United States Patent
Hoge et al.

(10) Patent No.: US 12,246,030 B2
(45) Date of Patent: Mar. 11, 2025

(54) METHODS FOR THERAPEUTIC ADMINISTRATION OF MESSENGER RIBONUCLEIC ACID DRUGS

(71) Applicant: ModernaTX, Inc., Cambridge, MA (US)

(72) Inventors: Stephen Hoge, Cambridge, MA (US); Tirtha Chakraborty, Cambridge, MA (US); Gilles Besin, Cambridge, MA (US); Ruchi Jain, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 18/167,984

(22) Filed: Feb. 13, 2023

(65) Prior Publication Data

US 2023/0338410 A1    Oct. 26, 2023

Related U.S. Application Data

(63) Continuation of application No. 17/036,374, filed on Sep. 29, 2020, now Pat. No. 11,590,157, which is a continuation of application No. 15/761,220, filed as application No. PCT/US2016/055582 on Oct. 5, 2016, now Pat. No. 10,849,920.

(60) Provisional application No. 62/350,149, filed on Jun. 14, 2016, provisional application No. 62/338,388, filed on May 18, 2016, provisional application No. 62/338,385, filed on May 18, 2016, provisional application No. 62/338,386, filed on May 18, 2016, provisional application No. 62/317,366, filed on Apr. 1, 2016, provisional application No. 62/317,271, filed on Apr. 1, 2016, provisional application No. 62/317,268, filed on Apr. 1, 2016, provisional application No. 62/237,462, filed on Oct. 5, 2015.

(51) Int. Cl.
| | |
|---|---|
| *C07H 21/04* | (2006.01) |
| *A61K 9/00* | (2006.01) |
| *A61K 9/127* | (2006.01) |
| *A61K 31/7115* | (2006.01) |
| *C12N 15/113* | (2010.01) |
| *C12N 15/67* | (2006.01) |

(52) U.S. Cl.
CPC ........ *A61K 31/7115* (2013.01); *A61K 9/0019* (2013.01); *A61K 9/127* (2013.01); *C12N 15/113* (2013.01); *C12N 15/67* (2013.01); *C12N 2310/141* (2013.01); *C12N 2800/107* (2013.01); *C12N 2800/22* (2013.01)

(58) Field of Classification Search
CPC ................. C12N 2310/141; C12N 15/113
See application file for complete search history.

(56) References Cited

U.S. PATENT DOCUMENTS

| | | | |
|---|---|---|---|
| 5,489,677 | A | 2/1996 | Sanghvi et al. |
| 6,310,197 | B1 | 10/2001 | Rogers |
| 6,849,405 | B2 | 2/2005 | Rogers |
| 7,183,395 | B2 | 2/2007 | Mauro et al. |
| 7,456,273 | B2 | 11/2008 | Mauro et al. |
| 8,039,214 | B2 | 10/2011 | Dahl et al. |
| 8,058,069 | B2 | 11/2011 | Yaworski et al. |
| 8,158,601 | B2 | 4/2012 | Chen et al. |
| 8,217,016 | B2 | 7/2012 | Hoerr et al. |
| 8,278,036 | B2 | 10/2012 | Kariko et al. |
| 8,329,887 | B2 | 12/2012 | Dahl et al. |
| 8,354,513 | B2 | 1/2013 | Mikesell et al. |
| 8,519,110 | B2 | 8/2013 | Kowalska et al. |
| 8,664,194 | B2 | 3/2014 | de Fougerolles et al. |
| 8,680,069 | B2 | 3/2014 | de Fougerolles et al. |
| 8,691,750 | B2 | 4/2014 | Constien et al. |
| 8,691,966 | B2 | 4/2014 | Kariko et al. |
| 8,710,200 | B2 | 4/2014 | Schrum et al. |
| 8,716,465 | B2 | 5/2014 | Rossi et al. |
| 8,748,089 | B2 | 6/2014 | Kariko et al. |

(Continued)

FOREIGN PATENT DOCUMENTS

| | | |
|---|---|---|
| CA | 2795695 A1 | 10/2011 |
| EP | 2221371 A1 | 8/2010 |

(Continued)

OTHER PUBLICATIONS

Newby et al. (PNAS, 2002, 99, 20, 12697-12702).*

(Continued)

*Primary Examiner* — Amy Rose Hudson
(74) *Attorney, Agent, or Firm* — Clark & Elbing LLP

(57) ABSTRACT

The disclosure features methods of reducing or inhibiting an anti-drug antibody response in a subject, as well as methods of reducing or inhibiting unwanted immune cell activation in a subject to be treated with a messenger RNA (mRNA), comprising administering to the subject a mRNA, e.g., a chemically modified messenger RNA (mmRNA), encoding a polypeptide of interest, wherein the mRNA comprises at least one microRNA (miR) binding site for a miR expressed in immune cells, such as miR-126 binding site and/or miR-142 binding site, such that an anti-drug antibody response to the polypeptide or interest, or unwanted immune cell activation (e.g., B cell activation, cytokine secretion), is reduced or inhibited in the subject. The disclosure further provides therapeutic treatment regimens designed to reduce or inhibit ADA or unwanted immune cell activation (e.g., B cell activation, cytokine secretion) in a subject being treated with mRNA-based therapeutics.

32 Claims, 39 Drawing Sheets

Specification includes a Sequence Listing.

(56) References Cited

U.S. PATENT DOCUMENTS

| | | |
|---|---|---|
| 8,754,062 B2 | 6/2014 | de Fougerolles et al. |
| 8,802,438 B2 | 8/2014 | Rossi et al. |
| 8,808,982 B2 | 8/2014 | Dahl et al. |
| 8,822,663 B2 | 9/2014 | Schrum et al. |
| 8,835,108 B2 | 9/2014 | Kariko et al. |
| 8,846,348 B2 | 9/2014 | Jendrisak et al. |
| 8,853,179 B2 | 10/2014 | Mauro et al. |
| 8,853,377 B2 | 10/2014 | Guild et al. |
| 8,871,230 B2 | 10/2014 | Rudolph et al. |
| 8,883,506 B2 | 11/2014 | Rossi et al. |
| 8,999,380 B2 | 4/2015 | Bancel et al. |
| 9,597,380 B2 | 3/2017 | Chakraborty et al. |
| 9,751,925 B2 | 9/2017 | Hoge et al. |
| 10,080,809 B2 | 9/2018 | Thess |
| 10,155,029 B2 | 12/2018 | Chakraborty et al. |
| 10,849,920 B2 | 12/2020 | Hoge et al. |
| 10,925,935 B2 | 2/2021 | Chakraborty et al. |
| 11,590,157 B2 | 2/2023 | Hoge et al. |
| 2003/0192068 A1 | 10/2003 | DeBoer et al. |
| 2005/0032730 A1 | 2/2005 | Von Der Mulbe et al. |
| 2005/0065333 A1 | 3/2005 | Seth |
| 2005/0261218 A1 | 11/2005 | Esau et al. |
| 2006/0188490 A1 | 8/2006 | Hoerr et al. |
| 2006/0247195 A1 | 11/2006 | Ray |
| 2007/0048776 A1 | 3/2007 | Mauro et al. |
| 2007/0143878 A1 | 6/2007 | Bhat et al. |
| 2008/0267873 A1 | 10/2008 | Hoerr et al. |
| 2009/0093049 A1 | 4/2009 | Mauro et al. |
| 2009/0286852 A1 | 11/2009 | Kariko et al. |
| 2010/0028943 A1 | 2/2010 | Thomas et al. |
| 2010/0041737 A1 | 2/2010 | Naldini et al. |
| 2010/0047261 A1 | 2/2010 | Hoerr et al. |
| 2010/0129877 A1 | 5/2010 | Sahin et al. |
| 2010/0189729 A1 | 7/2010 | Hoerr et al. |
| 2010/0196357 A1 | 8/2010 | Huang et al. |
| 2010/0239608 A1 | 9/2010 | Von Der Mulbe et al. |
| 2010/0258135 A1 | 10/2010 | Persson |
| 2010/0293625 A1 | 11/2010 | Reed |
| 2011/0045022 A1 | 2/2011 | Tsai |
| 2011/0065103 A1 | 3/2011 | Sahin et al. |
| 2011/0077287 A1 | 3/2011 | Von Der Mulbe et al. |
| 2011/0086904 A1 | 4/2011 | Russell |
| 2011/0124100 A1 | 5/2011 | Mauro et al. |
| 2011/0143397 A1 | 6/2011 | Kariko et al. |
| 2011/0151444 A1 | 6/2011 | Albers et al. |
| 2011/0244026 A1 | 10/2011 | Guild et al. |
| 2011/0247090 A1 | 10/2011 | Reed |
| 2011/0250237 A1 | 10/2011 | O'Hagan et al. |
| 2011/0300205 A1 | 12/2011 | Geall et al. |
| 2011/0311472 A1 | 12/2011 | Hoerr et al. |
| 2012/0027813 A1 | 2/2012 | Podda et al. |
| 2012/0046346 A1 | 2/2012 | Rossi et al. |
| 2012/0053333 A1 | 3/2012 | Mauro et al. |
| 2012/0065252 A1 | 3/2012 | Schrum et al. |
| 2012/0156251 A1 | 6/2012 | Brito et al. |
| 2012/0195917 A1 | 8/2012 | Sahin et al. |
| 2012/0195936 A1* | 8/2012 | Rudolph ............ A61K 48/0066 424/400 |
| 2012/0208278 A1 | 8/2012 | Yanik et al. |
| 2012/0237975 A1 | 9/2012 | Schrum et al. |
| 2012/0251618 A1 | 10/2012 | Schrum et al. |
| 2012/0301955 A1 | 11/2012 | Thomas et al. |
| 2012/0322864 A1 | 12/2012 | Rossi et al. |
| 2012/0322865 A1 | 12/2012 | Rossi et al. |
| 2013/0102034 A1 | 4/2013 | Schrum |
| 2013/0115272 A1 | 5/2013 | de Fougerolles et al. |
| 2013/0123481 A1 | 5/2013 | de Fougerolles et al. |
| 2013/0149375 A1 | 6/2013 | Geall |
| 2013/0156849 A1 | 6/2013 | de Fougerolles et al. |
| 2013/0165504 A1 | 6/2013 | Bancel et al. |
| 2013/0171241 A1 | 7/2013 | Geall |
| 2013/0177581 A1 | 7/2013 | Mauro et al. |
| 2013/0177639 A1 | 7/2013 | Geall et al. |
| 2013/0177640 A1 | 7/2013 | Geall et al. |
| 2013/0183355 A1 | 7/2013 | Jain et al. |
| 2013/0189295 A1 | 7/2013 | Aric et al. |
| 2013/0189351 A1 | 7/2013 | Geall |
| 2013/0189741 A1 | 7/2013 | Meis et al. |
| 2013/0195967 A1 | 8/2013 | Guild et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0203115 A1 | 8/2013 | Schrum et al. |
| 2013/0216561 A1 | 8/2013 | Govindan |
| 2013/0236974 A1 | 9/2013 | de Fougerolles |
| 2013/0237592 A1 | 9/2013 | de Fougerolles et al. |
| 2013/0237593 A1 | 9/2013 | de Fougerolles et al. |
| 2013/0237594 A1 | 9/2013 | de Fougerolles et al. |
| 2013/0244278 A1 | 9/2013 | de Fougerolles et al. |
| 2013/0244279 A1 | 9/2013 | de Fougerolles et al. |
| 2013/0244282 A1 | 9/2013 | Schrum et al. |
| 2013/0245096 A1 | 9/2013 | Abitbol |
| 2013/0245103 A1 | 9/2013 | de Fougerolles et al. |
| 2013/0245106 A1 | 9/2013 | de Fougerolles et al. |
| 2013/0245107 A1 | 9/2013 | de Fougerolles et al. |
| 2013/0252281 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2013/0273104 A1 | 10/2013 | Podda et al. |
| 2013/0273109 A1 | 10/2013 | Settembre et al. |
| 2014/0004593 A1 | 1/2014 | Boldog et al. |
| 2014/0010861 A1 | 1/2014 | Bancel et al. |
| 2014/0030292 A1 | 1/2014 | Franti et al. |
| 2014/0073687 A1 | 3/2014 | Chien et al. |
| 2014/0105930 A1 | 4/2014 | Springer |
| 2014/0105964 A1 | 4/2014 | Bancel et al. |
| 2014/0105965 A1 | 4/2014 | Bancel et al. |
| 2014/0105966 A1 | 4/2014 | Bancel et al. |
| 2014/0107189 A1 | 4/2014 | Bancel et al. |
| 2014/0113959 A1 | 4/2014 | Bancel et al. |
| 2014/0113960 A1 | 4/2014 | Bancel et al. |
| 2014/0141037 A1 | 5/2014 | Swanson et al. |
| 2014/0141067 A1 | 5/2014 | Bancel et al. |
| 2014/0141068 A1 | 5/2014 | Bancel et al. |
| 2014/0141070 A1 | 5/2014 | Geall et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161873 A1 | 6/2014 | Bancel et al. |
| 2014/0162934 A1 | 6/2014 | Constien et al. |
| 2014/0162962 A1 | 6/2014 | Constien et al. |
| 2014/0170175 A1 | 6/2014 | Constien et al. |
| 2014/0171485 A1 | 6/2014 | Bancel et al. |
| 2014/0178429 A1 | 6/2014 | Tsai |
| 2014/0178438 A1 | 6/2014 | Sahin et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0193484 A1 | 7/2014 | Bertholet Girardin et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0212498 A1 | 7/2014 | Brito et al. |
| 2014/0212504 A1 | 7/2014 | Weers et al. |
| 2014/0220083 A1 | 8/2014 | Brito et al. |
| 2014/0221465 A1 | 8/2014 | Bancel et al. |
| 2014/0227237 A1 | 8/2014 | June et al. |
| 2014/0227300 A1 | 8/2014 | Chin et al. |
| 2014/0227346 A1 | 8/2014 | Geall et al. |
| 2014/0242152 A1 | 8/2014 | Geall et al. |
| 2014/0243399 A1 | 8/2014 | Schrum et al. |
| 2014/0248312 A1 | 9/2014 | Rappuoli et al. |
| 2014/0248314 A1 | 9/2014 | Swanson et al. |

(56) References Cited

U.S. PATENT DOCUMENTS

| | | |
|---|---|---|
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0255472 A1 | 9/2014 | Geall et al. |
| 2014/0271829 A1 | 9/2014 | Lilja et al. |
| 2014/0275227 A1 | 9/2014 | Hoge et al. |
| 2014/0275229 A1 | 9/2014 | Bancel et al. |
| 2014/0288160 A1 | 9/2014 | Guild et al. |
| 2014/0294938 A1 | 10/2014 | Guild et al. |
| 2014/0294939 A1 | 10/2014 | Guild et al. |
| 2014/0294940 A1 | 10/2014 | Guild et al. |
| 2014/0308746 A1 | 10/2014 | Rossi et al. |
| 2014/0309277 A1 | 10/2014 | Baryza et al. |
| 2014/0315988 A1 | 10/2014 | Dahl et al. |
| 2014/0328825 A1 | 11/2014 | Meis et al. |
| 2014/0341995 A1 | 11/2014 | Rudolph et al. |
| 2014/0343129 A1 | 11/2014 | de Fougerolles et al. |
| 2014/0363876 A1 | 12/2014 | Jendrisak et al. |
| 2014/0370545 A1 | 12/2014 | Mauro et al. |
| 2014/0371302 A1 | 12/2014 | Afeyan et al. |
| 2014/0378538 A1 | 12/2014 | Bancel |
| 2015/0004217 A1 | 1/2015 | Guild et al. |
| 2015/0005372 A1 | 1/2015 | Hoge et al. |
| 2015/0017206 A1 | 1/2015 | Rueckl et al. |
| 2015/0017211 A1 | 1/2015 | de Fougerolles et al. |
| 2015/0030576 A1 | 1/2015 | Bancel |
| 2015/0038558 A1 | 2/2015 | Kariko et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0141498 A1 | 5/2015 | Mutzke |
| 2015/0141499 A1 | 5/2015 | Bancel et al. |
| 2015/0246139 A1 | 9/2015 | Bancel et al. |
| 2016/0022840 A1 | 1/2016 | Chakraborty et al. |
| 2017/0202979 A1 | 7/2017 | Chakraborty et al. |
| 2017/0252461 A1 | 9/2017 | Chakraborty et al. |
| 2017/0362605 A1 | 12/2017 | Chakraborty |
| 2018/0000091 A1 | 1/2018 | Eaton et al. |
| 2019/0185529 A1 | 6/2019 | Hoge et al. |
| 2019/0290742 A1 | 9/2019 | Chakraborty et al. |

FOREIGN PATENT DOCUMENTS

| | | | |
|---|---|---|---|
| EP | 2246422 A1 | 11/2010 | |
| EP | 2700708 A2 | 2/2014 | |
| WO | WO-1999014346 A2 | 3/1999 | |
| WO | WO-1999024595 A1 | 5/1999 | |
| WO | WO-2001055369 A1 | 8/2001 | |
| WO | WO-2004076622 A2 | 9/2004 | |
| WO | WO-2005005622 A2 | 1/2005 | |
| WO | WO-2006111512 A1 | 10/2006 | |
| WO | WO-2006128245 A1 | 12/2006 | |
| WO | WO-2007/000668 A2 | 1/2007 | |
| WO | WO-2007024708 A2 | 3/2007 | |
| WO | WO-2007064952 A2 | 6/2007 | |
| WO | WO-2007044627 A3 | 8/2007 | |
| WO | WO-2007025008 A3 | 9/2007 | |
| WO | WO-2008052770 A2 | 5/2008 | |
| WO | WO-2008083949 A2 | 7/2008 | |
| WO | WO-2008091799 A3 | 11/2008 | |
| WO | WO-2008140615 A2 | 11/2008 | |
| WO | WO-2009015071 A1 | 1/2009 | |
| WO | WO-2009075886 A1 | 6/2009 | |
| WO | WO-2009077134 A2 | 6/2009 | |
| WO | WO-2009127230 A1 | 10/2009 | |
| WO | WO-2010/017510 A1 | 2/2010 | |
| WO | WO-2010/042877 A1 | 4/2010 | |
| WO | WO-2010054406 A1 | 5/2010 | |
| WO | WO-2010055413 A1 | 5/2010 | |
| WO | WO-2010088537 A2 | 8/2010 | |
| WO | WO-2010098861 A1 | 9/2010 | |
| WO | WO-2010/125471 A2 | 11/2010 | |
| WO | WO-2010027903 A8 | 11/2010 | |
| WO | WO-2010129709 A1 | 11/2010 | |
| WO | WO-2011/012316 A3 | 2/2011 | |
| WO | WO-2011005786 A3 | 3/2011 | |
| WO | WO-2011025566 A1 | 3/2011 | |
| WO | WO-2011068810 A1 | 6/2011 | |
| WO | WO-2011071931 A2 | 6/2011 | |
| WO | WO-2011071936 A2 | 6/2011 | |
| WO | WO-2011088309 A1 | 7/2011 | |
| WO | WO-2011130624 A2 | 10/2011 | |
| WO | WO-2012019168 A2 | 2/2012 | |
| WO | WO-2012019630 A1 | 2/2012 | |
| WO | WO-2012009644 A3 | 3/2012 | |
| WO | WO-2012045075 A1 | 4/2012 | |
| WO | WO-2012045082 A2 | 4/2012 | |
| WO | WO-2012056440 A1 | 5/2012 | |
| WO | WO-2012089338 A1 | 7/2012 | |
| WO | WO-2012135805 A2 | 10/2012 | |
| WO | WO-2012138453 A1 | 10/2012 | |
| WO | WO-2012170889 A1 | 12/2012 | |
| WO | WO-2012170930 A1 | 12/2012 | |
| WO | WO-2013039857 A1 | 3/2013 | |
| WO | WO-2013/090186 A1 | 6/2013 | |
| WO | WO 2013/090648 A1 * | 6/2013 | ........... A61K 31/713 |
| WO | WO-2013103659 A1 | 7/2013 | |
| WO | WO-2013109713 A1 | 7/2013 | |
| WO | WO-2013120497 A1 | 8/2013 | |
| WO | WO-2013120498 A1 | 8/2013 | |
| WO | WO-2013120499 A1 | 8/2013 | |
| WO | WO-2013120500 A1 | 8/2013 | |
| WO | WO-2013120626 A1 | 8/2013 | |
| WO | WO-2013120627 A1 | 8/2013 | |
| WO | WO-2013120628 A1 | 8/2013 | |
| WO | WO-2013120629 A1 | 8/2013 | |
| WO | WO-2013/134349 A1 | 9/2013 | |
| WO | WO-2013131143 A1 | 9/2013 | |
| WO | WO-2013/151666 A2 | 10/2013 | |
| WO | WO-2013151663 A1 | 10/2013 | |
| WO | WO-2013151664 A1 | 10/2013 | |
| WO | WO-2013151665 A2 | 10/2013 | |
| WO | WO-2013151667 A1 | 10/2013 | |
| WO | WO-2013151668 A2 | 10/2013 | |
| WO | WO-2013151669 A1 | 10/2013 | |
| WO | WO-2013151670 A2 | 10/2013 | |
| WO | WO-2013151671 A1 | 10/2013 | |
| WO | WO-2013151672 A2 | 10/2013 | |
| WO | WO-2013151736 A2 | 10/2013 | |
| WO | WO-2014028429 A2 | 2/2014 | |
| WO | WO-2014/081507 A1 | 5/2014 | |
| WO | WO-2014093574 A1 | 6/2014 | |
| WO | WO-2014093924 A1 | 6/2014 | |
| WO | WO-2014/113089 A2 | 7/2014 | |
| WO | WO-2014144039 A1 | 9/2014 | |
| WO | WO-2014144711 A1 | 9/2014 | |
| WO | WO-2014144767 A1 | 9/2014 | |
| WO | WO-2014152027 A1 | 9/2014 | |
| WO | WO-2014152030 A1 | 9/2014 | |
| WO | WO-2014152031 A1 | 9/2014 | |
| WO | WO-2014152211 A1 | 9/2014 | |
| WO | WO-2014152540 A1 | 9/2014 | |
| WO | WO-2014158795 A1 | 10/2014 | |
| WO | WO-2014159813 A1 | 10/2014 | |
| WO | WO-2014164253 A1 | 10/2014 | |
| WO | WO-2014140856 A3 | 11/2014 | |
| WO | WO-2015006747 A2 | 1/2015 | |
| WO | WO-2015007871 A3 | 3/2015 | |
| WO | WO-2015034925 A1 | 3/2015 | |
| WO | WO-2015034928 A1 | 3/2015 | |
| WO | WO-2015038892 A1 | 3/2015 | |
| WO | WO-2015048744 A2 | 4/2015 | |
| WO | WO-2015051173 A2 | 4/2015 | |
| WO | WO-2015051214 A1 | 4/2015 | |
| WO | WO-2015058069 A1 | 4/2015 | |
| WO | WO-2015105926 A1 | 7/2015 | |
| WO | WO-2015073884 A3 | 11/2015 | |
| WO | WO-2016011306 A3 | 3/2016 | |

(56) References Cited

FOREIGN PATENT DOCUMENTS

| | | |
|---|---|---|
| WO | WO-2016100812 A1 | 6/2016 |
| WO | WO-2016170176 A1 | 10/2016 |
| WO | WO-2017/112943 A1 | 6/2017 |

OTHER PUBLICATIONS

Kormann et al. (Nature Biotechnology, 29, 2, 2011, 154-159).*
Tavernier et al. (Journal of Controlled Release 150 (2011) 238-247).*
U.S. Appl. No. 17/127,435, filed Dec. 18, 2020, Chakraborty et al.
U.S. Appl. No. 17/162,061, filed Jan. 29, 2021, Hoge et al.
Anadarini, S. et al., "Adenovirus vector-mediated in vivo gene transfer of OX40 ligand to tumor cells enhances antitumor immunity of tumor-bearing hosts," Cancer Research, vol. 64:3281-3287 (2004).
Anderson, B.R. et al., "Incorporation of pseudouridine into mRNA enhances translation by diminishing PKR activation," Nucleic Acids Research, vol. 38(17):5884-5892 (2010).
Annoni, A. et al., "In vivo delivery of a microRNA-regulated transgene induces antigen-specific regulatory T cells and promotes immunologic tolerance," Blood, vol. 114: 5152-5161 (2009).
Beilharz, T. et al., "Widespread use of poly(A) tail length control to accentuate expression of the yeast transcriptome," RNA, vol. 13(7): 982-997 (2007) Abstract.
Blum, E. et al., "Polyadenylation Promotes Degradation of 3'-Structured RNA by the <i>Escherichia coli</i> mRNA Degradosome in Vitro," J Bio Chem., vol. 274(7):4009-4016 (1999).
Bolukbasi, M.F. et al., "miR-1289 and "Zipcode"-like Sequence Enrich mRNAs in Microvesicles," Molecular Therapy—Nucleic Acids, vol. 1, e10: 10 pages (2012) doi:10.1038/mtna.2011.2.
Brown, B.D. et al., "Endogenous microRNA can be broadly exploited to regulate transgene expression according to tissue, lineage and differentiation state", Nature Biotechnology, vol. 25:1457-1467 (2007).
Brown, J.A. et al., "Formation of triple-helical structures by the 3'-end sequences of MALAT1 and MEN noncoding RNAs," PNAS, vol. 109 (47):19202-19207 (2012).
Cawood, R. et al., "Use of tissue-specific microRNA to control pathology of wild-type adenovirus without attenuation of its ability to kill cancer cells," PLOS Pathogens, Public Library of Science, vol. 5(5): e1000440: (2009).
Chappell, S. A., et al. "Biochemical and functional analysis of a 9-nt RNA sequence that affects translation efficiency in eukaryotic cells," PNAS, vol. 101 (26): 9590-9594 (2004).
Collins, F. et al., "Generation and initial analysis of more than 15,000 full-length human and mouse cDNA sequences, " PNAS, vol. 99(26):16899-16903 (2002).
Dannull, J. et al., "Enhancing the immunostimulatory function of dendritic cells by transfection with mRNA encoding OX40 ligand," Blood, vol. 105 (8):3206-3213 (2004).
Direct Submission Submitted (Feb. 5, 2001) National Institutes of Health, Mammalian Gene Collection (MGC), Bethesda, MD 20892-2590, USA <i>Homo sapiens</i> polypyrimidine tract binding protein 1, mRNA (cDNA clone MGC:8461 IMAGE:2821531), (Year:2001).
Ebert, M.S., et al., "MicroRNA sponges: competitive inhibitors of small RNAs in mammalian cells," Nat. Methods, vol. 4:721-726. (2007).
Extended European Search Report, European Application No. 14780126, dated Nov. 8, 2016, 11 pages.
Extended European Search Report, European Application No. 15871164. 8, dated May 25, 2018, 6 pages.
Extended European Search Report, European Application No. 18179340. 7, dated Nov. 9, 2018, 14 pages.
Fan, X. C., et al., "Overexpression of HuR, a nuclear-cytoplasmic shuttling protein, increases the in vivo stability of ARE-containing mRNAs," The EMBO Journal, vol. 17(12):3448-3460 (1998).
Helm, M., "Post-transcriptional nucleotide modification and alternative folding of RNA," Nucleic Acids Research, vol. 34(2): 721-733 (2006).
International Preliminary Report on Patentability, PCT/US2013/062531, dated Jul. 21, 2015, 19 pages.
International Preliminary Report on Patentability, PCT/US2013/062943, dated May 26, 2015, 11 pages.
International Preliminary Report on Patentability, PCT/US2014/021522, dated Sep. 15, 2015, 8 pages.
International Preliminary Report on Patentability, PCT/US2015/040835, dated Jan. 17, 2017, 9 pages.
International Preliminary Report on Patentability, PCT/US2015/066662, dated Jun. 20, 2017, 7 pages.
International Preliminary Report on Patentability, PCT/US2016/055582, dated Apr. 10, 2018, 8 pages.
International Search Report and Written Opinion, PCT/ US2015/40835, dated Jan. 4, 2016, 21 pages.
International Search Report and Written Opinion, PCT/US2013/062531, dated Jul. 3, 2014, 30 pages.
International Search Report and Written Opinion, PCT/US2013/062943, dated Jan. 7, 2014, 17 pages.
International Search Report and Written Opinion, PCT/US2014/021522, dated Sep. 4, 2014, 13 pages.
International Search Report and Written Opinion, PCT/US2014/053904, dated Feb. 11, 2015, 19 pages.
International Search Report and Written Opinion, PCT/US2014/053907, dated Dec. 18, 2014, 9 pages.
International Search Report and Written Opinion, PCT/US2015/066662, dated Mar. 7, 2016, 11 pages.
International Search Report and Written Opinion, PCT/US2016/055582, dated Mar. 13, 2017, 14 pages.
International Search Report and Written Opinion, PCT/US2016/068552, dated Mar. 21, 2017, 6 pages.
Kariko, K. et al., "Generating the optimal mRNA for therapy: HPLC purification eliminates immune activation and improves translation of nucleoside-modified, protein-encoding mRNA," Nucleic Acids Research, vol. 39 (21):e142-1 (2011).
Kariko K. et al., "Incorporation of pseudouridine into mRNA yields superior nonimmunogenic vector with increased translational capacity and biological stability," Molecular Therapy, Nature Publishing Group, vol. 16 (11):1833-1840 (2008).
Kariko, K. et al., "Suppression of RNA Recognition by Toll-like Receptors: The Impact of Nucleoside Modification and the Evolutionary Origin of RNA," Immunity, vol. 23: 165-175 (2005).
Kedde, M. et al., "A Pumilio-induced RNA structure switch in p27-3' UTR controls miR-221 and miR-222 accessibility," Nature Cell Biology, vol. 10(12)1014-1020 (2010).
Kore, A.R. et al., "Synthesis and biological validation of N7-(4-chlorophenoxyethyl) substituted dinucleotide cap analogs for mRNA translation," Bioorganic & Medicinal Chemistry, vol. 21:4570-4574 (2013).
Kormann, M.S. et al., "Expression of therapeutic proteins after delivery of chemically modified mRNA in mice," Nature Biotechnology, vol. 29(2):154-159 (2011).
Kron, M. et al., "miRNA-mediated silencing in hepatocytes can increase adaptive immune responses to adenovirus vector-delivered transgenic antigens," Molecular Therapy, vol. 19(8):1547-1557 (2011).
Lennox, KA, et al., "Chemical modification and design of anti-miRNA oligonucleotides," Gene Therapy, vol. 18 (12):1111-1120 (2011).
Leppek, K., et al., "Roquin Promotes Constitutive mRNA Decay via a Conserved Class of Stem-Loop Recognition Motifs," Cell, vol. 153: 869-881 (2013).
Limbach, PA., et al., "Summary: the modified nucleosides of RNA," Nucleic Acids Research, vol. 22 (12): 2183-2196 (1994).
Link, et al. "Structure of <i>Escherichia coli</i> Hfq bound to polyriboadenylate RNA," PNAS USA, vol. 106(46):19292-19297 (2009).
Lorenz, C. et al., "Protein expression from exogenous mRNA: Uptake by receptor-mediated endocytosis and trafficking via the lysosomal pathway," RNA Biology, vol. 8(4):627-636 (2011).

(56) References Cited

OTHER PUBLICATIONS

Lytle, J.R., et al., "Target mRNAs are repressed as efficiently by microRNA-binding sites in the 5' UTR as in the 3' UTR," PNAS, vol. 104(23): 9667-9672 (2007).
Meijer, H.A., et al., "Translational Repression and eIF4A2 Activity Are Critical for MicroRNA-Mediated Gene Regulation," Science vol. 340: 82-85 (2013).
Nemani, M. et al., "Activation of the human homologue of the *Drosophila* sina gene in apoptosis and tumor suppression," Proc. Natl. Acad. Sci. USA, vol. 93 (17):9039-9042 (1996).
Panek, J. et al., "An evolutionary conserved pattern of 18S rRNA sequence complementarity to mRNA 5' UTRs and its implications for eukaryotic gene translation regulation," Nucleic Acids Research, vol. 41(16):7625-7634 (2013).
Partial Supplementary European Search Report, European Application No. 15821578.0, dated May 30, 2018, 12 pages.
Peart, N. et al., "Non-mRNA 3' end formation: how the other half lives," Wiley Interdiscip Rev RNA, vol. 4(5):491-506 (2013) doi: 10.1002/wrna.1174. Epub Jun. 10, 2013.
Piccinini, A. et al., "Illustrating the interplay between the extracellular matrix and microRNAs," Int. J.Exp. Path., vol. 95:158-180 (2014).
Pichard, V. et al., "Specific Micro RNA-Regulated TetR-KRAB Transcriptional Control of Transgene Expression in Viral Vector-Transduced Cells," PLOS One, vol. 7(12): e51952: 10 pages (2012).
Probst J et al., "Spontaneous cellular uptake of exogenous messenger RNA in vivo is nucleic acid-specific, saturable and ion dependent," Gene Therapy, Nature Publishing Group, vol. 14: 1175-1180 (2007).
Rotondaro, L. et al., "Efficiency of different viral promoters in directing gene expression in mammalian cells: effect of 3'-untranslated sequences," Gene, vol. 168(2):195-198 (1996).
Rozenski, J., "The RNA Modification Database: 1999 update," Nucleic Acids Research, vol. 27(1):196-197 (1999).
Sahin, U. et al., "mRNA-based therapeutics—developing a new class of drugs," Nature Reviews Drug Discovery, vol. 13(10)759-780 (2014).
Savino, M. et al., "The Action Mechanism of the Myc Inhibitor Termed Omomyc May Give Clues on How to Target Myc for Cancer Therapy," PLOS One, vol. 6(7): e22284 (2011).
Singh, R. et al., "Nanoengineering artificial lipid envelopes around adenovirus by self-assembly," ACS Nano, vol. 2(5):1040-1050 (2008).
Smirnov, D.A. et al., "ATM Gene mutations result in both recessive and dominant expression phenotypes of genes and microRNAs", The American Journal of Human Genetics, vol. 83: 243-253 (2008).
Soucek, L. et al., "Modelling Myc inhibition as a cancer therapy," Nature, vol. 455 (7213):679-683 (2008).
Soucek, L. et al., "Omomyc, a potential Myc dominant negative, enhances Myc-induced apoptosis," Cancer Research, American Association of Cancer Research, vol. 62 (12):3507-3510 (2002).
Su, X., et al., "In vitro and in vivo mRNA delivery using lipid-enveloped pH-responsive polymer nanoparticles", Molecular Phamaceutics, vol. 8: 744-787 (2011).
Sullenger, B. et al., "Emerging clinical applications of RNA," Nature, vol. 418: 252-258 (2002).
Supplementary European Search Report, European Application No. 15821578.0, dated Sep. 3, 2018, 10 pages.
Suzuki, T. et al., "miR-122a-Regulated Expression of a Suicide Gene Prevents Hepatotoxicity Without Altering Antitumor Effects in Suicide Gene Therapy," Molecular Therapy, vol. 16(10): 1719-1726 (2008).
Taniguchi, K., et al., "Organ-specific PTB1-associated microRNAs determine expression of pyruvate kinase isoforms," Scientific Reports, vol. 5(8647), pp. 1-8 (2015).
Tavernier, G. et al., "mRNA as gene therapeutic: How to control protein expression," Journal of Controlled Release, vol. 150 (3):238-247(2011).
Tycowski, K. et al., "Conservation of a Triple-Helix-Forming RNA Stability Element in Noncoding and Genomic RNAs of Diverse Viruses," Cell Reports, vol. 2 (1):26-32 (2012).
Van Der Jeught, K. et al., "Targeting the tumor microenvironment to enhance antitumor immune responses," Oncotarget, vol. 6(3):1359-1381 (2014).
Van Tendeloo V., et al. "Highly efficient gene delivery by mRNA electroporation in human hematopoietic cells: superiority to lipofection and passive pulsing of mRNA and to electroporation of plasmid cDNA for tumor antigen loading of dendritic cells," Blood, vol. 98(1):49-56 (2001).
Van Tendeloo V., et al. "mRNA-based gene transfer as a tool for gene and cell therapy," Current Opinion in Molecular Therapeutics, Current Drugs, vol. 9(5):423-431 (2007).
Vinuesa, C. et al., "Logic and Extent of miRNA-Mediated Control of Autoimmune Gene Expression", Int Rev Immunol., vol. 28(3-4):112-138 (2009).
Wang Y. et al., "Systemic delivery of modified mRNA encoding herpes simplex virus 1 thymidine kinase for targeted cancer gene therapy", Mol Ther., vol. 21(2):358-367 (2013).
Warren, L. et al. "Highly efficient reprogramming to pluripotency and directed differentiation of human cells with synthetic modified mRNA," Cell Stem Cell., vol. 7(5):618-30 (2010).
Wellensiek, B., et al. "Genome-wide profiling of human cap-independent translation-enhancing elements," Nat Methods. vol. 10(8):747-750. (2013) doi: 10.1038/nmeth.2522.
Wellensiek, B. et al., "Supplementary Information for Genome-wide Profiling of Human Cap-Independent Translation Enhancing Elements," Nat Methods., 30 pages (2013) doi: 10.1038/nmeth.2522. Epub Jun. 16, 2013.
Wikipedia, Fiver prime untranslated region, 2018.
Wikipedia, Three prime untranslated region, 2018.
Wilusz J.E. et al., "A triple helix stabilizes the 3' ends of long noncoding RNAs that lack poly(A) tails," Genes & Development, vol. 26 (21):2392-2407 (2012).
Wilusz, J., et al., "3' end processing of a long nuclear-retained non-coding RNA yields a tRNA-like cytoplasmic RNA," Cell, vol. 135(5): 919-932. (2008).
Wolff, L. et al., "Effect of tissue-specific promoters and microRNA recognition elements on stability of transgene expression after hydrodynamic naked plasmid DNA delivery," Human Gene Therapy, vol. 20, pp. 374-388 (2009).
Yamamoto A. et al., "Current prospects for mRNA gene delivery," European Journal of Pharmaceutics and Biopharmaceutics, vol. 71(3):484-489 (2009).
Zhou, W. et al., "A positive feedback vector for identification of nucleotide sequences that enhance translation," PNAS, vol. 102 (18): 6273-6278 (2005).
Brown, B.D. et al., "A microRNA-regulated lentiviral vector mediates stable correction of hemophilia B mice," Blood, Dec. 2007, vol. 100, No. 13, 4144-4152.
Brown, B.D. et al., "Endogenous microRNA regulation suppresses transgene expression in hematopoietic lineages and enables stable gene transfer," Nature Medicine, May 2006, vol. 12, No. 5, pp. 585-591.
Chirmule et al., "Immunogenicity to Therapeutic Proteins: Impact on PK/PD and Efficacy," The AAPS Journal, Jun. 2012, vol. 14, No. 2, pp. 296-302.
De Groot and Scott, "Immunogenicity of protein therapeutics," Trends in Immunology, 2007, vol. 28, No. 11, pp. 482-490.
Fabian et al., "Regulation of mRNA Translation and Stability by microRNAs," Annu. Rev. Biochem. 2010, 79: 351-379.
Ferretti and La Cava, "miR-126, a new modulator of innate immunity," Cellular & Molecular Immunology (2014) 11, 215-217.
Gentner et al., "Identification of Hematopoietic Stem Cell-Specific miRNAs Enables Gene Therapy of Globoid Cell Leukodystrophy," Science Translational Medicine, Nov. 2010, vol. 2, Issue 2, 58ra84, 11 pages.
Majowicz et al., "Mir-142-3p target sequences reduce transgene-direct immunogenicity following intramuscular adeno-associated virus 1 vector-mediated gene delivey," J Gene Med 2013; 15: 219-232.

(56) References Cited

OTHER PUBLICATIONS

Martini and Guey, "A New Era for Rare Genetic Diseases: Messenger RNA Therapy," Human Gene Therapy, 2019, vol. 30, No. 10, pp. 1180-1189.
Matucci et al., "Anti-drug antibodies and clinical implications," Clinical Dermatology 2013; 1 (2): 77-80.
Notice of Opposition for European Application No. 16782372.3 dated Feb. 18, 2021, 44 pages.
Sakurai et al., "MicroRNA-regulated transgene expression systems for gene therapy and virotherapy," Frontiers in Bioscience Jun. 1, 2011, 16, 2389-2401.

\* cited by examiner

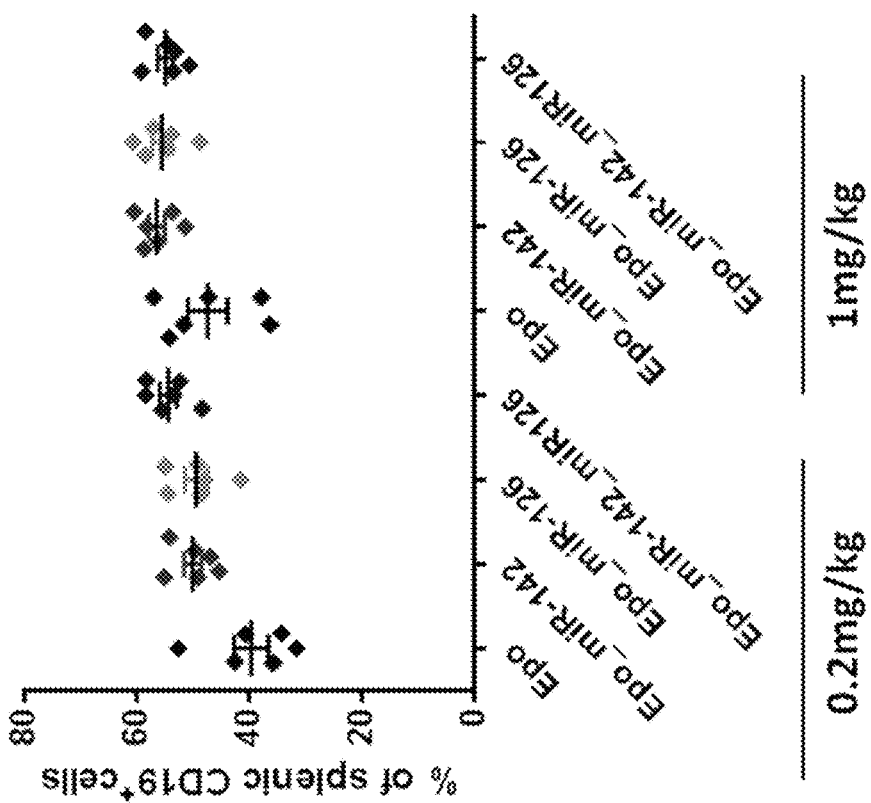
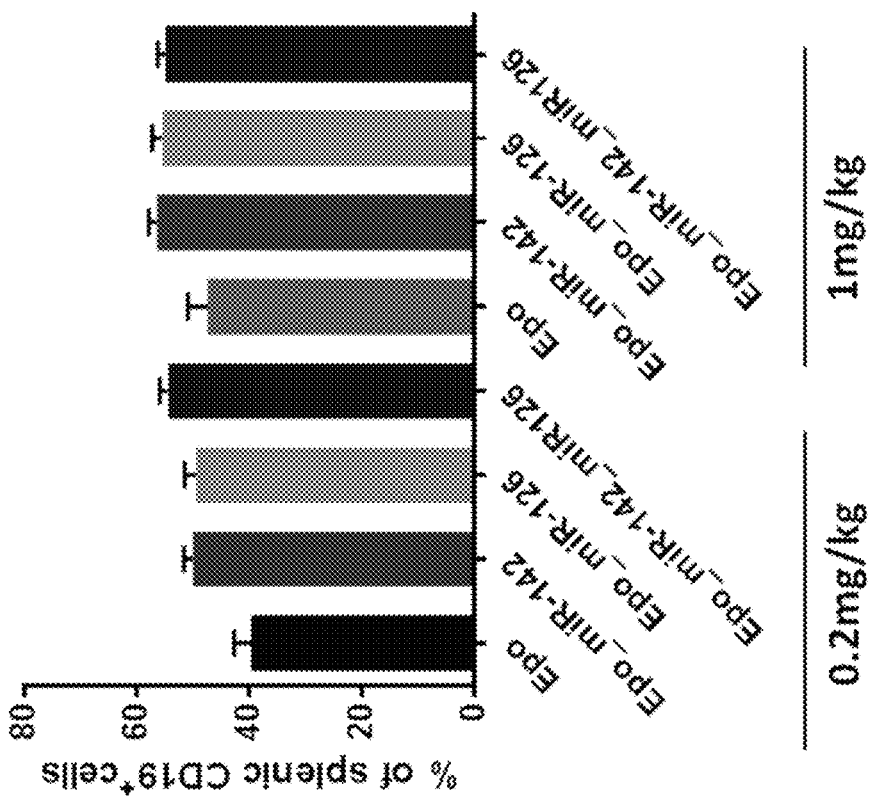
FIGURE 7

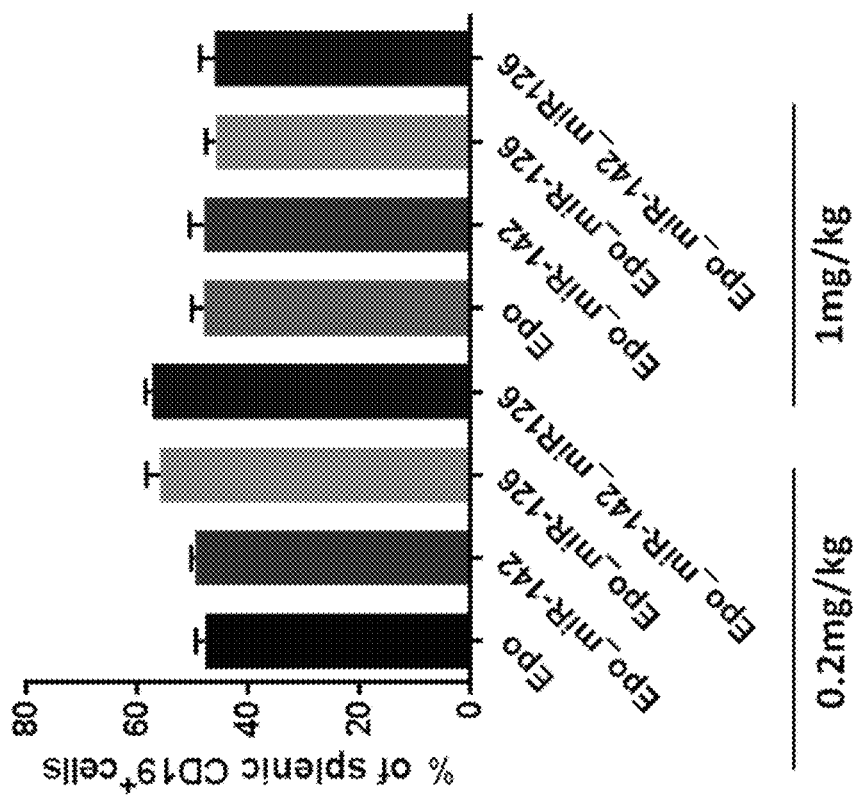
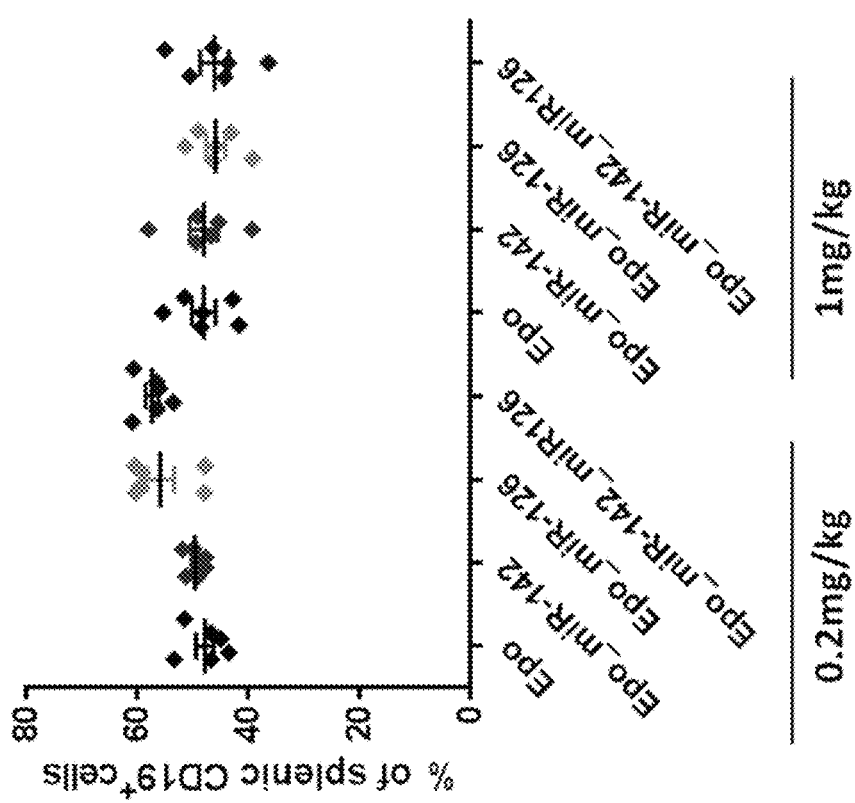
FIGURE 9

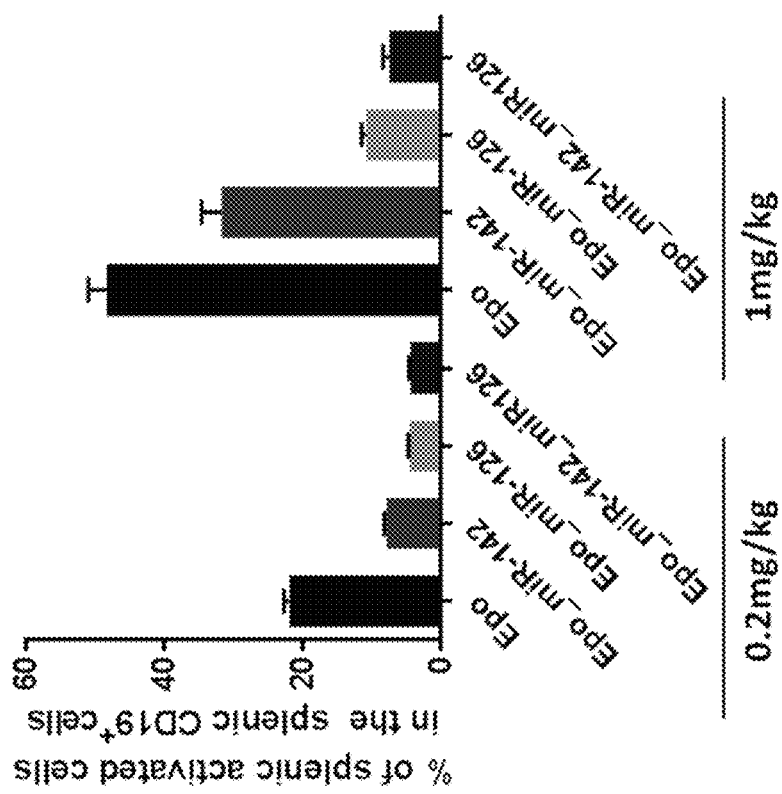
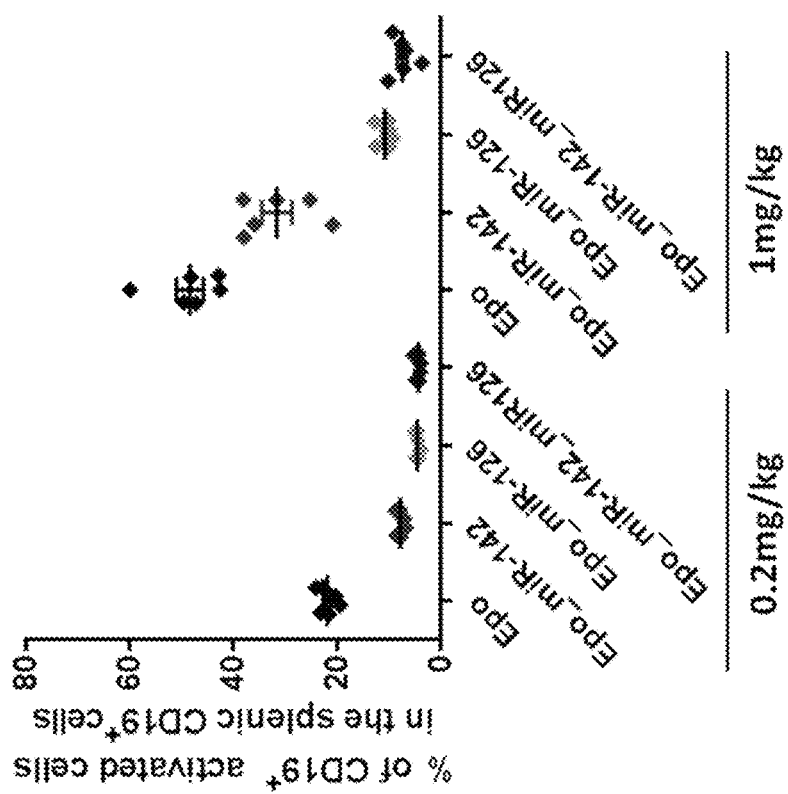
FIGURE 10

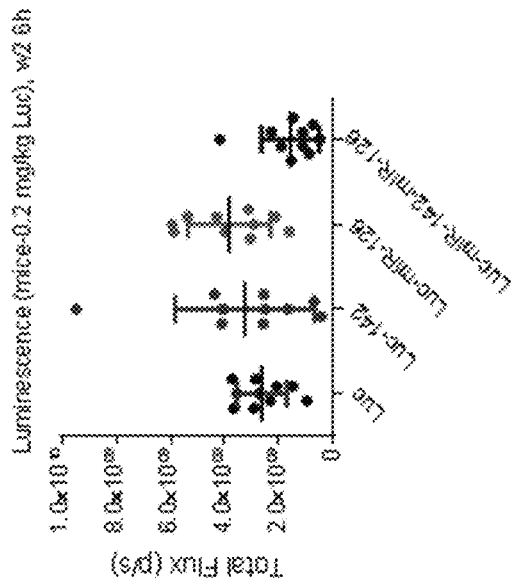
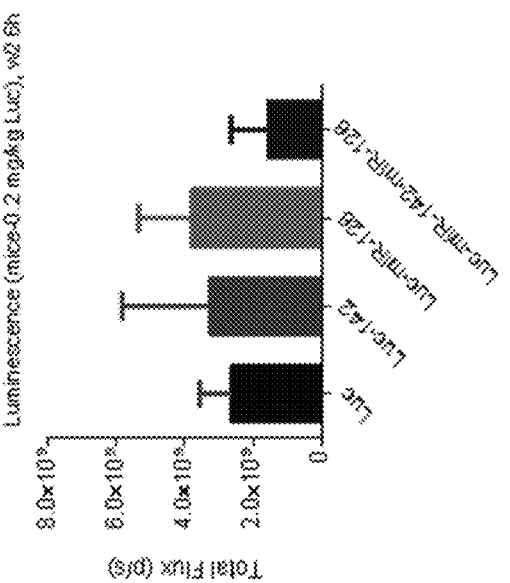
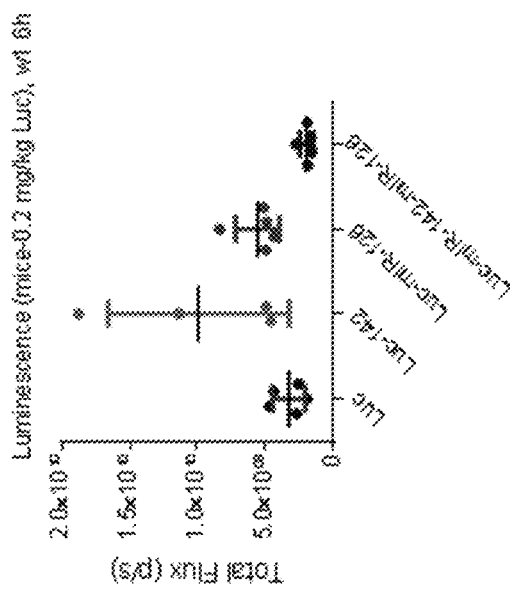
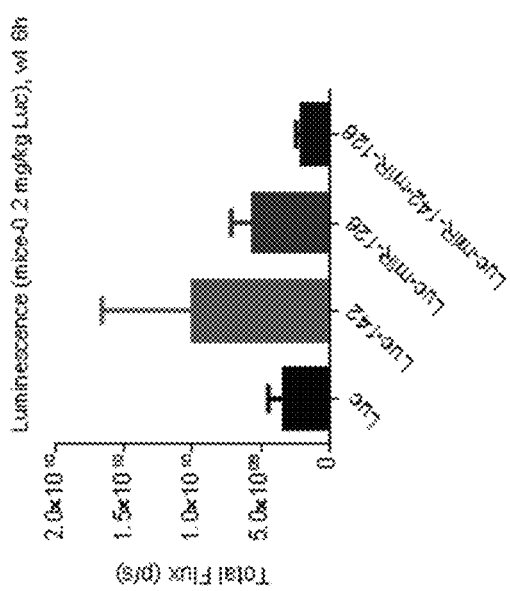
FIGURE 15A
FIGURE 15B

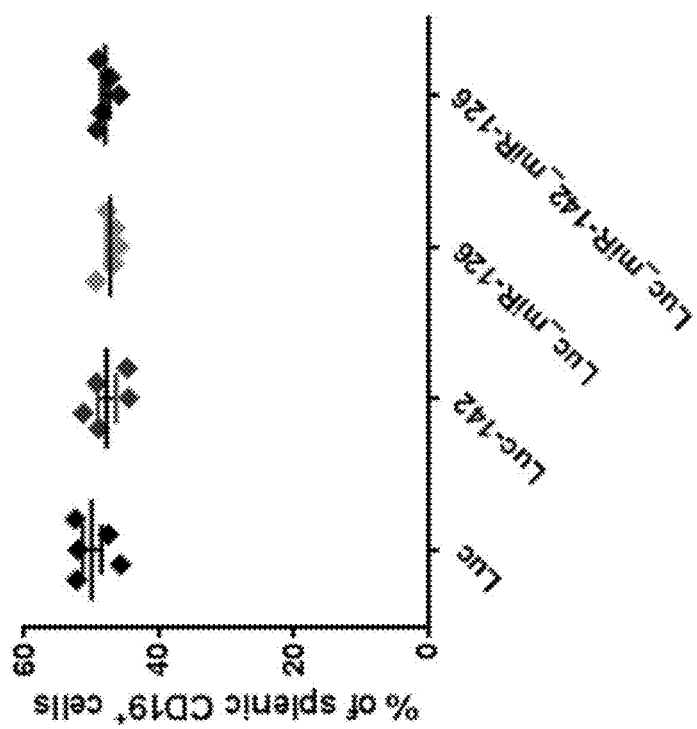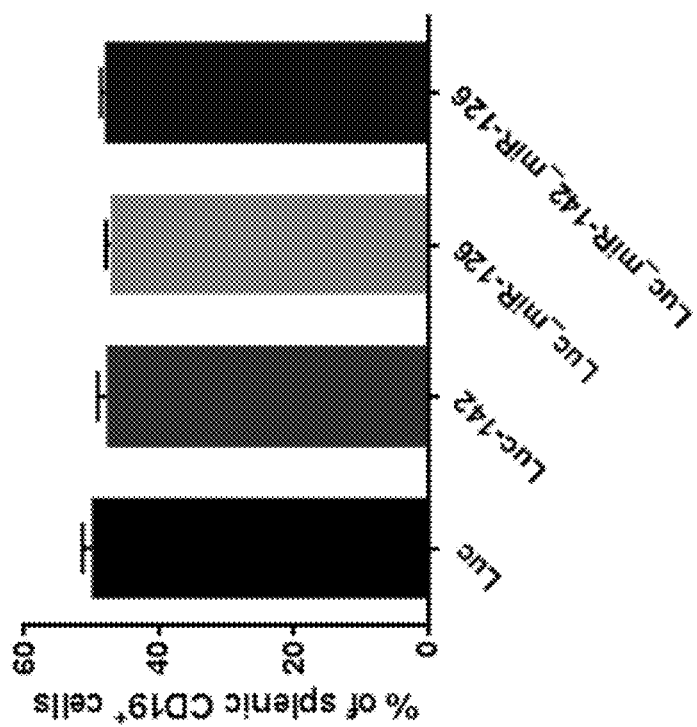
FIGURE 16

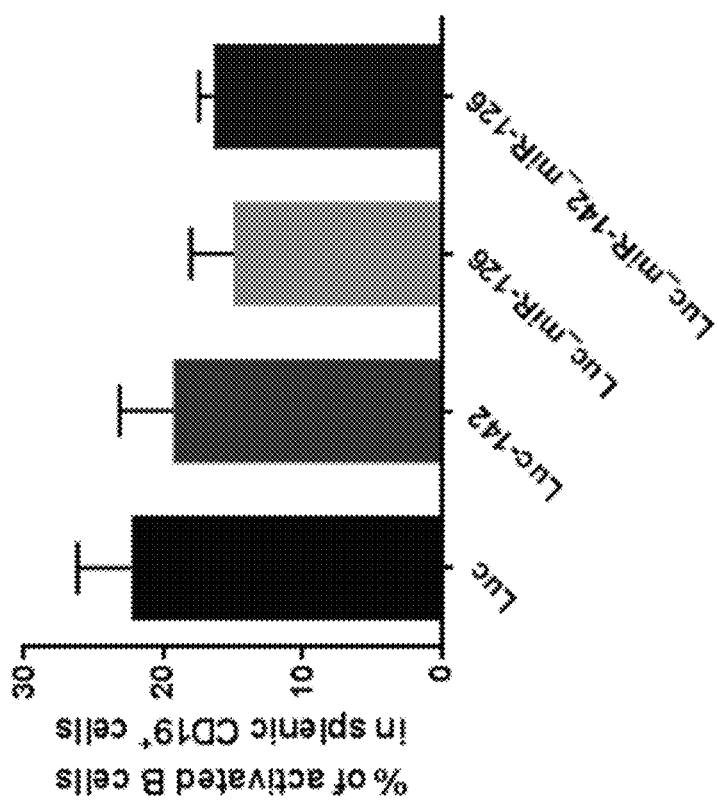
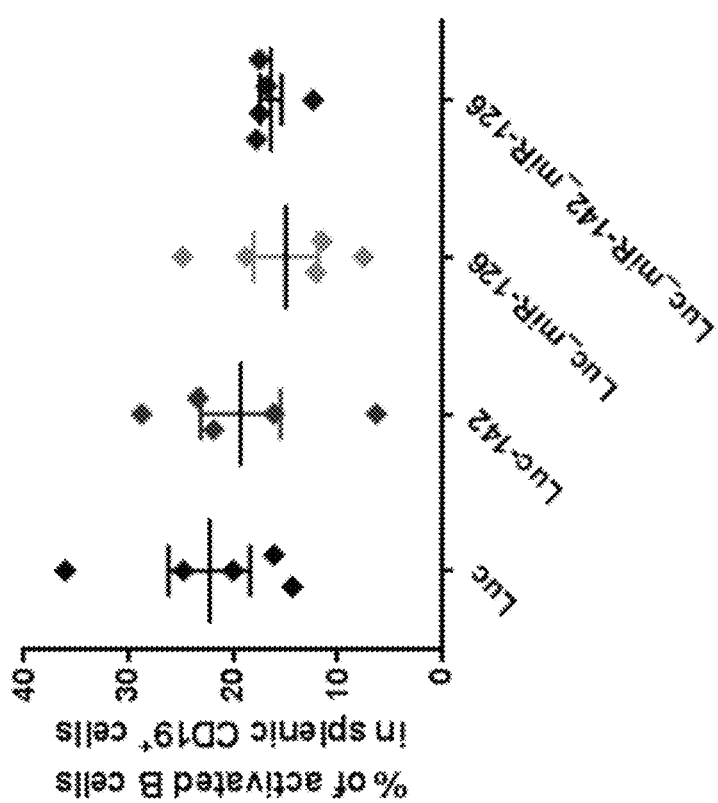
FIGURE 17

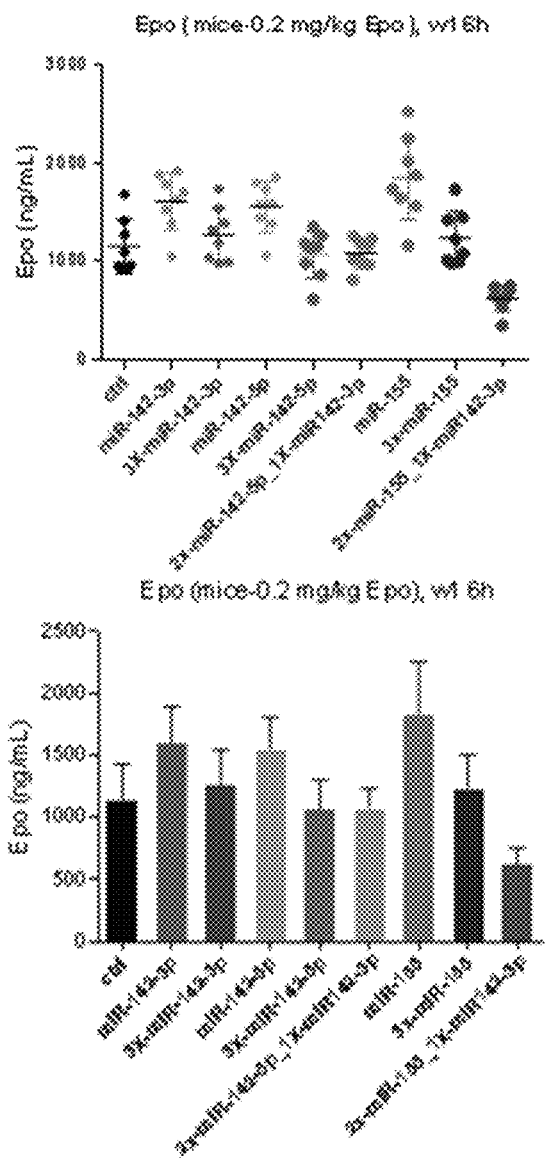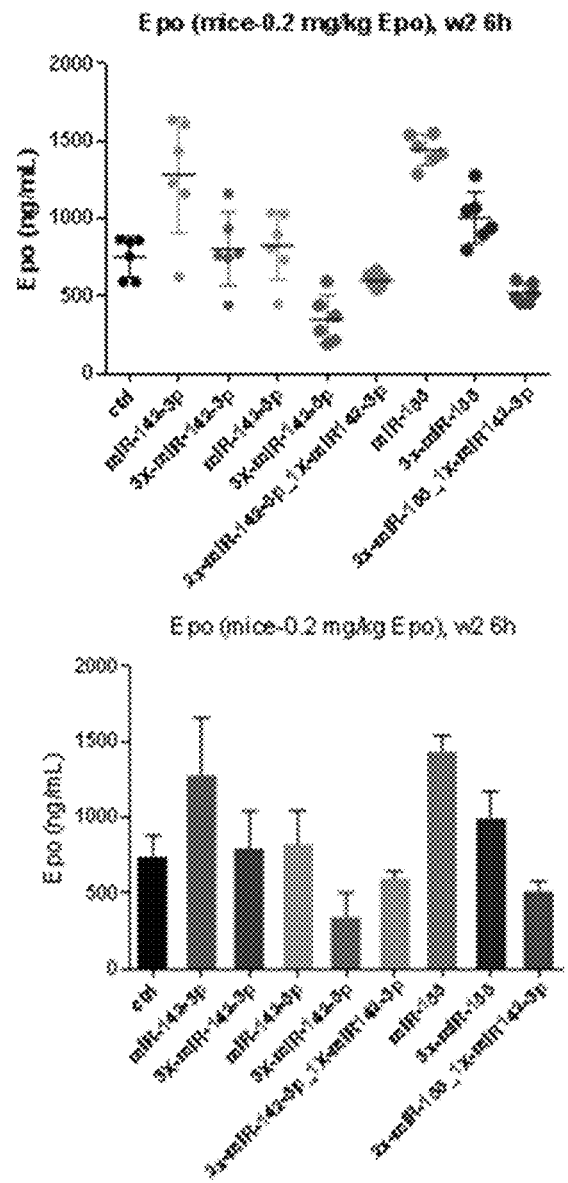
FIGURE 19A                                    FIGURE 19B

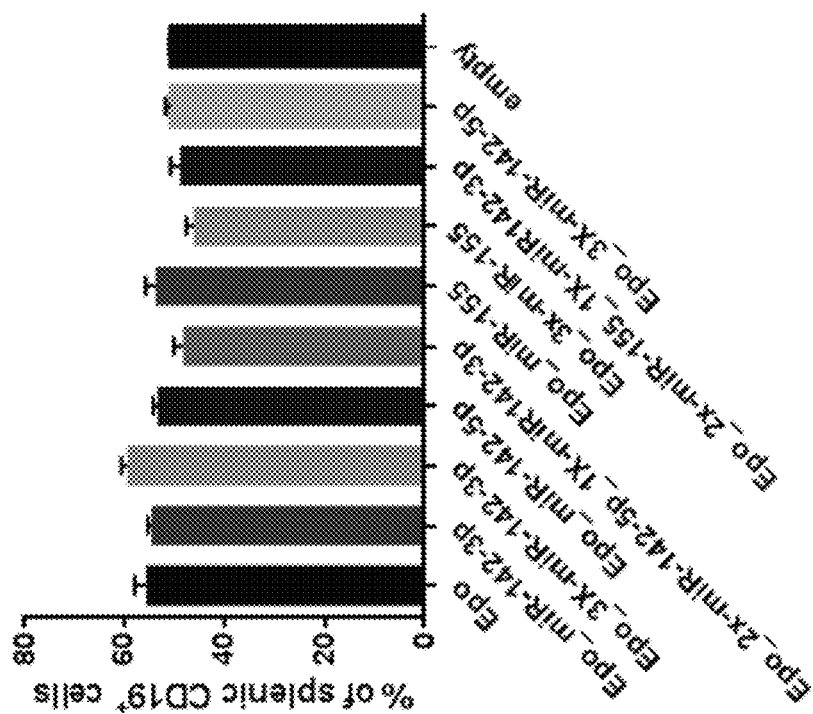
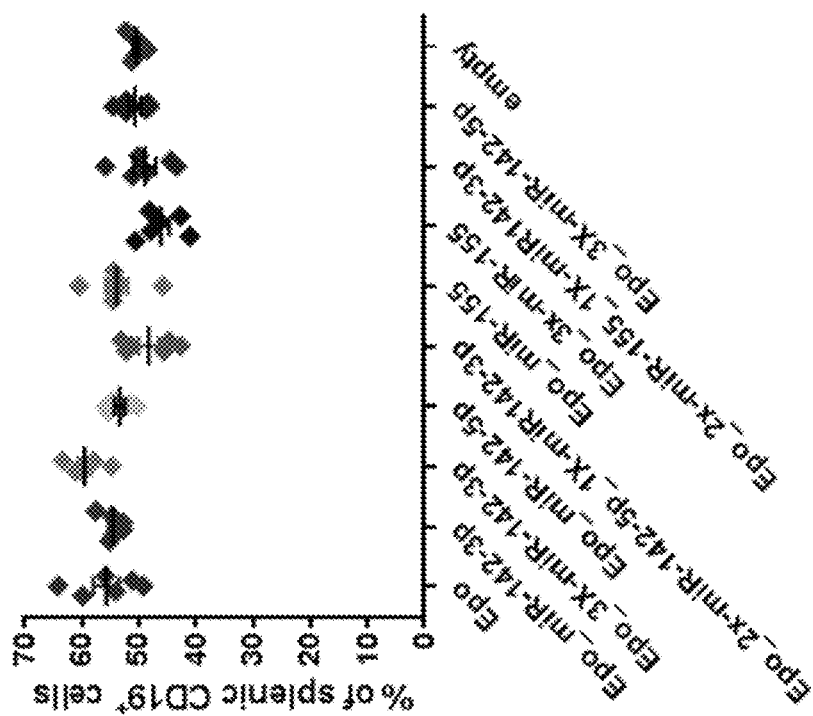
FIGURE 20

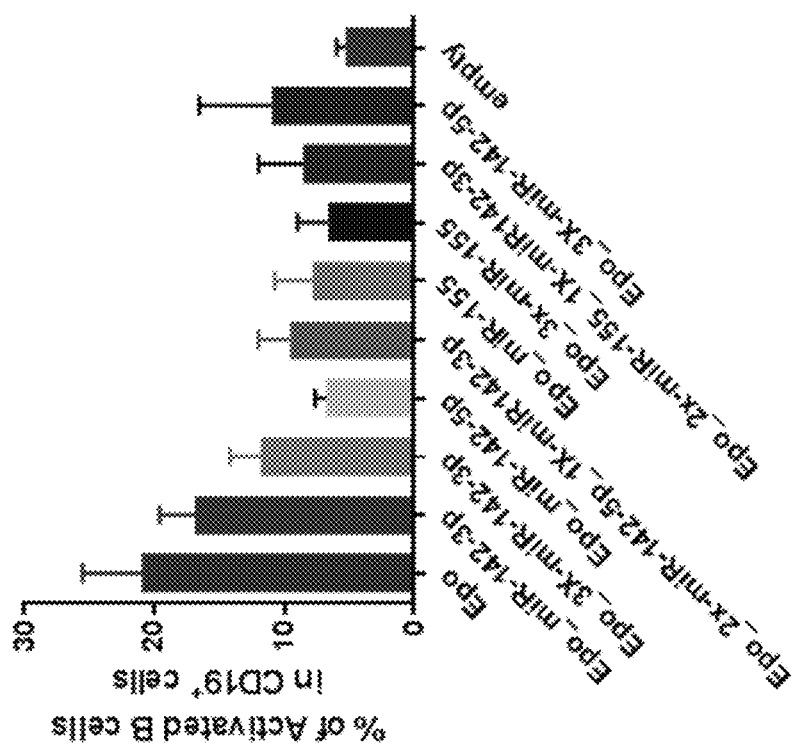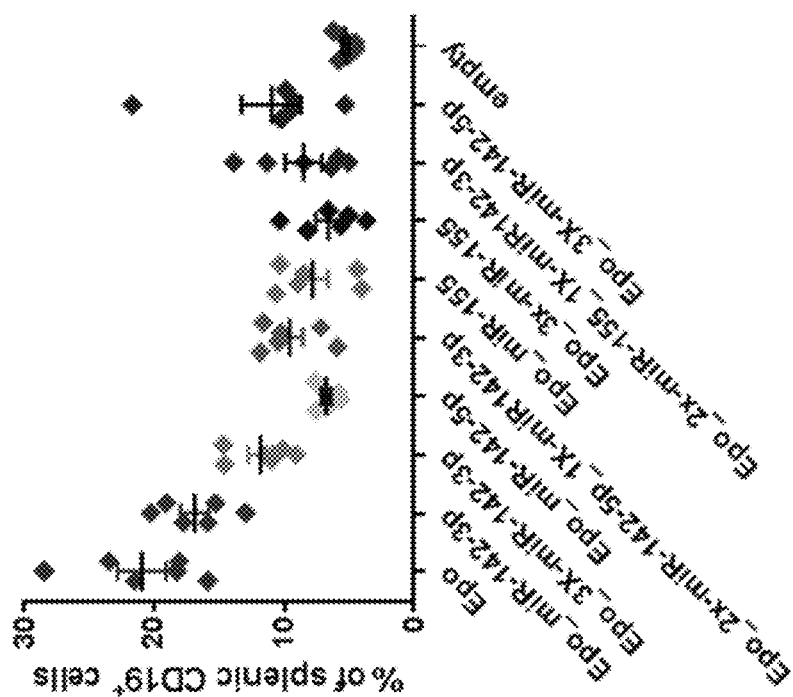
FIGURE 21

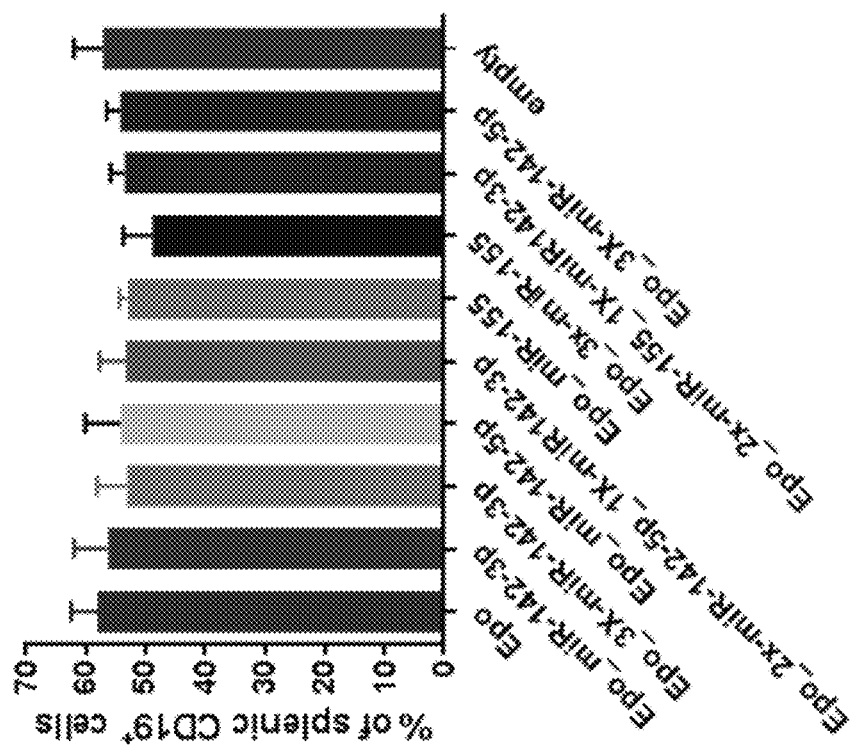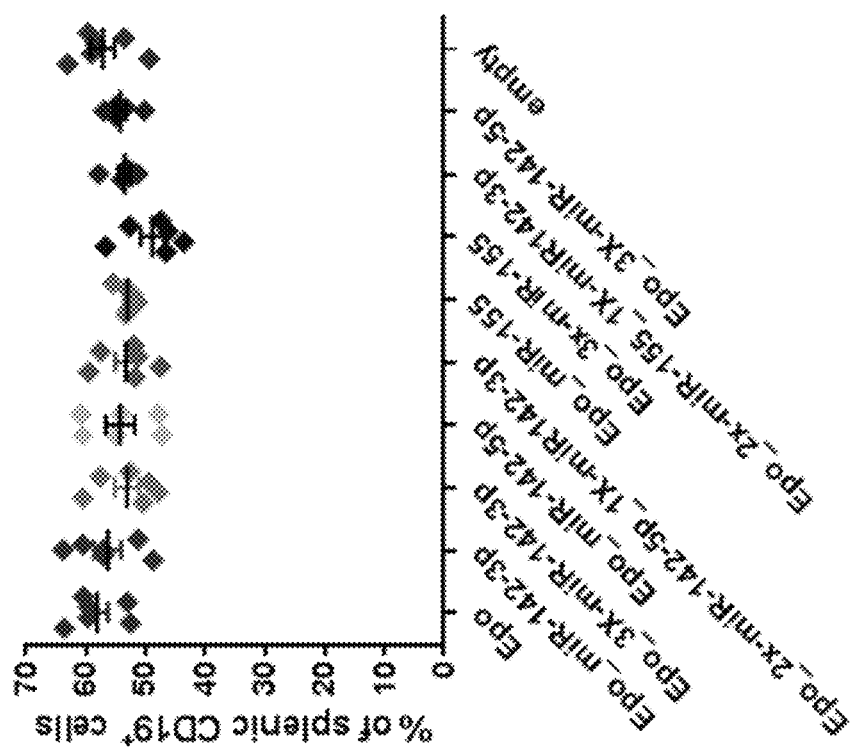
FIGURE 22

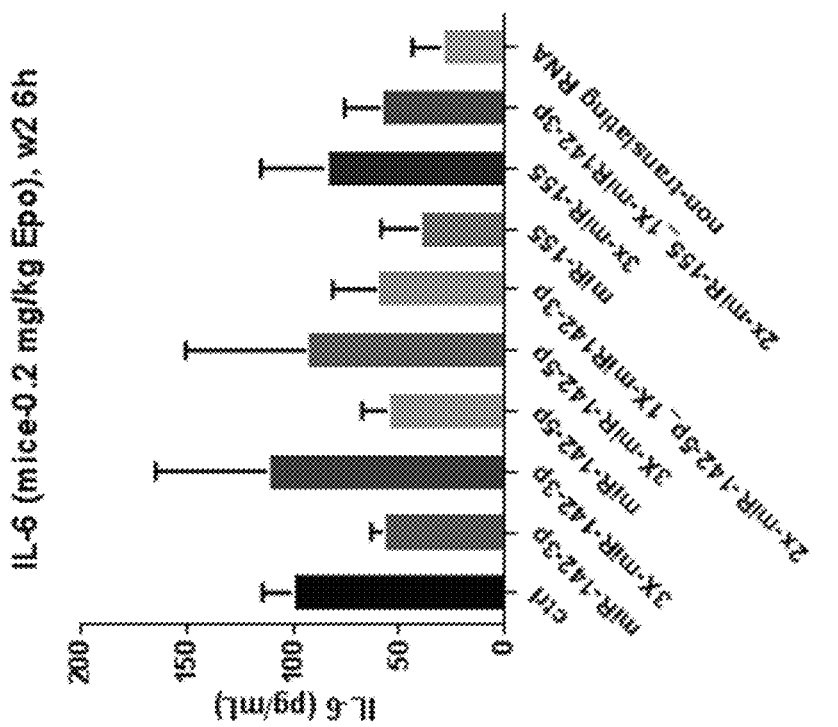
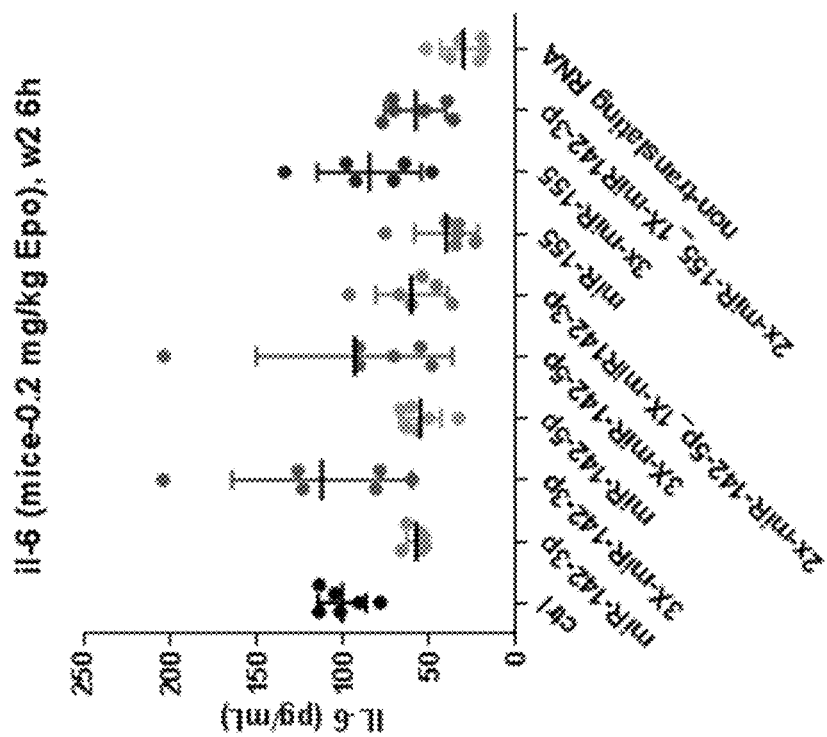
FIGURE 24A

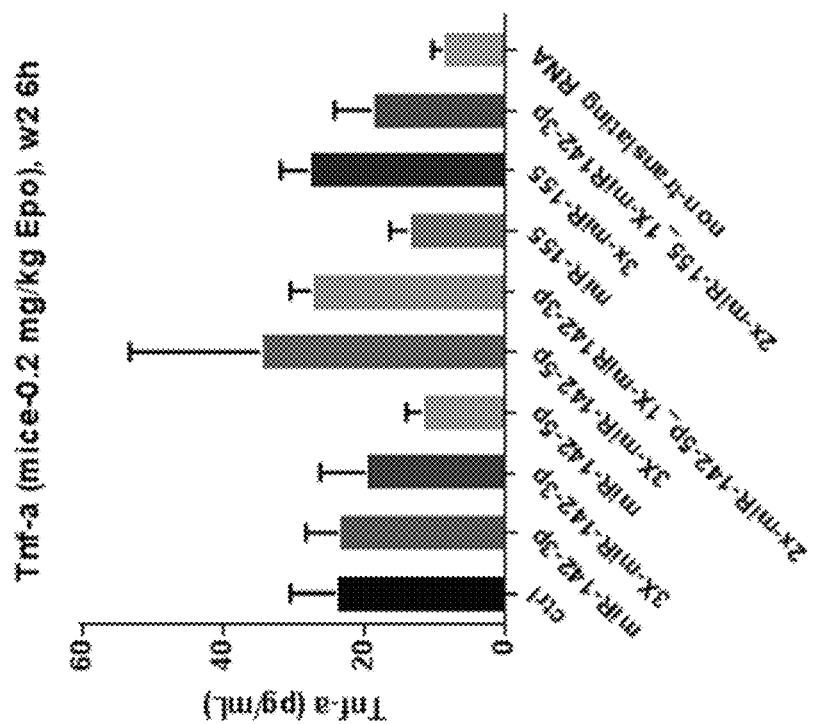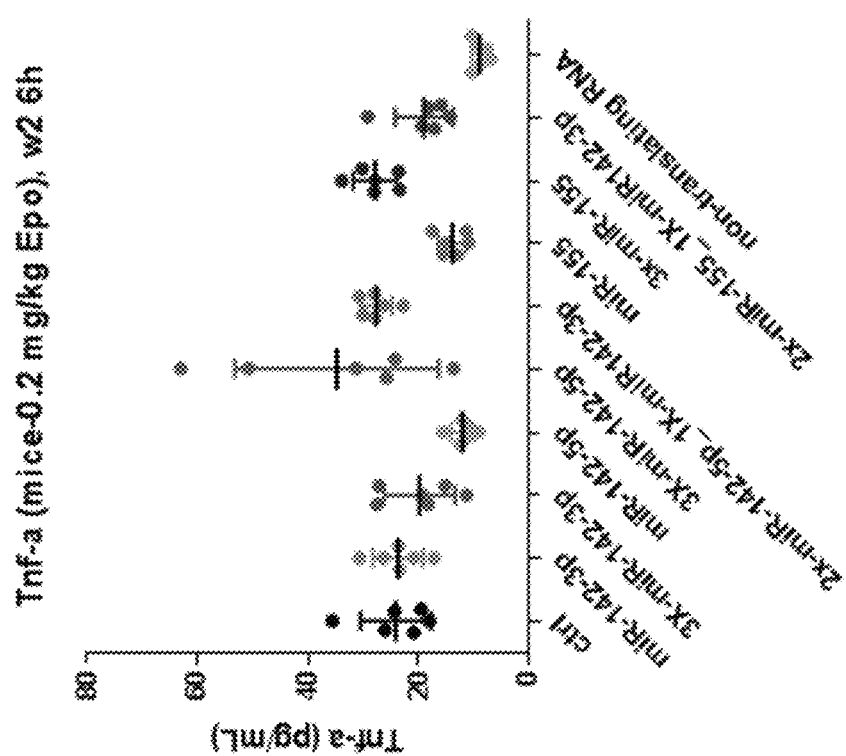
FIGURE 24B

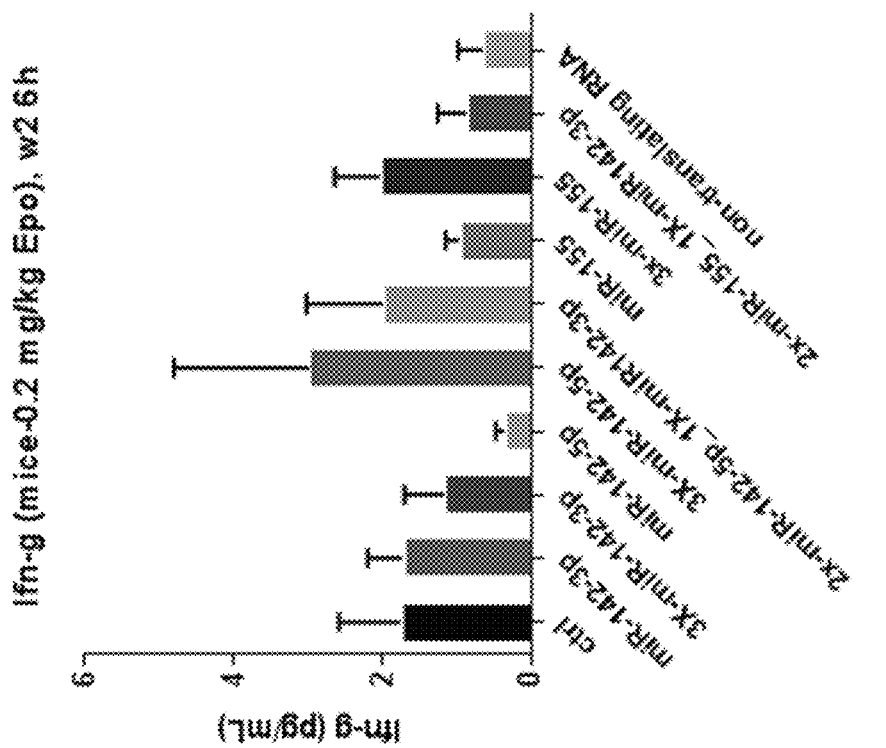
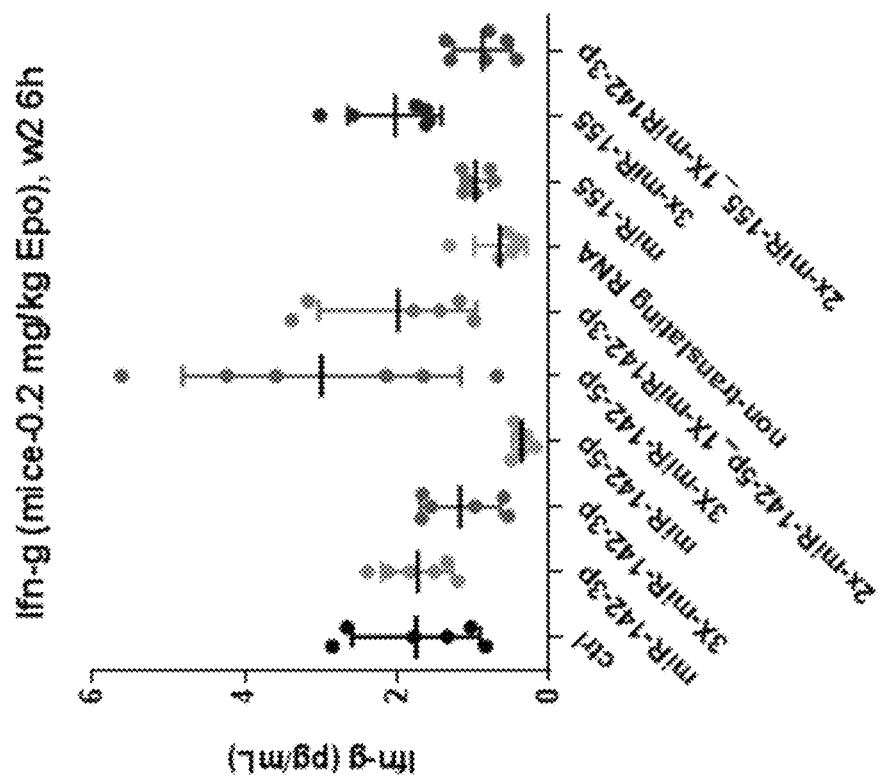
FIGURE 24C

Total CD11c+ cells

Activated CD11c+ cells

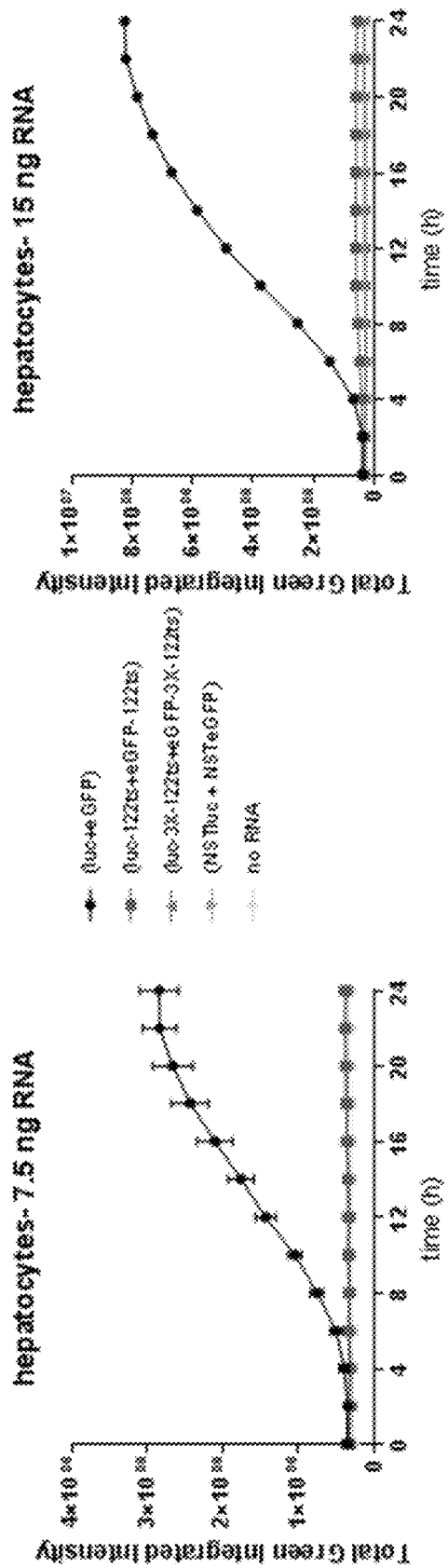
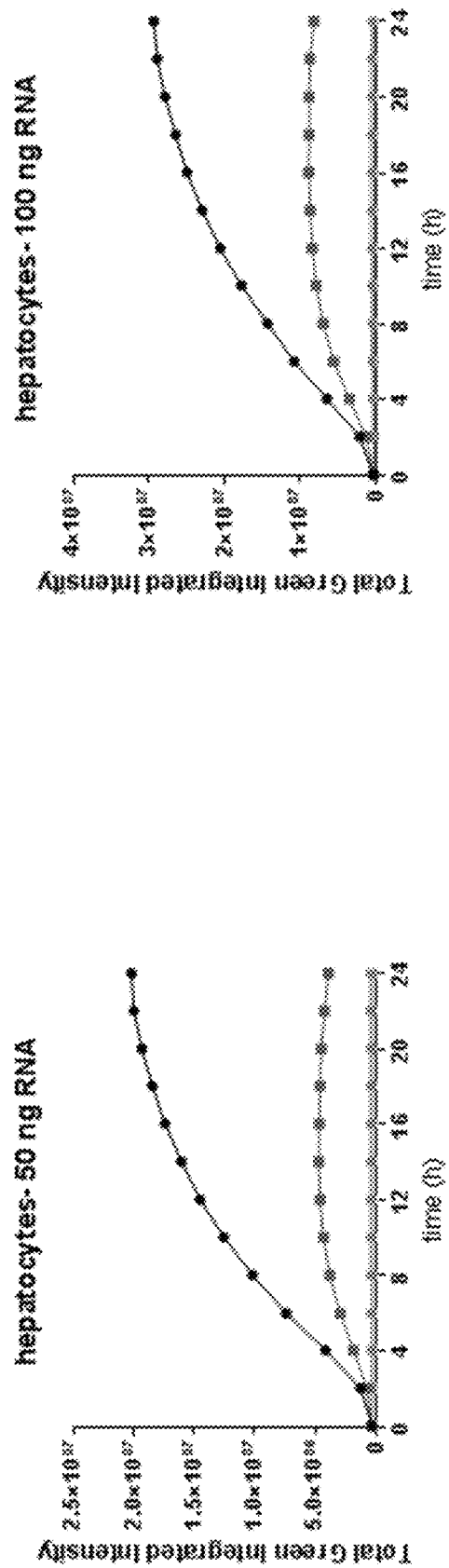
FIGURE 31A
FIGURE 31B
FIGURE 31C
FIGURE 31D

US 12,246,030 B2

METHODS FOR THERAPEUTIC ADMINISTRATION OF MESSENGER RIBONUCLEIC ACID DRUGS

RELATED APPLICATIONS

This application is a Continuation of U.S. application Ser. No. 17/036,378, filed Sep. 29, 2020, which is a Continuation of U.S. application Ser. No. 15/761,220, filed on Mar. 19, 2018, now U.S. Pat. No. 10,849,920, issued on Dec. 1, 2020, which is a 35 U.S.C. 371 national stage filing of International Application No. PCT/US2016/055582, filed on Oct. 5, 2016, which claims priority to U.S. Provisional Patent Application No. 62/237,462 filed Oct. 5, 2015; U.S. Provisional Patent Application No. 62/317,268 filed Apr. 1, 2016; U.S. Provisional Patent Application No. 62/317,271 filed Apr. 1, 2016; U.S. Provisional Patent Application No. 62/317,366 filed Apr. 1, 2016; U.S. Provisional Patent Application No. 62/338,385 filed May 18, 2016; U.S. Provisional Patent Application No. 62/338,386 filed May 18, 2016; U.S. Provisional Patent Application No. 62/338,388 filed May 18, 2016; and U.S. Provisional Patent Application No. 62/350,149 filed Jun. 14, 2016. The contents of the aforementioned applications are hereby incorporated by reference in their entireties.

REFERENCE TO SEQUENCE LISTING

The Sequence Listing associated with this application is provided electronically in XML file format and is hereby incorporated by reference into the specification. The name of the XML file containing the Sequence Listing is MRNA_103_C02US_SeqList_ST26.xml. The XML file is 135,305 bytes and was created on Jan. 17, 2023.

BACKGROUND OF THE INVENTION

Biologics, such as recombinant antibodies, cytokines and growth factors, have been shown to be effective in the treatment of a wide variety of diseases and the FDA has now approved a large number of such agents for use in humans (for a review, see Kinch, M. S. (2015) *Drug Discov. Today* 20:393-398). The vast majority of FDA approved biologics are protein-based agents. More recently, messenger RNA-based agents are being developed as a disruptive therapeutic modality. There are several reported examples of effective mRNA-based vaccines including both infectious disease vaccines and tumor vaccines (for respective reviews, see Marć M. A., et al. (2015) *Expert Opin Drug Deliv.* September 12:1-15 and Sahin, U., et al. (2014) *Nature Reviews Drug Discovery* 13:759-780). The use of mRNA-based agents is more-recently being pursued for therapeutic purposes, for example, using mRNA constructs that encode a therapeutic protein of interest.

Accordingly, new approaches and methods for use of mRNA-based agents in a subject, such as mRNA-based therapeutic agents, are needed, particularly methods that offer advantageous properties with regard to the safety and/or therapeutic efficacy of the mRNA-based agent in the subject.

SUMMARY OF THE INVENTION

The invention provides methods for use with mRNA-based agents to be administered to a subject, wherein the methods provide advantageous features for use of the mRNA-based agents in vivo. It has now been surprisingly discovered that administration to non-human primates of mRNA-based agents encoding a protein of interest can lead to development of an undesirable immune response in animals, wherein antibodies against the protein encoded by the mRNA can be detected in the animal. This is an unexpected result, since the animal was not administered a protein therapeutic, but rather an mRNA construct, and it was not expected that local production of the protein of interest in target tissues in vivo would lead to a response against the encoded protein product. The response observed in non-human primates has also been studied in other relevant animal model systems and is analogous to the art-recognized anti-drug antibody (ADA) response seen in both the fields of recombinant protein therapeutics and even small molecule therapeutics. A recognizable distinction in terminology is apparent to the skilled artisan in that a classic anti-drug antibody (ADA) response is generally understood to be in response to systemic administration of, for example, a recombinant protein therapeutic, which can generate antibodies directly to said protein therapeutic. In the field of mRNA therapeutics, the antibody responses observed in the herein-described animal studies are not to the mRNA-based drug per se. By contrast, the antibody responses are to the mRNA drug-encoded protein product. The skilled artisan can refer to such a phenomenon as anti-protein antibody (APA) but owing to the pharmacologically analogous effects, the instant application will utilize the art-recognized terminology of anti-drug antibody (ADA).

Remarkably, it has now also been discovered that inclusion in the mRNA construct of at least one microRNA (miR) binding site for a miR expressed in conventional immune cells or any cell that expresses TLR7 and/or TLR8 and secretes pro-inflammatory cytokines and/or chemokines (e.g., in immune cells of peripheral lymphoid organs and/or splenocytes and/or endothelial cells) results in dramatic inhibition of ADA responses in vivo. Accordingly, the disclosure provides methods for reducing or inhibiting anti-drug antibody responses in which a protein of interest is encoded by a messenger RNA (mRNA) that comprises at least one microRNA (miR) binding site for a miR expressed in conventional immune cells or any cell that expresses TLR7 and/or TLR8 and secretes pro-inflammatory cytokines and/or chemokines (e.g., in immune cells of peripheral lymphoid organs, such as spleen cells, e.g., splenic myeloid cells, and/or endothelial cells). In exemplary aspects, the disclosure provides methods for reducing or inhibiting anti-drug antibody responses in which a protein of interest is encoded by a messenger RNA (mRNA), e.g., modified messenger RNA (mmRNA), that comprises one or more modified nucleobases and the mRNA, e.g., mmRNA, further comprises at least one microRNA (miR) binding site for a miR expressed in conventional immune cells or any cell that expresses TLR7 and/or TLR8 and secretes pro-inflammatory cytokines and/or chemokines (e.g., in immune cells of peripheral lymphoid organs, such as spleen cells, e.g., splenic myeloid cells, and/or endothelial cells). In the methods of the disclosure, a subject is administered the mRNA, e.g., mmRNA, encoding the polypeptide of interest and comprising the binding site for the at least one immune cell-expressed miR such that an anti-drug antibody response to the polypeptide of interest is reduced or inhibited in the subject. In exemplary embodiments, the miR binding site is for a miR expressed abundantly or preferentially in immune cells (e.g., in immune cells of peripheral lymphoid organs and/or splenocytes). In exemplary embodiments, the miR binding site is included in an untranslated region (UTR) of the mRNA, e.g., mmRNA, encoding the protein of interest (e.g., the 3' UTR, the 5' UTR, or in both the 3' and 5' UTRs). Thus, in the methods of the disclosure, an anti-drug antibody response is reduced or inhibited by post-transcriptional regulation of mRNA, with a possible component from translational repression, by inclusion of at least one miR binding site, without the need to alter the amino acid sequence of the protein of interest.

In one embodiment, the at least one miR expressed in immune cells is a miR-142-3p microRNA binding site. In another embodiment, the at least one miR expressed in immune cells is a miR-126 microRNA binding site, such as a miR-126-3p binding site. Accordingly, the disclosure provides a method of reducing or inhibiting an anti-drug antibody response in a subject, comprising administering to the subject a messenger RNA (mRNA), e.g., a modified messenger RNA (mmRNA), encoding a polypeptide of interest, wherein the mRNA, e.g., mmRNA, comprises at least one miR-142-3p microRNA binding site and/or at least one miR-126 microRNA binding site, and wherein the mRNA, e.g., mmRNA, comprises one or more modified nucleobases, such that an anti-drug antibody response to the polypeptide of interest is reduced or inhibited in the subject. In one embodiment, the miR-142-3p microRNA binding site comprises the sequence shown in SEQ ID NO: 3. In one embodiment, the miR-126 binding site is a miR-126-3p binding site. In one embodiment, the miR-126-3p microRNA binding site comprises the sequence shown in SEQ ID NO: 26.

In other embodiments, the mRNA, e.g., mmRNA, comprises at least one microRNA binding site for a miR selected from the group consisting of miR-142, miR-146 miR-155, miR-126, miR-16, miR-21, miR-223, miR-24 and miR-27. A miR referred to by number herein can refer to either of the two mature microRNAs originating from opposite arms of the same pre-miRNA (e.g., either the 3p or 5p microRNA). All miRs referred to by number herein are intended to include both the 3p and 5p arms/sequences.

In another embodiment, the mRNA, e.g., mmRNA, comprises at least two miR binding sites for microRNAs expressed in immune cells. In various embodiments, the mRNA, e.g., mmRNA, comprises 1-4, one, two, three or four miR binding sites for microRNAs expressed in immune cells. These miR binding sites can be for microRNAs selected from the group consisting of miR-142 (including miR-142-3p and miR-142-5p), miR-146 (including miR-146-3p and miR-146-5p), miR-155, miR-126 (including miR-126-3p and miR-126-5p), miR-16, miR-21, miR-223, miR-24, miR-27, and combinations thereof. In another embodiment, the mRNA, e.g., mmRNA, comprises at least two miR binding sites for microRNAs expressed in immune cells, wherein one of the miR binding sites is for miR-142-3p. In various embodiments, the mRNA, e.g., mmRNA, comprises binding sites for miR-142-3p and miR-155, miR-142-3p and miR-146, or miR-142-3p and miR-126 (e.g., miR-126-3p). In another embodiment, the mRNA, e.g., mmRNA, comprises at least two miR binding sites for microRNAs expressed in immune cells, wherein one of the miR binding sites is for miR-126 (e.g, miR-126-3p). In various embodiments, the mRNA, e.g., mmRNA, comprises binding sites for miR-126 and miR-155, miR-126 and miR-146, or miR-126 and miR-142. In one embodiment, the mRNA, e.g., mmRNA, comprises a miR-142-3p binding site and a miR-126 binding site.

In one embodiment, the mRNA, e.g., mmRNA, comprises a 5' UTR, a codon optimized open reading frame encoding the polypeptide of interest, a 3' UTR comprising the at least one microRNA binding site for a miR expressed in immune cells, and a 3' tailing region of linked nucleosides. In various embodiments, the 3' UTR comprises 1-4, at least one, two, three or four microRNA binding sites for miRs expressed in immune cells, preferably abundantly or preferentially expressed in immune cells (e.g., in immune cells of peripheral lymphoid organs and/or splenocytes). In other embodiments, the 3' UTR comprises at least one miR-142-3p microRNA binding site or at least two miR binding sites for miRs expressed in immune cells, wherein one miR binding site is for miR-142-3p. In another embodiment, the 3' UTR comprises at least one miR-126 microRNA binding site or at least two miR binding sites for miRs expressed in immune cells, wherein one miR binding site is for miR-126. In one embodiment, the codon optimized open reading frame encoding the polypeptide of interest comprises a stop codon and the at least one microRNA binding site (e.g., a miR-142-3p binding site and/or a miR-126 binding site) is located within the 3' UTR 1-100 nucleotides after the stop codon. In another embodiment, the codon optimized open reading frame encoding the polypeptide of interest comprises a stop codon and the at least one microRNA binding site (e.g., a miR-142-3p binding site and/or a miR-126 binding site) is located within the 3' UTR 30-50 nucleotides after the stop codon. In another embodiment, the codon optimized open reading frame encoding the polypeptide of interest comprises a stop codon and the at least one microRNA binding site (e.g., a miR-142-3p microRNA binding site and/or a miR-126 microRNA binding site) is located within the 3' UTR at least 50 nucleotides after the stop codon.

In another embodiment, the mRNA, e.g., mmRNA, comprises a 5' UTR and 3'UTR which are heterologous to the coding region.

In another embodiment, the chemically modified mRNA, e.g., mmRNA, is fully modified. In other embodiments, the chemically modified mRNA, e.g., mmRNA, comprises one or more modified nucleobases described further herein.

In some embodiments, the mRNA comprises pseudouridine ($\psi$). In some embodiments, the mRNA comprises pseudouridine ($\psi$) and 5-methyl-cytidine ($m^5C$). In some embodiments, the mRNA comprises 1-methyl-pseudouridine ($m^1\psi$). In some embodiments, the mRNA comprises 1-methyl-pseudouridine ($m^1\psi$) and 5-methyl-cytidine ($m^5C$). In some embodiments, the mRNA comprises 2-thiouridine ($s^2U$). In some embodiments, the mRNA comprises 2-thiouridine and 5-methyl-cytidine ($m^5C$). In some embodiments, the mRNA comprises 5-methoxy-uridine ($mo^5U$). In some embodiments, the mRNA comprises 5-methoxy-uridine ($mo^5U$) and 5-methyl-cytidine ($m^5C$). In some embodiments, the mRNA comprises 2'-O-methyl uridine. In some embodiments, the mRNA comprises 2'-O-methyl uridine and 5-methyl-cytidine ($m^5C$). In some embodiments, the mRNA comprises comprises N6-methyl-adenosine ($m^6A$). In some embodiments, the mRNA comprises N6-methyl-adenosine ($m^6A$) and 5-methyl-cytidine ($m^5C$).

In some embodiments, the modified nucleobase is pseudouridine ($\psi$), N1-methylpseudouridine ($m^1\psi$), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is 1-methyl-pseudouridine (m$^1$ψ), 5-methoxy-uridine (mo$^5$U), 5-methyl-cytidine (m$^5$C), pseudouridine (ψ), α-thio-guanosine, or α-thio-adenosine. In some embodiments, an mRNA of the disclosure includes a combination of one or more of the aforementioned modified nucleobases (e.g., a combination of 2, 3 or 4 of the aforementioned modified nucleobases.)

In one embodiment, the mRNA, e.g., mmRNA, is administered intravenously encapsulated in a lipid nanoparticle. In one embodiment, the lipid nanoparticle is a liposome. In one embodiment, the lipid nanoparticle comprises a cationic and/or ionizable lipid. In one embodiment, the cationic and/or ionizable lipid is DLin-KC2-DMA or DLin-MC3-DMA.

In one embodiment, the polypeptide of interest is a therapeutic protein, a cytokine, a growth factor, an antibody or a fusion protein. Further examples of polypeptides of interest are described herein.

In one embodiment, the mRNA, e.g., mmRNA, is administered by once weekly infusion. In another embodiment, the infusion is intravenously. In another embodiment, the mRNA, e.g., mmRNA, is administered by once weekly infusion for at least 4 weeks. In another embodiment, the mRNA, e.g., mmRNA, is administered intratumorally. Suitable dosage regimens are described further herein.

In another embodiment, the disclosure provides a method of reducing or inhibiting an anti-drug antibody response following repeated administration of a polypeptide of interest to a subject, comprising administering to the subject intravenously a first dose of a mRNA, e.g., modified mRNA (mmRNA), encoding a polypeptide of interest encapsulated in an LNP, wherein the mRNA, e.g., mmRNA, comprises at least one miR-142-3p microRNA binding site and/or at least one miR-126 microRNA binding site, and wherein the mRNA, e.g., mmRNA, comprises one or more modified nucleobases; and administering to the subject intravenously a second dose of the mRNA, e.g., mmRNA, encapsulated in an LNP, such that an anti-drug antibody response to the polypeptide of interest is reduced or inhibited in the subject.

In another aspect, the disclosure provides a method of reducing or inhibiting an anti-drug antibody response following repeated administration of a polypeptide of interest to a subject, comprising
  (i) administering to the subject intravenously a first dose of a mRNA, e.g., modified mRNA (mmRNA), encoding a polypeptide of interest encapsulated in an LNP, wherein the mRNA, e.g., mmRNA, comprises at least one microRNA binding site for a miR expressed in immune cells (e.g., a miR-142-3p microRNA binding site and/or a miR-126 microRNA binding site), and wherein the mRNA, e.g., mmRNA, comprises one or more modified nucleobases:
  (ii) detecting a level of anti-drug antibodies in a sample from the subject; and
  (iii) administering to the subject intravenously a second dose of the mRNA, e.g., mmRNA, encapsulated in an LNP when the level of anti-drug antibodies in the sample is diminished, such that an anti-drug antibody response to the polypeptide of interest is reduced or inhibited in the subject.

In another aspect, the disclosure provides a method of reducing or inhibiting drug-related toxicity in a subject, comprising administering to the subject a messenger RNA (mRNA), e.g., a modified messenger RNA (mmRNA), encoding a polypeptide of interest, wherein the mRNA, e.g., mmRNA, comprises at least one microRNA binding site for a miR expressed in immune cells (e.g., a miR-142-3p microRNA binding site and/or a miR-126 microRNA binding site), and wherein the mRNA, e.g., mmRNA, comprises one or more modified nucleobases, such that drug-related toxicity to the polypeptide of interest is reduced or inhibited in the subject. In one embodiment, the drug-related toxicity to the polypeptide of interest is decreased blood cell counts (cytopenia) in the subject. In one embodiment, the drug-related toxicity to the polypeptide of interest is autoimmunity in the subject. In one embodiment, the drug-related toxicity to the polypeptide of interest is complement mediated effects in the subject. In one embodiment, the drug-related toxicity to the polypeptide of interest is decreased hematopoiesis in the subject. In other embodiments, the drug-related toxicity can be, for example, renal toxicity or liver toxicity.

Additionally, it has now further been discovered that inclusion of at least one binding site for a microRNA (miR) expressed in conventional immune cells or any cell that expresses TLR7 and/or TLR8 and secretes pro-inflammatory cytokines and/or chemokines (e.g., in immune cells of peripheral lymphoid organs, such as spleen cells, e.g., splenic myeloid cells, and/or endothelial cells), such as a miR-126 and/or miR-142 binding site(s), in an mRNA reduces or inhibits unwanted immune cell activation (e.g., B cell activation, cytokine secretion) in a subject to whom the mRNA is administered. It has been further discovered that inclusion of this at least one miR binding site(s) in an mRNA can reduce or inhibit accelerated blood clearance (ABC) of a lipid-comprising compound or composition in which the mRNA is administered. Moreover, inclusion of this at least on miR binding site(s) in an mRNA can reduce or inhibit proliferation and/or activation of plasmacytoid dendritic cells (pDCs) and/or reduce or inhibit production of IgMs against the lipid-comprising compound or composition in which the mRNA is administered by B cells, such as, for example, IgMs against phospholipid components (e.g., phosphatidylcholine) of the lipid-comprising compound or composition by B cells.

Accordingly, in one aspect, the disclosure provides methods for reducing or inhibiting unwanted immune cell activation in a subject administered an RNA, e.g., mRNA encoding a polypeptide of interest, the methods comprising administering to the subject an RNA, e.g., mRNA, e.g., a chemically modified messenger RNA (mmRNA), encoding a polypeptide of interest, which comprises at least one binding site for a microRNA (miR) expressed in conventional immune cells or any cell that expresses TLR7 and/or TLR8 and secretes pro-inflammatory cytokines and/or chemokines (e.g., in immune cells of peripheral lymphoid organs, such as spleen cells, e.g., splenic myeloid cells, and/or endothelial cells), such as a miR-126 and/or miR-142 microRNA binding site, such that unwanted immune cell activation is reduced or inhibited in the subject. In another aspect, the disclosure provides methods for reducing or inhibiting unwanted cytokine production in a subject administered an RNA, e.g., mRNA encoding a polypeptide of interest, the methods comprising administering to the subject an RNA, e.g., mRNA, e.g., a chemically modified messenger RNA (mmRNA), encoding a polypeptide of interest, which comprises at least one binding site for a microRNA (miR) expressed in conventional immune cells or any cell that expresses TLR7 and/or TLR8 and secretes pro-inflammatory cytokines and/or chemokines (e.g., in immune cells of peripheral lymphoid organs, such as spleen cells, e.g., splenic myeloid cells, and/or endothelial cells), such as a miR-126 and/or miR-142 microRNA binding site, such that unwanted cytokine production is reduced or inhibited in the subject. The RNA can be an mRNA, such as a chemically modified mRNA (referred to herein as an mmRNA) that comprises one or more modified nucleobases. The mmRNA can be fully modified (i.e., all nucleotides or nucleobases of a particular type are modified within the mmRNA), can be partially modified (i.e., a portion of nucleotides or nucleobases of a particular type are modified within the mRNA or can be a chimeric mRNA containing stretches of modified and unmodified nucleobases.

In one embodiment, reduction or inhibition of unwanted immune cell activation and/or cytokine production is determined compared to administration of a control RNA, e.g., mRNA, e.g., mmRNA, lacking the at least one binding site for a microRNA (miR) expressed in immune cells, such as a miR-126 and/or miR-142 microRNA binding site. In one embodiment, immune cell activation is decreased by at least 10%. In another embodiment, immune cell activation is decreased by at least 25%. In yet another embodiment, immune cell activation is decreased by at least 50%. In still another embodiment, immune cell activation is decreased without a corresponding decrease in expression of a polypeptide (e.g., therapeutic protein) of interest encoded by the mRNA.

In one embodiment, the immune cell activation is lymphocyte activation. In one embodiment, the lymphocyte activation is B cell activation. In one embodiment, B cell activation is determined by frequency of $CD19^+$ $CD86^+$ $CD69^+$ B cells. In another embodiment, B cell activation is determined by cytokine secretion, e.g., in the serum or by total splenic cells. In one embodiment, B cell activation is determined by secretion of interleukin-6 (IL-6), tumor necrosis factor $\alpha$ (TNF-$\alpha$) or interferon-$\gamma$ (IFN-$\gamma$), e.g., in the serum or by total splenic cells. In one embodiment, B cell activation is determined by secretion of IL-6, e.g., in the serum or by total splenic cells. In one embodiment, reduction or inhibition of cytokine production is determined by reduction or inhibition of interleukin-6 (IL-6), tumor necrosis factor $\alpha$ (TNF-$\alpha$) or interferon-$\gamma$ (IFN-$\gamma$) production. In another embodiment, reduction or inhibition of cytokine production is determined by reduction or inhibition of interleukin-6 (IL-6) production.

In another embodiment, the disclosure provides a method of reducing or inhibiting accelerated blood clearance in a subject repeatedly administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that accelerated blood clearance is reduced or inhibited in the subject upon repeat administration.

In some embodiments, the disclosure provides a method of reducing or inhibiting accelerated blood clearance in a subject administered a messenger RNA (mRNA) encoding a polypeptide of interest encapsulated in an lipid nanoparticle (LNP), comprising administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases; and administering to the subject intravenously a second dose of the chemically modified mRNA encapsulated in an LNP, such that accelerated blood clearance is reduced or inhibited in the subject.

In some embodiments, the disclosure provides a method of reducing or inhibiting production of IgM molecules that recognize polyethylene glycol (PEG) in a subject repeatedly administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that production of IgM molecules that recognize PEG are reduced or inhibited in the subject upon repeat administration.

In further embodiments, the disclosure provides a method of reducing or inhibiting activation of B1a cells in a subject repeatedly administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of B1a cells is reduced or inhibited in the subject upon repeat administration.

In some embodiments, the disclosure provides a method of reducing or inhibiting activation of plasmacytoid dendrtic cells in a subject repeatedly administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of plasmacytoid dendritic cells is reduced or inhibited in the subject upon repeat administration.

In further embodiments, the LNP does not activate B cells and/or does not induce production of IgM molecules capable of binding to the LNP, such that accelerated blood clearance is reduced or inhibited in the subject upon administration of one or more subsequent doses. In some embodiments, the IgM molecules recognize polyethylene glycol (PEG).

In some embodiments, the reduction or inhibition of accelerated blood clearance is determined compared to control administration of a chemically modified mRNA lacking the at least one microRNA binding site encapsulated in a lipid nanoparticle (LNP). In further embodiments, the accelerated blood clearance is reduced or inhibited without a corresponding reduction or inhibition in expression of the polypeptide of interest encoded by the chemically modified mRNA.

In some embodiments, the interval between two consecutive doses is less than 2 weeks. In other embodiments, the interval between two consecutive doses is less than 1 week.

In one embodiment, the mRNA, e.g., mmRNA, comprises a 5' UTR, a codon optimized open reading frame encoding a polypeptide of interest, a 3' UTR comprising the at least one binding site for a microRNA (miR) expressed in immune cells, such as a miR-126 (e.g., miR-126-3p) or miR-142 (e.g., miR-142-3p) microRNA binding site, and a 3' tailing region of linked nucleosides. In one embodiment, the codon optimized open reading frame encoding the polypeptide of interest comprises a stop codon and the at least one binding site for a microRNA expressed in immune cells (e.g., a miR-142-3p binding site and/or a miR-126-3p binding site) is located within the 3' UTR 1-100 nucleotides after the stop codon. In another embodiment, the codon optimized open reading frame encoding the polypeptide of interest comprises a stop codon and the at least one binding site for a microRNA (miR) expressed in immune cells, such as a miR-126 and/or miR-142 microRNA binding site is located within the 3' UTR 30-50 nucleotides after the stop codon. In another embodiment, the codon optimized open reading frame encoding the polypeptide of interest comprises a stop codon and the at least one binding site for a microRNA (miR) expressed in immune cells, such as a miR-126 and/or miR-142 microRNA binding site is located within the 3' UTR at least 50 nucleotides after the stop codon. In another embodiment, the codon optimized open reading frame encoding the polypeptide of interest comprises a stop codon and the at least one binding site for a microRNA expressed in immune cells (e.g., a miR-142-3p binding site and/or a miR-126-3p binding site) is located anywhere in the 3'UTR (e.g., after the first 100 nucleotides after the stop codon). In another embodiment, the mRNA, e.g., mmRNA, comprises a 5' UTR and 3'UTR which are heterologous to the open reading frame.

In various embodiments, the mRNA, e.g., mmRNA, comprises 1-4, one, two, three or four miR binding sites for microRNAs expressed in immune cells, wherein at least one of the miR binding sites is a miR-126 binding site. In one embodiment, the mRNA, e.g., mmRNA, comprises at least two microRNA binding sites for microRNAs expressed in immune cells, wherein at least one of the microRNA binding sites is a miR-126 binding site. In one embodiment, the mRNA, e.g., mmRNA, comprises a miR-126 binding site and a second microRNA binding site for a miR selected from the group consisting of miR-142-3p, miR-142-5p, miR-146-3p, miR-146-5p, miR-155, miR-16, miR-21, miR-223, miR-24 and miR-27. In another embodiment, the mRNA, e.g., mmRNA comprises a miR-126 (e.g., miR-126-3p) binding site and a miR-142 (e.g., miR-142-3p) binding site. In one embodiment, the mRNA, e.g., mmRNA, comprises at least three microRNA binding sites for microRNAs expressed in immune cells, wherein at least one of the microRNA binding sites is a miR-126 binding site. In one embodiment, the mRNA, e.g., mmRNA, comprises a miR-126 binding site, a miR-142 (e.g., miR_142-3p) binding site, and a third microRNA binding site for a miR selected from the group consisting of miR-146-3p, miR-146-5p, miR-155, miR-16, miR-21, miR-223, miR-24 and miR-27. In another embodiment, the mRNA, e.g., mmRNA, comprises a miR-126 binding site, a miR-142 (e.g., miR-142-3p) binding site, and a miR-155 binding site. In one embodiment, the mRNA, e.g., mmRNA, comprises at least four microRNA binding sites for microRNAs expressed in immune cells. In another embodiment, the mRNA, e.g., mmRNA, comprises a miR-126 binding site, a miR-142-3p binding site, a miR-142-5p binding site, and a miR-155 binding site. A miR referred to by number herein can refer to either of the two mature microRNAs originating from opposite arms of the same pre-miRNA (e.g., either the 3p or 5p microRNA). All miRs referred to by number herein are intended to include both the 3p and 5p arms/sequences.

In one embodiment, the miR-126-3p binding site comprises the sequence shown in SEQ ID NO: 26.

In one embodiment, the miR-142-3p binding site comprises the sequence shown in SEQ ID NO: 3.

In one embodiment, the miR-155 binding site comprises the sequence shown in SEQ ID NO: 35.

In some embodiments, the microRNA binding site binds a microRNA expressed in myeloid cells. In other embodiments, the microRNA binding site binds a microRNA expressed in plasmacytoid dendritic cells. In yet other embodiments, the microRNA binding site binds a microRNA expressed in macrophages.

In another embodiment, the mRNA, e.g., mmRNA, is fully modified for a particular chemical modification. Types of suitable chemical modification are described further herein. In other embodiments, the mRNA, e.g., mmRNA, comprises one or more modified nucleotides or nucleobases described further herein.

In some embodiments, the mRNA comprises pseudouridine ($\psi$). In some embodiments, the mRNA comprises pseudouridine ($\psi$) and 5-methyl-cytidine ($m^5C$). In some embodiments, the mRNA comprises 1-methyl-pseudouridine ($m^1\psi$). In some embodiments, the mRNA comprises 1-methyl-pseudouridine ($m^1\psi$) and 5-methyl-cytidine ($m^5C$). In some embodiments, the mRNA comprises 2-thiouridine ($s^2U$). In some embodiments, the mRNA comprises 2-thiouridine and 5-methyl-cytidine ($m^5C$). In some embodiments, the mRNA comprises 5-methoxy-uridine ($mo^5U$). In some embodiments, the mRNA comprises 5-methoxy-uridine ($mo^5U$) and 5-methyl-cytidine ($m^5C$). In some embodiments, the mRNA comprises 2'-O-methyl uridine. In some embodiments, the mRNA comprises 2'-O-methyl uridine and 5-methyl-cytidine ($m^5C$). In some embodiments, the mRNA comprises comprises N6-methyl-adenosine ($m^6A$). In some embodiments, the mRNA comprises N6-methyl-adenosine ($m^6A$) and 5-methyl-cytidine ($m^5C$).

In some embodiments, the modified nucleobase is pseudouridine ($\psi$), N1-methylpseudouridine ($m^1\psi$), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is 1-methyl-pseudouridine ($m^1\psi w$), 5-methoxy-uridine ($mo^5U$), 5-methyl-cytidine ($m^5C$), pseudouridine ($\psi$), α-thio-guanosine, or α-thio-adenosine. In some embodiments, an mRNA of the disclosure includes a combination of one or more of the aforementioned modified nucleobases (e.g., a combination of 2, 3 or 4 of the aforementioned modified nucleobases.)

In one embodiment, the mRNA, e.g., mmRNA, is administered intravenously encapsulated in a lipid nanoparticle. In one embodiment, the lipid nanoparticle is a liposome. In one embodiment, the lipid nanoparticle comprises a cationic and/or ionizable lipid. In one embodiment, the cationic and/or ionizable lipid is DLin-KC2-DMA or DLin-MC3-DMA.

In one embodiment, the mRNA, e.g., mmRNA, encodes a polypeptide of interest. In various embodiments, the polypeptide of interest is a therapeutic protein, a cytokine, a growth factor, an antibody or a fusion protein. Further examples of polypeptides of interest are described herein.

In one embodiment, the mRNA, e.g., mmRNA, is administered by once weekly infusion. In another embodiment, the infusion is intravenously. In another embodiment, the mRNA, e.g., mmRNA, is administered by once weekly infusion for at least 4 weeks. In another embodiment, the mRNA, e.g., mmRNA, is administered intratumorally. Suitable dosage regimens are described further herein.

In another embodiment, the disclosure provides a method of reducing or inhibiting unwanted immune cell activation (e.g., B cell activation) and/or unwanted cytokine production in a subject administered a messenger RNA (mRNA) encoding a polypeptide of interest, the method comprising administering to the subject intravenously a first dose of a mRNA, e.g., modified mRNA (mmRNA) encoding a polypeptide of interest encapsulated in an LNP, wherein the mRNA, e.g., mmRNA, comprises at least one binding site for a microRNA (miR) expressed in immune cells, such as a miR-126 microRNA binding site and/or at least one miR-142 microRNA binding site, and wherein the mRNA, e.g., mmRNA, comprises one or more modified nucleobases; and administering to the subject intravenously a second dose of the mRNA, e.g., mmRNA, encapsulated in an LNP, such that unwanted immune cell activation and/or unwanted cytokine production is reduced or inhibited in the subject.

In another aspect, the disclosure provides a method of reducing or inhibiting unwanted immune cell activation (e.g., B cell activation) and/or unwanted cytokine production in subject following repeated administration of a messenger RNA (mRNA) encoding a polypeptide of interest to a subject, comprising
(i) administering to the subject intravenously a first dose of a mRNA, e.g., modified mRNA (mmRNA) encoding a polypeptide of interest, encapsulated in an LNP, wherein the mRNA, e.g., mmRNA, comprises at least one binding site for a microRNA (miR) expressed in immune cells, such as a miR-126 microRNA binding site and/or at least one miR-142 microRNA binding site, and wherein the mRNA, e.g., mmRNA, comprises one or more modified nucleobases:
(ii) detecting a level of immune cell activation in a sample from the subject; and
(iii) administering to the subject intravenously a second dose of the mRNA, e.g., mmRNA, encapsulated in an LNP when the level of immune cell activation in the sample is diminished, such that unwanted immune cell activation and/or unwanted cytokine production is reduced or inhibited in the subject.

In yet another aspect, the disclosure provides a modified messenger RNA (mmRNA) encoding a polypeptide of interest, wherein the mmRNA comprises at least two different microRNA (miR) binding sites, wherein the microRNA is expressed in an immune cell of hematopoietic lineage or a cell that expresses TLR7 and/or TLR8 and secretes pro-inflammatory cytokines and/or chemokines, and wherein the mmRNA comprises one or more modified nucleobases. In some aspects, the immune cell of hematopoietic lineage is a lymphoid cell, such as a T cell, B cell, or NK cell. In some aspects, the immune cell of hematopoietic lineage is a myeloid cell, such as a monocyte, macrophage, neutrophil, basophil, eosinophil, erthyrocyte, dendritic cell, megakaryocyte, or platelet. In some aspects, the immune cell of hematopoietic lineage is a hematopoietic progenitor cell. In some aspects, the cell that expresses TLR7 and/or TLR8 and secretes pro-inflammatory cytokines and/or chemokines is an endothelial cell.

In some aspects of the disclosure, the mmRNA comprises at least two different microRNA binding sites, wherein the microRNA is abundant in the same or different cell type of interest. In some aspects the microRNA is abundant in multiple cell types of interest.

In some aspects, the disclosure provides an mmRNA comprising at least one first microRNA binding site of a microRNA abundant in an immune cell of hematopoietic lineage and at least one second microRNA binding site of a microRNA abundant in endothelial cells, wherein the mmRNA comprises one or more modified nucleobases.

In some aspects, the disclosure provides an mmRNA comprising at least one first microRNA binding site of a microRNA abundant in B cells and at least one second microRNA binding site of a microRNA abundant in endothelial cells, wherein the mmRNA comprises one or more modified nucleobases.

In some aspects, the disclosure provides an mmRNA comprising at least one first microRNA binding site of a microRNA abundant in plasmacytoid dendritic cells and at least one second microRNA binding site of a microRNA abundant in endothelial cells, wherein the mmRNA comprises one or more modified nucleobases.

In some aspects of the disclosure, the mmRNA comprises multiple copies (2, 3, 4 copies) of a first microRNA binding site and at least one copy of a second microRNA binding site. In some aspects, the mmRNA comprises 2 copies of a first microRNA binding site and 1 copy of a second microRNA binding site.

In some aspects, the disclosure provides an mmRNA comprising first and second microRNA binding sites of the same microRNA, such as, for example, microRNA binding sites of the 3p and 5p arms of the same microRNA.

Some aspects of the disclosure provide a modified messenger RNA (mmRNA) encoding a polypeptide of interest, wherein the mmRNA comprises at least two different microRNA (miR) binding sites, wherein the microRNA is selected from the group consisting of miR-126, miR-142, miR-144, miR-146, miR-150, miR-155, miR-16, miR-21, miR-223, miR-24, miR-27 and miR-26a, and wherein the mmRNA comprises one or more modified nucleobases. In some aspects, the microRNA is selected from the group consisting of miR126-3p, miR-142-3p, miR-142-5p, and miR-155. In some aspects, the at least one microRNA binding site is a miR-126 binding site, such as set forth in SEQ ID NO: 26. In some aspects, the at least one microRNA binding site is a miR-142 binding site, such as set forth in SEQ ID NO: 3.

In yet other aspects, the disclosure provide a modified messenger RNA (mmRNA) encoding a polypeptide of interest, wherein the mmRNA comprises at least two different microRNA (miR) binding sites, wherein one microRNA binding site is a miR-126 binding site and the second microRNA binding site is for a microRNA selected from the group consisting of miR-142-3p, miR-142-5p, miR-146-3p, miR-146-5p, miR-155, miR-16, miR-21, miR-223, miR-24 and miR-27, and wherein the mmRNA comprises one or more modified nucleobases.

In other aspects, the disclosure provide a modified messenger RNA (mmRNA) encoding a polypeptide of interest, wherein the mmRNA a miR-126-3p binding site and a miR-142-3p binding site, and wherein the mmRNA comprises one or more modified nucleobases. In some aspects the mmRNA comprises in the 5' or 3' UTR a single miR- 126-3p binding site as set forth in SEQ ID NO: 26 and a single miR-142-3p binding site as set forth in SEQ ID NO: 3. In some aspects the mmRNA comprises at least one miR-142-3p binding site and at least one 142-5p binding site, such as set forth in SEQ ID NO: 3 and SEQ ID NO: 51, respectively.

In yet other aspects, the disclosure provide a modified messenger RNA (mmRNA) encoding a polypeptide of interest, wherein the mmRNA comprises at least three different microRNA binding sites, wherein at least one of the microRNA binding sites is a miR-126 binding site, and wherein the mmRNA comprises one or more modified nucleobases.

In some aspects, the disclosure provide a modified messenger RNA (mmRNA) encoding a polypeptide of interest, wherein the mmRNA comprises at least three different microRNA binding sites, wherein at least one of the microRNA binding sites is a miR-142 binding site, and wherein the mmRNA comprises one or more modified nucleobases.

In yet other aspects, the disclosure provide a modified messenger RNA (mmRNA) encoding a polypeptide of interest, wherein the mmRNA comprises at least one miR-126-3p binding site, at least one miR-142-3p, and a third microRNA binding site for a microRNA selected from the group consisting of miR-146-3p, miR-146-5p, miR-155, miR-16, miR-21, miR-223, miR-24 and miR-27, and wherein the mmRNA comprises one or more modified nucleobases. In some aspects, the mmRNA comprises at least one miR-126-3p binding site, at least one miR-142-3p binding site, and at least one miR-155 binding site (e.g., a 155-5p binding site as set forth in the Sequence Listing). In some aspects, the mmRNA comprises at least one miR-126-3p binding site, at least one miR-142-3p binding site, at least one miR-142-5p binding site, and at least one miR-155 binding site.

In any of the preceding and related aspects, the disclosure provides an mmRNA comprising a 5' UTR, a codon optimized open reading frame encoding the polypeptide of interest, a 3' UTR, and a 3' tailing region of linked nucleosides, wherein the microRNA binding sites are located in the 5' UTR, 3' UTR, or both the 5' UTR and 3' UTR of the mmRNA. In some aspects, the microRNA binding sites are located in the 3' UTR of the mmRNA. In some aspects, the microRNA binding sites are located in the 5' UTR of the mmRNA. In some aspects, the microRNA binding sites are located in both the 5' UTR and 3' UTR of the mmRNA. In some aspects, the at least one microRNA binding site is located in the 3' UTR immediately adjacent to the stop codon of the coding region of the mmRNA. In some aspects, the at least one microRNA binding site is located in the 3' UTR 70-80 bases downstream of the stop codon of the coding region of the mmRNA. In some aspects, the at least one microRNA binding site is located in the 5' UTR immediately preceding the start codon of the coding region of the mmRNA. In some aspects, the at least one microRNA binding site is located in the 5' UTR 15-20 nucleotides preceding the start codon of the coding region of the mmRNA. In some aspects, the at least one microRNA binding site is located in the 5' UTR 70-80 nucleotides preceding the start codon of the coding region of the mmRNA.

In some aspects, the disclosure provides mmRNA comprising multiple copies of the same or different microRNA binding sites positioned immediately adjacent to each other or with a spacer of less than 5, 5-10, 10-15, or 15-20 nucleotides, in either the 5' UTR, 3' UTR or both. In some aspects, the mmRNA comprises multiple copies of the same microRNA binding site located in the 3' UTR, wherein the first microRNA binding site is positioned immediately adjacent to the stop codon and the second and third microRNA binding sites are positioned 30-40 bases downstream of the first microRNA binding site. In some aspects, the mmRNA comprises 2 copies of a first microRNA binding site and 1 copy of a second microRNA binding site located in the 3' UTR, wherein the first copy of the first microRNA binding site is positioned immediately adjacent to the stop codon, the second microRNA binding site is positioned 30-40 bases downstream of the first copy of the first microRNA binding site, and the second copy of the first microRNA binding site is positioned 30-40 bases downstream of the second microRNA binding site.

In any of the foregoing or related aspects, the disclosure provides a modified mRNA wherein the mmRNA is fully modified.

In any of the foregoing or related aspects, the disclosure provides an mmRNA comprising pseudouridine ($\psi$), pseudouridine ($\psi$) and 5-methyl-cytidine ($m^5C$), 1-methyl-pseudouridine ($m^1\psi$), 1-methyl-pseudouridine ($m^1\psi$) and 5-methyl-cytidine ($m^5C$), 2-thiouridine ($s^2U$), 2-thiouridine and 5-methyl-cytidine ($m^5C$), 5-methoxy-uridine ($mo^5U$), 5-methoxy-uridine ($mo^5U$) and 5-methyl-cytidine ($m^5C$), 2'-O-methyl uridine, 2'-O-methyl uridine and 5-methyl-cytidine ($m^5C$), N6-methyl-adenosine ($m^6A$) or N6-methyl-adenosine ($m^6A$) and 5-methyl-cytidine ($m^5C$).

In any of the foregoing or related aspects, the disclosure provides an mmRNA comprising pseudouridine ($\psi$), N1-methylpseudouridine ($m^1\psi$), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine, or combinations thereof.

In any of the foregoing or related aspects, the disclosure provides an mmRNA comprising 1-methyl-pseudouridine ($m^1\psi$), 5-methoxy-uridine ($mo^5U$), 5-methyl-cytidine ($m^5C$), pseudouridine ($\psi$), $\alpha$-thio-guanosine, or $\alpha$-thio-adenosine, or combinations thereof.

In any of the foregoing or related aspects, the disclosure provides an mmRNA encoding a polypeptide of interest, wherein the polypeptide of interest is a therapeutic protein, cytokine, growth factor, antibody or fusion protein.

In any of the foregoing or related aspects, the disclosure provides a lipid nanoparticle comprising a modified mRNA as described herein. In some aspects, the lipid nanoparticle comprises a liposome. In some aspects, the lipid nanoparticle comprises a cationic and/or ionizable lipid. In some aspects, the cationic and/or ionizable lipid is DLin-KC2-DMA or DLin-MC3-DMA.

In any of the foregoing or related aspects, the disclosure provides a pharmaceutical composition comprising the mmRNA or lipid nanoparticle as described herein, and a pharmaceutically acceptable carrier, diluent or excipient.

In any of the foregoing or related aspects, the disclosure provides an mmRNA, a lipid nanoparticle or a pharmaceutical composition as described herein, for use in reducing or inhibiting an anti-drug antibody response or inhibiting drug-related toxicity in a subject in need thereof.

In any of the foregoing or related aspects, the disclosure provides an mmRNA, a lipid nanoparticle or a pharmaceutical composition as described herein, for use in reducing or inhibiting unwanted immune cell activation or reducing or inhibiting unwanted cytokine production in a subject in need thereof.

In any of the foregoing or related aspects, the disclosure provides an mmRNA, a lipid nanoparticle or a pharmaceutical composition as described herein, for use in reducing or inhibiting accelerated blood clearance in a subject in need thereof.

In any of the foregoing or related aspects, the disclosure provides an mmRNA, a lipid nanoparticle or a pharmaceutical composition as described herein, for use in reducing or inhibiting production of IgM molecules that recognize polyethylene glycol (PEG) in a subject in need thereof.

The details of various embodiments of the disclosure are set forth in the description below. Other features, objects, and advantages of the disclosure will be apparent from the description and the drawings, and from the claims.

BRIEF DESCRIPTION OF THE DRAWINGS

FIG. 7 are graphs showing B cell frequency of mice treated with a single indicated dose (0.2 mg/kg or 1 mg/kg) of mmRNA encoding hEPO either lacking or containing a miR-142-3p binding site, a miR-126 binding site, or both the miR-142-3p and miR-126 binding sites, in the 3' UTR of the construct.

FIG. 9 are graphs showing B cell frequency of mice treated with two doses of the indicated dosage (0.2 mg/kg or 1 mg/kg) of mmRNA encoding hEPO either lacking or containing a miR-142-3p binding site, a miR-126 binding site, or both the miR-142-3p and miR-126 binding sites, in the 3' UTR of the construct.

FIG. 10 are graphs showing activated B cell frequency of mice treated with two doses of the indicated dosage (0.2 mg/kg or 1 mg/kg) of mmRNA encoding hEPO either lacking or containing a miR-142-3p binding site, a miR-126 binding site, or both the miR-142-3p and miR-126 binding sites, in the 3' UTR of the construct.

FIGS. 15A-B are graphs showing Luciferase (Luc) expression levels, as measured by whole body luminescence, in mice treated for 1 week (FIG. 15A) or two weeks (FIG. 15B) with 0.2 mg/kg mmRNA encoding Luc either lacking or containing a miR-142-3p binding site, a miR-126 binding site, or both the miR-142-3p and miR-126 binding sites, in the 3' UTR of the construct.

FIG. 16 are graphs showing total B cell frequency in mice treated with a 0.2 mg/kg mmRNA encoding Luc either lacking or containing a miR-142-3p binding site, a miR-126 binding site, or both the miR-142-3p and miR-126 binding sites, in the 3' UTR of the construct.

FIG. 17 are graphs showing activated B cell frequency in mice treated with 0.2 mg/kg mmRNA encoding Luc either lacking or containing a miR-142-3p binding site, a miR-126 binding site, or both the miR-142-3p and miR-126 binding sites, in the 3' UTR of the construct.

FIGS. 19A-B are graphs showing EPO expression levels in the serum of mice treated for 1 week (FIG. 19A) or two weeks (FIG. 19B) with 0.2 mg/kg mmRNA encoding EPO either lacking or containing a miR-142-3p binding site, a miR-142-5p binding site, a miR-155-5p binding site, or multiple copies or combinations thereof.

FIG. 20 are graphs showing total B cell frequency in mice treated for 1 week with 0.2 mg/kg mmRNA encoding EPO either lacking or containing a miR-142-3p binding site, a miR-142-5p binding site, a miR-155-5p binding site, or multiple copies or combinations thereof.

FIG. 21 are graphs showing activated B cell frequency in mice treated for 1 week with 0.2 mg/kg mmRNA encoding EPO either lacking or containing a miR-142-3p binding site, a miR-142-5p binding site, a miR-155-5p binding site, or multiple copies or combinations thereof.

FIG. 22 are graphs showing total B cell frequency in mice treated for two weeks with 0.2 mg/kg mmRNA encoding EPO either lacking or containing a miR-142-3p binding site, a miR-142-5p binding site, a miR-155-5p binding site, or multiple copies or combinations thereof.

FIGS. 24A-C are graphs showing secreted IL-6 levels (FIG. 24A), TNF-a levels (FIG. 24B) and IFN-γ levels (FIG. 24C) in mice treated for 2 weeks with 0.2 mg/kg mmRNA encoding EPO either lacking or containing a miR-142-3p binding site, a miR-142-5p binding site, a miR-155-5p binding site, or multiple copies or combinations thereof.

FIGS. 31A-D are graphs showing the level of expression of eGFP in primary hepatocytes transfected with an equimolar mixture of Luc and eGFP mRNA constructs in LNP, wherein the mRNA constructs contained either no recognizable miR sites (control), 1× or 3× miR-122 binding sites or a putative mRNA with similar sequence to the eGFP and Luc sequences (control), at doses of 7.5 ng (FIG. 31A), 15 ng (FIG. 31B), 50 ng (FIG. 31C) or 100 ng (FIG. 31D).

DETAILED DESCRIPTION

Figure 1:
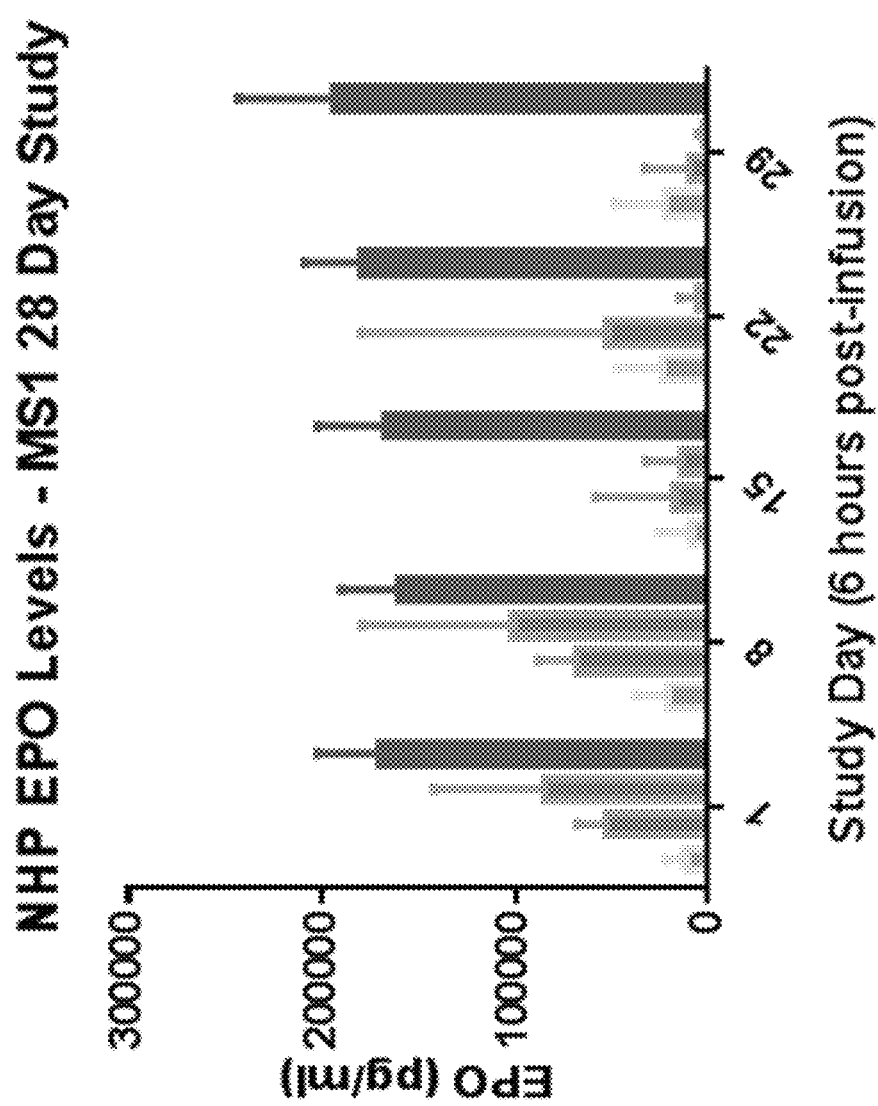
FIG. 1 is a bar graph showing the levels of human erythropoietin (hEPO) protein in cynomolgus macaques treated with mmRNA encoding hEPO (but lacking any miR binding sites) at the indicated doses, or with recombinant hEPO protein as a positive control, six hours post infusion on the indicated days of treatment.

One challenge associated with the clinical use of protein-based therapeutics is the development of an unwanted anti-drug antibody (ADA) response, wherein the patient's immune system generates antibodies against the therapeutic agent (for reviews, see e.g., Subramanyam, M. (2006) *J. Immunotoxicol.* 3:151-156; De Groot, A. S, and Scott, D. W. (2007) *Trends Immunol.* 28:482-490; Nechansky, A, and Kircheis, R. (2010) *Expert Opin. Drug. Discov.* 5:1067-1079). Development of ADA responses has been reported both for recombinant antibody biologics and for non-antibody biologics (see e.g., Brickelmaier, M. et al. (1999) *J. Immunol. Methods* 227:121-135; Ruf, P. et al. (2010) *Br. J. Clin. Pharmacol.* 69:617-625; Lundkvist, M. et al. (2013) *Mult. Scler.* 19:757-764). The ADA response can interfere with or neutralize the effect of the therapeutic agent, thereby impacting drug pharmacokinetics and efficacy. Neutralizing antibodies (NAB) are generally of more concern than binding antibodies (BAB) that are not neutralizing, but both may have clinical consequences.

Furthermore, allergic reactions, complement activation and other adverse events are often associated with the development of ADA, thereby impacting drug safety. Thus, ADA is a significant factor in the ability to use biologics for long-term treatment.

The use of modified mRNA, e.g., mRNAs (mmRNAs), as therapeutic agents offers an exciting alternative to protein-based therapeutics. mRNA therapeutics offer several advantages over the protein-based therapeutic art, including, for example, fidelity of encoded protein characteristics (because the protein is produced by the body's own translation apparatus), sensitive, tunable pharmacokinetic profile (protein expression may be transient, which may be favorable for some therapeutic approaches to better control pharmacokinetics and dosing), excellent safety profile (as revealed in various vaccine clinical trials), functionality in the cytoplasm without the need to travel to the nucleus resulting in protein translation almost immediately after mRNA administration, eliminates any risk of genomic integration, as well as ease of manufacturing, e.g., mRNAs are easily produced by various generic, in vitro processes, e.g., in vitro transcription reactions, without the need for living organisms. Furthermore, mRNA can be designed either to have self-adjuvanting properties, e.g., in vaccine applications, or to evade immunogenic activation, e.g., in therapeutic applications. It has now been discovered, however, that administration of mRNA encoding a protein of interest, particularly in instances where the mRNA administration leads directly or indirectly to expression of the encoded protein in immune cells, e.g., the spleen, also can lead to the development of an anti-drug antibody response to the protein encoded by the mRNA. It has surprisingly been demonstrated, however, that incorporation of at least one microRNA (miRNA) binding site for a miR expressed in immune cells (e.g., in immune cells of peripheral lymphoid organs and/or splenocytes) into the mRNA (mRNA) encoding the protein of interest can reduce the anti-drug antibody response to the protein of interest when the mRNA is administered to the subject.

Accordingly, the disclosure provides methods for reducing or inhibiting an anti-drug antibody (ADA) response to a protein of interest by means of post-transcriptional regulation, in particular in immune system tissue such as the spleen. The disclosure also provides methods of reducing drug-related toxicity in a subject by incorporation of at least one microRNA (miRNA) binding site for a miR expressed in immune cells into a mRNA (e.g., mmRNA) encoding a protein of interest. Preferred microRNA binding sites used in the methods of the disclosure are those that bind miRs expressed abundantly or preferentially in immune cells (e.g., in immune cells of peripheral lymphoid organs and/or splenocytes). A particularly preferred microRNA binding site is for miR-142-3p. Another particularly preferred microRNA binding site is for miR-126.

As described in Example 1, an in vivo study in which cynomolgus macaques were administered an mmRNA construct encoding human erythropoietin (hEPO) led to the observations that the levels of hEPO declined over time in the animals. Furthermore, reticulocytopenia and reduced bone marrow hematopoiesis were also observed. These results suggested the possibility that anti-drug antibodies were being generated in the animals, which was confirmed by ELISA analysis of serum. While in no way being bound by theory, prior experience with the mRNA delivery system used in the study (using lipid nanoparticles, LNPs) demonstrated that the mRNA distributed primarily to the liver but also to the spleen and, thus, this distribution could lead to heightened immunity to the protein being made that is encoded by the mRNA. Again while not being bound by theory or mechanism, it is possible that expression of encoded protein manufactured in the spleen (delivered based on the LNP distribution to the spleen by direct delivery via the blood flow or indirectly via professional antigen presenting cells) could lead to T cell dependent antibody production via the presentation of appropriate epitopes (i.e., from the protein of interest) to T cells.

To address this, as described in Example 2, additional mRNA constructs were designed that included at least one microRNA (miRNA) binding site for a miR expressed in immune cells (e.g., at least one binding site for miR-142-3p). Administration of the miR-containing mRNA construct in vivo led to a significant reduction in the development of ADA responses in the recipient animals.

Another challenge associated with the clinical use of protein-based therapeutics in the art is the development of unwanted immune cell activation (e.g., B cell activation) against the therapeutic protein, leading to immune-mediated side effects. It has now been discovered, however, that administration of mRNA, e.g., encoding a protein of interest, particularly in instances where the mRNA administration leads directly or indirectly to expression of the encoded protein in immune cells, e.g., splenocytes, also can lead to the development unwanted immune cell activation (e.g., B cell activation, including cytokine production). It has surprisingly been demonstrated, however, that incorporation of at least one binding site for a microRNA (miRNA) that is expressed in peripheral lymphoid tissue and/or endothelial cells, in particular at least one miR-126 and/or miR-142 binding site, into the mRNA (mRNA) can reduce or inhibit unwanted immune cell activation when the mRNA is administered to the subject. Accordingly, the disclosure provides compositions and methods for reducing or inhibiting unwanted immune cell activation when using mRNA-based therapeutic agents by means of post-transcriptional regulation, in particular in immune system tissue such as peripheral lymphoid organs or the spleen.

Experiments described in Example 3 demonstrated that incorporation of a miR-126 or miR-142 (e.g., miR-142-3p) binding site, or the two sites in combination, into mRNA constructs encoding a protein of interest, led to a reduced frequency of activated B cells, as well as reduced levels of cytokine production (IL-6, TNF-α, IFN-γ), in animals administered the constructs, as compared to animals treated with constructs lacking the miR binding site(s). The effect of the miR-126 binding site alone was more potent than the effect of the miR-142 binding site alone, with the strongest effects being seen with the two sites used in combination. Frequency of B cell activation and cytokine production are early indicators of a mounting immune response in vivo, including antibody responses. Thus, these results indicate that inclusion of a miR-126 binding site in an mRNA construct (alone or in combination with a miR-142-3p binding site) can lead to a reduction in the development of ADA responses to the encoded protein in the recipient animal.

While in no way being bound by theory, the inclusion of a miR-126 binding site in an mRNA construct can lead to reduced or inhibited immune cell activation by one or more possible mechanisms, based on the expression pattern of miR-126. MicroRNA-126 is known to be highly and selectively expressed in plasmacytoid dendritic cells (pDCs) and regulates the maturation, survival and effector functions of these cells (Agudo, J. et al. (2014) *Nat. Immunol.* 15:54-62; Cella, M, and Trinchieri, G. (2014) *Nat. Immunol.* 15:8-9). Plasmacytoid dendritic cells account for less than 0.1% of peripheral blood mononuclear cells and 0.4-0.6% of total splenic cells, can differentiate into dendritic cells upon activation, produce interferons and serve as a link between innate and adaptive immunity, as well as playing a role in antigen presentation (for reviews on pDCs, see e.g., Jegalian, A. G. et al. (2009) *Adv. Anat. Pathol.* 16:392-404; Reizis, B. et al. (2011) *Annu. Rev. Immunol.* 29:163-183; Tel, J. et al. (2012) *Cancer Immunol. Immunotherap.* 61:1279-1288). Furthermore, pDCs are also involved in promoting B cell activation and differentiation and in stimulating cytokine production (see e.g., Douag, I. et al. (2009) *J. Immunol.* 182:1991-2001; Ding. C. et al. (2009) *J. Immunol.* 183:7140-7149; Gujer, C. et al. (2011) *J. Leukoc. Biol.* 89:811-821). Thus, the reduced frequency of B cell activation and the reduced cytokine production observed by the inclusion of a miR-126 binding site in an mRNA construct may result, for example, from inhibition of the antigen presenting function of the pDCs and/or from inability of pDCs to launch an effective response against foreign nucleic acids and/or from inhibition of the maturation and survival of the pDCs, thereby leading to reduced promotion of B cell activation and reduced cytokine production, the overall result of these effects then being a reduced ADA response in vivo against the protein encoded by the mRNA construct.

Additionally, miR-126 is known to be expressed in endothelial cells (see e.g., Fish, J. E. et al. (2008) *Dev. Cell.* 15:272-284: Wang, S. et al. (2008) *Dev. Cell.* 15:-261-271). Accordingly, the effect of inclusion of a miR-126 binding site in an mRNA construct may be related to the abundance of miR-126 in endothelial cells. Thus, inclusion of a miR-126 binding site in an mRNA construct may lead to reduced expression of the encoded protein in endothelial cells in vivo, resulting in reduced antigen presentation by the endothelial cells, leading to a concomitant reduction in frequency of B cell activation and reduced cytokine production, resulting in reduced ADA responses against the encoded protein in vivo.

As demonstrated in Example 6, inclusion of a miR-142 and/or miR-126 binding site in an mRNA construct leads to reduced total frequency of $CD11c^+$ dendritic cells, as well as reduced frequency of activated dendritic cells ($CD11c^+$ $CD70^+$ $CD86^+$ cells) within the $CD11c^+$ splenic cell population. In contrast, inclusion of a miR-142 and/or miR-126 binding site in mRNA constructs did not affect the frequency of $CD27^+$ $CD19^+$ B cells in splenic $CD19^+$ B cells, nor did it affect the level of CD27 expression in the $CD27^+$ $CD19^+$ B cell population. Furthermore, proliferation of naïve B cells was reduced when incubated with pDCs isolated from mice treated with the miR binding site(s)-containing constructs, as compared to treatment with an mRNA construct lacking the miR binding site(s). Thus, this experimental data supports the proposed mechanism that inhibition of B cell activation and inhibition of cytokine production in mice treated with modified mRNA constructs including one or a combination of miR binding site(s) results from decreased frequency and/or activation of pDCs, thereby leading to decreased B cell stimulation, likely resulting from decreased CD70-CD27 interactions or reduced dendritic cells cytokine secretion.

A separate challenge exists with the use of lipid-comprising compounds and compositions, such as lipid nanoparticles (LNPs), to deliver therapeutic agents, e.g., modified mRNA, wherein the agents are rapidly cleared from the blood upon second and subsequent administrations (i.e., accelerated blood clearance (ABC)). The mechanism includes the recognition of lipid-comprising compounds or compositions (e.g., LNPs) by B cells, in particular, by B1a cells, through CD36 and/or TLR recognition of the lipid components, such as phosphatidylcholine. Activated B1a cells secrete IgM, in particular, natural IgM, which can contribute to ABC (e.g., via an acute phase response-type mechanism. Phospholilid component (e.g., DSPC) of a lipid-comprising compound or composition (e.g., LNP) can also activate platelets, for example, in circulation. Activated platelets can aggregate and bind to macrophages, which subsequently release inflammatory cytokines and migrate to the spleen. The sequesteration of lipid-comprising compounds or compositions (e.g., LNPs) to the spleen happens almost immediately after administration.

It has been discovered that ABC is mediated, at least in part, by B cells, specifically B1a cells. These B cells are normally responsible for secreting natural IgM antibodies, which are polyreactive, meaning that they are able to bind to a variety of antigens, albeit with relatively low affinity for each. Upon administration of a first dose of an agent, B1a cells bind the agent and are activated, thereby secreting natural IgM that binds to the agent, such as phosphatidylcholine. A second or subsequent dose of a lipid-comprising compound or composition is then targeted by circulating IgM and rapidly cleared. Conventional B cells, referred to herein as B2 cells or CD19 (+) B cells, are also implicated in ABC. Specifically, conventional B cells are able to mount first an IgM response followed by an IgG response concomitant with a memory response. The conventional B cells react against the administered agent and the polyethylene glycol (PEG) and contribute to IgM (and eventually IgG) that mediates ABC. Previous solutions to this challenge have focused on supressing the immune response in subject administered LNP compositions. In particular, co-medication regimens (e.g., antihistamines, non-steroidal anti-inflammatory drugs (NSAIDs), steroids, corticosteroids, and the like) have been used to supress the immune system. It has now been discovered, however, that incorporation of at least one microRNA binding site for a microRNA expressed in immune cells (e.g., miR-126, miR-142, miR-155 and combinations thereof) into a modified mRNA construct can reduce or inhibit ABC when the lipid-comprising compound or composition comprising the modified mRNA is administered to a subject. Specifically, it has been discovered that incorporation of at least one microRNA binding site into a modified mRNA can reduce or inhibit plasmacytoid dendritic cell proliferation and/or activation and/or reduce or inhibit production of anti-PEG IgMs. For example, as demonstrated in Example 7, inclusion of the at least one miR binding site(s) in the mRNA construct leads to decreased levels of serum anti-PEG IgM antibodies in mice administered a lipid-comprising compound or composition comprising the mRNA constructs.

Multiple possible mechanisms exist by which the inclusion of at least one microRNA binding site(s), as described herein, into a modified mRNA construct being delivered by lipid-comprising compounds or compositions leads to reduction or inhibition of ABC. In one embodiment, the mechanism of action of the miRNA binding site(s) is a microRNA "sponge", wherein the miRNA binding site(s) in the construct "soaks up" microRNAs that bind to the binding site(s). This can lead to deregulation of natural targets of the specific microRNA as this microRNA is less/not available to regulate them. This scenario mimics the effects of a microRNA knock-down/knock-out. In examples where proper regulation of the natural targets of the microRNA is necessary for the cell's ability to act as an effective immune cell, this microRNA-spone-type effect renders the cell incapable of producing an immune response. It is also possible that deregulation of an endogenous target of the microRNA disrupts the homeostasis of the cell (e.g., calcium signaling), leading to a stress response (e.g., unfolded protein response). Alternatively, it is possible that inclusion of the microRNA-binding in the mRNA suppresses expression from this mRNA in the specific microRNA-harboring cell-type. It is also possible that inclusion of the micro-RNA binding site leads to degradation of the mRNA before a sensor like TLR7 can recognize it. The latter two mechanisms are postulated to be dependent on RNA-induced silencing complex (RISC)-mediated cleavage of an mRNA comprising a one or more binding sites for a microRNA (miR) expressed in immune cells. It is also possible that these mechanisms act in concert, both leading to the miR-mediated observed effects described herein.

Regardless of the mechanisms involved, the resulting impact of the inclusion of at least one microRNA binding site(s), as described herein, into a mRNA construct is that immune cells which recognize the lipid-comprising compounds or compositions (e.g., pDCs, B cells (e.g., circulating B cells, macrophages), are not activated and therefore do not migrate to the spleen to activate B cells (e.g, splenic B cells). In addition, cytokine production (e.g., IL-6) is reduced or inhibited which further prevents activation of the immune cells. The reduction or inhibition of B cell activation results in a reduction or inhibition of natural IgMs (e.g., by B1a cells), IgMs and IgGs. The production of these molecules are essential for ABC and therefore the reduction or inhibition of their production reduces or inhibits ABC overall.

Accordingly, the disclosure provides methods for reducing or inhibiting ABC when using lipid-comprising compounds or compositions comprising modified mRNA encoding a polypeptide of interest.

Various aspects of the disclosure are described further in the subsections below:

mRNA

The disclosure provides isolated RNAs, in particular mRNAs, e.g., chemically modified mRNAs, that encode a polypeptide of interest and that include at least one microRNA binding site (e.g., miR-126 and/or miR-142 binding sites). In other embodiments, the disclosure provides RNAs, e.g., chemically modified RNAs, that include at least one microRNA binding site (e.g., miR-126 and/or miR-142 binding sites), but that do not necessarily encode a polypeptide of interest. The latter RNAs also may lack other typical features of mRNAs (such as the mRNA features described below), yet include the miR-126 and/or miR-142 binding site(s).

An RNA may be a naturally or non-naturally occurring RNA, e.g., mRNA. An mRNA may include one or more modified nucleobases, nucleosides, or nucleotides, as described below, in which case it may be referred to as a "chemically modified mRNA", also referred to herein as a "modified mRNA" or "mmRNA." As described herein "nucleoside" is defined as a compound containing a sugar molecule (e.g., a pentose or ribose) or derivative thereof in combination with an organic base (e.g., a purine or pyrimidine) or a derivative thereof (also referred to herein as "nucleobase"). As described herein, "nucleotide" is defined as a nucleoside including a phosphate group.

An mRNA may include a 5' untranslated region (5'UTR), a 3' untranslated region (3'UTR), and/or a coding region (e.g., an open reading frame). An mRNA may include any suitable number of base pairs, including hundreds (e.g., 200, 300, 400, 500, 600, 700, 800, or 900) or thousands (e.g., 1000, 2000, 3000, 4000, 5000, 6000, 7000, 8000, 9000, 10,000) of base pairs. Any number (e.g., all, some, or none) of nucleobases, nucleosides, or nucleotides may be an analog of a canonical species, substituted, modified, or otherwise non-naturally occurring. In certain embodiments, all of a particular nucleotide or nucleobase type may be modified.

In one embodiment, the mRNA comprises a first flanking region located at the 5' terminus of an open reading frame (coding region) and a second flanking region located at the 3' terminus of the open reading frame (coding region), wherein the first flanking region comprises a 5' untranslated region (5' UTR) and the second flanking region comprises a 3' untranslated region (3 'UTR). In one embodiment, the 5'UTR and the 3'UTR of the mRNA are not derived from the same species. In one embodiment, the 5'UTR and/or the 3'UTR of the mRNA are not derived from beta-globin. In one embodiment, the 5' untranslated region is heterologous to the coding region of the mRNA. In another embodiment, the 3' untranslated region is heterologous to the coding region of the mRNA. In yet another embodiment, the 5' untranslated region and the 3' untranslated region are heterologous to the coding region of the mRNA. In yet another embodiment, the mRNA comprises at least two stop codons.

The sequence of a non-limiting example of a 5' UTR suitable for use in the mRNA constructs is shown in SEQ ID NO: 53. The sequence of a non-limiting example of a 3' UTR suitable for use in the mRNA constructs is shown in SEQ ID NO: 30. Other suitable 5' and 3' UTRs suitable for use in the mRNA constructs are well known in the art.

For example, suitable 5' UTRs include those from the β-globin gene (see e.g., Kariko et al. (2008) *Mol. Therap.* 16:1833-40: U.S. Pat. Nos. 8,278,063, 9,012,219), the α-globin gene (see e.g., U.S. Pat. No. 9,012,219), the human cytochrome b-245 α polypeptide gene (CYBA) (see e.g., Ferizi et al. (2015) *Lab. Chip.* 23:1456-1464), the hydroxysteroid (17-β) dehydrogenase gene (HSD17B4) (see e.g., Thess et al. (2015) *Mol. Therap.* 23:1456-1464: WO 2015/024667), the TOP gene (see e.g., WO/2015101414, WO2015/101415, WO2015/062738, WO2015/024667, WO2015/024667), the ribosomal protein Large 32 (L32) gene (see e.g., WO2015/101414, WO2015/101415, WO2015/062738) and the ATP51 gene (see e.g., WO2015/024667), as well as viral 5' UTRs, including those from Tobacco etch virus (TEV) (see e.g., Katalin et al. (2012) *Mol. Therap.* 20:948-953: U.S. Pat. Nos. 8,278,063, 9,012, 219), Venezuelan equine encephalitis virus (VEEV), (see e.g., Andries et al. (2015) *J. Control Release* 217:337-344) and the CMV immediate-early 1 (IE1) gene (see e.g., US20140206753, WO2014/089486, WO2013/185069, WO2014/144196, WO2014/152659, WO2014/152940, WO2014/152774, WO2014/153052). Synthetic 5' UTRs have been described and are also suitable for use (see e.g., Mandal and Rossi (2013) *Nat. Protocol* 5:68-82).

Additionally, for example, suitable 3' UTRs include those from the β-globin gene (see e.g., Kariko et al. (2008) *Mol. Therap.* 16:1833-40; U.S. Pat. No. 8,278,063: U.S. Pat. No. 9,012,219; WO2007/036366, US 2011/0065103, WO2011/015347, WO2012/072096, WO2013/143555, WO2014/071963), the α-globin gene (see e.g., U.S. Pat. No. 9,012, 219: WO2015/101414, WO2015/101415, WO2015024667), the human cytochrome b-245 α polypeptide gene (CYBA) (see e.g., Ferizi et al. (2015) *Lab. Chip.* 23:1456-1464), the albumin gene (see e.g., Thess et al. (2015) *Mol. Therap.* 23:1456-1464), the human growth hormone (hGH) gene (see e.g., US20140206753, WO2013/185069, WO2014/089486, WO2014/144196, WO2014//152659, WO2014152940, WO2014/152774, WO2014/153052), the ribosomal rps9 protein gene (see e.g., WO2015/101414), the FIG. 4 gene (see e.g., WO2015/101415), the human albumin7 gene (see e.g., WO2015/101415, WO2015/101414, WO2015/06273, WO2015/024667, WO2105/062737), as well as viral 3' UTRs, including those from Venezuelan equine encephalitis virus (VEEV), (see e.g., Andries et al. (2015) *J. Control Release* 217:337-344).

In some embodiments, an mRNA as described herein may include a 5' cap structure, a chain terminating nucleotide, a Kozak sequence (also known as a Kozak consensus sequence), a stem loop, a poly A sequence, and/or a polyadenylation signal. In other embodiments, the mRNA lacks a poly A sequence and/or a polyadenylation signal but rather contains an alternative structure for stabilizing the mRNA.

A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., m$^7$G (5')ppp (5')G, commonly written as m$^7$GpppG. A cap species may also be an anti-reverse cap analog. A non-limiting list of possible cap species includes m$^7$GpppG, m$^7$Gpppm$^7$G, m$^{7_3'}$dGpppG, m$_2^{7,O3'}$GpppG, m$_2^{7,O3'}$GppppG, m$_2^{7,}$$_{O2'}$GppppG, m$^7$Gpppm$^7$G, m$^7$3'dGpppG, m$_2^{7,O3'}$GpppG, m$_2^{7,O3'}$GppppG, and m$_2^{7,O2'}$GppppG. In various embodiments, the mRNA can comprise a 5' terminal cap selected from the group consisting of Cap0, Cap1, ARCA, inosine, N1-methyl-guanosine, 2'fluoro-guanosine, 7-deaza-guanosine, 8-oxo-guanosine, 2-amino-guanosine, LNA-guanosine, and 2-azido-guanosine. In one embodiment, the 5' terminal cap is Cap1.

An mRNA may instead or additionally include a chain terminating nucleoside. For example, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxythymine. In some embodiments, incorporation of a chain terminating nucleotide into an mRNA, for example at the 3'-terminus may result in stabilization of the mRNA, as described, for example, in International Patent Publication No. WO 2013/103659.

An mRNA may instead or additionally include a stem loop, such as a histone stem loop. A stem loop may include 2, 3, 4, 5, 6, 7, 8, or more nucleotide base pairs. For example, a stem loop may include 4, 5, 6, 7, or 8 nucleotide base pairs. A stem loop may be located in any region of an mRNA. For example, a stem loop may be located in, before, or after an untranslated region (a 5' untranslated region or a 3' untranslated region), a coding region, or a polyA sequence or tail. In some embodiments, a stem loop may affect one or more function(s) of an mRNA, such as initiation of translation, translation efficiency, and/or transcriptional termination.

An mRNA may instead or additionally include a polyA sequence and/or polyadenylation signal. A polyA sequence may be comprised entirely or mostly of adenine nucleotides or analogs or derivatives thereof. A polyA sequence may be a tail located adjacent to a 3' untranslated region of an mRNA. In some embodiments, a polyA sequence may affect the nuclear export, translation, and/or stability of an mRNA.

In some embodiments, an mRNA is a bicistronic mRNA comprising a first coding region and a second coding region with an intervening sequence comprising an internal ribosome entry site (IRES) sequence that allows for internal translation initiation between the first and second coding regions, or with an intervening sequence encoding a self-cleaving peptide, such as a 2A peptide. IRES sequences and 2A peptides are typically used to enhance expression of multiple proteins from the same vector. A variety of IRES sequences are known and available in the art and may be used, including, e.g., the encephalomyocarditis virus IRES.

In one embodiment, the polynucleotides of the present disclosure may include a sequence encoding a self-cleaving peptide. The self-cleaving peptide may be, but is not limited to, a 2A peptide. A variety of 2A peptides are known and available in the art and may be used, including e.g., the foot and mouth disease virus (FMDV) 2A peptide, the equine rhinitis A virus 2A peptide, the *Thosea asigna* virus 2A peptide, and the porcine teschovirus-1 2A peptide. 2A peptides are used by several viruses to generate two proteins from one transcript by ribosome-skipping, such that a normal peptide bond is impaired at the 2A peptide sequence, resulting in two discontinuous proteins being produced from one translation event. As a non-limiting example, the 2A peptide may have the protein sequence: GSGATNFSLLKQAGDVEENPGP (SEQ ID NO: 4), fragments or variants thereof. In one embodiment, the 2A peptide cleaves between the last glycine and last proline. As another non-limiting example, the polynucleotides of the present disclosure may include a polynucleotide sequence encoding the 2A peptide having the protein sequence GSGATNFSLLKQAGDVEENPGP (SEQ ID NO: 4) fragments or variants thereof. One example of a polynucleotide sequence encoding the 2A peptide is: GGAAGCGGAGC-TACTAACTTCAGCCTGCTGAAGCAGGCTGGA-GACGTGGAGGAG AACCCTGGACCT (SEQ ID NO: 5). In one illustrative embodiment, a 2A peptide is encoded by the following sequence: 5'-TCCGGACTCAGATCCGGG-GATCTCAAAATTGTCGCTCCTGT-CAAACAAACTCTTA ACTTTGATTTACT-CAAACTGGCTGGGGATGTAGAAAGCAATCCAGGTC-CACTC-3' (SEQ ID NO: 6). The polynucleotide sequence of the 2A peptide may be modified or codon optimized by the methods described herein and/or are known in the art.

In one embodiment, this sequence may be used to separate the coding regions of two or more polypeptides of interest. As a non-limiting example, the sequence encoding the 2A peptide may be between a first coding region A and a second coding region B (A-2Apep-B). The presence of the 2A peptide results in the cleavage of one long protein into protein A, protein B and the 2A peptide. Protein A and protein B may be the same or different peptides or polypeptides of interest.

Modified mRNAs

In some embodiments, an mRNA of the disclosure comprises one or more modified nucleobases, nucleosides, or nucleotides (termed "chemically modified mRNAs", also referred to herein as "modified mRNAs" or "mmRNAs"). In some embodiments, modified mRNAs may have useful properties, including enhanced stability, intracellular retention, enhanced translation, and/or the lack of a substantial induction of the innate immune response of a cell into which the mRNA is introduced, as compared to a reference unmodified mRNA. Therefore, use of modified mRNAs may enhance the efficiency of protein production, intracellular retention of nucleic acids, as well as possess reduced immunogenicity.

In some embodiments, an mRNA, includes one or more (e.g., 1, 2, 3 or 4) different modified nucleobases, nucleosides, or nucleotides. In some embodiments, an mRNA includes one or more (e.g., 1, 2, 3, 4, 5, 6, 7, 8, 9, 10, 20, 30, 40, 50, 60, 70, 80, 90, 100, or more) different modified nucleobases, nucleosides, or nucleotides. In some embodiments, the modified mRNA, may have reduced degradation in a cell into which the mmRNA is introduced, relative to a corresponding unmodified mRNA.

In one embodiment, the mRNA comprises at least one nucleoside (or nucleotide) modification. In another embodiment, the mRNA comprises at least one modification as compared to the chemical structure of an A, G, U or C ribonucleoside. In yet another embodiment, the mRNA is an isolated polynucleotide comprising:

(a) a first region of linked nucleosides, said first region encoding a polypeptide of interest;

(b) a first flanking region located 5' relative to said first region comprising a 5' untranslated region (5'UTR) and at least one 5' terminal cap;

(c) a second flanking region located 3' relative to said first region comprising a 3' untranslated region (3'UTR) and a 3' tailing sequence of linked nucleosides;

wherein said polynucleotide comprises at least one chemically modified nucleoside.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine ($\tau m^5s^2U$), 1-taurinomethyl-4-thio-pseudouridine, 5-methyl-uridine ($m^5U$, i.e., having the nucleobase deoxy thymine), 1-methyl-pseudouridine ($m^1\psi$), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxy propyl) uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxy carbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), α-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^4_2Cm$), 1-thio-cytidine, 2-F-ara-cytidine, 2'-F-cytidine, and 2'-OH-ara-cytidine.

In some embodiments, the modified nucleobase is a modified adenine. Exemplary nucleobases and nucleosides having a modified adenine include α-thio-adenosine, 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2m^6A$), N6-isopentenyl-adenosine (16A), 2-methylthio-N6-isopentenyl-adenosine ($ms^2i^6A$), N6-(cis-hydroxyisopentenyl) adenosine ($io^6A$), 2-methylthio-N6-(cis-hydroxyisopentenyl) adenosine ($ms^2io^6A$), N6-glycinylcarbamoyl-adenosine ($g^6A$), N6-threonylcarbamoyl-adenosine ($t^6A$), N6-methyl-N6-threonylcarbamoyl-adenosine ($m^6t^6A$), 2-methylthio-N6-threonylcarbamoyl-adenosine ($ms^2g^6A$), N6,N6-dimethyl-adenosine ($m^6_2A$), N6-hydroxynorvalylcarbamoyl-adenosine ($hn^6A$), 2-methylthio-N6-hydroxynorvalylcarbamoyl-adenosine ($ms^2hn^6A$), N6-acetyl-adenosine ($ac^6A$), 7-methyl-adenine, 2-methylthio-adenine, 2-methoxy-adenine, α-thio-adenosine, 2'-O-methyl-adenosine (Am), N6,2'-O-dimethyl-adenosine ($m^6Am$), N6,N6,2'-O-trimethyl-adenosine ($m^6_2Am$), 1,2'-O-dimethyl-adenosine ($m^1Am$), 2'-O-ribosyladenosine (phosphate) (Ar (p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include α-thio-guanosine, inosine (I), 1-methyl-inosine ($m^1I$), wyosine (imG), methylwyosine (mimG), 4-demethyl-wyosine (imG-14), isowyosine (imG2), wybutosine (yW), peroxywybutosine (ozyW), hydroxy wybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine ($preQ_0$), 7-aminomethyl-7-deaza-guanosine ($preQ_1$), archaeosine ($G^+$), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^2_2G$), N2,7-dimethyl-guanosine ($m^{2,7}G$), N2, N2,7-dimethyl-guanosine ($m^{2,2,7}G$), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine ($m^2Gm$), N2,N2-dimethyl-2'-O-methyl-guanosine ($m^2_2Gm$), 1-methyl-2'-O-methyl-guanosine ($m^1Gm$), N2,7-dimethyl-2'-O-methylguanosine (m$^{2,7}$Gm), 2'-O-methyl-inosine (Im), 1,2'-O-dimethyl-inosine (m$^1$Im), 2'-O-ribosylguanosine (phosphate) (Gr (p)), 1-thio-guanosine, 06-methyl-guanosine, 2'-F-ara-guanosine, and 2'-F-guanosine.

In some embodiments, an mmRNA, of the disclosure includes a combination of one or more of the aforementioned modified nucleobases (e.g., a combination of 2, 3 or 4 of the aforementioned modified nucleobases).

In some embodiments, the modified nucleobase is pseudouridine (ψ), N1-methylpseudouridine (m$^1$ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, an mmRNA of the disclosure includes a combination of one or more of the aforementioned modified nucleobases (e.g., a combination of 2, 3 or 4 of the aforementioned modified nucleobases).

In some embodiments, the modified nucleobase is a modified cytosine. Exemplary nucleobases and nucleosides having a modified cytosine include N4-acetyl-cytidine (ac$^4$C), 5-methyl-cytidine (m$^5$C), 5-halo-cytidine (e.g., 5-iodo-cytidine), 5-hydroxy methyl-cytidine (hm$^5$C), 1-methyl-pseudoisocytidine, 2-thio-cytidine (s$^2$C), 2-thio-5-methyl-cytidine. In some embodiments, an mmRNA, of the disclosure includes a combination of one or more of the aforementioned modified nucleobases (e.g., a combination of 2, 3 or 4 of the aforementioned modified nucleobases).

In some embodiments, the modified nucleobase is a modified adenine. Exemplary nucleobases and nucleosides having a modified adenine include 7-deaza-adenine, 1-methyl-adenosine (m$^1$A), 2-methyl-adenine (m$^2$A), N6-methyl-adenosine (m$^6$A). In some embodiments, an mmRNA, of the disclosure includes a combination of one or more of the aforementioned modified nucleobases (e.g., a combination of 2, 3 or 4 of the aforementioned modified nucleobases).

In some embodiments, the modified nucleobase is a modified guanine. Exemplary nucleobases and nucleosides having a modified guanine include inosine (I), 1-methyl-inosine (m$^1$I), wyosine (imG), methylwyosine (mimG), 7-deaza-guanosine, 7-cyano-7-deaza-guanosine (preQ$_0$), 7-aminomethyl-7-deaza-guanosine (preQ$_1$), 7-methyl-guanosine (m$^7$G), 1-methyl-guanosine (m$^1$G), 8-oxo-guanosine, 7-methyl-8-oxo-guanosine. In some embodiments, an mmRNA of the disclosure includes a combination of one or more of the aforementioned modified nucleobases (e.g., a combination of 2, 3 or 4 of the aforementioned modified nucleobases).

In some embodiments, the modified nucleobase is 1-methyl-pseudouridine (m$^1$ψ), 5-methoxy-uridine (mo$^5$U), 5-methyl-cytidine (m$^5$C), pseudouridine (ψ), α-thio-guanosine, or α-thio-adenosine. In some embodiments, an mmRNA of the disclosure includes a combination of one or more of the aforementioned modified nucleobases (e.g., a combination of 2, 3 or 4 of the aforementioned modified nucleobases).

In some embodiments, the mmRNA, comprises pseudouridine (ψ). In some embodiments, the mmRNA, comprises pseudouridine (ψ) and 5-methyl-cytidine (m$^5$C). In some embodiments, the mmRNA, comprises 1-methyl-pseudouridine (m$^1$ψ). In some embodiments, the mmRNA comprises 1-methyl-pseudouridine (m$^1$ψ) and 5-methyl-cytidine (m$^5$C). In some embodiments, the mmRNA, comprises 2-thiouridine (s$^2$U). In some embodiments, the mmRNA, comprises 2-thiouridine and 5-methyl-cytidine (m$^5$C). In some embodiments, the mmRNA, comprises 5-methoxy-uridine (mo$^5$U). In some embodiments, the RNA, e.g., comprises 5-methoxy-uridine (mo$^5$U) and 5-methyl-cytidine (m$^5$C). In some embodiments, the mmRNA, comprises 2'-O-methyl uridine. In some embodiments, the mmRNA, comprises 2'-O-methyl uridine and 5-methyl-cytidine (m$^5$C). In some embodiments, the mmRNA, comprises N6-methyl-adenosine (m$^6$A). In some embodiments, the mmRNA, comprises N6-methyl-adenosine (m$^6$A) and 5-methyl-cytidine (m$^5$C).

In certain embodiments, an mmRNA, of the disclosure is uniformly modified (i.e., fully modified, modified throughout the entire sequence) for a particular modification. For example, an mmRNA, can be uniformly modified with 1-methyl-pseudouridine (m$^1$ψ) or with 5-methyl-cytidine (m$^5$C), meaning that all uridine or cytosine residues in the mmRNA, sequence are replaced with 1-methyl-pseudouridine (m$^1$ψ) or with 5-methyl-cytidine (m$^5$C), respectively. Similarly, mmRNAs, of the disclosure can be uniformly modified for any type of nucleoside residue present in the sequence by replacement with a modified residue such as those set forth above.

In some embodiments, an mRNA of the disclosure may be modified in a coding region (e.g., an open reading frame encoding a polypeptide). In other embodiments, an mRNA may be modified in regions besides a coding region. For example, in some embodiments, a 5'-UTR and/or a 3'-UTR are provided, wherein either or both may independently contain one or more different nucleoside modifications. In such embodiments, nucleoside modifications may also be present in the coding region.

Examples of nucleoside modifications and combinations thereof that may be present in mmRNAs, of the present disclosure include, but are not limited to, those described in PCT Patent Application Publications: WO2012045075, WO2014081507, WO2014093924, WO2014164253, and WO2014159813.

The mmRNAs, of the disclosure can include a combination of modifications to the sugar, the nucleobase, and/or the internucleoside linkage. These combinations can include any one or more modifications described herein.

Examples of modified nucleosides and modified nucleoside combinations are provided below in Table 1 and Table 2. These combinations of modified nucleotides can be used to form the mmRNAs, of the disclosure. In certain embodiments, the modified nucleosides may be partially or completely substituted for the natural nucleotides of the mmRNAs, of the disclosure. As a non-limiting example, the natural nucleotide uridine may be substituted with a modified nucleoside described herein. In another non-limiting example, the natural nucleoside uridine may be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9% of the natural uridines) with at least one of the modified nucleoside disclosed herein.

TABLE 1

Combinations of Nucleoside Modifications

| Modified Nucleotide | Modified Nucleotide Combination |
|---|---|
| α-thio-cytidine | α-thio-cytidine/5-iodo-uridine |
| | α-thio-cytidine/N1-methyl-pseudouridine |

TABLE 1-continued

Combinations of Nucleoside Modifications

| Modified Nucleotide | Modified Nucleotide Combination |
|---|---|
| | α-thio-cytidine/α-thio-uridine |
| | α-thio-cytidine/5-methyl-uridine |
| | α-thio-cytidine/pseudo-uridine |
| | about 50% of the cytosines are α-thio-cytidine |
| pseudoisocytidine | pseudoisocytidine/5-iodo-uridine |
| | pseudoisocytidine/N1-methyl-pseudouridine |
| | pseudoisocytidine/α-thio-uridine |
| | pseudoisocytidine/5-methyl-uridine |
| | pseudoisocytidine/pseudouridine |
| | about 25% of cytosines are pseudoisocytidine |
| | pseudoisocytidine/about 50% of uridines are N1-methyl-pseudouridine and about 50% of uridine are pseudouridine |
| | pseudoisocytidine/about 25% of uridines are N1-methyl-pseudouridine and about 25% of uridines are pseudouridine |
| pyrrolo-cytidine | pyrrolo-cytidine/5-iodo-uridine |
| | pyrrolo-cytidine/N1-methyl-pseudouridine |
| | pyrrolo-cytidine/α-thio-uridine |
| | pyrrolo-cytidine/5-methyl-uridine |
| | pyrrolo-cytidine/pseudouridine |
| | about 50% of the cytosines are pyrrolo-cytidine |
| 5-methyl-cytidine | 5-methyl-cytidine/5-iodo-uridine |
| | 5-methyl-cytidine/N1-methyl-pseudouridine |
| | 5-methyl-cytidine/α-thio-uridine |
| | 5-methyl-cytidine/5-methyl-uridine |
| | 5-methyl-cytidine/pseudouridine |
| | about 25% of cytosines are 5-methyl-cytidine |
| | about 50% of cytosines are 5-methyl-cytidine |
| | 5-methyl-cytidine/5-methoxy-uridine |
| | 5-methyl-cytidine/5-bromo-uridine |
| | 5-methyl-cytidine/2-thio-uridine |
| | 5-methyl-cytidine/about 50% of uridines are 2-thio-uridine |
| | about 50% of uridines are 5-methyl-cytidine/about 50% of uridines are 2-thio-uridine |
| N4-acetyl-cytidine | N4-acetyl-cytidine/5-iodo-uridine |
| | N4-acetyl-cytidine/N1-methyl-pseudouridine |
| | N4-acetyl-cytidine/α-thio-uridine |
| | N4-acetyl-cytidine/5-methyl-uridine |
| | N4-acetyl-cytidine/pseudouridine |
| | about 50% of cytosines are N4-acetyl-cytidine |
| | about 25% of cytosines are N4-acetyl-cytidine |
| | N4-acetyl-cytidine/5-methoxy-uridine |
| | N4-acetyl-cytidine/5-bromo-uridine |
| | N4-acetyl-cytidine/2-thio-uridine |
| | about 50% of cytosines are N4-acetyl-cytidine/about 50% of uridines are 2-thio-uridine |

TABLE 2

Modified Nucleosides and Combinations Thereof 1-(2,2,2-Trifluoroethyl)pseudo-UTP
1-Ethyl-pseudo-UTP
1-Methyl-pseudo-U-alpha-thio-TP
1-methyl-pseudouridine TP, ATP, GTP, CTP
1-methyl-pseudo-UTP/5-methyl-CTP/ATP/GTP
1-Propyl-pseudo-UTP
25% 5-Aminoallyl-CTP + 75% CTP/25% 5-Methoxy-UTP + 75% UTP
25% 5-Aminoallyl-CTP + 75% CTP/75% 5-Methoxy-UTP + 25% UTP
25% 5-Bromo-CTP + 75% CTP/25% 5-Methoxy-UTP + 75% UTP
25% 5-Bromo-CTP + 75% CTP/75% 5-Methoxy-UTP + 25% UTP
25% 5-Bromo-CTP + 75% CTP/1-Methyl-pseudo-UTP
25% 5-Carboxy-CTP + 75% CTP/25% 5-Methoxy-UTP + 75% UTP
25% 5-Carboxy-CTP + 75% CTP/75% 5-Methoxy-UTP + 25% UTP
25% 5-Ethyl-CTP + 75% CTP/25% 5-Methoxy-UTP + 75% UTP
25% 5-Ethyl-CTP + 75% CTP/75% 5-Methoxy-UTP + 25% UTP
25% 5-Ethynyl-CTP + 75% CTP/25% 5-Methoxy-UTP + 75% UTP
25% 5-Ethynyl-CTP + 75% CTP/75% 5-Methoxy-UTP + 25% UTP
25% 5-Fluoro-CTP + 75% CTP/25% 5-Methoxy-UTP + 75% UTP
25% 5-Fluoro-CTP + 75% CTP/75% 5-Methoxy-UTP + 25% UTP
25% 5-Formyl-CTP + 75% CTP/25% 5-Methoxy-UTP + 75% UTP
25% 5-Formyl-CTP + 75% CTP/75% 5-Methoxy-UTP + 25% UTP
25% 5-Hydroxymethyl-CTP + 75% CTP/25% 5-Methoxy-UTP + 75% UTP
25% 5-Hydroxymethyl-CTP + 75% CTP/75% 5-Methoxy-UTP + 25% UTP
25% 5-Iodo-CTP + 75% CTP/25% 5-Methoxy-UTP + 75% UTP
25% 5-Iodo-CTP + 75% CTP/75% 5-Methoxy-UTP + 25% UTP
25% 5-Methoxy-CTP + 75% CTP/25% 5-Methoxy-UTP + 75% UTP
25% 5-Methoxy-CTP + 75% CTP/75% 5-Methoxy-UTP + 25% UTP
25% 5-Methyl-CTP + 75% CTP/25% 5-Methoxy-UTP + 75% 1-Methyl-pseudo-UTP
25% 5-Methyl-CTP + 75% CTP/25% 5-Methoxy-UTP + 75% UTP
25% 5-Methyl-CTP + 75% CTP/50% 5-Methoxy-UTP + 50% 1-Methyl-pseudo-UTP
25% 5-Methyl-CTP + 75% CTP/50% 5-Methoxy-UTP + 50% UTP
25% 5-Methyl-CTP + 75% CTP/5-Methoxy-UTP
25% 5-Methyl-CTP + 75% CTP/75% 5-Methoxy-UTP + 25% 1-Methyl-pseudo-UTP
25% 5-Methyl-CTP + 75% CTP/75% 5-Methoxy-UTP + 25% UTP
25% 5-Phenyl-CTP + 75% CTP/25% 5-Methoxy-UTP + 75% UTP
25% 5-Phenyl-CTP + 75% CTP/75% 5-Methoxy-UTP + 25% UTP
25% 5-Trifluoromethyl-CTP + 75% CTP/25% 5-Methoxy-UTP + 75% UTP
25% 5-Trifluoromethyl-CTP + 75% CTP/75% 5-Methoxy-UTP + 25% UTP
25% 5-Trifluoromethyl-CTP + 75% CTP/1-Methyl-pseudo-UTP
25% N4-Ac-CTP + 75% CTP/25% 5-Methoxy-UTP + 75% UTP
25% N4-Ac-CTP + 75% CTP/75% 5-Methoxy-UTP + 25% UTP
25% N4-Bz-CTP + 75% CTP/25% 5-Methoxy-UTP + 75% UTP
25% N4-Bz-CTP + 75% CTP/75% 5-Methoxy-UTP + 25% UTP TABLE 2-continued Modified Nucleosides and Combinations Thereof 25% N4-Methyl-CTP + 75% CTP/25% 5-Methoxy-UTP + 75% UTP
25% N4-Methyl-CTP + 75% CTP/75% 5-Methoxy-UTP + 25% UTP
25% Pseudo-iso-CTP + 75% CTP/25% 5-Methoxy-UTP + 75% UTP
25% Pseudo-iso-CTP + 75% CTP/75% 5-Methoxy-UTP + 25% UTP
25% 5-Bromo-CTP/75% CTP/Pseudo-UTP
25% 5-methoxy-UTP/25% 5-methyl-CTP/ATP/GTP
25% 5-methoxy-UTP/5-methyl-CTP/ATP/GTP
25% 5-methoxy-UTP/75% 5-methyl-CTP/ATP/GTP
25% 5-methoxy-UTP/CTP/ATP/GTP
25% 5-metoxy-UTP/50% 5-methyl-CTP/ATP/GTP
2-Amino-ATP
2-Thio-CTP
2-thio-pseudouridine TP, ATP, GTP, CTP
2-Thio-pseudo-UTP
2-Thio-UTP
3-Methyl-CTP
3-Methyl-pseudo-UTP
4-Thio-UTP
50% 5-Bromo-CTP + 50% CTP/1-Methyl-pseudo-UTP
50% 5-Hydroxymethyl-CTP + 50% CTP/1-Methyl-pseudo-UTP
50% 5-methoxy-UTP/5-methyl-CTP/ATP/GTP
50% 5-Methyl-CTP + 50% CTP/25% 5-Methoxy-UTP + 75% 1-Methyl-pseudo-UTP
50% 5-Methyl-CTP + 50% CTP/25% 5-Methoxy-UTP + 75% UTP
50% 5-Methyl-CTP + 50% CTP/50% 5-Methoxy-UTP + 50% 1-Methyl-pseudo-UTP
50% 5-Methyl-CTP + 50% CTP/50% 5-Methoxy-UTP + 50% UTP
50% 5-Methyl-CTP + 50% CTP/5-Methoxy-UTP
50% 5-Methyl-CTP + 50% CTP/75% 5-Methoxy-UTP + 25% 1-Methyl-pseudo-UTP
50% 5-Methyl-CTP + 50% CTP/75% 5-Methoxy-UTP + 25% UTP
50% 5-Trifluoromethyl-CTP + 50% CTP/1-Methyl-pseudo-UTP
50% 5-Bromo-CTP/50% CTP/Pseudo-UTP
50% 5-methoxy-UTP/25% 5-methyl-CTP/ATP/GTP
50% 5-methoxy-UTP/50% 5-methyl-CTP/ATP/GTP
50% 5-methoxy-UTP/75% 5-methyl-CTP/ATP/GTP
50% 5-methoxy-UTP/CTP/ATP/GTP
5-Aminoallyl-CTP
5-Aminoallyl-CTP/5-Methoxy-UTP
5-Aminoallyl-UTP
5-Bromo-CTP
5-Bromo-CTP/5-Methoxy-UTP
5-Bromo-CTP/1-Methyl-pseudo-UTP
5-Bromo-CTP/Pseudo-UTP
5-bromocytidine TP, ATP, GTP, UTP
5-Bromo-UTP
5-Carboxy-CTP/5-Methoxy-UTP
5-Ethyl-CTP/5-Methoxy-UTP
5-Ethynyl-CTP/5-Methoxy-UTP
5-Fluoro-CTP/5-Methoxy-UTP
5-Formyl-CTP/5-Methoxy-UTP
5-Hydroxy-methyl-CTP/5-Methoxy-UTP
5-Hydroxymethyl-CTP
5-Hydroxymethyl-CTP/1-Methyl-pseudo-UTP
5-Hydroxymethyl-CTP/5-Methoxy-UTP
5-hydroxymethyl-cytidine TP, ATP, GTP, UTP
5-Iodo-CTP/5-Methoxy-UTP
5-Me-CTP/5-Methoxy-UTP
5-Methoxy carbonyl methyl-UTP
5-Methoxy-CTP/5-Methoxy-UTP
5-methoxy-uridine TP, ATP, GTP, UTP
5-methoxy-UTP
5-Methoxy-UTP
5-Methoxy-UTP/N6-Isopentenyl-ATP
5-methoxy-UTP/25% 5-methyl-CTP/ATP/GTP
5-methoxy-UTP/5-methyl-CTP/ATP/GTP
5-methoxy-UTP/75% 5-methyl-CTP/ATP/GTP
5-methoxy-UTP/CTP/ATP/GTP
5-Methyl-2-thio-UTP
5-Methylaminomethyl-UTP
5-Methyl-CTP/5-Methoxy-UTP
5-Methyl-CTP/5-Methoxy-UTP(cap 0)
5-Methyl-CTP/5-Methoxy-UTP(No cap)
5-Methyl-CTP/25% 5-Methoxy-UTP + 75% 1-Methyl-pseudo-UTP
5-Methyl-CTP/25% 5-Methoxy-UTP + 75% UTP
5-Methyl-CTP/50% 5-Methoxy-UTP + 50% 1-Methyl-pseudo-UTP
5-Methyl-CTP/50% 5-Methoxy-UTP + 50% UTP
5-Methyl-CTP/5-Methoxy-UTP/N6-Me-ATP
5-Methyl-CTP/75% 5-Methoxy-UTP + 25% 1-Methyl-pseudo-UTP
5-Methyl-CTP/75% 5-Methoxy-UTP + 25% UTP
5-Phenyl-CTP/5-Methoxy-UTP TABLE 2-continued Modified Nucleosides and Combinations Thereof 5-Trifluoro-methyl-CTP/5-Methoxy-UTP
5-Trifluoromethyl-CTP
5-Trifluoromethyl-CTP/5-Methoxy-UTP
5-Trifluoromethyl-CTP/1-Methyl-pseudo-UTP
5-Trifluoromethyl-CTP/Pseudo-UTP
5-Trifluoromethyl-UTP
5-trifluromethylcytidine TP, ATP, GTP, UTP
75% 5-Aminoallyl-CTP + 25% CTP/25% 5-Methoxy-UTP + 75% UTP
75% 5-Aminoallyl-CTP + 25% CTP/75% 5-Methoxy-UTP + 25% UTP
75% 5-Bromo-CTP + 25% CTP/25% 5-Methoxy-UTP + 75% UTP
75% 5-Bromo-CTP + 25% CTP/75% 5-Methoxy-UTP + 25% UTP
75% 5-Carboxy-CTP + 25% CTP/25% 5-Methoxy-UTP + 75% UTP
75% 5-Carboxy-CTP + 25% CTP/75% 5-Methoxy-UTP + 25% UTP
75% 5-Ethyl-CTP + 25% CTP/25% 5-Methoxy-UTP + 75% UTP
75% 5-Ethyl-CTP + 25% CTP/75% 5-Methoxy-UTP + 25% UTP
75% 5-Ethynyl-CTP + 25% CTP/25% 5-Methoxy-UTP + 75% UTP
75% 5-Ethynyl-CTP + 25% CTP/75% 5-Methoxy-UTP + 25% UTP
75% 5-Fluoro-CTP + 25% CTP/25% 5-Methoxy-UTP + 75% UTP
75% 5-Fluoro-CTP + 25% CTP/75% 5-Methoxy-UTP + 25% UTP
75% 5-Formyl-CTP + 25% CTP/25% 5-Methoxy-UTP + 75% UTP
75% 5-Formyl-CTP + 25% CTP/75% 5-Methoxy-UTP + 25% UTP
75% 5-Hydroxymethyl-CTP + 25% CTP/25% 5-Methoxy-UTP + 75% UTP
75% 5-Hydroxymethyl-CTP + 25% CTP/75% 5-Methoxy-UTP + 25% UTP
75% 5-Iodo-CTP + 25% CTP/25% 5-Methoxy-UTP + 75% UTP
75% 5-Iodo-CTP + 25% CTP/75% 5-Methoxy-UTP + 25% UTP
75% 5-Methoxy-CTP + 25% CTP/25% 5-Methoxy-UTP + 75% UTP
75% 5-Methoxy-CTP + 25% CTP/75% 5-Methoxy-UTP + 25% UTP
75% 5-methoxy-UTP/5-methyl-CTP/ATP/GTP
75% 5-Methyl-CTP + 25% CTP/25% 5-Methoxy-UTP + 75% 1-Methyl-pseudo-UTP
75% 5-Methyl-CTP + 25% CTP/25% 5-Methoxy-UTP + 75% UTP
75% 5-Methyl-CTP + 25% CTP/50% 5-Methoxy-UTP + 50% 1-Methyl-pseudo-UTP
75% 5-Methyl-CTP + 25% CTP/50% 5-Methoxy-UTP + 50% UTP
75% 5-Methyl-CTP + 25% CTP/5-Methoxy-UTP
75% 5-Methyl-CTP + 25% CTP/75% 5-Methoxy-UTP + 25% 1-Methyl-pseudo-UTP
75% 5-Methyl-CTP + 25% CTP/75% 5-Methoxy-UTP + 25% UTP
75% 5-Phenyl-CTP + 25% CTP/25% 5-Methoxy-UTP + 75% UTP
75% 5-Phenyl-CTP + 25% CTP/75% 5-Methoxy-UTP + 25% UTP
75% 5-Trifluoromethyl-CTP + 25% CTP/25% 5-Methoxy-UTP + 75% UTP
75% 5-Trifluoromethyl-CTP + 25% CTP/75% 5-Methoxy-UTP + 25% UTP
75% 5-Trifluoromethyl-CTP + 25% CTP/1-Methyl-pseudo-UTP
75% N4-Ac-CTP + 25% CTP/25% 5-Methoxy-UTP + 75% UTP
75% N4-Ac-CTP + 25% CTP/75% 5-Methoxy-UTP + 25% UTP
75% N4-Bz-CTP + 25% CTP/25% 5-Methoxy-UTP + 75% UTP
75% N4-Bz-CTP + 25% CTP/75% 5-Methoxy-UTP + 25% UTP
75% N4-Methyl-CTP + 25% CTP/25% 5-Methoxy-UTP + 75% UTP
75% N4-Methyl-CTP + 25% CTP/75% 5-Methoxy-UTP + 25% UTP
75% Pseudo-iso-CTP + 25% CTP/25% 5-Methoxy-UTP + 75% UTP
75% Pseudo-iso-CTP + 25% CTP/75% 5-Methoxy-UTP + 25% UTP
75% 5-Bromo-CTP/25% CTP/1-Methyl-pseudo-UTP
75% 5-Bromo-CTP/25% CTP/Pseudo-UTP
75% 5-methoxy-UTP/25% 5-methyl-CTP/ATP/GTP
75% 5-methoxy-UTP/50% 5-methyl-CTP/ATP/GTP
75% 5-methoxy-UTP/75% 5-methyl-CTP/ATP/GTP
75% 5-methoxy-UTP/CTP/ATP/GTP
8-Aza-ATP
Alpha-thio-CTP
CTP/25% 5-Methoxy-UTP + 75% 1-Methyl-pseudo-UTP
CTP/25% 5-Methoxy-UTP + 75% UTP
CTP/50% 5-Methoxy-UTP + 50% 1-Methyl-pseudo-UTP
CTP/50% 5-Methoxy-UTP + 50% UTP CTP/5-Methoxy-UTP
CTP/5-Methoxy-UTP
CTP/5-Methoxy-UTP (cap 0)
CTP/5-Methoxy-UTP(No cap)
CTP/75% 5-Methoxy-UTP + 25% 1-Methyl-pseudo-UTP
CTP/75% 5-Methoxy-UTP + 25% UTP
CTP/UTP(No cap)
N1-Me-GTP
N4-Ac-CTP
N4Ac-CTP/1-Methyl-pseudo-UTP
N4Ac-CTP/5-Methoxy-UTP
N4-acetyl-cytidine TP, ATP, GTP, UTP
N4-Bz-CTP/5-Methoxy-UTP
N4-methyl CTP
N4-Methyl-CTP/5-Methoxy-UTP
Pseudo-iso-CTP/5-Methoxy-UTP
PseudoU-alpha-thio-TP
pseudouridine TP, ATP, GTP, CTP
pseudo-UTP/5-methyl-CTP/ATP/GTP TABLE 2-continued Modified Nucleosides and Combinations Thereof UTP-5-oxyacetic acid Me ester
Xanthosine According to the disclosure, polynucleotides of the disclosure may be synthesized to comprise the combinations or single modifications of Table 1 or Table 2.

Where a single modification is listed, the listed nucleoside or nucleotide represents 100 percent of that A, U, G or C nucleotide or nucleoside having been modified. Where percentages are listed, these represent the percentage of that particular A, U, G or C nucleobase triphosphate of the total amount of A, U, G, or C triphosphate present. For example, the combination: 25% 5-Aminoallyl-CTP+75% CTP/25% 5-Methoxy-UTP+75% UTP refers to a polynucleotide where 25% of the cytosine triphosphates are 5-Aminoallyl-CTP while 75% of the cytosines are CTP; whereas 25% of the uracils are 5-methoxy UTP while 75% of the uracils are UTP. Where no modified UTP is listed then the naturally occurring ATP, UTP, GTP and/or CTP is used at 100% of the sites of those nucleotides found in the polynucleotide. In this example all of the GTP and ATP nucleotides are left unmodified.

The mRNAs of the present disclosure, or regions thereof, may be codon optimized. Codon optimization methods are known in the art and may be useful for a variety of purposes: matching codon frequencies in host organisms to ensure proper folding, bias GC content to increase mRNA stability or reduce secondary structures, minimize tandem repeat codons or base runs that may impair gene construction or expression, customize transcriptional and translational control regions, insert or remove proteins trafficking sequences, remove/add post translation modification sites in encoded proteins (e.g., glycosylation sites), add, remove or shuffle protein domains, insert or delete restriction sites, modify ribosome binding sites and mRNA degradation sites, adjust translation rates to allow the various domains of the protein to fold properly, or to reduce or eliminate problem secondary structures within the polynucleotide. Codon optimization tools, algorithms and services are known in the art; non-limiting examples include services from GeneArt (Life Technologies), DNA2.0 (Menlo Park, CA) and/or proprietary methods. In one embodiment, the mRNA sequence is optimized using optimization algorithms, e.g., to optimize expression in mammalian cells or enhance mRNA stability.

In certain embodiments, the present disclosure includes polynucleotides having at least 80%, at least 85%, at least 90%, at least 95%, at least 98%, or at least 99% sequence identity to any of the polynucleotide sequences described herein.

The mRNAs, of the present disclosure may be produced by means available in the art, including but not limited to in vitro transcription (IVT) and synthetic methods. Enzymatic (IVT), solid-phase, liquid-phase, combined synthetic methods, small region synthesis, and ligation methods may be utilized. In one embodiment, mRNAs, are made using IVT enzymatic synthesis methods. Methods of making polynucleotides by IVT are known in the art and are described in International Application PCT/US2013/30062, the contents of which are incorporated herein by reference in their entirety. Accordingly, the present disclosure also includes polynucleotides, e.g., DNA, constructs and vectors that may be used to in vitro transcribe an mRNA described herein.

Non-natural modified nucleobases may be introduced into polynucleotides, e.g., mRNA, during synthesis or post-synthesis. In certain embodiments, modifications may be on internucleoside linkages, purine or pyrimidine bases, or sugar. In particular embodiments, the modification may be introduced at the terminal of a polynucleotide chain or anywhere else in the polynucleotide chain; with chemical synthesis or with a polymerase enzyme. Examples of modified nucleic acids and their synthesis are disclosed in PCT application No. PCT/US2012/058519. Synthesis of modified polynucleotides is also described in Verma and Eckstein, Annual Review of Biochemistry, vol. 76, 99-134 (1998).

Either enzymatic or chemical ligation methods may be used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1 (3), 165-187 (1990).

microRNA Binding Sites for miRs Expressed in Immune Cells microRNAs (or miRNA) are 19-25 nucleotide long (commonly 19-23 nucleotides long, most typically 22 nucleotides long) noncoding RNAs that bind to the 3'UTR of nucleic acid molecules and post-translationally down-regulate gene expression either by reducing nucleic acid molecule stability or by inhibiting translation. The mRNAs of the disclosure may comprise one or more microRNA target sequences or sites, microRNA binding sequences or sites, sequence complementary to a microRNA sequences, or sequence complementary to a microRNA seed region or sequence. Such sequences may correspond to any known microRNA such as those taught in US Publication US2005/0261218 and US Publication US2005/0059005, the contents of which are incorporated herein by reference in their entirety. A microRNA sequence comprises a "seed" region or sequence, i.e., a sequence in the region of positions 2-8 of the mature microRNA, which sequence has perfect Watson-Crick complementarity to the miRNA target sequence. The bases of the microRNA seed region or sequence have complete complementarity with the target sequence. microRNAs derive enzymatically from regions of RNA transcripts that fold back on themselves to form short hairpin structures often termed a pre-miRNA (precursor-miRNA). The pre-miRNA typically has a two-nucleotide overhang at its 3' end, and has 3' hydroxyl and 5' phosphate groups. This precursor-mRNA is processed in the nucleus and subsequently transported to the cytoplasm where it is further processed by DICER (a RNase III enzyme), to form a mature microRNA of approximately 22 nucleotides. The mature microRNA is then incorporated into a ribonuclear particle to form the RNA-induced silencing complex, RISC, which mediates gene silencing. Art-recognized nomenclature for mature miRNAs typically designates the arm of the pre-miRNA from which the mature miRNA derives; "5p" means the microRNA is from the 5 prime arm of the pre-miRNA hairpin and "3p" means the microRNA is from the 3 prime end of the pre-miRNA hairpin. A miR referred to by number herein can refer to either of the two mature microRNAs originating from opposite arms of the same pre-miRNA (e.g., either the 3p or 5p microRNA). All miRs referred to herein are intended to include both the 3p and 5p arms/sequences, unless particularly specified by the 3p or 5p designation.

In some embodiments, an mRNA of the disclosure may include one or more microRNA (miRNA) binding sites. As used herein, the term "microRNA (miRNA) binding site" refers to a sequence within a polynucleotide, e.g., within a DNA or within an RNA transcript, that has sufficient complementarity to all or a region of a miRNA to interact with, associate with or bind to the miRNA. In exemplary embodiments, miRNA binding sites are included in mRNAs, for example, in the 5' UTR and/or 3' UTR of an mRNA. A miR binding site sequence having sufficient complementarity to the miR refers to a degree of complementarity sufficient to facilitate miR-mediated regulation of the mRNA, e.g., miR-mediated translational repression or degradation of the mRNA. In exemplary aspects of the disclosure, a miR binding site sequence having sufficient complementarity to the miR refers to a degree of complementarity sufficient to facilitate miR-mediated degradation of the mRNA, e.g., miR-guided RISC-mediated cleavage of mRNA. The miR binding site can have complementarity to, for example, a 19-25 nucleotide long miR sequence, to a 19-23 nucleotide long miR, most typically to a 22 nucleotide long miR sequence. A miR binding site may be complementary to only a portion of a miR, e.g., to a portion 1, 2, 3 or 4 nucleotides shorter that a naturally-occurring miR. Full or complete complementarity (e.g., fully complementary or completely complementary over all or a significant portion of a naturally-occurring miR) is preferred when the desired regulation is mRNA degradation. In some embodiments, a miRNA binding site includes a sequence that has complementarity (e.g., partial or complete complementarity) with an miRNA seed sequence. In particular embodiments, the miRNA binding site includes a sequence that has complete complementarity with a miRNA seed sequence. In some embodiments, a miRNA binding site includes a sequence that has complementarity (e.g., partial or complete complementarity) with a miRNA sequence. In particular embodiments, the miRNA binding site includes a sequence that has complete complementarity with a miRNA sequence. In some embodiments, a miRNA binding site has complete complementarity with a miRNA sequence but for 1, 2 or 3 nucleotide substitutions, terminal additions, and/or truncations.

One or more miR binding sequences can be incorporated in an mRNA of the disclosure for one or more of a variety of different purposes. For example, incorporation of one or more miRNA binding sites into an mRNA of the disclosure may target the molecule for degradation or reduced translation, provided the miRNA in question is available (e.g., expressed in a target cell or tissue.) In some embodiments, incorporation of one or more miRNA binding sites into an mRNA of the disclosure may reduce the hazard of off-target effects upon nucleic acid molecule delivery and/or enable tissue-specific regulation of expression of a polypeptide encoded by the mRNA. In yet other embodiments, incorporation of one or more miRNA binding sites into an mRNA of the disclosure can modulate immune responses upon nucleic acid delivery in vivo. In further embodiments, incorporation of one or more miRNA binding sites into an mRNA of the disclosure can modulate accelerated blood clearance (ABC) of lipid-comprising compounds and compositions described herein.

Representative miRNAs were selected based on expression and abundance in immune cells of the hematopoietic lineage, such as B cells, T cells, macrophages, dendritic cells, and cells that are known to express TLR7/TLR8 and/or able to secrete cytokines such as endothelial cells and platelets. The miRNA set thus included miRs that may be responsible in part for the immunogenicity of these cells, and such that a corresponding miR-site incorporation in the mRNA could lead to destabilization of the mRNA and/or suppression of translation from these mRNAs in the specific cell type. Non-limiting representative examples include miR-142, miR-144, miR-150, miR-155 and miR-223, which are specific for many of the hematopoietic cells; miR-142, miR150, miR-16 and miR-223, which are expressed in B cells; miR-223, miR-451, miR-26a, miR-16, which are expressed in progenitor hematopoietic cells; and miR-126, which is expressed in plasmacytoid dendritic cells, platelets and endothelial cells. For further discussion of tissue expression of miRs see e.g., Teruel-Montoya, R. et al. (2014) PLOS One 9; e102259; Landgraf, P. et al. (2007) Cell 129:1401-1414; Bissels, U. et al. (2009) RNA 15:2375-2384. As is evidenced, any one miR-site incorporation in the 3'UTR and/or 5' UTR may mediate such effects in multiple cell types of interest (e.g., miR-142 is abundant in both B cells and dendritic cells).

It is beneficial to target the same cell type with multiple miRs and to incorporate binding sites to each of the 3p and 5p arm if both are abundant (e.g., both miR-142-3p and miR 142-5p are abundant in hematopoietic stem cells). Thus, for example, in certain embodiments, an mRNA construct contains two or more (e.g., two, three, four or more) miR bindings sites from: (i) the group consisting of miR-142, miR-144, miR-150, miR-155 and miR-223 (which are expressed in many hematopoietic cells); or (ii) the group consisting of miR-142, miR150, miR-16 and miR-223 (which are expressed in B cells); or the group consisting of miR-223, miR-451, miR-26a, miR-16 (which are expressed in progenitor hematopoietic cells).

It is also beneficial to combine various miRs such that multiple cell types of interest are targeted at the same time (e.g., miR-142 and miR-126 to target many cells of the hematopoietic lineage and endothelial cells). Thus, for example, in certain embodiments, an mRNA construct contains two or more (e.g., two, three, four or more) miR bindings sites, wherein: (i) at least one of the miRs targets cells of the hematopoietic lineage (e.g., miR-142, miR-144, miR-150, miR-155 or miR-223) and at least one of the miRs targets plasmacytoid dendritic cells, platelets or endothelial cells (e.g., miR-126); or (ii) at least one of the miRs targets B cells (e.g., miR-142, miR150, miR-16 or miR-223) and at least one of the miRs targets plasmacytoid dendritic cells, platelets or endothelial cells (e.g., miR-126); or (iii) at least one of the miRs targets progenitor hematopoietic cells (e.g., miR-223, miR-451, miR-26a or miR-16) and at least one of the miRs targets plasmacytoid dendritic cells, platelets or endothelial cells (e.g., miR-126); or (iv) at least one of the miRs targets cells of the hematopoietic lineage (e.g., miR-142, miR-144, miR-150, miR-155 or miR-223), at least one of the miRs targets B cells (e.g., miR-142, miR150, miR-16 or miR-223) and at least one of the miRs targets plasmacytoid dendritic cells, platelets or endothelial cells (e.g., miR-126); or any other possible combination of the foregoing four classes of miR binding sites (i.e., those targeting the hematopoietic lineage, those targeting B cells, those targeting progenitor hematopoietic cells and/or those targeting plamacytoid dendritic cells/platelets/endothelial cells).

Accordingly, in one embodiment, to modulate immune responses, an mRNA can comprise one or more miR binding sequences that bind to one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) reduces or inhibits immune cell activation (e.g., B cell activation, as measured by frequency of activated B cells) and/or cytokine production (e.g., production of IL-6, IFN-γ and/or TNFα). Furthermore, it has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) can reduce or inhibit an anti-drug antibody (ADA) response against a protein of interest encoded by the mRNA.

In another embodiment, to modulate accelerated blood clearance of an mRNA delivered in a lipid-comprising compound or composition, the mRNA can comprise one or more miR binding sequences that bind to one or more miRs expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miR binding sites reduces or inhibits accelerated blood clearance (ABC) of the lipid-comprising compound or composition for use in delivering the mRNA. Furthermore, it has now been discovered that incorporation of one or more miR binding sites into an mRNA reduces serum levels of anti-PEG anti-IgM (e.g, reduces or inhibits the acute production of IgMs that recognize polyethylene glycol (PEG) by B cells) and/or reduces or inhibits proliferation and/or activation of plasmacytoid dendritic cells following administration of a lipid-comprising compound or composition comprising the mRNA.

Such miR sequences may correspond to any known microRNA expressed in immune cells, including but not limited to those taught in US Publication US2005/0261218 and US Publication US2005/0059005, the contents of which are incorporated herein by reference in their entirety. Non-limiting examples of miRs expressed in immune cells include those expressed in spleen cells, myeloid cells, dendritic cells, plasmacytoid dendritic cells, B cells, T cells and/or macrophages. For example, miR-142-3p, miR-142-5p, miR-16, miR-21, miR-223, miR-24 and miR-27 are expressed in myeloid cells, miR-155 is expressed in dendritic cells, B cells and T cells, miR-146 is upregulated in macrophages upon TLR stimulation and miR-126 is expressed in plasmacytoid dendritic cells. In certain embodiments, the miR(s) is expressed abundantly or preferentially in immune cells. For example, miR-142 (miR-142-3p and/or miR-142-5p), miR-126 (miR-126-3p and/or miR-126-5p), miR-146 (miR-146-3p and/or miR-146-5p) and miR-155 (miR-155-3p and/or miR155-5p) are expressed abundantly in immune cells. These microRNA sequences are known in the art and, thus, one of ordinary skill in the art can readily design binding sequences or target sequences to which these microRNAs will bind based upon Watson-Crick complementarity.

Accordingly, in various embodiments, the mRNA comprises at least one microRNA binding site for a miR selected from the group consisting of miR-142, miR-146, miR-155, miR-126, miR-16, miR-21, miR-223, miR-24 and miR-27. In another embodiment, the mRNA comprises at least two miR binding sites for microRNAs expressed in immune cells. In various embodiments, the mRNA comprises 1-4, one, two, three or four miR binding sites for microRNAs expressed in immune cells. In another embodiment, the mRNA comprises three miR binding sites. These miR binding sites can be for microRNAs selected from the group consisting of miR-142, miR-146, miR-155, miR-126, miR-16, miR-21, miR-223, miR-24, miR-27, and combinations thereof. In one embodiment, the mRNA comprises two or more (e.g., two, three, four) copies of the same miR binding site expressed in immune cells, e.g., two or more copies of a miR binding site selected from the group of miRs consisting of miR-142, miR-146, miR-155, miR-126, miR-16, miR-21, miR-223, miR-24, miR-27.

For example, in one embodiment, the mRNA comprises three copies of the same miR binding site. As described in Example 8, in certain embodiments, use of three copies of the same miR binding site can exhibit beneficial properties as compared to use of a single miR binding site. Non-limiting examples of sequences for 3' UTRs containing three miR bindings sites are shown in SEQ ID NO: 38 (three miR-142-3p binding sites), SEQ ID NO: 40 (three miR-142-5p binding sites) and SEQ ID NO: 54 (three miR-122 binding sites).

In another embodiment, the mRNA comprises two or more (e.g., two, three, four) copies of at least two different miR binding sites expressed in immune cells. Non-limiting examples of sequences of 3' UTRs containing two or more different miR binding sites are shown in SEQ ID NO: 33 (one miR-142-3p binding site and one miR-126-3p binding site), SEQ ID NO: 47 (one miR-142-3p binding site and one miR-122-5p binding site), SEQ ID NO: 41 (two miR-142-5p binding sites and one miR-142-3p binding sites) and SEQ ID NO: 44 (two miR-155-5p binding sites and one miR-142-3p binding sites).

In another embodiment, the mRNA comprises at least two miR binding sites for microRNAs expressed in immune cells, wherein one of the miR binding sites is for miR-142-3p. In various embodiments, the mRNA comprises binding sites for miR-142-3p and miR-155 (miR-155-3p or miR-155-5p), miR-142-3p and miR-146 (miR-146-3 or miR-146-5p), or miR-142-3p and miR-126 (miR-126-3p or miR-126-5p).

In another embodiment, the mRNA comprises at least two miR binding sites for microRNAs expressed in immune cells, wherein one of the miR binding sites is for miR-126-3p. In various embodiments, the mRNA comprises binding sites for miR-126-3p and miR-155 (miR-155-3p or miR-155-5p), miR-126-3p and miR-146 (miR-146-3p or miR-146-5p), or miR-126-3p and miR-142 (miR-142-3p or miR-142-5p).

In another embodiment, the mRNA comprises at least two miR binding sites for microRNAs expressed in immune cells, wherein one of the miR binding sites is for miR-142-5p. In various embodiments, the mRNA comprises binding sites for miR-142-5p and miR-155 (miR-155-3p or miR-155-5p), miR-142-5p and miR-146 (miR-146-3 or miR-146-5p), or miR-142-5p and miR-126 (miR-126-3p or miR-126-5p).

In yet another embodiment, the mRNA comprises at least two miR binding sites for microRNAs expressed in immune cells, wherein one of the miR binding sites is for miR-155-5p. In various embodiments, the mRNA comprises binding sites for miR-155-5p and miR-142 (miR-142-3p or miR-142-5p), miR-155-5p and miR-146 (miR-146-3 or miR-146-5p), or miR-155-5p and miR-126 (miR-126-3p or miR-126-5p).

In exemplary embodiments, the one or more miR binding sites are positioned within the 3'UTR, the 5' UTR, or both the 3' and 5' UTRs, such that the mRNA has the desired properties. The miR binding site can be positioned within the 3' UTR immediately following the stop codon of the coding region within the mRNA construct (or, if there are multiple copies of a stop codon in the construct, immediately following the final stop codon) or the miR binding site(s) can be positioned further downstream of the stop codon, in which case there are 3' UTR bases between the stop codon and the miR binding site(s). For example, three non-limiting examples of possible insertion sites for a miR in a 3' UTR are shown in SEQ ID NOs: 48, 49 and 50, which show a 3' UTR sequence with a miR-142-3p site inserted in one of three different possible insertion sites, respectively, within the 3' UTR. Furthermore, one or more miR binding sites can be positioned within the 5' UTR at one or more possible insertion sites. For example, three non-limiting examples of possible insertion sites for a miR in a 5' UTR are described further in Example 9 and shown in SEQ ID NOs: 55, 56 and 57, which show a 5' UTR sequence with a miR-142-3p site inserted into one of three different possible insertion sites, respectively, within the 5' UTR. Additionally, SEQ ID NOs: 58, 59 and 60 show a 5' UTR sequence with a miR-122 site inserted into one of three different possible insertion sites, respectively, within the 5' UTR.

In one embodiment, a codon optimized open reading frame encoding a polypeptide of interest comprises a stop codon and the at least one microRNA binding site is located within the 3' UTR 1-100 nucleotides after the stop codon. In one embodiment, the codon optimized open reading frame encoding the polypeptide of interest comprises a stop codon and the at least one microRNA binding site for a miR expressed in immune cells is located within the 3' UTR 30-50 nucleotides after the stop codon. In another embodiment, the codon optimized open reading frame encoding the polypeptide of interest comprises a stop codon and the at least one microRNA binding site for a miR expressed in immune cells is located within the 3' UTR at least 50 nucleotides after the stop codon. In other embodiments, the codon optimized open reading frame encoding the polypeptide of interest comprises a stop codon and the at least one microRNA binding site for a miR expressed in immune cells is located within the 3' UTR immediately after the stop codon, or within the 3' UTR 15-20 nucleotides after the stop codon or within the 3' UTR 70-80 nucleotides after the stop codon. In other embodiments, the 3'UTR comprises more than one miR binding site (e.g., 2-4 miR binding sites), wherein there can be a spacer region (e.g., of 10-100, 20-70 or 30-50 nucleotides in length) between each miR binding site. In another embodiment, the 3' UTR comprises a spacer region between the end of the miR binding site(s) and the poly A tail nucleotides. For example, a spacer region of 10-100, 20-70 or 30-50 nucleotides in length can be situated between the end of the miR binding site(s) and the beginning of the poly A tail.

In one embodiment, a codon optimized open reading frame encoding a polypeptide of interest comprises a start codon and the at least one microRNA binding site is located within the 5' UTR 1-100 nucleotides before (upstream of) the start codon. In one embodiment, the codon optimized open reading frame encoding the polypeptide of interest comprises a start codon and the at least one microRNA binding site for a miR expressed in immune cells is located within the 5' UTR 10-50 nucleotides before (upstream of) the start codon. In another embodiment, the codon optimized open reading frame encoding the polypeptide of interest comprises a start codon and the at least one microRNA binding site for a miR expressed in immune cells is located within the 5' UTR at least 25 nucleotides before (upstream of) the start codon. In other embodiments, the codon optimized open reading frame encoding the polypeptide of interest comprises a start codon and the at least one microRNA binding site for a miR expressed in immune cells is located within the 5' UTR immediately before the start codon, or within the 5' UTR 15-20 nucleotides before the start codon or within the 5' UTR 70-80 nucleotides before the start codon. In other embodiments, the 5'UTR comprises more than one miR binding site (e.g., 2-4 miR binding sites), wherein there can be a spacer region (e.g., of 10-100, 20-70 or 30-50 nucleotides in length) between each miR binding site.

In one embodiment, the 3' UTR comprises more than one stop codon, wherein at least one miR binding site is positioned downstream of the stop codons. For example, a 3' UTR can comprise 1, 2 or 3 stop codons. Non-limiting examples of triple stop codons that can be used include: UGAUAAUAG, UGAUAGUAA, UAAUGAUAG, UGAUAAUAA, UGAUAGUAG, UAAUGAUGA, UAAUAGUAG, UGAUGAUGA, UAAUAAUAA and UAGUAGUAG. Within a 3' UTR, for example, 1, 2, 3 or 4 miR binding sites, e.g., miR-142-3p binding sites, can be positioned immediately adjacent to the stop codon(s) or at any number of nucleotides downstream of the final stop codon. When the 3' UTR comprises multiple miR binding sites, these binding sites can be positioned directly next to each other in the construct (i.e., one after the other) or, alternatively, spacer nucleotides can be positioned between each binding site.

In one embodiment, the 3' UTR comprises three stop codons with a single miR-142-3p binding site located downstream of the 3rd stop codon. Non-limiting examples of sequences of 3' UTR having three stop codons and a single miR-142-3p binding site located at different positions downstream of the final stop codon are shown in SEQ ID Nos: 31 and 48-50.

In one embodiment, the mmRNA comprises a 5' UTR, a codon optimized open reading frame encoding a polypeptide of interest, a 3' UTR comprising the at least one microRNA binding site for a miR expressed in immune cells, and a 3' tailing region of linked nucleosides. In various embodiments, the 3' UTR comprises 1-4, at least two, one, two, three or four microRNA binding sites for miRs expressed in immune cells, preferably abundantly or preferentially expressed in immune cells.

In one embodiment, the at least one miR expressed in immune cells is a miR-142-3p microRNA binding site. In one embodiment, the miR-142-3p microRNA binding site comprises the sequence shown in SEQ ID NO: 3. In one embodiment, the 3' UTR of the mRNA comprising the miR-142-3p microRNA binding site comprises the sequence shown in SEQ ID NO: 2.

In one embodiment, the at least one miR expressed in immune cells is a miR-126 microRNA binding site. In one embodiment, the miR-126 binding site is a miR-126-3p binding site. In one embodiment, the miR-126-3p microRNA binding site comprises the sequence shown in SEQ ID NO: 26. In one embodiment, the 3' UTR of the mmRNA comprising the miR-126-3p microRNA binding site comprises the sequence shown in SEQ ID NO: 27.

Non-limiting exemplary sequences for miRs to which a microRNA binding site(s) of the disclosure can bind include the following: miR-142-3p (SEQ ID NO: 8), miR-142-5p (SEQ ID NO: 9), miR-146-3p (SEQ ID NO: 10), miR-146-5p (SEQ ID NO: 11), miR-155-3p (SEQ ID NO: 12), miR-155-5p (SEQ ID NO: 13), miR-126-3p (SEQ ID NO: 14), miR-126-5p (SEQ ID NO: 15), miR-16-3p (SEQ ID NO: 16), miR-16-5p (SEQ ID NO: 17), miR-21-3p (SEQ ID NO: 18), miR-21-5p (SEQ ID NO: 19), miR-223-3p (SEQ ID NO: 20), miR-223-5p (SEQ ID NO: 21), miR-24-3p (SEQ ID NO: 22), miR-24-5p (SEQ ID NO: 23), miR-27-3p (SEQ ID NO: 24) and miR-27-5p (SEQ ID NO: 25). Other suitable miR sequences expressed in immune cells (e.g., abundantly or preferentially expressed in immune cells) are known and available in the art, for example at the University of Manchester's microRNA database, miRBase. Sites that bind any of the aforementioned miRs can be designed based on Watson-Crick complementarity to the miR, typically 100% complementarity to the miR, and inserted into an mRNA construct of the disclosure as described herein.

In yet other embodiments, the therapeutic window and/or differential expression (e.g., tissue-specific expression) of a polypeptide of the disclosure may be altered by incorporation of a miRNA binding site into an mRNA encoding the polypeptide. Examples of tissues where microRNA are known to regulate mRNA, and thereby protein expression, include, but are not limited to, liver (e.g., miR-122), muscle (e.g., miR-133, miR-206, and miR-208), endothelial cells (e.g., miR-17-92, and miR-126), myeloid cells (e.g., miR-142-3p, miR-142-5p, miR-16, miR-21, miR-223, miR-24, and miR-27), adipose tissue (e.g., let-7, and miR-30c), heart (e.g., miR-Id and miR-149), kidney (e.g., miR-192, miR-194, and miR-204), and lung epithelial cells (e.g., let-7, miR-133, and miR-126). Thus, in various embodiments, an mRNA can comprise one or more binding site for any of the afore-mentioned miRs, alone or in combination, to regulate thereby regulate tissue expression of an encoded protein of interest.

For example, an mRNA may include one or more miRNA binding sites that are bound by miRNAs that have higher expression in one tissue type as compared to another. In another example, an mRNA may include one or more miRNA binding sites that are bound by miRNAs that have lower expression in a cancer cell as compared to a non-cancerous cell of the same tissue of origin. When present in a cancer cell that expresses low levels of such an miRNA, the polypeptide encoded by the mRNA typically will show increased expression. If the polypeptide is able to induce apoptosis, this may result in preferential cell killing of cancer cells as compared to normal cells.

For example, liver cancer cells (e.g., hepatocellular carcinoma cells) typically express low levels of miR-122 as compared to normal liver cells. Therefore, an mRNA encoding a polypeptide that includes at least one miR-122 binding site (e.g., in the 3'-UTR of the mRNA) will typically express comparatively low levels of the polypeptide in normal liver cells and comparatively high levels of the polypeptide in liver cancer cells. If the polypeptide is able to induce apoptosis, this can cause preferential cell killing of liver cancer cells (e.g., hepatocellular carcinoma cells) as compared to normal liver cells.

Accordingly, as a non-limiting example of incorporation a miR binding site(s) into a mRNA to modulate tissue expression of an encoded protein of interest, mRNAs of the disclosure may include at least one miR-122 binding site. For example, a mRNA of the disclosure may include a miR-122 binding site that includes a sequence with partial or complete complementarity with a miR-122 seed sequence. In some embodiments, a miR-122 seed sequence may correspond to nucleotides 2-7 of a miR-122. In some embodiments, a miR-122 seed sequence may be 5'-GGAGUG-3'. In some embodiments, a miR-122 seed sequence may be nucleotides 2-8 of a miR-122. In some embodiments, a miR-122 seed sequence may be 5'-GGAGUGU-3'. In some embodiments, the miR-122 binding site includes a nucleotide sequence of 5'-UAUUUAGUGUGAUAAUGGCGUU-3' (SEQ ID NO: 45) or 5'-CAAACACCAUUGUCACA-CUCCA-3' (SEQ ID NO: 46) or a complement thereof. In some embodiments, inclusion of at least one miR-122 binding site in an mRNA may dampen expression of a polypeptide encoded by the mRNA in a normal liver cell as compared to other cell types that express low levels of miR-122. In other embodiments, inclusion of at least one miR-122 binding site in an mRNA may allow increased expression of a polypeptide encoded by the mRNA in a liver cancer cell (e.g., a hepatocellular carcinoma cell) as compared to a normal liver cell.

In yet another embodiment, the mRNA (e.g., the 3' UTR thereof) can comprise at least one miR binding site for a miR expressed in immune cells, to thereby reduce or inhibit immune activation (e.g., B cell activation, cytokine production, ADA responses) upon nucleic acid delivery in vivo, and can comprise at least one miR binding site for modulating tissue expression of an encoded protein of interest. For example, in one embodiment, the mRNA comprises a miR-122 binding site, to thereby allow increased expression of a polypeptide encoded by the mRNA in a liver cancer cell (e.g., a hepatocellular carcinoma cell) as compared to a normal liver cell, and also comprises one or more miR binding sites for a miR expressed in immune cells, e.g., selected from the group consisting of miR-142, miR-146, miR-155, miR-126, miR-16, miR-21, miR-223, miR-24, miR-27.

In another embodiment, the mRNA (e.g., the 3' UTR thereof) can comprise at least one miR binding site to thereby reduce or inhibit accelerated blood clearance, for example by reducing or inhibiting production of IgMs, e.g., against PEG, by B cells and/or reducing or inhibiting proliferation and/or activation of pDCs, and can comprise at least one miR binding site for modulating tissue expression of an encoded protein of interest. For example, in one embodiment, the mRNA comprises a miR-122 binding site, to thereby allow increased expression of a polypeptide encoded by the mRNA in a liver cancer cell (e.g., a hepatocellular carcinoma cell) as compared to a normal liver cell, and also comprises one or more miR binding sites, e.g., selected from the group consisting of miR-142, miR-146, miR-155, miR-126, miR-16, miR-21, miR-223, miR-24, miR-27.

In one embodiment, the mRNA comprises a miR-122 binding site and a miR-142-3p binding site. In another embodiment, the mRNA comprises a miR-122 binding site and a miR-142-5p binding site. In another embodiment, the mRNA comprises a miR-122 binding site and a miR-126-3p binding site. In another embodiment, the mRNA comprises a miR-122 binding site and a miR-155-5p binding site. In another embodiment, the mRNA comprises a miR-122 binding site and a miR-126-3p binding site. In another embodiment, the mRNA comprises a miR-122 binding site, a miR-142 (miR-142-3p or 142-5p) binding site and a miR- 126 (miR-126-3p or miR-126-5p) binding site. In another embodiment, the mRNA comprises a miR-122 binding site, a miR-142 (miR-142-3p or 142-5p) binding site and a miR-155 (miR-155-3p or miR-155-5p) binding site. In another embodiment, the mRNA comprises a miR-122 binding site, a miR-126 (miR-126-3p or 126-5p) binding site and a miR-155 (miR-155-3p or miR-155-5p) binding site. In yet another embodiment, the mRNA comprises a miR-122 binding site, a miR-142 (miR-142-3p or miR-142-5p) binding site, a miR-126 (miR-126-3p or 126-5p) binding site and a miR-155 (miR-155-3p or miR-155-5p) binding site. In any of these embodiments, the miR-122 binding site can be a miR-122-5p binding site.

A non-limiting example of a 3' UTR sequence that comprises both a miR-142-3p binding site and a miR-122-5p binding site is shown in SEQ ID NO: 47. The structure of the 3' UTR of SEQ ID NO: 47 includes three stop codons at it's 5' end, followed immediately by a single miR-142-3p binding site, followed downstream by spacer nucleotides and then a single miR-122-5p binding site. The distance between the miR binding sites (e.g., miR-142-3p and miR-122-5p) can vary considerably: a number of different constructs have been tested with differing placement of the two miR binding sites and all have been functional. In certain embodiments, a nucleotide spacer is positioned between the two miR binding sites of a sufficient length to allow binding of RISC to each one. In one embodiment, the two miR binding sites are positioned about 40 bases apart from each other and the overall length of the 3' UTR is approximately 100-110 bases.

Proteins of Interest

The mRNAs of the disclosure can encode a protein of interest, typically a protein having therapeutic properties for use in a subject. The protein of interest can be essentially any protein that can be encoded by the mRNA. In particular, a protein of interest can be one that stimulates immune cell activation (e.g., B cell activation), such as eliciting an anti-drug antibody (ADA) response in a subject and, thus, for which reducing or inhibiting immune cell activation (e.g., reducing the ADA response) in the subject is desirable. In various embodiments, the protein of interest can be, for example, a therapeutic protein, a cytokine, a growth factor, an antibody or a fusion protein. Non-limiting examples of therapeutic proteins include, for example, blood factors (such as Factor VIII and Factor VII), complement factors, Low Density Lipoprotein Receptor (LDLR) and MUT1. Non-limiting examples of cytokines include, for example, interleukins, interferons, chemokines, lymphokines and the like. Non-limiting examples of growth factors include erythropoietin, EGFs, PDGFs, FGFs, TGFs, IGFs, TNFs, CSFs, MCSFs, GMCSFs and the like. Non-limiting examples of antibodies include, for example, adalimumab, infliximab, rituximab, ipilimumab, tocilizumab, canakinumab, itolizumab, tralokinumab. Non-limiting examples of fusion proteins include, for example, etanercept, abatacept and belatacept.

In one embodiment, the protein of interest is human erythropoietin. In one embodiment, the mRNA encodes human erythropoietin and comprises a microRNA binding site that binds miR-142-3p, such as the mRNA having the sequence shown in SEQ ID NO: 1. In another embodiment, the mRNA encodes human erythropoietin and comprises a microRNA binding site that binds miR-126, such as the mRNA having the sequence shown in SEQ ID NO: 28. In yet another embodiment, the mRNA encodes human erythropoietin and comprises a microRNA binding site that binds miR-142-3p and a microRNA binding site that binds miR-126, such as the mRNA having the sequence shown in SEQ ID NO: 29. In another embodiment, the protein of interest is LDLR (for use in inhibiting cholesterol). In another embodiment, the protein of interest is MUT1 (for use in the treatment of methylmalonic acidemia (MMA)). In yet other embodiments, the protein of interest encoded by the mmRNA is a therapeutic antibody, including but not limited to the antibodies listed above.

Nanoparticles

The mRNAs, of the disclosure may be formulated in nanoparticles or other delivery vehicles, e.g., to protect them from degradation when delivered to a subject. Illustrative nanoparticles are described in Panyam, J. & Labhasetwar, V. (2003) *Adv. Drug Deliv. Rev.* 55, 329-347 and Peer, D. et al. (2007) *Nature Nanotech.* 2, 751-760. In certain embodiments, an RNA, e.g., mRNA, of the disclosure is encapsulated within a nanoparticle. In particular embodiments, a nanoparticle is a particle having at least one dimension (e.g., a diameter) less than or equal to 1000 nM, less than or equal to 500 nM or less than or equal to 100 nM. In particular embodiments, a nanoparticle includes a lipid. Lipid nanoparticles include, but are not limited to, liposomes and micelles. Any of a number of lipids may be present, including cationic and/or ionizable lipids, anionic lipids, neutral lipids, amphipathic lipids, PEGylated lipids, and/or structural lipids. Such lipids can be used alone or in combination. In particular embodiments, a lipid nanoparticle comprises one or more RNAs, e.g., mRNAs, described herein, e.g., a mmRNA encoding a polypeptide of interest and comprising at least microRNA one binding site for a miR expressed in immune cells.

In some embodiments, the lipid nanoparticle formulations of the mRNAs, described herein may include one or more (e.g., 1, 2, 3, 4, 5, 6, 7, or 8) cationic and/or ionizable lipids. Such cationic lipids include, but are not limited to, 3-(didodecylamino)-N1,N1,4-tridodecyl-1-piperazineethanamine (KL10), N1-[2-(didodecylamino)ethyl]-N1, N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 2-({8-[(3β)-cholest-5-en-3-yloxy]octyl} oxy)-N,N-dimethyl-3-[(9Z,12Z)-octadeca-9,12-dien-1-yloxy]propan-1-amine (Octyl-CLinDMA), (2R)-2-({8-[(3B)-cholest-5-en-3-yloxy]octyl} oxy)-N,N-dimethyl-3-[(9Z,12Z)-octadeca-9,12-dien-1-yloxy] propan-1-amine (Octyl-CLinDMA (2R)), (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).N,N-dioleyl-N,N-dimethylammonium chloride ("DODAC"): N-(2,3-dioleyloxy) propyl-N,N—N-triethylammonium chloride ("DOTMA"); N,N-distearyl-N, N-dimethylammonium bromide ("DDAB"): N-(2,3-dioleoyloxy) propyl-N,N,N-trimethylammonium chloride ("DOTAP"): 1,2-Dioleyloxy-3-trimethylaminopropane chloride salt ("DOTAP.Cl"); 3-β-(N—(N',N'-dimethylaminoethane)-carbamoyl) cholesterol ("DC-Chol"), N-(1-(2,3-dioleyloxy) propyl)-N-2-(sperminecarboxamido)ethyl)-N, N-dimethyl-ammonium trifluoracetate ("DOSPA"), dioctadecylamidoglycyl carboxyspermine ("DOGS"), 1,2-dioleoyl-3-dimethylammonium propane ("DODAP"), N,N-dimethyl-2,3-dioleyloxy) propylamine ("DODMA"), and N-(1,2-dimyristyloxyprop-3-yl)-N, N-dimethyl-N-hydroxyethyl ammonium bromide ("DMRIE"). Additionally, a number of commercial preparations of cationic and/or ionizable lipids can be used, such as, e.g., LIPOFECTINR (including DOTMA and DOPE, available from GIBCO/BRL), and LIPOFECTAMINER; (including DOSPA and DOPE, available from GIBCO/BRL). KL10, KL22, and KL25 are described, for example, in U.S. Pat. No. 8,691,750, which is incorporated herein by reference in its entirety. In particular embodiments, the lipid is DLin-MC3-DMA or DLin-KC2-DMA.

Anionic lipids suitable for use in lipid nanoparticles of the disclosure include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

Neutral lipids suitable for use in lipid nanoparticles of the disclosure include, but are not limited to, diacylphosphatidylcholine, diacylphosphatidylethanolamine, ceramide, sphingomyelin, dihydrosphingomyelin, cephalin, and cerebrosides. Lipids having a variety of acyl chain groups of varying chain length and degree of saturation are available or may be isolated or synthesized by well-known techniques. Additionally, lipids having mixtures of saturated and unsaturated fatty acid chains can be used. In some embodiments, the neutral lipids used in the disclosure are DOPE, DSPC, DPPC, POPC, or any related phosphatidylcholine. In some embodiments, the neutral lipid may be composed of sphingomyelin, dihydrosphingomyeline, or phospholipids with other head groups, such as serine and inositol.

In some embodiments, amphipathic lipids are included in nanoparticles of the disclosure. Exemplary amphipathic lipids suitable for use in nanoparticles of the disclosure include, but are not limited to, sphingolipids, phospholipids, and aminolipids. In some embodiments, a phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholestery lhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoetha nolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. Other phosphorus-lacking compounds, such as sphingolipids, glycosphingolipid families, diacylglycerols, and β-acyloxyacids, may also be used. Additionally, such amphipathic lipids can be readily mixed with other lipids, such as triglycerides and sterols.

In some embodiments, the lipid component of a nanoparticle of the disclosure may include one or more PEGylated lipids. A PEGylated lipid (also known as a PEG lipid or a PEG-modified lipid) is a lipid modified with polyethylene glycol. The lipid component may include one or more PEGylated lipids. A PEGylated lipid may be selected from the non-limiting group consisting of PEG-modified phosphatidylethanolamines, PEG-modified phosphatidic acids, PEG-modified ceramides, PEG-modified dialkylamines, PEG-modified diacylglycerols, and PEG-modified dialkylglycerols. For example, a PEGylated lipid may be PEG-c-DOMG, PEG-DMG, PEG-DLPE, PEG-DMPE, PEG-DPPC, or a PEG-DSPE lipid.

A lipid nanoparticle of the disclosure may include one or more structural lipids. Exemplary, non-limiting structural lipids that may be present in the lipid nanoparticles of the disclosure include cholesterol, fecosterol, sitosterol, campesterol, stigmasterol, brassicasterol, ergosterol, tomatidine, tomatine, ursolic acid, or alpha-tocopherol).

In some embodiments, one or more mRNAs, of the disclosure may be formulated in a lipid nanoparticle having a diameter from about 1 nm to about 900 nm, e.g., about 1 nm to about 100 nm, about 1 nm to about 200 nm, about 1 nm to about 300 nm, about 1 nm to about 400 nm, about 1 nm to about 500 nm, about 1 nm to about 600 nm, about 1 nm to about 700 nm, about 1 nm to 800 nm, about 1 nm to about 900 nm. In some embodiments, the nanoparticle may have a diameter from about 10 nm to about 300 nm, about 20 nm to about 200 nm, about 30 nm to about 100 nm, or about 40 nm to about 80 nm. In some embodiments, the nanoparticle may have a diameter from about 30 nm to about 300 nm, about 40 nm to about 200 nm, about 50 nm to about 150 nm, about 70 to about 110 nm, or about 80 nm to about 120 nm. In one embodiment, an mRNA, may be formulated in a lipid nanoparticle having a diameter from about 10 to about 100 nm including ranges in between such as, but not limited to, about 10) to about 20 nm, about 10) to about 30 nm, about 10 to about 40) nm, about 10 to about 50 nm, about 10 to about 60 nm, about 10 to about 70 nm, about 10 to about 80 nm, about 10) to about 90 nm, about 20 to about 30 nm, about 20 to about 40) nm, about 20 to about 50 nm, about 20 to about 60 nm, about 20 to about 70 nm, about 20 to about 80 nm, about 20 to about 90 nm, about 20 to about 100 nm, about 30 to about 40) nm, about 30 to about 50 nm, about 30 to about 60 nm, about 30 to about 70 nm, about 30 to about 80 nm, about 30 to about 90 nm, about 30 to about 100 nm, about 40 to about 50) nm, about 40) to about 60 nm, about 40) to about 70 nm, about 40 to about 80 nm, about 40) to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm, and/or about 90 to about 100 nm. In one embodiment, an mRNA may be formulated in a lipid nanoparticle having a diameter from about 30 nm to about 300 nm, about 40 nm to about 200 nm, about 50 nm to about 150 nm, about 70 to about 110 nm, or about 80 nm to about 120 nm including ranges in between.

In some embodiments, a lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, or greater than 950 nm.

In some embodiments, the particle size of the lipid nanoparticle may be increased and/or decreased. The change in particle size may be able to help counter a biological reaction such as, but not limited to, inflammation, or may increase the biological effect of the mRNA, delivered to a patient or subject.

In certain embodiments, it is desirable to target a nanoparticle, e.g., a lipid nanoparticle, of the disclosure using a targeting moiety that is specific to a cell type and/or tissue type. In some embodiments, a nanoparticle may be targeted to a particular cell, tissue, and/or organ using a targeting moiety. In particular embodiments, a nanoparticle comprises one or more mRNA described herein and a targeting moiety. Exemplary non-limiting targeting moieties include ligands, cell surface receptors, glycoproteins, vitamins (e.g., riboflavin) and antibodies (e.g., full-length antibodies, antibody fragments (e.g., Fv fragments, single chain Fv (scFv) fragments, Fab' fragments, or F(ab')2 fragments), single domain antibodies, camelid antibodies and fragments thereof, human antibodies and fragments thereof, monoclonal antibodies, and multispecific antibodies (e.g., bispecific antibodies)). In some embodiments, the targeting moiety may be a polypeptide. The targeting moiety may include the entire polypeptide (e.g., peptide or protein) or fragments thereof. A targeting moiety is typically positioned on the outer surface of the nanoparticle in such a manner that the targeting moiety is available for interaction with the target, for example, a cell surface receptor. A variety of different targeting moieties and methods are known and available in the art, including those described, e.g., in Sapra et al., *Prog. Lipid Res.* 42 (5): 439-62, 2003 and Abra et al., *J. Liposome Res.* 12:1-3, 2002.

In some embodiments, a lipid nanoparticle (e.g., a liposome) may include a surface coating of hydrophilic polymer chains, such as polyethylene glycol (PEG) chains (see, e.g., Allen et al., *Biochimica et Biophysica Acta* 1237:99-108, 1995; DeFrees et al., *Journal of the American Chemistry Society* 118:6101-6104, 1996; Blume et al., *Biochimica et Biophysica Acta* 1149:180-184, 1993: Klibanov et al., *Journal of Liposome Research* 2:321-334, 1992: U.S. Pat. No. 5,013,556; Zalipsky, *Bioconjugate Chemistry* 4:296-299, 1993; Zalipsky, *FEBS Letters* 353:71-74, 1994; Zalipsky, in *Stealth Liposomes* Chapter 9 (Lasic and Martin, Eds) CRC Press, Boca Raton Fla., 1995. In one approach, a targeting moiety for targeting the lipid nanoparticle is linked to the polar head group of lipids forming the nanoparticle. In another approach, the targeting moiety is attached to the distal ends of the PEG chains forming the hydrophilic polymer coating (see, e.g., Klibanov et al., *Journal of Liposome Research* 2:321-334, 1992; Kirpotin et al., *FEBS Letters* 388:115-118, 1996).

Standard methods for coupling the targeting moiety or moieties may be used. For example, phosphatidylethanolamine, which can be activated for attachment of targeting moieties, or derivatized lipophilic compounds, such as lipid-derivatized bleomycin, can be used. Antibody-targeted liposomes can be constructed using, for instance, liposomes that incorporate protein A (see, e.g., Renneisen et al., *J. Bio. Chem.*, 265:16337-16342, 1990 and Leonetti et al., *Proc. Natl. Acad. Sci.* (USA), 87:2448-2451, 1990). Other examples of antibody conjugation are disclosed in U.S. Pat. No. 6,027,726. Examples of targeting moieties can also include other polypeptides that are specific to cellular components, including antigens associated with neoplasms or tumors. Polypeptides used as targeting moieties can be attached to the liposomes via covalent bonds (see, for example Heath, Covalent Attachment of Proteins to Liposomes, 149 *Methods in Enzymology* 111-119 (Academic Press, Inc. 1987)). Other targeting methods include the biotin-avidin system.

In some embodiments, a lipid nanoparticle of the disclosure includes a targeting moiety that targets the lipid nanoparticle to a cell including, but not limited to, hepatocytes, colon cells, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells (including primary tumor cells and metastatic tumor cells). In particular embodiments, the targeting moiety targets the lipid nanoparticle to a hepatocyte. In other embodiments, the targeting moiety targets the lipid nanoparticle to a colon cell. In some embodiments, the targeting moiety targets the lipid nanoparticle to a liver cancer cell (e.g., a hepatocellular carcinoma cell) or a colorectal cancer cell (e.g., a primary tumor or a metastasis).

Pharmaceutical Compositions

The present disclosure includes pharmaceutical compositions comprising an mRNA or a nanoparticle (e.g., a lipid nanoparticle) described herein, in combination with one or more pharmaceutically acceptable excipient, carrier or diluent. In particular embodiments, the mRNA, is present in a nanoparticle, e.g., a lipid nanoparticle. In particular embodiments, the mRNA or nanoparticle is present in a pharmaceutical composition. In various embodiments, the mRNA, present in the pharmaceutical composition is encapsulated in a nanoparticle, e.g., a lipid nanoparticle.

Pharmaceutical compositions may optionally include one or more additional active substances, for example, therapeutically and/or prophylactically active substances. Pharmaceutical compositions of the present disclosure may be sterile and/or pyrogen-free. General considerations in the formulation and/or manufacture of pharmaceutical agents may be found, for example, in *Remington: The Science and Practice of Pharmacy* $21^{st}$ ed., Lippincott Williams & Wilkins, 2005 (incorporated herein by reference in its entirety). In particular embodiments, a pharmaceutical composition comprises an mRNA and a lipid nanoparticle, or complexes thereof.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may include between 0.1% and 100%, e.g., between 0.5% and 70%, between 1% and 30%, between 5% and 80%, or at least 80% (w/w) active ingredient. In some embodiments, the active agent is an mRNA encoding a protein of interest and at least one microRNA binding site for a miR expressed in immune cells, such as a miR-142-3p binding site.

The mRNAs, of the disclosure can be formulated using one or more excipients to: (1) increase stability; (2) increase cell transfection; (3) permit the sustained or delayed release (e.g., from a depot formulation of the mRNA); (4) alter the biodistribution (e.g., target the mRNA to specific tissues or cell types); (5) increase the translation of a polypeptide encoded by the mmRNA in vivo; and/or (6) alter the release profile of a polypeptide encoded by the mRNA in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, lipidoids, liposomes, lipid nanoparticles (e.g., liposomes and micelles), polymers, lipoplexes, core-shell nanoparticles, peptides, proteins, carbohydrates, cells transfected with mRNAs (e.g., for transplantation into a subject), hyaluronidase, nanoparticle mimics and combinations thereof. Accordingly, the formulations of the disclosure can include one or more excipients, each in an amount that together increases the stability of the mRNA, increases cell transfection by the mRNA, increases the expression of a polypeptide encoded by the mRNA, and/or alters the release profile of a mRNA-encoded polypeptide. Further, the mRNAs of the present disclosure may be formulated using self-assembled nucleic acid nanoparticles.

Various excipients for formulating pharmaceutical compositions and techniques for preparing the composition are known in the art (see Remington: *The Science and Practice of Pharmacy*, 21st Edition, A. R. Gennaro, Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition. Excipients may include, for example: antiadherents, antioxidants, binders, coatings, compression aids, disintegrants, dyes (colors), emollients, emulsifiers, fillers (diluents), film formers or coatings, glidants (flow enhancers), lubricants, preservatives, printing inks, sorbents, suspending or dispersing agents, sweeteners, and waters of hydration. Exemplary excipients include, but are not limited to: buty lated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

In some embodiments, the formulations described herein may include at least one pharmaceutically acceptable salt. Examples of pharmaceutically acceptable salts that may be included in a formulation of the disclosure include, but are not limited to, acid addition salts, alkali or alkaline earth metal salts, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In some embodiments, the formulations described herein may contain at least one type of polynucleotide. As a non-limiting example, the formulations may contain 1, 2, 3, 4, 5 or more than 5 mRNAs described herein.

Liquid dosage forms for e.g., parenteral administration include, but are not limited to, pharmaceutically acceptable emulsions, microemulsions, nanoemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and/or suspending agents. In certain embodiments for parenteral administration, compositions are mixed with solubilizing agents such as CREMAPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In some embodiments, pharmaceutical compositions including at least one mRNA described herein are administered to mammals (e.g., humans). Although the descriptions of pharmaceutical compositions provided herein are principally directed to pharmaceutical compositions that are suitable for administration to humans, it will be understood by the skilled artisan that such compositions are generally suitable for administration to any other animal, e.g., to a non-human mammal. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates: mammals, including commercially relevant mammals such as cattle, pigs, horses, sheep, cats, dogs, mice, and/or rats; and/or birds, including commercially relevant birds such as poultry, chickens, ducks, geese, and/or turkeys. In particular embodiments, a subject is provided with two or more mRNAs described herein, e.g., a first mRNA encoding a first polypeptide of interest and comprising at least one microRNA binding site for a miR expressed in immune cells and a second mRNA encoding a second polypeptide of interest and comprising at least one microRNA binding site for a miR expressed in immune cells. In particular embodiments, the first and second mmRNAs are provided to the subject at the same time or at different times, e.g., sequentially. In particular embodiments, the first and second mRNAs are provided to the subject in the same pharmaceutical composition or formulation, e.g., to facilitate uptake of both mRNAs by the same cells.

Inhibition of Immune Cell Activation and Cytokine Production

The methods of the disclosure allow for reducing or inhibiting unwanted immune cell activation and/or unwanted cytokine production in a subject being treated with an mRNA-based therapeutic, such as unwanted immune cell activation and/or cytokine production that is stimulated by a polypeptide of interest (e.g., therapeutic agent) encoded by the mRNA-based therapeutic, by inclusion of at least one miR-126 (e.g., miR-126-3p) and/or miR-142 (e.g., miR-142-3p) binding site in the mRNA construct. In one embodiment, the immune cell activation is lymphocyte activation. In one embodiment, the immune cell activation is B cell activation. In another embodiment, the immune cell activation is T cell activation. In yet other embodiments, the immune cell activation is macrophage activation, dendritic cell activation, NK cell activation, basophil activation or eosinophil activation. In one embodiment, reduction or inhibition of unwanted immune cell activation is determined compared to control administration of an mmRNA, lacking the at least one miR-126 or miR-142 microRNA binding site. In various embodiments, the immune cell activation is decreased by at least 5%, by at least 10%, by at least 15%, by at least 20%, by at least 25%, by at least 30%, by at least 35%, by at least 40%, by at least 45%, by at least 50%, by at least about 60%, by at least about 70%, by at least about 80%, by about 5%-50%, by about 10%-50%, by about 15%-50%, by about 20%-50%, by about 25%-50%, by about 10%-80%, by about 10%-70%, by about 10%-60%, by about 20%-80%, by about 20%-70%, by about 20%-60%, by about 20%-40% or by about 25%-75%.

The level of immune cell activation can be evaluated by essentially any method established in the art for assessing immune cell activation, such as the frequency of an activated immune cell population, typically assessed by detection of cells expressing cell-surface activation markers, or levels of production of one or more cytokines indicative of immune cell activation. In one embodiment, the immune cell activation is B cell activation, wherein the level of B cell activation is determined by measuring the frequency of activated B cells, such as the frequency of activated B cells among the splenic B cell population. B cell surface markers indicative of B cell activation are well known in the art (see e.g., Maddalay, R. et al. (2010) *FEBS Letters* 584:4883-4894). In one embodiment, B cell activation is determined by frequency of $CD19^+CD86^+CD69'B$ cells. In another embodiment, the immune cell activation is B cell activation, wherein the level of B cell activation is determined by cytokine secretion, such as by secretion of interleukin-6 (IL-6), tumor necrosis factor α (TNF-α) or interferon-γ (IFN-γ), e.g., in the serum of treated subjects. In one embodiment, B cell activation is determined by secretion of IL-6, e.g., in the serum of treated subjects. In other embodiments, the unwanted cytokine production that is reduced or inhibited is production of interleukin-6 (IL-6), tumor necrosis factor α (TNF-α) or interferon-γ (IFN-γ), e.g., in the serum of treated subjects. In another embodiment, the unwanted cytokine production that is reduced or inhibited is production of interleukin-6 (IL-6).

In one embodiment, the immune cell activation is plasmacytoid dendritic cell (pDC) activation, wherein the level of pDC activation is determined by measuring the frequency of activated pDC, such as the frequency of activated pDCs among the splenic pDC population. pDC surface markers indicative of activation are well known in the art (see e.g., Dzionek. A., et al., (2002) *Hum Immunol*. Vol. 63 (12): 1133-48). In one embodiment, pDC activation is determined by frequency of $CD11c^+CD70^+CD86^+$ cells.

In one embodiment, unwanted immune cell activation and/or unwanted cytokine production is decreased without a corresponding decrease in expression of a polypeptide of interest encoded by the mmRNA. Thus, the methods of the disclosure allow for inhibiting or reducing immune cell activation (e.g., B cell activation, cytokine production) in a subject treated with an mRNA encoding a polypeptide of interest that is a therapeutic agent without significantly affecting the level of expression of the therapeutic agent in the subject.

A standard metric that can be used in the methods of the disclosure is the measure of the ratio of the level or amount of encoded polypeptide (protein) produced in a cell, tissue or organism to the level or amount of one or more (or a panel) of cytokines whose expression is triggered in the cell, tissue or organism as a result of administration or contact with the chemically modified mRNA. Such ratios are referred to herein as the Protein: Cytokine Ratio or "PC" Ratio. The higher the PC ratio, the more efficacious the chemically modified mRNA (polynucleotide encoding the protein measured). Preferred PC Ratios, by cytokine, of the present disclosure may be greater than 1, greater than 10, greater than 100, greater than 1000, greater than 10.000 or more. Modified mRNAs having higher PC Ratios than a modified mRNA of a different or unmodified construct are preferred.

The PC ratio may be further qualified by the percent modification present in the mRNA. For example, normalized to a 100% modified mRNA, the protein production as a function of cytokine (or risk) or cytokine profile can be determined.

In one embodiment, the present disclosure provides a method for determining, across chemistries, cytokines or percent modification, the relative efficacy of any particular modified mRNA comprising at least one miR-126 and/or miR-142 binding site by comparing the PC Ratio of the modified mRNA including the miR-126 and/or miR-142 binding site(s) to the PC ratio of the same construct without the miR-126 and/or miR-142 binding site(s).

In one embodiment, the level of expression of a polypeptide of interest encoded by the mmRNA in the serum of a mammal (e.g., human) can be at least 50 pg/ml at least two hours after administration. In another embodiment, the level of expression of a polypeptide of interest encoded by the mmRNA in the serum of a mammal (e.g., human) can remain above 50 pg/ml for at least 72 hours after administration. In another embodiment, the level of expression of a polypeptide of interest encoded by the mmRNA in the serum of a mammal (e.g., human) can remain above 60 µg/ml for at least 72 hours after administration.

Inhibition of B1a Cells/Inhibition of Accelerated Blood Clearance

The spleen has been previously implicated in ABC, although the precise mechanism(s) responsible for ABC have not previously been understood. The spleen is composed of red pulp (red blood cell-rich), white pulp (lymphocyte-rich), and the marginal zone (located between the red and white pulp and outside the marginal sinus). Antigens entering the spleen are retained in the marginal zone, where blood-flow is reduced to allow interaction between antigens and immune effector cells (e.g., B cells) (Harms et al. *Infect. Immuno*. Vol. 64:4220-4225, 1996). The spleen's role in accelerated blood clearance is thought to be significant. Biodistribution data demonstrates that lipid-comprising compounds or compositions (e.g., LNPs) are taken up by the spleen (data not shown). Histological evaluation shows uptake of LNPs in the marginal zone rapidly after dosing (e.g., IV dosing). Within the spleen, LNPs can interact with splenic B cells, contributing to various elements of the immune response to the LNPs. For example, certain components of the LNPs (e.g., PEG components) can interact with CD19+ B cells in the spleen, resulting in binding, internalization, membrane fusion, and/or activation of such cells, resulting in production of IgG and/or IgM molecules specific for components of the LNPs, leading to accelerated blood clearance, for example, on second or subsequent dosing with the LNPs.

Surprisingly, it has also been demonstrated herein that particular cells of the immune system, namely, pDCs, also contribute to the ABC phenomenon. It has been demonstrated herein that inclusion of miR binding sites (e.g., miR-126 binding sites) can lead to reduction of unwanted immune responses (e.g., ADA) against proteins encoded by LNP-encapsulated mRNAs, for example, modified mRNAs. It has now also been surprisingly demonstrated that inclusion of miR binding sites, in particular, miR-126 binding sites, can lead to reduction in further unwanted immune responses against LNPs encapsulating the mRNAs. miR-126 (e.g., miR-126-3p) is highly expressed in pDCs and is, in fact, upregulated during activation of pDCs. pDCs synergistically increase B cell activation in response to nucleic acids and other forms of activation via cytokine secretion and plasma cell activation. Moreover, "miR-126-3p low" pDCs (e.g., pDC in which miR-126 has been knocked down or knocked out) are activation impaired (e.g., unable to launch an effective immune response to nucleic acids, secrete IFN-α/β secretion, IL-6 secretion, etc., inability to migrate to spleen upon activation and the like). As demonstrated herein, inclusion of miR-126 binding sites in mRNAs results in low B cell activation and low serum IL-6 over several weeks of repeat dosing of LNP-encapsulated mRNAs. Protein expression is maintained over similar dosing schedules. Suprisingly, anti-PEG IgM responses are dramatically diminished over weeks of repeat dosing. Thus, an unexpected benefit of inclusion of miR-126 binding sites in mRNA, in particular, in LNP-encapsulated mRNA, is reduction of ABC.

In the spleen, for example, in the marginal zone of the spleen, certain if these key immune cells can interact either directly or indirectly, e.g., as a result of cytokine production (e.g., IL-6).

Without wishing to be bound by theory, this disclosure provides evidence that miRs expressed in immune cells present in the marginal zone participate in accelerated blood clearance. When an mRNA of the disclosure includes one or more miR binding sites that bind to one or more miRs expressed in immune cells, the miR of interest is downregulated (e.g., antagonized and/or degraded). The inclusion of at least one miR binding site that binds to at least one miR expressed in immune cells results in decreased production of IgM molecules capable of binding lipid components (e.g., PEG lipids), compared to mRNA without the at least one miR binding site. Given the known role of IgM molecules in accelerated blood clearance, the ability of a miR binding site that binds a miR expressed in immune cells to inhibit or reduce production of IgM molecules, indicates an important role of miRs expressed in immune cells, specifically in the marginal zone of the spleen, in accelerated blood clearance.

The methods of the disclosure allow for reducing or inhibiting accelerated blood clearance in a subject repeatedly administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that accelerated blood clearance is reduced or inhibited in the subject upon repeat administration.

In other embodiments, accelerated blood clearance is reduced or inhibited in a subject administered a messenger RNA (mRNA) encoding a polypeptide of interest encapsulated in an lipid nanoparticle (LNP), by administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases; and administering to the subject intravenously a second dose of the chemically modified mRNA encapsulated in an LNP, such that accelerated blood clearance is reduced or inhibited in the subject.

In some embodiments, accelerated blood clearance is reduced or inhibited in a subject administered multiple doses of a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that accelerated blood clearance is reduced or inhibited in the subject upon administration of one or more subsequent doses.

In other embodiments, accelerated blood clearance is reduced or inhibited in a subject administered a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that accelerated blood clearance is reduced or inhibited in the subject upon administration of a subsequent dose of the mRNA.

In further embodiments, accelerated blood clearance is reduced or inhibited in a subject repeatedly administered a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, wherein the chemically modified mRNA comprises one or more modified nucleobases, and wherein the LNP does not activate B cells and/or does not induce production of IgM molecules capable of binding to the LNP, such that accelerated blood clearance is reduced or inhibited in the subject upon repeat administration.

In further embodiments, accelerated blood clearance is reduced or inhibited in a subject administered a messenger RNA (mRNA) encoding a polypeptide of interest encapsulated in an lipid nanoparticle (LNP), by administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases; and administering to the subject intravenously a second dose of the chemically modified mRNA encapsulated in an LNP, wherein the LNP does not activate B cells and/or does not induce production of IgM molecules capable of binding to the LNP, such that accelerated blood clearance is reduced or inhibited in the subject.

In other embodiments, accelerated blood clearance is reduced or inhibited in a subject administered multiple doses of a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, wherein the chemically modified mRNA comprises one or more modified nucleobases, and wherein the LNP does not activate B cells and/or does not induce production of IgM molecules capable of binding to the LNP, such that accelerated blood clearance is reduced or inhibited in the subject upon administration of one or more subsequent doses.

In some embodiments, accelerated blood clearance is reduced or inhibited in a subject administered a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, wherein the chemically modified mRNA comprises one or more modified nucleobases, and wherein the LNP does not activate B cells and/or does not induce production of IgM molecules capable of binding to the LNP, such that accelerated blood clearance is reduced or inhibited in the subject upon administration of a subsequent dose of the mRNA.

In some embodiments, the disclosure provides a method of reducing or inhibiting production of IgM molecules that recognize polyethylene glycol (PEG) in a subject repeatedly administered a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that production of IgM molecules that recognize PEG are reduced or inhibited in the subject upon repeat administration.

In some embodiments, production of IgM molecules that recognize polyethylene glycol (PEG) is reduced or inhibited in a subject administered a messenger RNA (mRNA) encoding a polypeptide of interest encapsulated in an lipid nanoparticle (LNP), by administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases; and administering to the subject intravenously a second dose of the chemically modified mRNA encapsulated in an LNP, such that production of IgM molecules that recognize PEG are reduced or inhibited in the subject.

In some embodiments, production of IgM molecules that recognize polyethylene glycol (PEG) is reduced or inhibited in a subject administered multiple doses of a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that production of IgM molecules that recognize PEG are reduced or inhibited in the subject upon administration of one or more subsequent doses.

In other embodiments, production of IgM molecules that recognize polyethylene glycol (PEG) is reduced or inhibited in a subject administered a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that production of IgM molecules that recognize PEG are reduced or inhibited in the subject upon administration of a subsequent dose of the mRNA.

In further embodiments, the disclosure provides a method of reducing or inhibiting activation of B1a cells in a subject repeatedly administered a messenger RNA (mRNA) encoding a polypeptide of interest encapsulated in an lipid nanoparticle (LNP), by comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of B1a cells is reduced or inhibited in the subject upon repeat administration.

In some embodiments, activation of B1a cells is reduced or inhibited in a subject administered a messenger RNA (mRNA) encoding a polypeptide of interest encapsulated in an lipid nanoparticle (LNP), by administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases; and administering to the subject intravenously a second dose of the chemically modified mRNA encapsulated in an LNP, such that activation of B1a cells is reduced or inhibited in the subject.

In other embodiments, activation of B1a cells is reduced or inhibited in a subject administered multiple doses of a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of B1a cells is reduced or inhibited in the subject upon administration of one or more subsequent doses.

In some embodiments, activation of B1a cells is reduced or inhibited in a subject administered a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of B1a cells is reduced or inhibited in the subject upon administration of a subsequent dose of the mRNA.

In further embodiments, the disclosure provides a method of reducing or inhibiting activation of plasmacytoid dendrtic cells in a subject repeatedly administered a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of plasmacytoid dendritic cells is reduced or inhibited in the subject upon repeat administration.

In some embodiments, activation of plasmacytoid dendritic cells is reduced or inhibited in a subject administered a messenger RNA (mRNA) encoding a polypeptide of interest encapsulated in an lipid nanoparticle (LNP), by administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases; and administering to the subject intravenously a second dose of the chemically modified mRNA encapsulated in an LNP, such that activation of plasmacytoid dendritic cells is reduced or inhibited in the subject.

In some embodiments, activation of plasmacytoid dendritic cells is reduced or inhibited in a subject administered multiple doses of a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of plasmacytoid dendritic cells is reduced or inhibited in the subject upon administration of one or more subsequent doses.

In some embodiments, activation of plasmacytoid dendritic cells is reduced or inhibited in a subject administered a messenger RNA (mRNA) encoding a polypeptide of interest encapsulated in an lipid nanoparticle (LNP), by administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of plasmacytoid dendritic cells is reduced or inhibited in the subject upon administration of a subsequent dose of the mRNA.

In further embodiments, the mRNA encoding a polypeptide of interest encapsulated in a lipid nanoparticle (LNP) does not activate B cells and/or does not induce production of IgM molecules capable of binding to the LNP. In some embodiments the mRNA encoding a polypeptide of interest encapsulated in a lipid nanoparticle (LNP) does not activate B cells. In other embodiments, the mRNA encoding a polypeptide of interest encapsulated in a lipid nanoparticle (LNP) does not induce production of IgM molecules capable of binding to the LNP.

In some embodiments, reduction or inhibition of accelerated blood clearance is determined compared to control administration of a chemically modified mRNA lacking the at least one microRNA binding site encapsulated in a lipid nanoparticle (LNP). In other embodiments, accelerated blood clearance is reduced or inhibited without a corresponding reduction or inhibition in expression of the polypeptide of interest encoded by the chemically modified mRNA.

In further embodiments, wherein the interval between two consecutive doses is less than 2 weeks. In some embodiments, the interval between two consecutive doses is less than 1 week.

In some embodiments, the IgM molecules recognize polyethylene glycol (PEG).

Methods of the Disclosure

In one aspect, the disclosure pertains to a method of reducing or inhibiting an anti-drug antibody response in a subject, comprising administering to the subject a modified messenger RNA (mmRNA) encoding a polypeptide of interest, wherein the mmRNA comprises at least one microRNA binding site for a miR expressed in immune cells (e.g., miR-142-3p and/or miR-126-3p), and wherein the mmRNA comprises one or more modified nucleobases, such that an anti-drug antibody response to the polypeptide of interest is reduced or inhibited in the subject. As described above, in various embodiments, the mmRNA can comprise, for example, two or more, 1-4, one, two, three or four binding sites for one or more miRs expressed in immune cells. In certain embodiments, the mmRNA comprises at least two binding sites for at least two different miRs expressed in immune cells. For example, the mmRNA can comprise a first binding site for miR-142-3p and a second binding site for a different miR expressed in an immune cell, such as miR-155, miR-146 (miR-146-3p and/or miR-146-5p) or miR-126. Alternatively, the mmRNA can comprise a first binding site for miR-126 (e.g., miR-126-3p) and a second binding site for a different miR expressed in an immune cell, such as miR-142 (mir-142-3p and/or miR-142-5p), miR-155 or miR-146 (miR-146-3p and/or miR-146-5p). In one embodiment, the mmRNA comprises a first binding site for miR-142-3p and a second binding site for miR-126.

In related embodiments, the subject is provided with or administered a nanoparticle (e.g., a lipid nanoparticle) comprising the mmRNA. In further related embodiments, the subject is provided with or administered a pharmaceutical composition of the disclosure to the subject. In particular embodiments, the pharmaceutical composition comprises an mmRNA encoding a polypeptide of interest and comprising at least one miR binding site as described herein, or it comprises a nanoparticle comprising the mmRNA. In particular embodiments, the mmRNA is present in a nanoparticle, e.g., a lipid nanoparticle. In particular embodiments, the mmRNA or nanoparticle is present in a pharmaceutical composition.

In one embodiment, the mmRNA is administered intravenously encapsulated in a lipid nanoparticle. In one embodiment, the mmRNA is administered by once weekly infusion (e.g., intravenous infusion, such as via a pump). In one embodiment, the mmRNA is administered by once weekly infusion for at least 4 weeks.

In another embodiment, the disclosure provides a method of reducing or inhibiting an anti-drug antibody response following repeated administration of a polypeptide of interest to a subject, comprising administering to the subject intravenously a first dose of a modified mRNA (mmRNA) encoding a polypeptide of interest encapsulated in an LNP, wherein the mmRNA comprises at least one binding site for a miR expressed in immune cells (e.g., a miR-142-3p microRNA binding site and/or a miR-126 microRNA binding site), and wherein the mmRNA comprises one or more modified nucleobases; and administering to the subject intravenously a second dose of the mmRNA encapsulated in an LNP, such that an anti-drug antibody response to the polypeptide of interest is reduced or inhibited in the subject.

In another aspect, the disclosure provides a method of reducing or inhibiting an anti-drug antibody response following repeated administration of a polypeptide of interest to a subject, comprising
(i) administering to the subject intravenously a first dose of a modified mRNA (mmRNA) encoding a polypeptide of interest encapsulated in an LNP, wherein the mmRNA comprises at least one microRNA binding site for a miR expressed in immune cells (e.g., a miR-142-3p microRNA binding site and/or a miR-126 microRNA binding site), and wherein the mmRNA comprises one or more modified nucleobases;
(ii) detecting a level of anti-drug antibodies in a sample from the subject; and
(iii) administering to the subject intravenously a second dose of the mmRNA encapsulated in an LNP when the level of anti-drug antibodies in the sample is diminished, such that an anti-drug antibody response to the polypeptide of interest is reduced or inhibited in the subject.

Given the ability of the methods of the disclosure to reduce or inhibit expression of the protein of interest encoded by the mmRNA in the spleen of the subject to which the mmRNA is administered, the disclosure further provides methods for reducing toxicity of mmRNA-based therapeutics. Accordingly, in another aspect, the disclosure provides a method of reducing or inhibiting drug-related toxicity in a subject, comprising administering to the subject a modified messenger RNA (mmRNA) encoding a polypeptide of interest, wherein the mmRNA comprises at least one binding site for a miR expressed in immune cells (e.g., a miR-142-3p microRNA binding site and/or a miR-126 microRNA binding site), and wherein the mmRNA comprises one or more modified nucleobases, such that drug-related toxicity to the polypeptide of interest is reduced or inhibited in the subject. In one embodiment, the drug-related toxicity to the polypeptide of interest is decreased blood cell counts (cytopenia) in the subject. In one embodiment, the drug-related toxicity to the polypeptide of interest is autoimmunity in the subject. In one embodiment, the drug-related toxicity to the polypeptide of interest is complement-mediated effects in the subject. In one embodiment, the drug-related toxicity to the polypeptide of interest is decreased hematopoiesis in the subject. In other embodiments, the drug-related toxicity can be, for example, renal toxicity or liver toxicity.

In another aspect, the disclosure pertains to a method of reducing or inhibiting unwanted immune cell activation in a subject administered an RNA, e.g., a messenger RNA (mRNA), comprising administering to the subject an RNA, e.g., a mRNA (e.g., a chemically modified mRNA or mmRNA), wherein the mRNA, e.g., chemically modified RNA or mmRNA, comprises at least one miR-126 and/or miR-142 microRNA binding site, and wherein the mRNA, e.g., chemically modified mRNA or mmRNA, comprises one or more modified nucleobases, such that unwanted immune cell activation is reduced or inhibited in the subject. In another aspect, the disclosure pertains to a method of reducing or inhibiting unwanted cytokine production in a subject administered an RNA, e.g., a messenger RNA (mRNA), the method comprising administering to the subject an RNA, e.g., a mRNA (e.g., a chemically modified mRNA or mmRNA), wherein the mRNA, e.g., chemically modified mRNA or mmRNA, comprises at least one miR-126 and/or miR-142 microRNA binding site, and wherein the mRNA, e.g., chemically modified mmRNA comprises one or more modified nucleobases, such that unwanted cytokine production is reduced or inhibited in the subject.

As described above, in various embodiments, the chemically modified mRNA (referred to as mmRNA) can comprise, for example, two or more, 1-4, one, two, three or four binding sites for one or more miRs expressed in immune cells. In certain embodiments, the mmRNA, comprises at least two binding sites for at least two different miRs expressed in immune cells. For example, the mmRNA, can comprise a first binding site for miR-126 and a second binding site for a different miR expressed in an immune cell, such as miR-142 (miR-142-3p and/or miR-142-5p), miR-155 or miR-146 (miR-146-3p and/or miR-146-5p). Alternatively, the mmRNA, can comprise a first binding site for miR-142 (miR-142-3p and/or miR-142-5p) and a second binding site for a different miR expressed in an immune cell, such as miR-126, miR-155 or miR-146 (miR-146-3p and/or miR-146-5p). In one embodiment, the mmRNA comprises a first binding site for miR-142-3p and a second binding site for miR-126.

In certain embodiments, the mRNA encodes a polypeptide of interest (e.g., a therapeutic agent), wherein unwanted immune cell activation occurs in response to the polypeptide of interest.

In related embodiments, the subject is provided with or administered a nanoparticle (e.g., a lipid nanoparticle) comprising the mRNA, e.g., mmRNA. In further related embodiments, the subject is provided with or administered a pharmaceutical composition of the disclosure to the subject. In particular embodiments, the pharmaceutical composition comprises an mmRNA encoding a polypeptide of interest and comprising at least one miR binding site as described herein, or it comprises a nanoparticle comprising the mmRNA. In particular embodiments, the mmRNA is present in a nanoparticle, e.g., a lipid nanoparticle. In particular embodiments, the mmRNA or nanoparticle is present in a pharmaceutical composition.

In one embodiment, the mRNA, e.g., mmRNA is administered intravenously encapsulated in a lipid nanoparticle. In one embodiment, the mRNA, e.g., mmRNA is administered by once weekly infusion (e.g., intravenous infusion, such as via a pump). In one embodiment, the mRNA, e.g., mmRNA is administered by once weekly infusion for at least 4 weeks.

In another embodiment, the disclosure provides a method of reducing or inhibiting unwanted immune cell activation (e.g., lymphocyte activation, B cell activation) or unwanted cytokine production in a subject administered a messenger RNA (mRNA), the method comprising administering to the subject intravenously a first dose of a mRNA, e.g., chemically modified mRNA (mmRNA) encapsulated in an LNP, wherein the mRNA, e.g., mmRNA comprises at least one miR-126 and/or miR-142 microRNA binding site,
    and wherein the mRNA, eg., mmRNA, comprises one or more modified nucleobases; and administering to the subject intravenously a second dose of the mRNA, e.g., mmRNA, encapsulated in an LNP, such that unwanted immune cell activation or unwanted cytokine production is reduced or inhibited in the subject.

In certain embodiments, the mRNA encodes a polypeptide of interest (e.g., a therapeutic agent), wherein unwanted immune cell activation and/or unwanted cytokine production occurs in response to the polypeptide of interest.

In another aspect, the disclosure provides a method of reducing or inhibiting unwanted immune cell activation (e.g., lymphocyte activation, B cell activation) or unwanted cytokine production in a subject following repeated administration of a messenger RNA (mRNA) to the subject, the method comprising:
(i) administering to the subject intravenously a first dose of a mRNA, e.g., chemically modified mRNA (mmRNA) encapsulated in an LNP, wherein the mRNA, e.g., mmRNA comprises at least one miR-126 and/or miR-142 microRNA binding site, and wherein the mRNA, e.g., mmRNA comprises one or more modified nucleobases;
(ii) detecting a level of immune cell activation in a sample from the subject; and
(iii) administering to the subject intravenously a second dose of the mRNA, e.g., mmRNA encapsulated in an LNP when the level of immune cell activation in the sample is diminished, such that unwanted immune cell activation or unwanted cytokine production is reduced or inhibited in the subject.

In certain embodiments, the mRNA, e.g., mmRNA, encodes a polypeptide of interest (e.g., a therapeutic agent), wherein unwanted immune cell activation or unwanted cytokine production occurs in response to the polypeptide of interest.

ADA Assays

ADA assays (bioassays) can be used to assay for both neutralizing antibodies (NABs) and non-neutralizing, binding antibodies (BABs). NAB assays can include both cell based assays, for example, cell proliferation assays, biomarker assays, gene expression assays, gene reporter assays, antibody-dependent cell-mediated cytotoxicity (ADCC) assays, complement-dependent cytotoxicity (CDC) assays, and the like, as well as non-cell based assays, for example, competitive ligand-binding (CLBA) assays, surface plasmon resonance (SPR), enzyme-linked immunosorbent assay (ELISA), electro-chemiluminescence (ECL), e.g., electro-chemiluminescence immunoassay (ECLIA), dissociation-enhanced lanthanide fluorescent immunoassay (DELFIA®), Gyros® anti-drug antibody (ADA) immunoassay's, fluorescent-enzyme immunoassay (FEIA), ristocetin-induced platelet aggregation (RIPA), and the like.

In exemplary aspects, the therapeutic regimen can include conducting one or more ADA assays before or during a therapeutic regimen. In exemplary embodiments, the ADA assay is a NAB assay. In such instances, the bioassay should be related to product mechanism of action, otherwise the assay will not be informative as to the effect of NAB on clinical pharmacology. In preferred embodiments, cell-based NABs are featured in the therapeutic regimen of the disclosure. If neutralizing cell-based assays are not feasible/available competitive ligand binding assays or alternatives may be suitable. However, when these are used, it is preferably demonstrated that the assays reflect neutralizing capacity/potential in an appropriate manner.

In addition to directly measuring the ADA response, the level of immune cell activation also can be evaluated as a measure of a developing antibody response. The level of immune cell activation can be evaluated by essentially any method established in the art for assessing immune cell activation, such as the frequency of an activated immune cell population, typically assessed by detection of cells expressing cell-surface activation markers, or levels of production of one or more cytokines indicative of immune cell activation. In one embodiment, the immune cell activation is B cell activation, wherein the level of B cell activation is determined by measuring the frequency of activated B cells, such as the frequency of activated B cells among the splenic B cell population. B cell surface markers indicative of B cell activation are well known in the art (see e.g., Maddalay, R. et al. (2010)) *FEBS Letters* 584:4883-4894). In one embodiment, B cell activation is determined by frequency of $CD19^+CD86^+CD69^+B$ cells. In another embodiment, the immune cell activation is B cell activation, wherein the level of B cell activation is determined by cytokine secretion, such as by secretion of interleukin-6 (IL-6), tumor necrosis factor α (TNF-α) or interferon-γ (IFN-γ), e.g., in the serum of treated subjects. In one embodiment, B cell activation is determined by secretion of IL-6, e.g., in the serum of treated subjects. In other embodiments, the unwanted cytokine production that is reduced or inhibited is production of interleukin-6 (IL-6), tumor necrosis factor α (TNF-α) or interferon-γ (IFN-γ), e.g., in the serum of treated subjects. In another embodiment, the unwanted cytokine production that is reduced or inhibited is production of interleukin-6 (IL-6).

Administration of Pharmaceutical Compositions

A pharmaceutical composition including one or more RNAs, e.g., mRNAs, of the disclosure may be administered to a subject by any suitable route. In some embodiments, compositions of the disclosure are administered by one or more of a variety of routes, including parenteral (e.g., subcutaneous, intracutaneous, intravenous, intraperitoneal, intramuscular, intraarticular, intraarterial, intrasynovial, intrasternal, intrathecal, intralesional, or intracranial injection, as well as any suitable infusion technique), oral, trans- or intra-dermal, interdermal, rectal, intravaginal, topical (e.g., by powders, ointments, creams, gels, lotions, and/or drops), mucosal, nasal, buccal, enteral, vitreal, intratumoral, sublingual, intranasal: by intratracheal instillation, bronchial instillation, and/or inhalation: as an oral spray and/or powder, nasal spray, and/or aerosol, and/or through a portal vein catheter. In some embodiments, a composition may be administered intravenously, intramuscularly, intradermally, intra-arterially, intratumorally, subcutaneously, or by inhalation. However, the present disclosure encompasses the delivery of compositions of the disclosure by any appropriate route taking into consideration likely advances in the sciences of drug delivery. In general, the most appropriate route of administration will depend upon a variety of factors including the nature of the pharmaceutical composition including one or more mRNAs (e.g., its stability in various bodily environments such as the bloodstream and gastrointestinal tract), and the condition of the patient (e.g., whether the patient is able to tolerate particular routes of administration). In one embodiment, the composition is administered parenterally. In another embodiment, the composition is administered intravenously. In another embodiment, the composition is administered intratumorally.

In certain embodiments, compositions of the disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.1 mg/kg to about 10 mg/kg, from about 1 mg/kg to about 5 mg/kg, from about 2 mg/kg to about 5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, or from about 0.1 mg/kg to about 1 mg/kg in a given dose, where a dose of 1 mg/kg provides 1 mg of mRNA or nanoparticle per 1 kg of subject body weight. In particular embodiments, a dose of about 0.005 mg/kg to about 5 mg/kg of mRNA or nanoparticle of the disclosure may be administrated. In particular embodiments, a dose of about 0.002 mg/kg to about 2 mg/kg of mRNA or nanoparticle of the disclosure may be administrated. In particular embodiments, a dose of about 0.02 mg/kg to about 0.2 mg/kg of mRNA or nanoparticle of the disclosure may be administrated.

A dose may be administered one or more times per day, in the same or a different amount, to obtain a desired level of mRNA, expression and/or effect (e.g., a therapeutic effect). The desired dosage may be delivered, for example, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In some embodiments, a single dose may be administered, for example, prior to or after a surgical procedure or in the instance of an acute disease, disorder, or condition.

The specific therapeutically effective, prophylactically effective, or otherwise appropriate dose level for any particular patient will depend upon a variety of factors including the severity and identify of a disorder being treated, if any: the one or more mRNAs employed: the specific composition employed: the age, body weight, general health, sex, and diet of the patient: the time of administration, route of administration, and rate of excretion of the specific pharmaceutical composition employed: the duration of the treatment: drugs used in combination or coincidental with the specific pharmaceutical composition employed; and like factors well known in the medical arts.

In some embodiments, a pharmaceutical composition of the disclosure may be administered in combination with another agent, for example, another therapeutic agent, a prophylactic agent, and/or a diagnostic agent. By "in combination with," it is not intended to imply that the agents must be administered at the same time and/or formulated for delivery together, although these methods of delivery are within the scope of the present disclosure. For example, one or more compositions including one or more different mRNAs may be administered in combination. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of compositions of the disclosure, or imaging, diagnostic, or prophylactic compositions thereof in combination with agents that improve their bioavailability, reduce and/or modify their metabolism, inhibit their excretion, and/or modify their distribution within the body.

Exemplary therapeutic agents that may be administered in combination with the compositions of the disclosure include, but are not limited to, cytotoxic, chemotherapeutic, and other therapeutic agents. Cytotoxic agents may include, for example, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, rachelmycin, and analogs thereof. Radioactive ions may also be used as therapeutic agents and may include, for example, radioactive iodine, strontium, phosphorous, palladium, cesium, iridium, cobalt, yttrium, samarium, and praseodymium. Other therapeutic agents may include, for example, antimetabolites (e.g., methotrexate, 6-mercaptopurine, 6-thioguanine, cytarabine, and 5-fluorouracil, and decarbazine), alkylating agents (e.g., mechlorethamine, thiotepa, chlorambucil, rachelmycin, melphalan, carmustine, lomustine, cyclophosphamide, busulfan, dibromomannitol, streptozotocin, mitomycin C, and cis-dichlorodiamine platinum (II) (DDP), and cisplatin), anthracyclines (e.g., daunorubicin and doxorubicin), antibiotics (e.g., dactinomycin, bleomycin, mithramycin, and anthramycin), and antimitotic agents (e.g., vincristine, vinblastine, taxol, and maytansinoids).

The particular combination of therapies (therapeutics or procedures) to employ in a combination regimen will take into account compatibility of the desired therapeutics and/or procedures and the desired therapeutic effect to be achieved.

It will also be appreciated that the therapies employed may achieve a desired effect for the same disorder (for example, a composition useful for treating cancer may be administered concurrently with a chemotherapeutic agent), or they may achieve different effects (e.g., control of any adverse effects).

Other Embodiments

This disclosure relates to the following embodiments:

In some aspects, the disclosure relates to methods of reducing or inhibiting an anti-drug antibody response in a subject, comprising administering to the subject a modified messenger RNA (mmRNA) encoding a polypeptide of interest, wherein the mmRNA comprises at least one miR-142-3p microRNA binding site, and wherein the mmRNA comprises one or more modified nucleobases, such that an anti-drug antibody response to the polypeptide of interest is reduced or inhibited in the subject.

In other aspects, the disclosure relates to methods of reducing or inhibiting an anti-drug antibody response following repeated administration of a polypeptide of interest to a subject, comprising administering to the subject intravenously a first dose of a modified mRNA (mmRNA) encoding a polypeptide of interest encapsulated in an LNP, wherein the mmRNA comprises at least one miR-142-3p microRNA binding site, and wherein the mmRNA comprises one or more modified nucleobases; and administering to the subject intravenously a second dose of the mmRNA encapsulated in an LNP, such that an anti-drug antibody response to the polypeptide of interest is reduced or inhibited in the subject.

In yet further aspects, the disclosure relates to methods of reducing or inhibiting an anti-drug antibody response following repeated administration of a polypeptide of interest to a subject, comprising
  (i) administering to the subject intravenously a first dose of a modified mRNA (mmRNA) encoding a polypeptide of interest encapsulated in an LNP, wherein the mmRNA comprises at least one miR-142-3p microRNA binding site,
  and wherein the mmRNA comprises one or more modified nucleobases;
  (ii) detecting a level of anti-drug antibodies in a sample from the subject; and
  (iii) administering to the subject intravenously a second dose of the mmRNA encapsulated in an LNP when the level of anti-drug antibodies in the sample is diminished, such that an anti-drug antibody response to the polypeptide of interest is reduced or inhibited in the subject.

In some aspects, the disclosure relates to methods of reducing or inhibiting drug-related toxicity in a subject, comprising administering to the subject a modified messenger RNA (mmRNA) encoding a polypeptide of interest, wherein the mmRNA comprises at least one miR-142-3p microRNA binding site, and wherein the mmRNA comprises one or more modified nucleobases, such that drug-related toxicity to the polypeptide of interest is reduced or inhibited in the subject.

In other aspects, the disclosure relates to methods of reducing or inhibiting drug-related toxicity in a subject, comprising administering to the subject a modified messenger RNA (mmRNA) encoding a polypeptide of interest, wherein the mmRNA comprises at least one miR-126 microRNA binding site, and wherein the mmRNA comprises one or more modified nucleobases, such that drug-related toxicity to the polypeptide of interest is reduced or inhibited in the subject.

In some embodiments of the foregoing aspects, drug-related toxicity to the polypeptide of interest is decreased blood cell counts (cytopenia) in the subject. In other embodiments of the foregoing aspects, drug-related toxicity to the polypeptide of interest is autoimmunity in the subject. In further embodiments of the foregoing aspects, drug-related toxicity to the polypeptide of interest is complement mediated effects in the subject. In some embodiments of the foregoing aspects, drug-related toxicity to the polypeptide of interest is decreased hematopoiesis in the subject. In other embodiments of the foregoing aspects, drug-related toxicity is renal toxicity or liver toxicity.

In some aspects, the disclosure relates to methods of reducing or inhibiting an anti-drug antibody response in a subject, comprising administering to the subject a modified messenger RNA (mmRNA) encoding a polypeptide of interest, wherein the mmRNA comprises at least one miR-126 microRNA binding site, and wherein the mmRNA comprises one or more modified nucleobases, such that an anti-drug antibody response to the polypeptide of interest is reduced or inhibited in the subject.

In other aspects, the disclosure relates to methods of reducing or inhibiting an anti-drug antibody response following repeated administration of a polypeptide of interest to a subject, comprising administering to the subject intravenously a first dose of a modified mRNA (mmRNA) encoding a polypeptide of interest encapsulated in an LNP, wherein the mmRNA comprises at least one miR-126 microRNA binding site, and wherein the mmRNA comprises one or more modified nucleobases; and administering to the subject intravenously a second dose of the mmRNA encapsulated in an LNP, such that an anti-drug antibody response to the polypeptide of interest is reduced or inhibited in the subject.

In yet further aspects, the disclosure relates to methods of reducing or inhibiting an anti-drug antibody response following repeated administration of a polypeptide of interest to a subject, comprising
  (i) administering to the subject intravenously a first dose of a modified mRNA (mmRNA) encoding a polypeptide of interest encapsulated in an LNP, wherein the mmRNA comprises at least one miR-126 microRNA binding site, and wherein the mmRNA comprises one or more modified nucleobases;
  (ii) detecting a level of anti-drug antibodies in a sample from the subject; and
  (iii) administering to the subject intravenously a second dose of the mmRNA encapsulated in an LNP when the level of anti-drug antibodies in the sample is diminished, such that an anti-drug antibody response to the polypeptide of interest is reduced or inhibited in the subject.

In some aspects, the disclosure relates to methods of reducing or inhibiting unwanted immune cell activation in a subject administered a messenger RNA (mRNA) encoding a polypeptide of interest, the method comprising administering to the subject a chemically modified mRNA encoding the polypeptide of interest, wherein the chemically modified mRNA comprises at least one microRNA binding site for a microRNA expressed in immune cells, and wherein the chemically modified mRNA comprises one or more modified nucleobases, such that unwanted immune cell activation is reduced or inhibited in the subject.

In some embodiments of the foregoing aspects, reduction or inhibition of unwanted immune cell activation is determined compared to control administration of a chemically modified mRNA lacking the at least one microRNA binding site. In other embodiments of the foregoing aspects, the reduction or inhibition of unwanted immune cell activation is reduction or inhibition of lymphocyte activation.

In some embodiments of the foregoing aspects, the reduction or inhibition of lymphocyte activation is reduction or inhibition of B cell activation. In other embodiments of the foregoing aspects, reduction or inhibition of B cell activation is determined by frequency of $CD19^+CD86^+CD69^+B$ cells.

In some embodiments of the foregoing aspects, the reduction or inhibition of unwanted immune cell activation causes reduced or inhibited cytokine production. In some embodiments of the foregoing aspects, immune cell activation is decreased by at least 10%. In further embodiments of the foregoing aspects, immune cell activation is decreased by at least 25%. In some embodiments of the foregoing aspects, immune cell activation is decreased by at least 50%. In other embodiments of the foregoing aspects, wherein immune cell activation is decreased without a corresponding decrease in expression of the polypeptide of interest encoded by the chemically modified mRNA.

In some aspects, the disclosure relates to methods of reducing or inhibiting unwanted immune cell activation in a subject administered a messenger RNA (mRNA) encoding a polypeptide of interest, comprising administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases; and administering to the subject intravenously a second dose of the chemically modified mRNA encapsulated in an LNP, such that unwanted immune cell activation is reduced or inhibited in the subject.

In other aspects, the disclosure relates to methods of reducing or inhibiting unwanted immune cell activation in a subject following repeated administration of a messenger RNA (mRNA) encoding a polypeptide of interest to the subject, comprising
(i) administering to the subject intravenously a first dose of a chemically modified mRNA encapsulated in a lipid nanoparticle (LNP), wherein the chemically modified mRNA comprises at least one microRNA binding site for a microRNA expressed in immune cells,
and wherein the chemically modified mRNA comprises one or more modified nucleobases;
(ii) detecting a level of immune cell activation in a sample from the subject; and
(iii) administering to the subject intravenously a second dose of the chemically modified mRNA encapsulated in an LNP when the level of immune cell activation in the sample is diminished, such that unwanted immune cell activation is reduced or inhibited in the subject.

In some embodiments of the foregoing aspects, the reduced or inhibited unwanted immune cell activation is reduced or inhibited B cell activation. In some embodiments of the foregoing aspects, the reduced or inhibited unwanted immune cell activation causes reduced or inhibited cytokine production.

In some aspects, the disclosure relates to methods of reducing or inhibiting unwanted cytokine production in a subject administered a messenger RNA (mRNA) encoding a polypeptide of interest, the method comprising administering to the subject a chemically modified mRNA encoding the polypeptide of interest, wherein the chemically modified mRNA comprises at least one microRNA binding site for a microRNA expressed in immune cells, and wherein the chemically modified mRNA comprises one or more modified nucleobases, such that unwanted cytokine production is reduced or inhibited in the subject.

In some embodiments of the foregoing aspects, reduction or inhibition of unwanted cytokine production is determined compared to control administration of a chemically modified mRNA lacking the at least one microRNA binding site for a microRNA expressed in immune cells. In other embodiments of the foregoing aspects, the reduced or inhibited cytokine production is reduced or inhibited production of interleukin-6 (IL-6), tumor necrosis factor □ (TNF-□) or interferon-(IFN-□). In some embodiments of the foregoing aspects, the reduced or inhibited cytokine production is reduced or inhibited production of interleukin-6 (IL-6).

In some embodiments of the foregoing aspects, cytokine production is decreased by at least 10%. In some embodiments of the foregoing aspects, cytokine production is decreased by at least 25%. In some embodiments of the foregoing aspects, cytokine production is decreased by at least 50%. In some embodiments of the foregoing aspects, cytokine production is decreased without a corresponding decrease in expression of the polypeptide of interest encoded by the chemically modified mRNA.

In yet further aspects, the disclosure relates to methods of reducing or inhibiting accelerated blood clearance in a subject repeatedly administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that accelerated blood clearance is reduced or inhibited in the subject upon repeat administration.

In some aspects, the disclosure relates to methods of reducing or inhibiting accelerated blood clearance in a subject administered a messenger RNA (mRNA) encoding a polypeptide of interest encapsulated in an lipid nanoparticle (LNP), comprising administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases; and administering to the subject intravenously a second dose of the chemically modified mRNA encapsulated in an LNP, such that accelerated blood clearance is reduced or inhibited in the subject.

In other aspects, the disclosure relates to methods of reducing or inhibiting accelerated blood clearance in a subject administered multiple doses of a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that accelerated blood clearance is reduced or inhibited in the subject upon administration of one or more subsequent doses.

In yet further aspects, the disclosure relates to methods of reducing or inhibiting accelerated blood clearance in a subject administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that accelerated blood clearance is reduced or inhibited in the subject upon administration of a subsequent dose of the mRNA.

In some aspects, the disclosure relates to methods of reducing or inhibiting accelerated blood clearance in a subject repeatedly administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, wherein the chemically modified mRNA comprises one or more modified nucleobases, and wherein the LNP does not activate B cells and/or does not induce production of IgM molecules capable of binding to the LNP, such that accelerated blood clearance is reduced or inhibited in the subject upon repeat administration.

In other aspects, the disclosure relates to methods of reducing or inhibiting accelerated blood clearance in a subject administered a messenger RNA (mRNA) encoding a polypeptide of interest encapsulated in an lipid nanoparticle (LNP), comprising administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases; and administering to the subject intravenously a second dose of the chemically modified mRNA encapsulated in an LNP, wherein the LNP does not activate B cells and/or does not induce production of IgM molecules capable of binding to the LNP, such that accelerated blood clearance is reduced or inhibited in the subject.

In yet further aspects, the disclosure relates to methods of reducing or inhibiting accelerated blood clearance in a subject administered multiple doses of a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, wherein the chemically modified mRNA comprises one or more modified nucleobases, and wherein the LNP does not activate B cells and/or does not induce production of IgM molecules capable of binding to the LNP, such that accelerated blood clearance is reduced or inhibited in the subject upon administration of one or more subsequent doses.

In some aspects, the disclosure relates to methods of reducing or inhibiting accelerated blood clearance in a subject administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, wherein the chemically modified mRNA comprises one or more modified nucleobases, and wherein the LNP does not activate B cells and/or does not induce production of IgM molecules capable of binding to the LNP, such that accelerated blood clearance is reduced or inhibited in the subject upon administration of a subsequent dose of the mRNA.

In other aspects, the disclosure relates to methods of reducing or inhibiting production of IgM molecules that recognize polyethylene glycol (PEG) in a subject repeatedly administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that production of IgM molecules that recognize PEG are reduced or inhibited in the subject upon repeat administration.

In some aspects, the disclosure relates to methods of reducing or inhibiting production of IgM molecules that recognize polyethylene glycol (PEG) in a subject administered a messenger RNA (mRNA) encoding a polypeptide of interest encapsulated in an lipid nanoparticle (LNP), comprising administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases; and administering to the subject intravenously a second dose of the chemically modified mRNA encapsulated in an LNP, such that production of IgM molecules that recognize PEG are reduced or inhibited in the subject.

In other aspects, the disclosure relates to methods of reducing or inhibiting production of IgM molecules that recognize polyethylene glycol (PEG) in a subject administered multiple doses of a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that production of IgM molecules that recognize PEG are reduced or inhibited in the subject upon administration of one or more subsequent doses.

In some aspects, the disclosure relates to methods of reducing or inhibiting production of IgM molecules that recognize polyethylene glycol (PEG) in a subject administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that production of IgM molecules that recognize PEG are reduced or inhibited in the subject upon administration of a subsequent dose of the mRNA.

In yet further aspects, the disclosure relates to methods of reducing or inhibiting activation of B1a cells in a subject repeatedly administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of B1a cells is reduced or inhibited in the subject upon repeat administration.

In some aspects, the disclosure relates to methods of reducing or inhibiting activation of B1a cells in a subject administered a messenger RNA (mRNA) encoding a polypeptide of interest encapsulated in an lipid nanoparticle (LNP), comprising administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases; and administering to the subject intravenously a second dose of the chemically modified mRNA encapsulated in an LNP, such that activation of B1a cells is reduced or inhibited in the subject.

In other aspects, the disclosure relates to methods of reducing or inhibiting activation of B1a cells in a subject administered multiple doses of a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of B1a cells is reduced or inhibited in the subject upon administration of one or more subsequent doses.

In some aspects, the disclosure relates to methods of reducing or inhibiting activation of B1a cells in a subject administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of B1a cells is reduced or inhibited in the subject upon administration of a subsequent dose of the mRNA.

In other aspects, the disclosure relates to methods of reducing or inhibiting activation of plasmacytoid dendritic cells in a subject repeatedly administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of plasmacytoid dendritic cells is reduced or inhibited in the subject upon repeat administration.

In yet further aspects, the disclosure relates to methods of reducing or inhibiting activation of plasmacytoid dendritic cells in a subject administered a messenger RNA (mRNA) encoding a polypeptide of interest encapsulated in an lipid nanoparticle (LNP), comprising administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases; and administering to the subject intravenously a second dose of the chemically modified mRNA encapsulated in an LNP, such that activation of plasmacytoid dendritic cells is reduced or inhibited in the subject.

In some aspects, the disclosure relates to methods of reducing or inhibiting activation of plasmacytoid dendritic cells in a subject administered multiple doses of a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of plasmacytoid dendritic cells is reduced or inhibited in the subject upon administration of one or more subsequent doses.

In other aspects, the disclosure relates to methods of reducing or inhibiting activation of plasmacytoid dendritic cells in a subject administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that activation of plasmacytoid dendritic cells is reduced or inhibited in the subject upon administration of a subsequent dose of the mRNA.

In some embodiments of the foregoing aspects, the mRNA encoding a polypeptide of interest encapsulated in a lipid nanoparticle (LNP) does not activate B cells and/or does not induce production of IgM molecules capable of binding to the LNP. In some embodiments of the foregoing aspects, the mRNA encoding a polypeptide of interest encapsulated in a lipid nanoparticle (LNP) does not activate B cells. In some embodiments of the foregoing aspects, the mRNA encoding a polypeptide of interest encapsulated in a lipid nanoparticle (LNP) does not induce production of IgM molecules capable of binding to the LNP.

In some embodiments of the foregoing aspects, reduction or inhibition of accelerated blood clearance is determined compared to control administration of a chemically modified mRNA lacking the at least one microRNA binding site encapsulated in a lipid nanoparticle (LNP). In some embodiments of the foregoing aspects, accelerated blood clearance is reduced or inhibited without a corresponding reduction or inhibition in expression of the polypeptide of interest encoded by the chemically modified mRNA. In some embodiments of the foregoing aspects, the interval between two consecutive doses is less than 2 weeks. In some embodiments of the foregoing aspects, the interval between two consecutive doses is less than 1 week.

In some embodiments of the foregoing aspects, the IgM molecules recognize polyethylene glycol (PEG).

In any of the foregoing aspects, the mmRNA described herein is administered intravenously encapsulated in a lipid nanoparticle. In any of the foregoing aspects, the mmRNA described herein is administered by once weekly infusion.

In any of the foregoing aspects, the mmRNA described herein comprises a 5' UTR, a codon optimized open reading frame encoding the polypeptide of interest, a 3' UTR comprising the at least one miR-142-3p microRNA binding site, and a 3' tailing region of linked nucleosides. In some embodiments, the mmRNA described herein comprises a 5' UTR and 3'UTR which are heterologous to the coding region. In some embodiments, the mmRNA described herein is fully modified. In some embodiments, the mmRNA described herein is fully modified for a particular chemical modification.

In any of the foregoing aspects, the mmRNA described herein comprises pseudouridine (ψ), pseudouridine (ψ) and 5-methyl-cytidine ($m^5C$), 1-methyl-pseudouridine ($m^1ψ$), 1-methyl-pseudouridine ($m^1ψ$) and 5-methyl-cytidine ($m^5C$), 2-thiouridine ($s^2U$), 2-thiouridine and 5-methyl-cytidine ($m^5C$), 5-methoxy-uridine ($mo^5U$), 5-methoxy-uridine ($mo^5U$) and 5-methyl-cytidine ($m^5C$), 2"-O-methyl uridine, 2'-O-methyl uridine and 5-methyl-cytidine ($m^5C$), N6-methyl-adenosine ($m^6A$) or N6-methyl-adenosine ($m^6A$) and 5-methyl-cytidine ($m^5C$).

In any of the foregoing aspects, the mmRNA described herein comprises pseudouridine (ψ), N1-methylpseudouridine ($m^1ψ$), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine, or combinations thereof.

In some embodiments, the mmRNA described herein comprises 1-methyl-pseudouridine ($m^1ψ$), 5-methoxy-uridine ($mo^5U$), 5-methyl-cytidine ($m^5C$), pseudouridine (ψ), α-thio-guanosine, or α-thio-adenosine, or combinations thereof.

In any of the foregoing aspects, the polypeptide of interest is a therapeutic protein, cytokine, growth factor, antibody or fusion protein.

In any of the foregoing aspects, the lipid nanoparticle is a liposome. In some embodiments, the lipid nanoparticle comprises a cationic and/or ionizable lipid. In some embodiments, the cationic and/or ionizable lipid is DLin-KC2-DMA or DLin-MC3-DMA.

In any of the foregoing aspects, mmRNA comprises at least two microRNA binding sites, wherein at least one of the microRNA binding sites is a miR-142-3p microRNA binding site. In any of the foregoing aspects, the mmRNA comprises a miR-142-3p binding site and a second microRNA binding site for a miR selected from the group consisting of miR-142-5p, miR-146-3p, miR-146-5p, miR-155, miR-126, miR-16, miR-21, miR-223, miR-24 and miR-27.

In any of the foregoing aspects, the chemically modified mRNA comprises a 5' UTR, a codon optimized open reading frame encoding the polypeptide of interest, a 3' UTR comprising the at least one microRNA binding site, and a 3' tailing region of linked nucleosides.

In any of the foregoing aspects, the codon optimized open reading frame encoding the polypeptide of interest comprises a stop codon and wherein the at least one microRNA binding site is located within the 3' UTR 1-100 nucleotides after the stop codon. In some embodiments, the codon optimized open reading frame encoding the polypeptide of interest comprises a stop codon and wherein the at least one microRNA binding site is located within the 3' UTR at least 50 nucleotides after the stop codon.

In any of the foregoing aspects, the chemically modified mRNA comprises a 5' UTR, a codon optimized open reading frame encoding the polypeptide of interest, a 3' UTR comprising the at least one microRNA binding site for a microRNA expressed in immune cells, and a 3' tailing region of linked nucleosides.

In any of the foregoing aspects, the codon optimized open reading frame encoding the polypeptide of interest comprises a stop codon and wherein the at least one miR-142-3p microRNA binding site is located within the 3' UTR 30-50 nucleotides after the stop codon. In some embodiments, the codon optimized open reading frame encoding the polypeptide of interest comprises a stop codon and wherein the at least one miR-142-3p microRNA binding site is located within the 3' UTR at least 50 nucleotides after the stop codon.

In any of the foregoing aspects, the codon optimized open reading frame encoding the polypeptide of interest comprises a stop codon and wherein the at least one miR-126 microRNA binding site is located within the 3' UTR 30-50 nucleotides after the stop codon. In some embodiments, the codon optimized open reading frame encoding the polypeptide of interest comprises a stop codon and wherein the at least one miR-126 microRNA binding site is located within the 3' UTR at least 50 nucleotides after the stop codon.

In any of the foregoing aspects, the mmRNA comprises a 5' UTR, a codon optimized open reading frame encoding the polypeptide of interest, a 3' UTR comprising the at least one miR-126 microRNA binding site, and a 3' tailing region of linked nucleosides. In any of the foregoing aspects, the mmRNA comprises at least two microRNA binding sites. In some embodiments, the mmRNA comprises at least two microRNA binding sites, wherein at least one of the microRNA binding sites is a miR-126 microRNA binding site. In some embodiments, the mmRNA comprises a miR-126 binding site and a second microRNA binding site for a miR selected from the group consisting of miR-142-3p, miR-142-5p, miR-146-3p, miR-146-5p, miR-155, miR-16, miR-21, miR-223, miR-24 and miR-27. In some embodiments, the chemically modified mRNA comprises a miR-126 binding site and a miR-142 binding site. In some embodiments, the mmRNA construct comprises a miR-126 binding site and a miR-142-3p binding site.

In any of the foregoing aspects, the microRNA binding site is a miR-142-3p binding site. In some embodiments, the miR-142-3p binding site comprises the sequence shown in SEQ ID NO: 3.

In any of the foregoing aspects, the microRNA binding site is a miR-126 microRNA binding site. In some embodiments, the miR-126 binding site comprises the sequence shown in SEQ ID NO: 26.

In any of the foregoing aspects, the microRNA binding site is a miR-155 microRNA binding site. In some embodiments, the miR-155 binding site comprises the sequence shown in SEQ ID NO: 35.

In any of the foregoing aspects, the microRNA binding site binds a microRNA expressed in myeloid cells. In any of the foregoing aspects, the microRNA binding site binds a microRNA expressed in plasmacytoid dendritic cells. In any of the foregoing aspects, the microRNA binding site binds a microRNA expressed in macrophages.

Definitions

Accelerated blood clearance (ABC): As used herein, "accelerated blood clearance" or "ABC" refers to a phenomenon in which certain exogenously administered agents are rapidly cleared from the blood upon second and subsequence administrations.

Administering: As used herein, "administering" refers to a method of delivering a composition to a subject or patient. A method of administration may be selected to target delivery (e.g., to specifically deliver) to a specific region or system of a body. For example, an administration may be parenteral (e.g., subcutaneous, intracutaneous, intravenous, intraperitoneal, intramuscular, intraarticular, intraarterial, intrasynovial, intrasternal, intrathecal, intralesional, or intracranial injection, as well as any suitable infusion technique), oral, trans- or intra-dermal, interdermal, rectal, intravaginal, topical (e.g., by powders, ointments, creams, gels, lotions, and/or drops), mucosal, nasal, buccal, enteral, vitreal, intratumoral, sublingual, intranasal: by intratracheal instillation, bronchial instillation, and/or inhalation: as an oral spray and/or powder, nasal spray, and/or aerosol, and/or through a portal vein catheter.

Anti-drug antibody: As used herein, the term "anti-drug antibody", or "ADA", refers to antibodies generated in a subject against a therapeutic protein present in the subject. A classical anti-drug antibody (ADA) response is understood in the art to result from systemic administration of a recombinant therapeutic protein to the subject. Moreover, as used herein with respect to mRNA therapeutics, an ADA response is intended to encompass the antibody responses observed in the herein-described animal studies wherein antibodies were generated that bind to the therapeutic protein encoded by the mRNA therapeutic (i.e., antibodies generated against the protein encoded by the mRNA drug). Such antibody responses to the therapeutic protein encoded by the mRNA drug are also referred to as anti-protein antibody (APA) responses, which terminology can be used interchangeably herein with ADA responses.

Apoptosis: As used herein, "apoptosis" refers to a form of cell death in which a programmed sequence of events leads to the death of a cell. Hallmarks of apoptosis include morphological changes, cell shrinkage, caspase activation, nuclear and cytoplasmic condensation, and alterations in plasma membrane topology. Biochemically, apoptotic cells are characterized by increased intracellular calcium concentration, fragmentation of chromosomal DNA, and expression of novel cell surface components. In particular embodiments, a cell undergoing apoptosis may undergo mitochondrial outer membrane permeabilization (MOMP).

Approximately, about: As used herein, the terms "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Binding Antibody (BAB): As used herein, a "binding antibody" or "BAB" refers to an antibody that is capable of binding to, i.e., interacting with, a target antigen, such as a therapeutic protein. The term binding antibody is intended to encompass neutralizing antibodies (i.e., antibodies that bind to the target antigen and inhibit the functional activity of the antigen) and non-neutralizing antibodies (i.e., antibodies that bind to the target antigen but that do not inhibit the functional activity of the antigen).

Cancer: As used herein, "cancer" is a condition involving abnormal and/or unregulated cell growth. The term cancer encompasses benign and malignant cancers. Exemplary non-limiting cancers include adrenal cortical cancer, advanced cancer, anal cancer, aplastic anemia, bileduct cancer, bladder cancer, bone cancer, bone metastasis, brain tumors, brain cancer, breast cancer, childhood cancer, cancer of unknown primary origin, Castleman disease, cervical cancer, colorectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer (e.g., hepatocellular carcinoma), non-small cell lung cancer, small cell lung cancer, lung carcinoid tumor, lymphoma of the skin, malignant mesothelioma, multiple myeloma, myelodysplasia syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor and secondary cancers caused by cancer treatment. In particular embodiments, the cancer is liver cancer (e.g., hepatocellular carcinoma) or colorectal cancer. In other embodiments, the cancer is a blood-based cancer or a hematopoetic cancer.

Conjugated: As used herein, the term "conjugated," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. In some embodiments, two or more moieties may be conjugated by direct covalent chemical bonding. In other embodiments, two or more moieties may be conjugated by ionic bonding or hydrogen bonding.

Contacting: As used herein, the term "contacting" means establishing a physical connection between two or more entities. For example, contacting a cell with an mRNA or a lipid nanoparticle composition means that the cell and mRNA or lipid nanoparticle are made to share a physical connection. Methods of contacting cells with external entities both in vivo, in vitro, and ex vivo are well known in the biological arts. In exemplary embodiments of the disclosure, the step of contacting a mammalian cell with a composition (e.g., an isolated mRNA, nanoparticle, or pharmaceutical composition of the disclosure) is performed in vivo. For example, contacting a lipid nanoparticle composition and a cell (for example, a mammalian cell) that may be disposed within an organism (e.g., a mammal) may be performed by any suitable administration route (e.g., parenteral administration to the organism, including intravenous, intramuscular, intradermal, and subcutaneous administration). For a cell present in vitro, a composition (e.g., a lipid nanoparticle or an isolated mRNA) and a cell may be contacted, for example, by adding the composition to the culture medium of the cell and may involve or result in transfection. Moreover, more than one cell may be contacted by a nanoparticle composition.

Drug-related toxicity: As used herein, the term "drug-related toxicity", or simply "toxicity", refers to undesirable in vivo effects that may result from expression in a subject of a therapeutic protein encoded by an mRNA, for example as a result of an immune response being stimulated against the encoded therapeutic protein, such as the generation of antibodies that bind to (and potentially neutralize) the encoded therapeutic protein. Thus, the term "drug-related toxicity" is intended to encompass the in vivo adverse effects resulting from an unwanted immune response against the encoded therapeutic protein, including but not limited to hematological effects (e.g., hematoxicity), renal effects, autoimmune effects, liver effects and the like.

Encapsulate: As used herein, the term "encapsulate" means to enclose, surround, or encase. In some embodiments, a compound, polynucleotide (e.g., an mRNA), or other composition may be fully encapsulated, partially encapsulated, or substantially encapsulated. For example, in some embodiments, an mRNA of the disclosure may be encapsulated in a lipid nanoparticle, e.g., a liposome.

Effective amount: As used herein, the term "effective amount" of an agent is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent. In some embodiments, a therapeutically effective amount is an amount of an agent to be delivered (e.g., nucleic acid, therapeutic agent, diagnostic agent or prophylactic agent) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Identity: As used herein, the term "identity" refers to the overall relatedness between polymeric molecules, e.g., between polynucleotide molecules (e.g., DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in *Computational Molecular Biology*, Lesk, A. M., ed., Oxford University Press, New York, 1988: *Biocomputing: Informatics and Genome Projects*, Smith, D. W., ed., Academic Press, New York, 1993; *Sequence Analysis in Molecular Biology*, von Heinje, G., Academic Press, 1987; *Computer Analysis of Sequence Data*, Part I, Griffin, A. M., and Griffin, H. G., eds., Humana Press, New Jersey, 1994; and *Sequence Analysis Primer*, Gribskov, M, and Devereux, J., eds., M Stockton Press, New York, 1991: each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., *SIAM J Applied Math.*, 48:1073 (1988): incorporated herein by reference. Techniques for determining identity are codified in publicly available computer programs. Exemplary computer software to determine homology between two sequences include, but are not limited to, GCG program package, Devereux et al., *Nucleic Acids Research,* 12 (1): 387, 1984, BLASTP, BLASTN, and FASTA, Altschul, S. F. et al., *J. Molec. Biol.,* 215, 403, 1990.

Fragment: A "fragment," as used herein, refers to a portion. For example, fragments of proteins may include polypeptides obtained by digesting full-length protein isolated from cultured cells or obtained through recombinant DNA techniques.

Hematotoxicity: As used herein, the term "hematotoxicity" refers to toxicological events (e.g., resulting from drug-related toxicity) occurring in the hematopoietic system, including but not limited to cytopenias (e.g., reticulocytopenia, thrombocytopenia, neutropenia), decreased hematopoiesis and anemia. While not intended to be limited by mechanism, hematotoxicity in a subject can result from the development of an immune response against a therapeutic protein encoded by an mRNA administered to the subject, e.g., as a result of antibodies being generated against the therapeutic protein, and thus hematotoxicity can be a subset of drug-related toxicities.

Heterologous: As used herein, "heterologous" indicates that a sequence (e.g., an amino acid sequence or the polynucleotide that encodes an amino acid sequence) is not normally present in a given polypeptide or polynucleotide. For example, an amino acid sequence that corresponds to a domain or motif of one protein may be heterologous to a second protein.

Hydrophobic amino acid: As used herein, a "hydrophobic amino acid" is an amino acid having an uncharged, nonpolar side chain. Examples of naturally occurring hydrophobic amino acids are alanine (Ala), valine (Val), leucine (Leu), isoleucine (Ile), proline (Pro), phenylalanine (Phe), methionine (Met), and tryptophan (Trp).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Liposome: As used herein, by "liposome" is meant a structure including a lipid-containing membrane enclosing an aqueous interior. Liposomes may have one or more lipid membranes. Liposomes include single-layered liposomes (also known in the art as unilamellar liposomes) and multi-layered liposomes (also known in the art as multilamellar liposomes).

Metastasis: As used herein, the term "metastasis" means the process by which cancer spreads from the place at which it first arose as a primary tumor to distant locations in the body. A secondary tumor that arose as a result of this process may be referred to as "a metastasis."

mRNA: As used herein, an "mRNA" refers to a messenger ribonucleic acid. An mRNA may be naturally or non-naturally occurring. For example, an mRNA may include modified and/or non-naturally occurring components such as one or more nucleobases, nucleosides, nucleotides, or linkers. An mRNA may include a cap structure, a chain terminating nucleoside, a stem loop, a polyA sequence, and/or a polyadenylation signal. An mRNA may have a nucleotide sequence encoding a polypeptide. Translation of an mRNA, for example, in vivo translation of an mRNA inside a mammalian cell, may produce a polypeptide. Traditionally, the basic components of an mRNA molecule include at least a coding region, a 5'-untranslated region (5'UTR), a 3'UTR, a 5' cap and a poly A sequence.

microRNA (miRNA): As used herein, a "microRNA (miRNA)" is a small non-coding RNA molecule which may function in post-transcriptional regulation of gene expression (e.g., by RNA silencing, such as by cleavage of the mRNA, destabilization of the mRNA by shortening its polyA tail, and/or by interfering with the efficiency of translation of the mRNA into a polypeptide by a ribosome). A mature miRNA is typically about 22-23 nucleotides long.

microRNA (miRNA) (miR) binding site: As used herein, a "microRNA (miRNA) (miR) binding site" refers to a miRNA (miR) target site or a miRNA (miR) recognition site, or any nucleotide sequence to which a miRNA (miR) binds or associates. In some embodiments, a miRNA (miR) binding site represents a nucleotide location or region of a polynucleotide (e.g., an mRNA) to which at least the "seed" region of a miRNA (miR) binds. It should be understood that "binding" may follow traditional Watson-Crick hybridization rules or may reflect any stable association of the miRNA with the target sequence at or adjacent to the microRNA site. When referring to a miRNA (miR) binding site, a miRNA (miR) sequence is to be understood as having complementarity (e.g., partial, substantial, or complete (or full) complementarity) with the miRNA that binds to the miRNA binding site. A miRNA (miR) binding site can be partially complementary to a miRNA (miR), e.g., to an endogenous miRNA (miR), as is the case when the miRNA (miR) may exert translational control and/or transcript stability control of its corresponding mRNA. Alternatively, a miRNA (miR) binding site can be fully complementary (complete complementarity) to a miRNA (miR), e.g., to an endogenous miRNA (miR), as is the case when the miRNA (miR) may exert post-transcriptional and/or translational control of its corresponding mRNA. In preferred aspects of the disclosure, a miRNA (miR) binding site is fully complementary to a miRNA (miR), e.g., to an endogenous miRNA (miR), and may cause cleavage of the mRNA comprising said miRNA (miR) in cells and/or tissues in vivo, where the corresponding miR is expressed, e.g., endogenously expressed, miRNA seed: As used herein, a "seed" region of a miRNA refers to a sequence in the region of positions 2-8 of a mature miRNA, which typically has perfect Watson-Crick complementarity to the miRNA binding site. A miRNA seed may include positions 2-8 or 2-7 of a mature miRNA. In some embodiments, a miRNA seed may comprise 7 nucleotides (e.g., nucleotides 2-8 of a mature miRNA), wherein the seed-complementary site in the corresponding miRNA binding site is flanked by an adenine (A) opposed to miRNA position 1. In some embodiments, a miRNA seed may comprise 6 nucleotides (e.g., nucleotides 2-7 of a mature miRNA), wherein the seed-complementary site in the corresponding miRNA binding site is flanked by an adenine (A) opposed to miRNA position 1. When referring to a miRNA binding site, a miRNA seed sequence is to be understood as having complementarity (e.g., partial, substantial, or complete (or full) complementarity) with the seed sequence of the miRNA that binds to the miRNA binding site.

Modified: As used herein "modified" refers to a changed state or structure of a molecule of the disclosure. Molecules may be modified in many ways including chemically, structurally, and functionally. In one embodiment, the mRNA molecules of the present disclosure are modified by the introduction of non-natural nucleosides and/or nucleotides. e.g., as it relates to the natural ribonucleotides A, U, G, and C. Noncanonical nucleotides such as the cap structures are not considered "modified" although they differ from the chemical structure of the A, C, G, U ribonucleotides.

Nanoparticle: As used herein, "nanoparticle" refers to a particle having any one structural feature on a scale of less than about 1000 nm that exhibits novel properties as compared to a bulk sample of the same material. Routinely, nanoparticles have any one structural feature on a scale of less than about 500 nm, less than about 200 nm, or about 100 nm. Also routinely, nanoparticles have any one structural feature on a scale of from about 50 nm to about 500 nm, from about 50 nm to about 200 nm or from about 70 to about 120 nm. In exemplary embodiments, a nanoparticle is a particle having one or more dimensions of the order of about 1-1000 nm. In other exemplary embodiments, a nanoparticle is a particle having one or more dimensions of the order of about 10-500 nm. In other exemplary embodiments, a nanoparticle is a particle having one or more dimensions of the order of about 50-200 nm. A spherical nanoparticle would have a diameter, for example, of between about 50-100 or 70-120 nanometers. A nanoparticle most often behaves as a unit in terms of its transport and properties. It is noted that novel properties that differentiate nanoparticles from the corresponding bulk material typically develop at a size scale of under 1000 nm, or at a size of about 100 nm, but nanoparticles can be of a larger size, for example, for particles that are oblong, tubular, and the like. Although the size of most molecules would fit into the above outline, individual molecules are usually not referred to as nanoparticles.

Neutralizing Antibody (NAB): As used herein, a "neutralizing antibody" or "NAB" refers to an antibody that is capable of binding to (i.e., interacting with) a target antigen, (such as a therapeutic protein) and inhibiting at least one functional activity of the antigen. Binding of a neutralizing antibody to its target antigen may cause partial inhibition of at least one functional activity of antigen or complete inhibition of at least one functional activity of the antigen. In certain instances, binding of a neutralizing antibody to its target antigen may cause partial or complete inhibition of all functional activities of the target antigen.

Nucleic acid: As used herein, the term "nucleic acid" is used in its broadest sense and encompasses any compound and/or substance that includes a polymer of nucleotides. These polymers are often referred to as polynucleotides. Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

Patient: As used herein, "patient" refers to a subject who may seek or be in need of treatment, requires treatment, is receiving treatment, will receive treatment, or a subject who is under care by a trained professional for a particular disease or condition. In particular embodiments, a patient is a human patient.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipient: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: buty lated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines: alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two: generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, *Pharmaceutical Salts: Properties. Selection, and Use,* P. H. Stahl and C. G. Wermuth (eds.), Wiley-VCH, 2008, and Berge et al., *Journal of Pharmaceutical Science,* 66, 1-19 (1977), each of which is incorporated herein by reference in its entirety.

Polypeptide: As used herein, the term "polypeptide" or "polypeptide of interest" refers to a polymer of amino acid residues typically joined by peptide bonds that can be produced naturally (e.g., isolated or purified) or synthetically.

Subject: As used herein, the term "subject" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants. In some embodiments, a subject may be a patient.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of a disease, disorder, and/or condition.

Targeting moiety: As used herein, a "targeting moiety" is a compound or agent that may target a nanoparticle to a particular cell, tissue, and/or organ type.

Therapeutic Agent: The term "therapeutic agent" refers to any agent that, when administered to a subject, has a therapeutic, diagnostic, and/or prophylactic effect and/or elicits a desired biological and/or pharmacological effect.

Transfection: As used herein, the term "transfection" refers to methods to introduce a species (e.g., a polynucleotide, such as a mRNA) into a cell.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Preventing: As used herein, the term "preventing" refers to partially or completely inhibiting the onset of one or more symptoms or features of a particular infection, disease, disorder, and/or condition.

Tumor: As used herein, a "tumor" is an abnormal growth of tissue, whether benign or malignant.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

EQUIVALENTS AND SCOPE

Those skilled in the art will recognize, or be able to ascertain using no more than routine experimentation, many equivalents to the specific embodiments in accordance with the disclosure described herein. The scope of the present disclosure is not intended to be limited to the Description below, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

The disclosure will be more fully understood by reference to the following examples. They should not, however, be construed as limiting the scope of the disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Modified mRNA Encoding hEPO Elicits an Anti-Drug Antibody (ADA) Response in Non-Human Primates In this example, modified mRNA (mmRNA) encoding human erythropoietin (hEPO), but lacking any miR binding sites, was administered to cynomolgus macaques in a four week study to examine expression of hEPO in the animals.

mmRNA encoding hEPO was formulated into MC3 lipid nanoparticles (LNP), which include MC3 50%, DSPC 10%, Cholesterol 38.5%, PEG-DMG 1.5%, N: P~5.5. (Values are based on mol. %). The mmRNA construct contained a Cap 1 5' Cap structure (7mG(5')ppp(5')NlmpNp), was fully modified with 5-methylcytosine and 1-methylpseudouridine and comprised a 140 nucleotide poly A tail. The mmRNA construct lacked the presence of any inserted miR binding sites. The nucleotide sequence of this hEPO-encoding construct without any inserted miR binding sites is shown in SEQ ID NO: 7 (without the polyA tail shown).

The study comprised seven groups of animals. The negative control group was treated with PBS. Three treatment groups were treated with one of three different doses of the hEPO-encoding mmRNA LNP, at either 0.02 mg/kg/dose, 0.1 mg/kg/dose or 0.2 mg/kg/dose. The low dose was selected to achieve at least 2 times the therapeutically effective exposure for human EPO, whereas the high dose was selected to achieve at least 10 times the levels of hEPO exposure over the therapeutically effective dose. The positive control group was treated with recombinant hEPO protein at a dose of 6000 U/kg. Two other controls groups were treated with either LNP containing an irrelevant mmRNA (non-translating mRNA form) or with LNP alone. The dose schedule was once per week for four consecutive weeks (for a total of 5 doses) by IV infusion. Infusions were for 60 minutes (IV) via pumps. The four week dosing period was followed by a four-week recovery evaluation period (control and high dose only).

The levels of expression of hEPO in the macaques was measured by ELISA six hours post infusion on each of the treatment days (days 1, 8, 15, 22 and 29). The results are shown in FIG. 1. The results demonstrate that the macaques treated with the low dose of mmRNA (0.02 mg/kg/dose) exhibited a therapeutically effective level of hEPO that was maintained at approximately the same level throughout the four-week study. In contrast, in the macaques treated with the mid- and high-doses of mmRNA (0.1 mg/kg/dose and 0.2 mg/kg/dose), EPO levels declined starting between days 8 and 15 of the study and remained low for the duration of the study. Reticulocyte counts revealed a persistent reticulocytopenia in the animals treated at the mid- and high-doses of mmRNA (0.1 mg/kg/dose and 0.2 mg/kg/dose). Furthermore, histological analysis revealed decreased hematopoiesis in the bone marrow of the animals treated with the mid- or high-doses of mmRNA. The reticulocytopenia and decreased hematopoiesis in the animals treated with the higher doses of mmRNA suggested that an anti-drug antibody (ADA) response may have developed over time in the animals.

To determine whether an ADA response against human EPO was present, ELISAs were performed on serum from the animals to detect the presence of cynomolgus macaque anti-human EPO antibodies. Blood was collected by femoral venipuncture and serum was collected at room temperature and allowed to clot for at least 30 minutes, followed by centrifugation for 10 minutes in a refrigerated (4° C.) centrifuge at 2700 rpm. Standard ELISA methods were used for the detection of anti-human EPO IgG in the serum. Samples were analyzed in duplicate.

A series of negative control results were used to establish a threshold level, above which would constitute a "positive" result in the assay. Representative quantitative ELISA results for the negative control samples, which thereby were used to set a threshold level, are shown below in Table 3:

TABLE 3

Results for the Anti- human EPO Antibody Analysis
Negative control (NC) results

| Assay ID: Replicate | hAB Prod-01[a] $A_{450nm}$ | hAB Prod-02[a] $A_{450nm}$ | hAB Prod-03 $A_{450nm}$ |
|---|---|---|---|
| 1 | 0.345 | 0.440 | 0.364 |
| 2 | 0.406 | 0.392 | 0.351 |
| 3 | 0.360 | 0.412 | 0.353 |
| 4 | 0.427 | 0.395 | 0.309 |
| 5 | 0.391 | 0.390 | 0.325 |
| 6 | 0.402 | 0.398 | 0.364 |
| 7 | 0.397 | 0.377 | 0.368 |
| 8 | 0.401 | 0.379 | 0.353 |
| 9 | 0.392 | 0.429 | 0.326 |
| 10 | 0.392 | 0.376 | 0.345 |
| 11 | 0.412 | 0.375 | 0.358 |
| 12 | 0.386 | 0.378 | 0.353 |
| Mean | 0.393 | 0.395 | 0.347 |
| SD | 0.022 | 0.022 | 0.018 |
| % CV | 5.6 | 5.5 | 5.2 |
| n | 12 | 12 | 12 |

[a]Results accepted in deviation, refer to Positive Control Samples for the anti-human EPO antibody analysis.

The ELISA results for the seven different animal groups used in the study are shown below in Table 4:

TABLE 4

Cynomolgus Macaque Anti-Human EPO Antibody Response

| Animal Number | PBS | mmRNA hEPO 0.02 mg/kg | mmRNA hEPO 0.1 mg/kg | mmRNA hEPO 0.2 mg/kg | Recomb. hEPO 6000 U/kg | Empty LNP 0.2 mg/kg | NTX in LNP 0.2 mg/kg |
|---|---|---|---|---|---|---|---|
| 1 | − | − | + | + | − | − | − |
| 2 | − | − | − | + | +++ | − | − |
| 3 | − | − | + | + | ++ | SI. + | − |
| 4 | − | − | − | + | +++ | − | − |
| 5 | − | + | + | ++ | ++ | | |
| 6 | − | − | − | + | +++ | | |
| 7 | − | | | + | | | |
| 8 | SI. + | | | ++ | | | |
| 9 | − | | | ++ | | | |
| 10 | − | | | ++ | | | |
| Total | 1/10 | 1/6 | 3/6 | 10/10 | 5/6 | 1/4 | 0/4 |

The results demonstrate that all of the cynomolgus monkeys treated with the highest dose of hEPO-encoding mmRNA (0.2 mg/kg/dose), and 50% of the cynomolgus monkeys treated with the mid-level dose (0.1 mg/kg/dose) exhibited an ADA response against human EPO. This was an unexpected finding and led the inventors to design and test additional mmRNA constructs to attempt to reduce the ADA response to the encoded protein in non-human primates. The results of those studies are described in Example 2.

Figure 2:
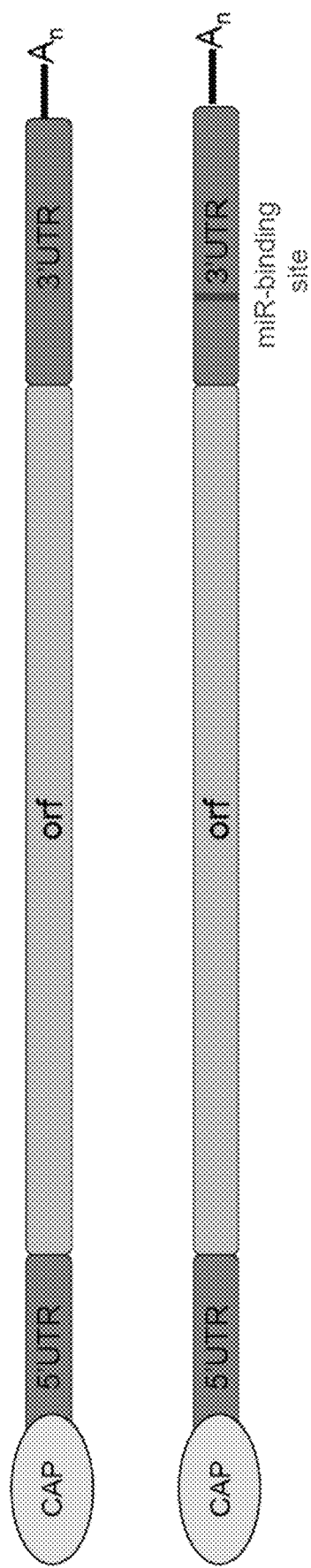
FIG. 2 is a schematic diagram of mRNA constructs without and with an inserted miR site(s) in the 3' UTR.

Example 2: Incorporation of an miR-142-3p Binding Site into mmRNA Inhibits an ADA Response to the Encoded Protein In this example, a human EPO-encoding mmRNA construct was prepared that incorporated an miR-142-3p binding site into the 3' UTR of the construct. The mmRNA construct comprised a Cap 1 5' cap (7mG(5')ppp(5')NlmpNp), was fully modified with 5-methylcytosine and 1-methylpseudouridine and comprised a polyA tail of approximately 140 nucleotides. A schematic diagram of the construct is shown in FIG. 2. The nucleotide sequence of this human EPO-encoding mmRNA is shown in SEQ ID NO: 1 (without the poly A tail). The nucleotide sequence of the 3' UTR comprising the miR-142-3p binding site is shown in SEQ ID NO: 2. The nucleotide sequence of the miR-142-3p binding site is shown in SEQ ID NO: 3. Other than the addition of the miR-142-3p binding site, the mmRNA construct and the LNP preparation were the same as in Example 1.

Cynomolgus macaque monkeys were treated with the construct comprising hEPO-encoding mmRNA with the miR-142-3p binding site in the LNP at a dose of 0.2 mg/kg/day. This dose previously had been shown to elicit an ADA response against hEPO using a construct lacking the miR-142-3p binding site (see Example 1). A four week study was conducted, in which animals were treated on days 1, 8, 15, 22 and 29 as described in Example 1. Intravenous infusions (60 minutes) were given via a temporary indwelling catheter into the brachial or saphenous vein.

To examine whether an ADA response against hEPO was elicited in the animals, ELISAs were performed on serum from the animals, as described in Example 1, to detect the presence of cynomolgus macaque anti-human EPO antibodies.

The results for the four animals (1301, 1302, 1303 and 1304), at each of the five time points for treatment at a dose of 0.2/mg/kg, are shown below in Table 5. The status of the sample as being "negative" or "positive" was determined relative a threshold value set based on the results for negative control samples, as described in Example 1.

TABLE 5

Cynomolgus Macaque Anti-Human EPO Antibody Response

| Sample ID | Time Point | Mean A450$_{nm}$ Value | Status (Pos/Neg) |
|---|---|---|---|
| 1301 | Day 1 predose | 0.254 | Negative |
| | Day 8 predose | 0.255 | Negative |
| | Day 15 predose | 0.255 | Negative |
| | Day 22 predose | 0.229 | Negative |
| | Day 29 predose | 0.230 | Negative |
| 1302 | Day 1 predose | 0.107 | Negative |
| | Day 8 predose | 0.115 | Negative |
| | Day 15 predose | 0.174 | Negative |
| | Day 22 predose | 0.243 | Negative |
| | Day 29 predose | 0.282 | Negative |
| 1303 | Day 1 predose | 0.224 | Negative |
| | Day 8 predose | 0.244 | Negative |
| | Day 15 predose | 0.485 | Positive |
| | Day 22 predose | 1 | Positive |
| | Day 29 predose | 0.991 | Positive |

TABLE 5-continued

Cynomolgus Macaque Anti-Human EPO Antibody Response

| Sample ID | Time Point | Mean A450$_{nm}$ Value | Status (Pos/Neg) |
|---|---|---|---|
| 1304 | Day 1 predose | 0.142 | Negative |
| | Day 8 predose | 0.162 | Negative |
| | Day 15 predose | 0.189 | Negative |
| | Day 22 predose | 0.1287 | Negative |
| | Day 29 predose | 0.379 | Negative |

The results showed that only one of the four treated monkeys (1303) exhibited an ADA response against hEPO. Thus, when the miR-142-3p binding site was incorporated into the hEPO-encoding mmRNA construct, only 25% of the animals treated with the high dose (0.2 mg/kg) of the construct exhibited an ADA against the encoded protein (Table 5), whereas treatment with the same dose using a construct that lacked the miR-142.p3 binding site resulted in 100% of the animals exhibiting an ADA against the encoded protein (Table 4).

Figure 3:
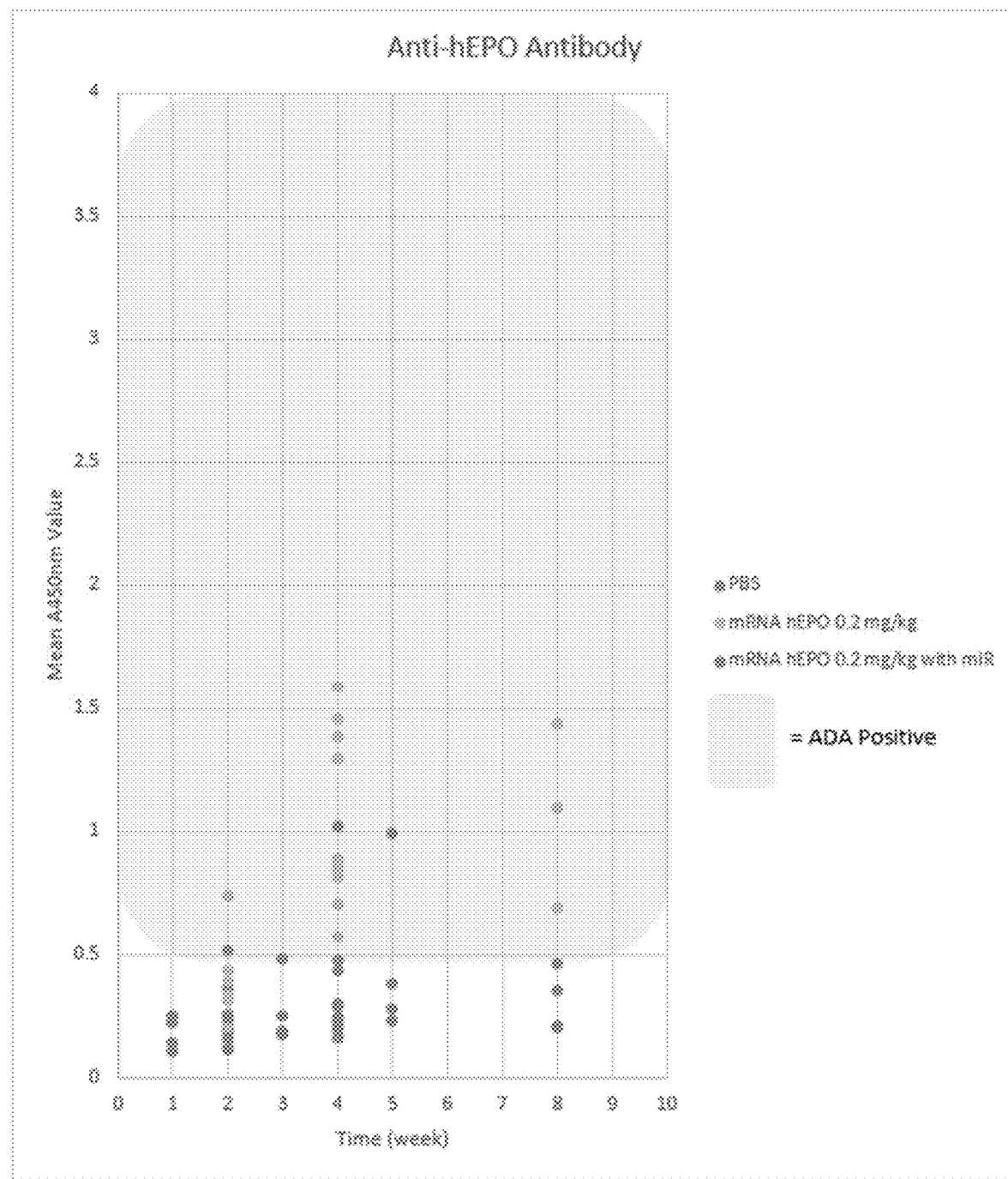
FIG. 3 is a graph comparing the anti-hEPO antibody levels in cynomolgus macaques treated with PBS or with 0.2 mg/kg of an mmRNA encoding hEPO, either lacking or containing a miR-142-3p binding site in the 3' UTR of the construct. Animals positive for an anti-drug antibody (ADA) response are indicated.

FIG. 3 shows a comparison of the ELISA results for the monkeys treated with 0.2 mg/kg of the mRNA construct lacking the miR-142-3p binding site and the ELISA results for the monkeys treated with 0.2 mg/kg of the mRNA construct containing the miR-142-3p binding site, showing the levels of anti-hEPO antibodies in the animals over time. Animals exhibiting an anti-drug-antibody (ADA) response are indicated. The results clearly demonstrate that significantly more ADA responses were observed in the animals treated with the construct lacking the miR binding site as compared to the construct containing the miR binding site.

In a follow-up study in cynomolgus macaque monkeys, very similar results to the pilot study described above were observed. Administration of an hEPO-encoding mmRNA construct lacking the miR-142.p3 binding site resulted in 100% of the animals exhibiting an ADA against the encoded protein, whereas incorporation of a miR-142-3p binding site into the construct resulted in only 50% of the animals exhibiting an ADA against the encoded protein. Incorporation of three miR-142-3p binding sites into the construct did not lead to enhanced effects, thereby demonstrating that a single miR-142-3p binding site was sufficient for reduction of ADA against the encoded protein.

Accordingly, these results demonstrate that incorporation of a miR-142-3p binding site into the mmRNA construct is effective in reducing or eliminating an ADA response against the encoded protein.

Example 3: Incorporation of an miR-126 or miR-142 Binding Site into mmRNA Inhibits B Cell Activation and Cytokine Expression In this example, human EPO-encoding mmRNA constructs were prepared that incorporated either a miR-142-3p binding site or a miR-126-3p binding site, or both the miR-142-3p and miR-126-3p binding sites, into the 3' UTR of the construct. The mmRNA constructs were administered to mice to examine the effects of incorporating the miR binding sites on various immune parameters in the mice.

The mmRNA constructs contained a Cap 1 5' Cap structure (7mG(5')ppp(5')NlmpNp), were fully modified with 5-methylcytosine and 1-methylpseudouridine and comprised a 140 nucleotide poly A tail. The control mmRNA construct lacked the presence of any inserted miR binding sites. The nucleotide sequence of this control hEPO-encoding construct without any inserted miR binding sites is shown in SEQ ID NO: 7 (without the polyA tail shown). The nucleotide sequence of the hEPO-encoding construct with the inserted miR-142-3p binding site is shown in SEQ ID NO: 1 (without the poly A tail shown). The nucleotide sequence of the hEPO-encoding construct with the inserted miR-126-3p site is shown in SEQ ID NO: 28 (without the poly A tail shown). The nucleotide sequence of the hEPO-encoding construct with the inserted miR-142-3p and miR-126-3p sites is shown in SEQ ID NO: 29 (without the poly A tail shown). A schematic diagram of exemplary mmRNA constructs is shown in FIG. 2. The mmRNA constructs encoding hEPO were formulated into MC3 lipid nanoparticles (LNP), which include MC3 50%, DSPC 10%, Cholesterol 38.5%, PEG-DMG 1.5%, N: P~5.5. (Values are based on mol. %).

In an initial study, groups of 30 mice each were assigned to the following treatment groups: (i) hEpo construct without any miR binding sites: (ii) hEpo construct with miR-142-3p binding site: (iii) hEpo construct with miR-126-3p binding site; and (iv) hEpo construct with miR-142-3p and miR-126-3p binding sites. The mmRNAs were administered intravenously to C57Bl/6 mice at a dose of 0.05 mg/kg. The dosing regimen was Days 1, 8, 15, 22, 29 and 36. For each treatment group, 5 mice per group were dosed on each dosing day for a total of 6 doses. The additional 25 mice in each group were broken into 5 subsets such that 5 mice were dosed once on each of dosing days 8, 15, 22, 29 and 36, for a total of one dose per mouse.

Figure 4A:
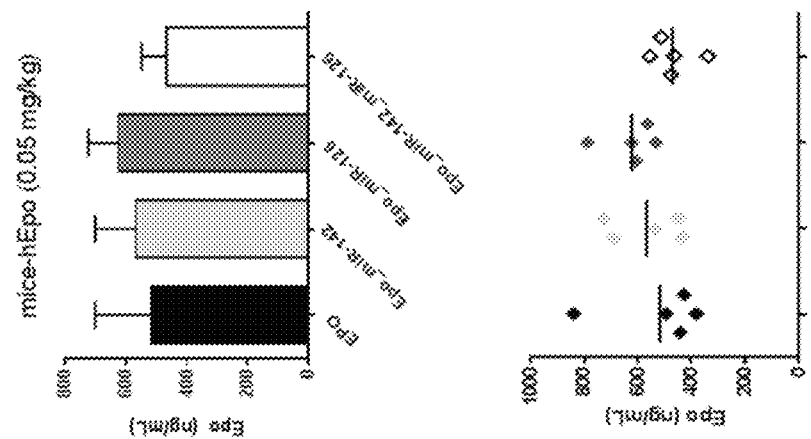
FIGS. 4A-C are graphs showing protein expression levels (FIG. 4A), B cell frequency (FIG. 4B) and activated B cell frequency (FIG. 4C) in mice treated with 0.05 mg/kg mmRNA encoding hEPO either lacking or containing a miR-142-3p binding site, a miR-126 binding site, or both the miR-142-3p and miR-126 binding sites, in the 3' UTR of the construct.
Figure 4B:
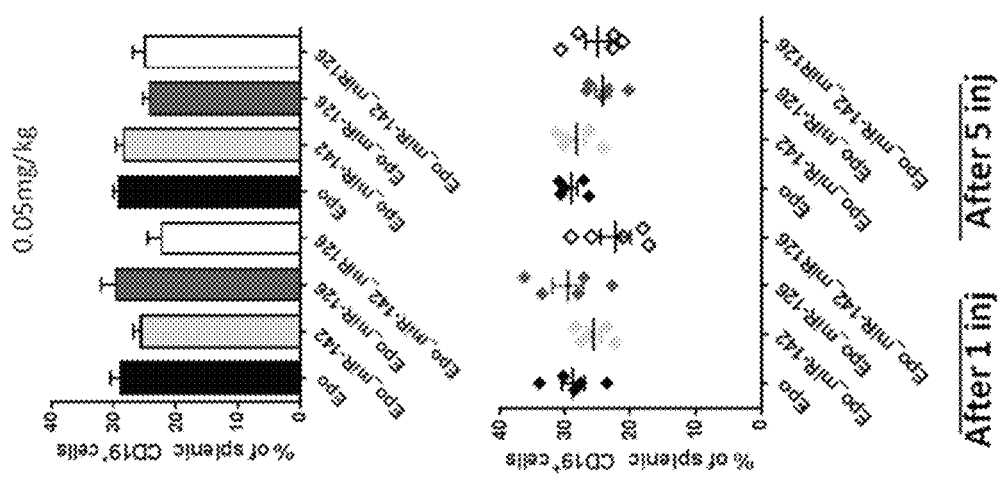
Figure 4C:
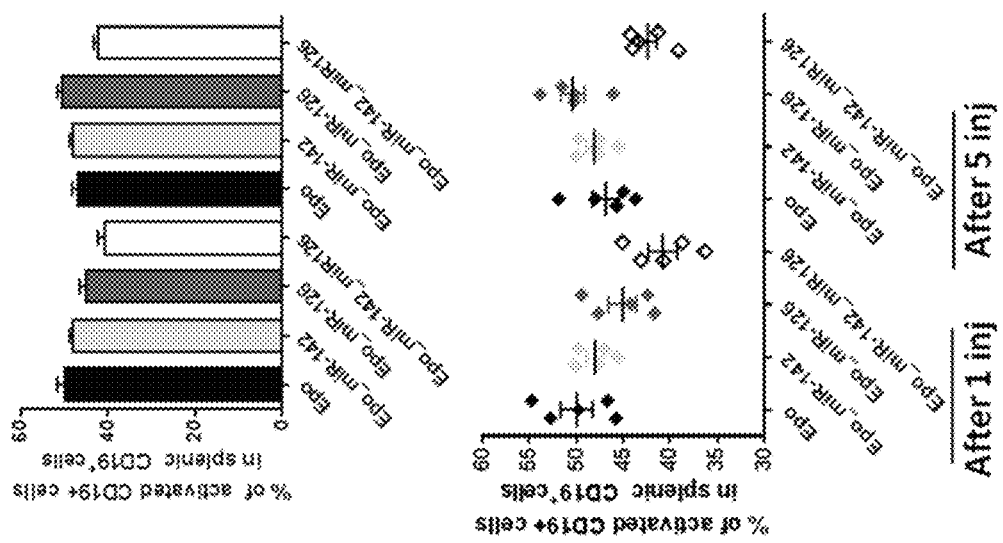

Following treatment, mice were examined for: (i) protein expression from the mmRNA construct by measuring hEpo (in ng/ml), (ii) B cell frequency by measuring % of splenic CD19+ cells, and (iii) activated B cell frequency by measuring % of activated CD19+ cells in splenic CD19+ cells. The results for these three read-outs are shown in FIGS. 4A, B and C, respectively. The results from this initial study demonstrated that there was no noticeable difference in protein expression by inclusion of the miR-142-3p or miR-126 binding sites, alone or in combination, but there was a small but statistically significant decrease in B cell activation observed by inclusion of the miR-126-3p binding site, alone or in combination with the miR-142-3p binding site in the mmRNA constructs.

To study this initial observation further, a second set of experiments was conducted to test the mmRNA constructs at a higher dose (to provide the most sensitivity) and with a higher number of mice per group (to increase the statistical confidence). The dosage regimen was Days 1 and 8. Twelve mice per group were dosed intravenously on Day 1 with either 0.2 mg/kg or 1 mg/kg of one of the four different mmRNA constructs described above (hEpo: hEpo+miR-142-3p: hEPO+miR-126-3p: or hEpo+miR-142-3p/miR-126-3p), formulated in the MC3 LNP. At six hours post-dosing on Day 1, serum was collected for analysis of protein level expression by Epo ELISA. Also, at six hours post-dosing on Day 1, spleens were harvested from six of the mice for B cell analysis. The remaining six mice per group were dosed again on Day 8, followed by serum collection and spleen harvesting at 6 hours post-dosing for further analysis.

Figure 5A:
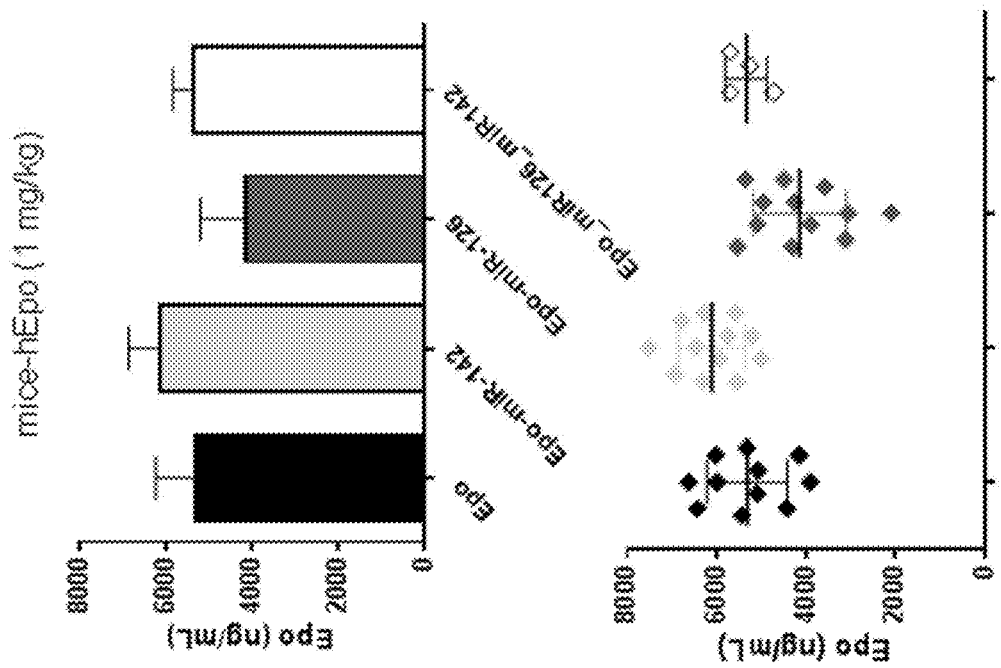
FIGS. 5A-B are graphs showing protein expression levels for mice treated with a single dose of 0.2 mg/kg (FIG. 5A) or 1 mg/kg (FIG. 5B) of mmRNA encoding hEPO either lacking or containing a miR-142-3p binding site, a miR-126 binding site, or both the miR-142-3p and miR-126 binding sites, in the 3' UTR of the construct.
Figure 5B:
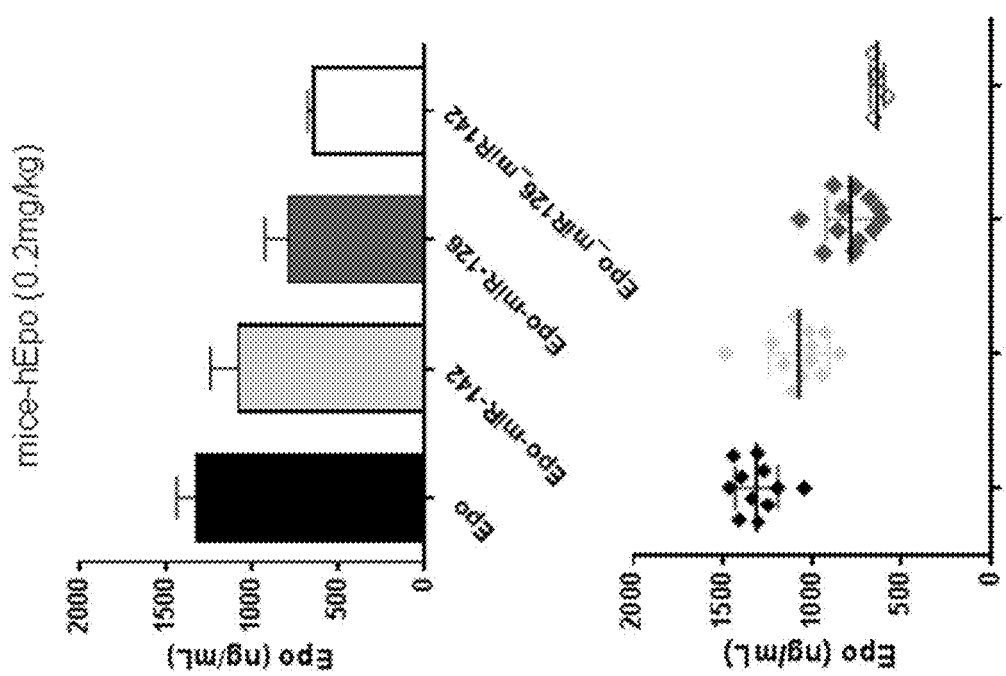
Figures 6A, 6B:
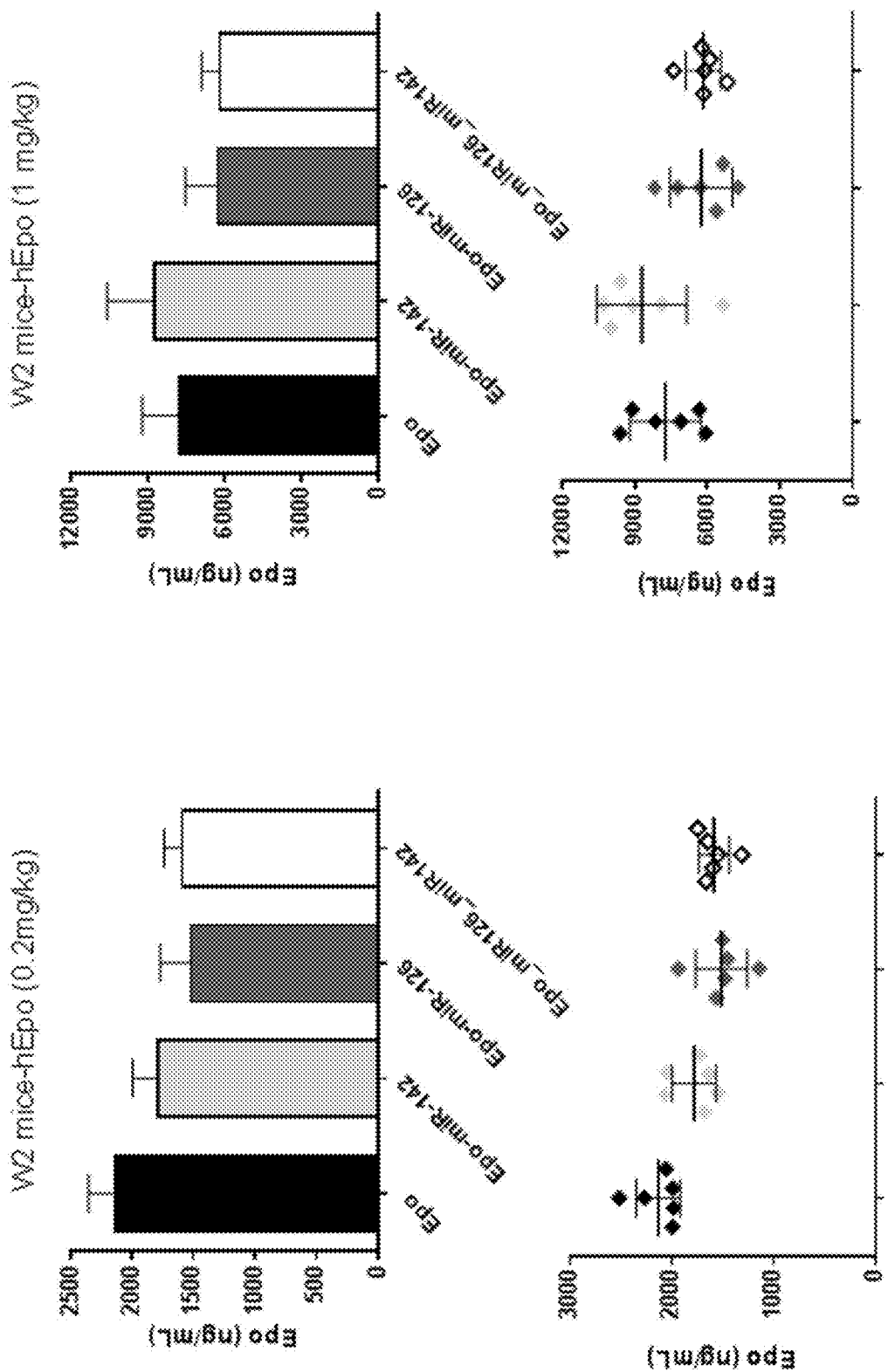
FIGS. 6A-B are graphs showing protein expression levels for mice treated with two doses of 0.2 mg/kg (FIG. 6A) or 1 mg/kg (FIG. 6B) of mmRNA encoding hEPO either lacking or containing a miR-142-3p binding site, a miR-126 binding site, or both the miR-142-3p and miR-126 binding sites, in the 3' UTR of the construct.
Figure 29:
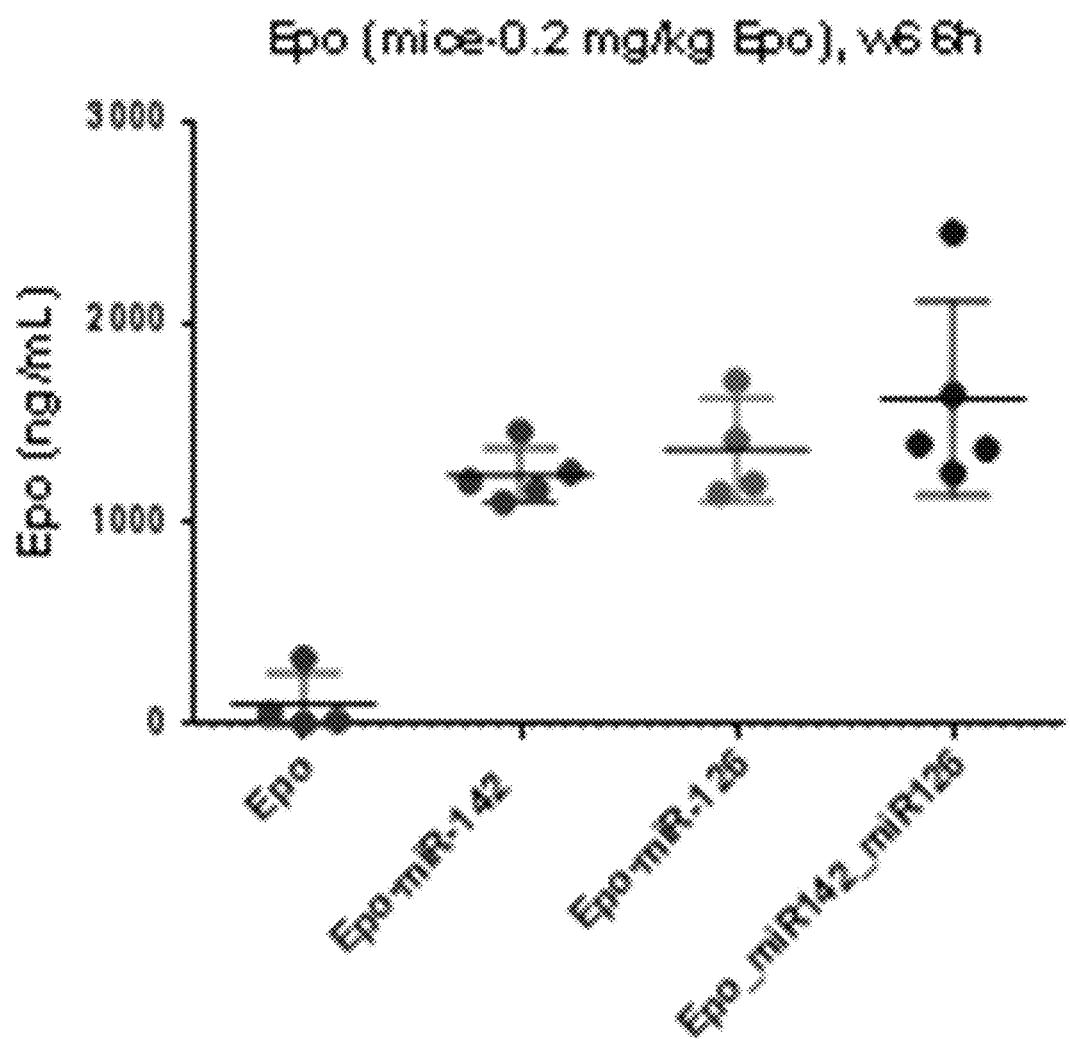
FIG. 29 is a graph showing EPO expression levels in the serum of mice treated for 6 weeks with 0.2 mg/kg mmRNA encoding EPO either lacking or containing a miR-142-3p binding site, a miR-126 binding site, or both the miR-142-3p and miR-126 binding sites, in the 3' UTR of the construct.

The results for the protein expression are shown in FIGS. 5A-B (for one dose, at either 0.2 mg/kg in FIG. 5A or 1 mg/kg in FIG. 5B) and FIGS. 6A-B (for two doses, at either 0.2 mg/kg for FIG. 6A or 1 mg/kg for FIG. 6B). The results demonstrated that the level of expression of the protein of interest encoded by the mmRNA construct is not significantly affected by the inclusion of the miR binding site(s) (miR-142-3p, miR-126-3p or both) in the construct. Protein expression was further monitored through week 6 of the study. Expression was reduced by week 4 and expression at week 5 was reduced almost to baseline (data not shown). At week 6, almost all mice in the control group lacked expression whereas inclusion of the miR binding site(s) in the mRNA construct (miR-142-3p, miR-126-3p or both) maintained significant levels of expression (FIG. 29).

Figure 8:
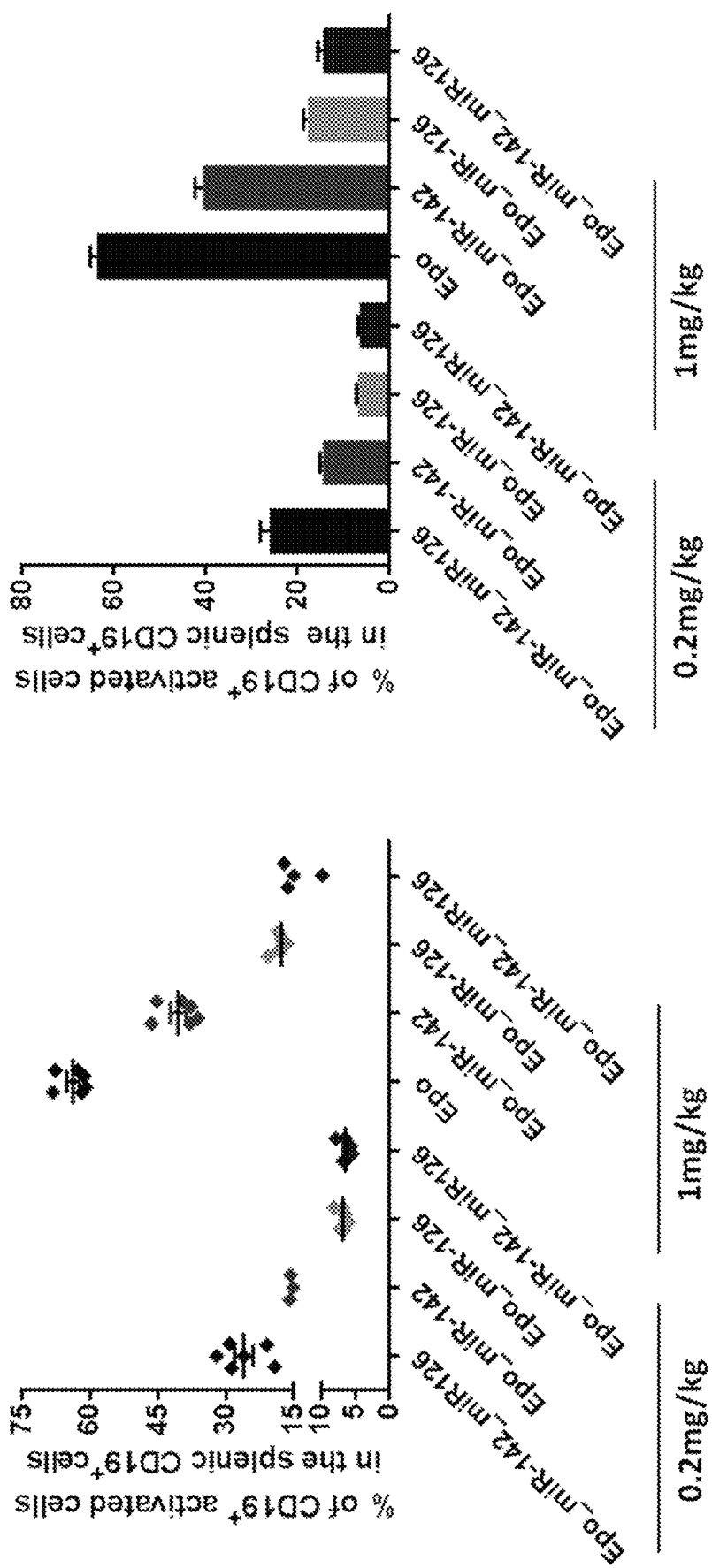
FIG. 8 are graphs showing activated B cell frequency of mice treated with a single indicated dose (0.2 mg/kg or 1 mg/kg) of mmRNA encoding hEPO either lacking or containing a miR-142-3p binding site, a miR-126 binding site, or both the miR-142-3p and miR-126 binding sites, in the 3' UTR of the construct.

The results for the B cell frequency and the activated B cell frequency for the single dose treatment are shown in FIGS. 7 and 8, respectively. The results for the B cell frequency and the activated B cell frequency for the two dose treatment are shown in FIGS. 9 and 10, respectively. These results showed that overall B cell frequency was not significantly affected by the inclusion of the miRs in the mmRNA constructs, but that B cell activation is slightly decreased in the presence of the miR-142-3p binding site and significantly reduced by the presence of the miR-126-3p binding site (alone or in combination with the miR-142-3p binding site). B cell frequency and activated B cell frequency were measured weekly through week 6 of the study and similar results were observed throughout the course of the study, with total B cell frequencies not being significantly affected by inclusion of the miR binding site(s) but with activated B cell frequencies being inhibited by the presence of either the miR-142-3p or miR-126-3p binding site alone, or both miR binding sites in combination.

Figure 11B:
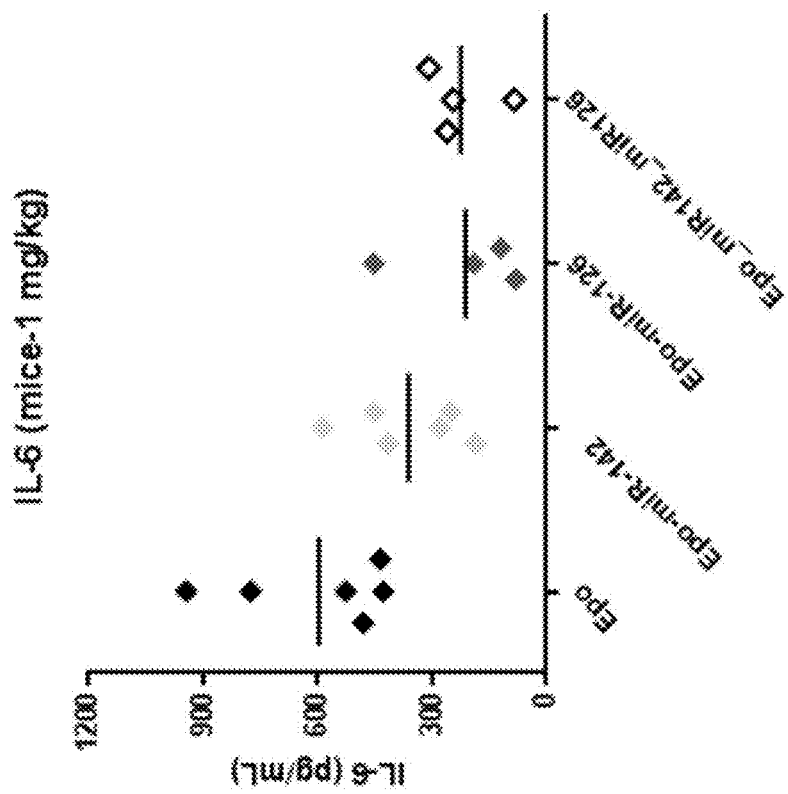
FIGS. 11A-B are graphs showing IL-6 levels in mice treated with a single dose of 0.2 mg/kg (FIG. 11A) or 1 mg/kg (FIG. 11B) of mmRNA encoding hEPO either lacking or containing a miR-142-3p binding site, a miR-126 binding site, or both the miR-142-3p and miR-126 binding sites, in the 3' UTR of the construct.
Figure 11A:
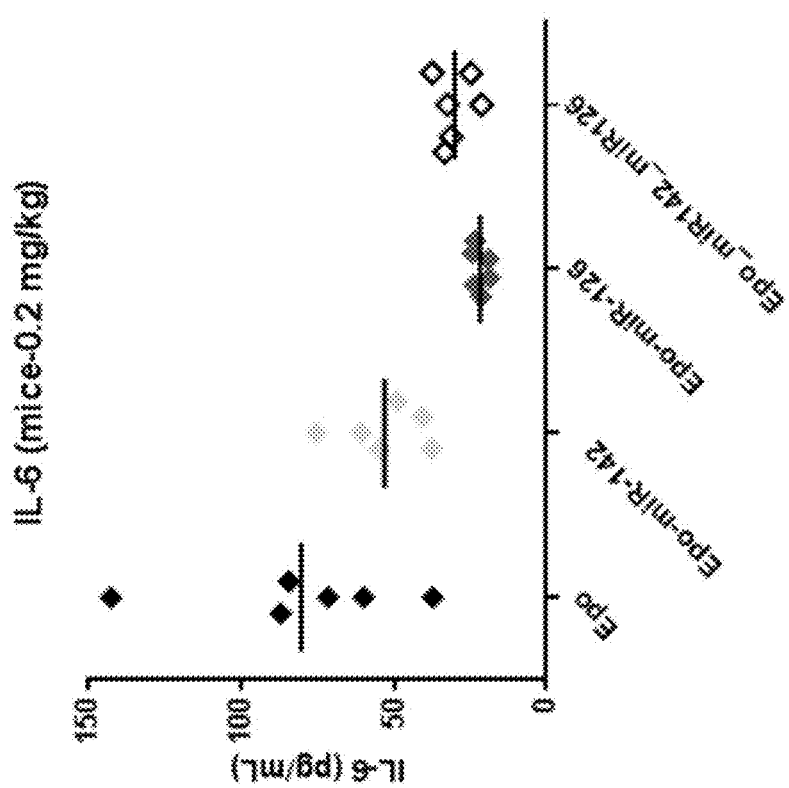
Figures 12A, 12B:
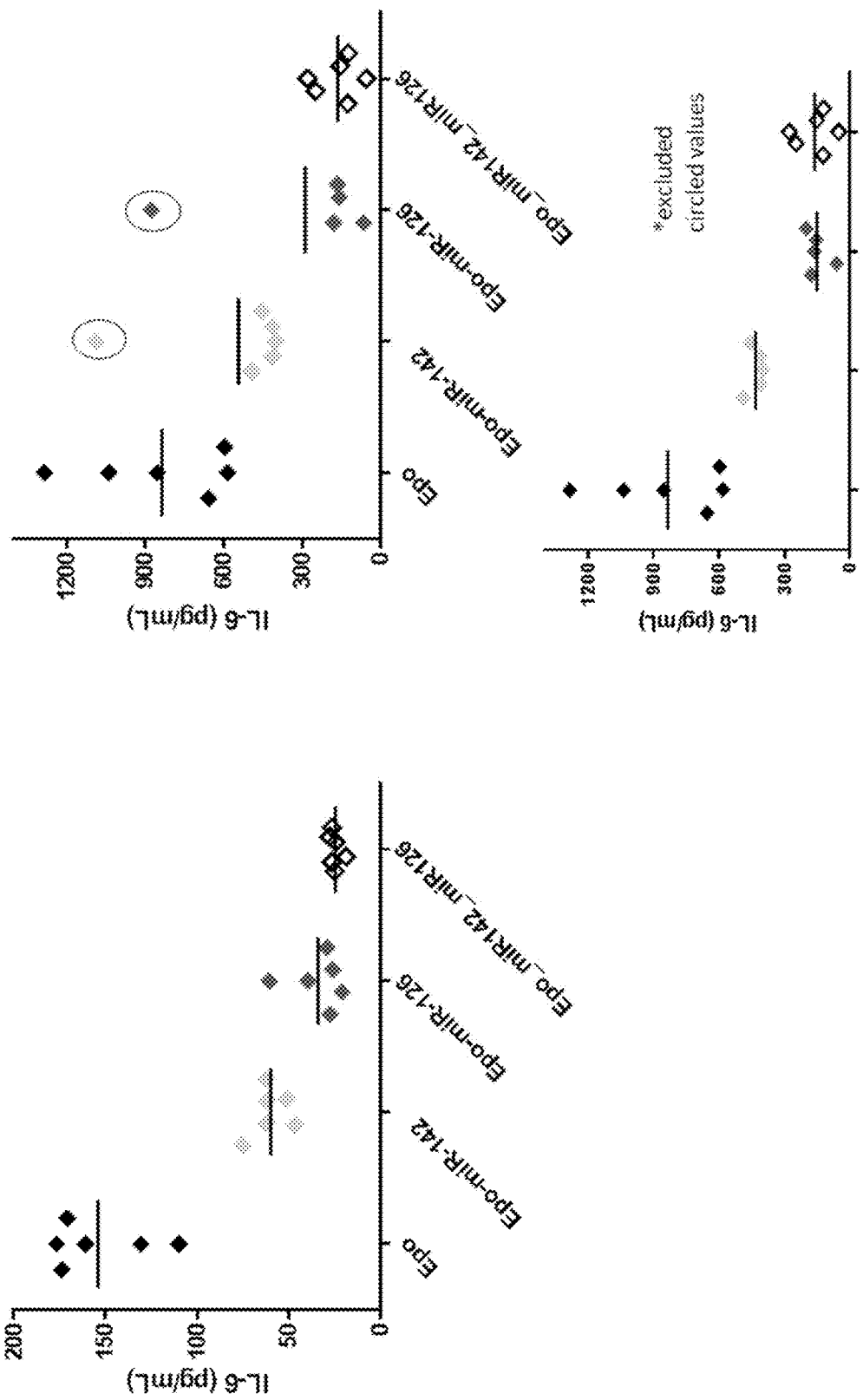
FIGS. 12A-B are graphs showing IL-6 levels in mice treated with two doses of 0.2 mg/kg (FIG. 12A) or 1 mg/kg (FIG. 12B) of mmRNA encoding hEPO either lacking or containing a miR-142-3p binding site, a miR-126 binding site, or both the miR-142-3p and miR-126 binding sites, in the 3' UTR of the construct.

The results for IL-6 expression for the mice treated with one dose are shown in FIGS. 11A-B (0.2 mg/kg for FIG. 11A and 1 mg/kg for FIG. 11B) and for mice treated with two doses are shown in FIGS. 12A-B (0.2 mg/kg for FIG. 12A and 1 mg/kg for FIG. 12B). These results demonstrate that IL-6 expression is decreased in the presence of the miR-142-3p binding site and reduced even further by the presence of the miR-126-3p binding site (alone or in combination with the miR-142-3p binding site).

Figure 13A:
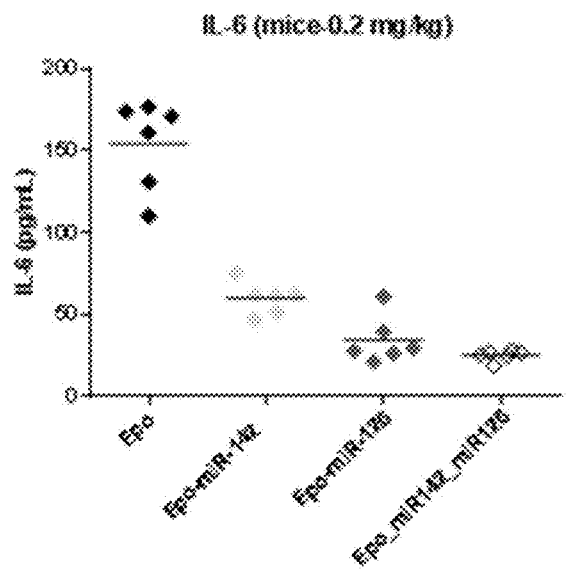
FIGS. 13A-C are graphs showing IL-6 levels (FIG. 13A), TNF-α levels (FIG. 13B) and IFN-γ levels (FIG. 13C) in mice treated with two doses of 0.2 mg/kg mmRNA encoding hEPO either lacking or containing a miR-142-3p binding site, a miR-126 binding site, or both the miR-142-3p and miR-126 binding sites, in the 3' UTR of the construct.
Figure 13B:
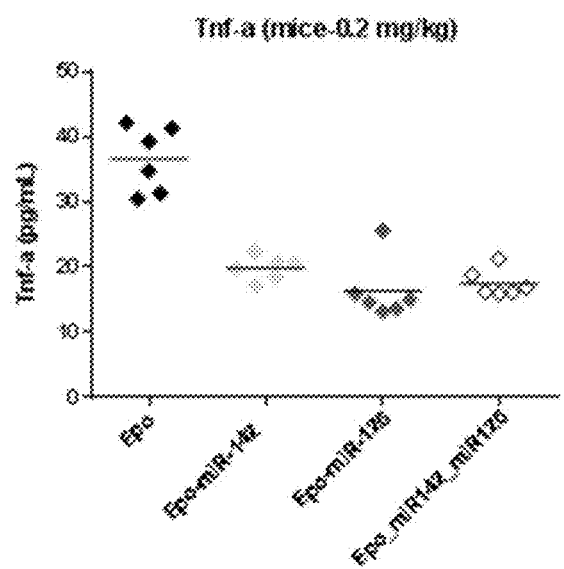
Figure 13C:
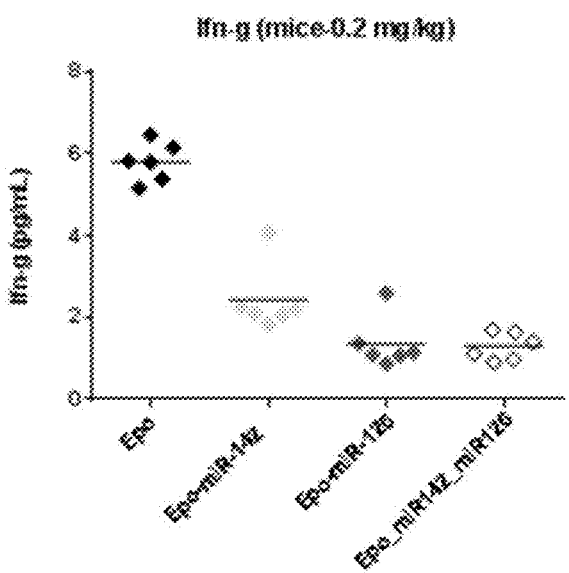
Figures 14A, 14B, 14C:
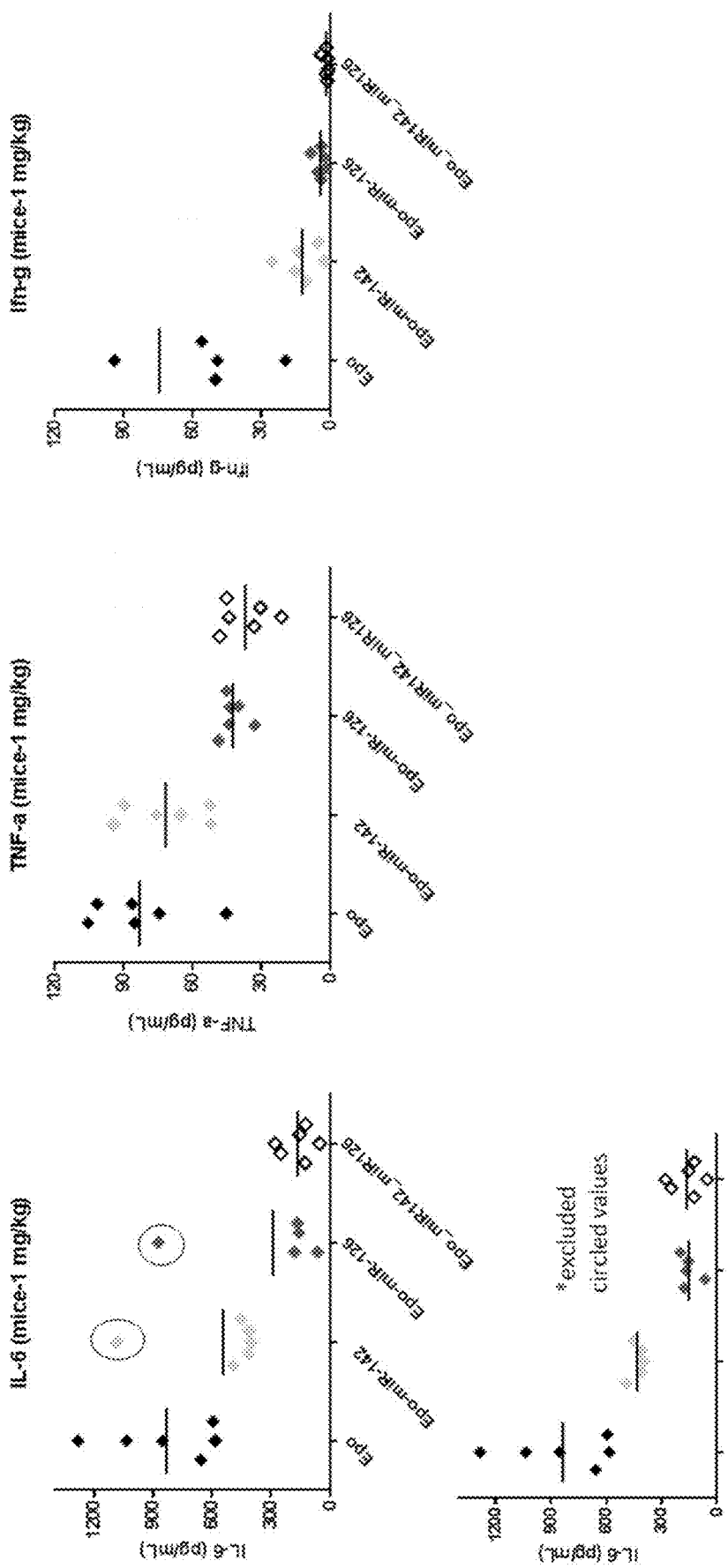
FIGS. 14A-C are graphs showing IL-6 levels (FIG. 14A), TNF-α levels (FIG. 14B) and IFN-γ levels (FIG. 14C) in mice treated with two doses of 1 mg/kg mmRNA encoding hEPO either lacking or containing a miR-142-3p binding site, a miR-126 binding site, or both the miR-142-3p and miR-126 binding sites, in the 3' UTR of the construct.

Cytokine expression was further examined by measuring TNF-$\alpha$ and IFN-$\gamma$ levels as well as IL-6 levels. The results for these three cytokines for mice treated with two doses at 0.2 mg/kg are shown in FIGS. 13A (IL-6), 13B (TNF-$\alpha$) and 13C (IFN-$\gamma$) and for mice treated with two doses at 1 mg/kg are shown in FIGS. 14A (IL-6), 14B (TNF-$\alpha$) and 14C (IFN-$\gamma$). These results demonstrate that expression of all three cytokines (IL-6, TNF-$\alpha$ and IFN-$\gamma$) is decreased in the presence of the miR-142-3p binding site and reduced even further by the presence of the miR-126-3p binding site (alone or in combination with the miR-142-3p binding site).

Cytokine expression was further monitored weekly through week 6 of the study, which demonstrated that levels of all three cytokines in the serum, IL-6, IFN-$\gamma$ and TNF-$\alpha$, were significantly inhibited by the presence of either the miR-142-3p or miR-126-3p binding site alone, or both miR binding sites in combination, in the mRNA construct.

Thus, the studies described above demonstrate that incorporation into an mRNA construct of a miR-126-3p binding site, a miR-142-3p binding site or both miR binding sites in combination, results in a reduced frequency of B cell activation and in reduced secretion of a panel of different immune-stimulating cytokines (IL-6, TNF-$\alpha$, IFN-$\gamma$) in vivo in animals treated with the mRNA construct, while having a minimal impact on the expression of a protein of interest encoded by the mRNA construct in the treated animal.

Example 4: Additional Studies Incorporating miR-126 and/or miR-142 Binding Sites into mmRNA Constructs In this example, luciferase-encoding mmRNA constructs were prepared that incorporated either a miR-142-3p binding site or a miR-126-3p binding site, or both the miR-142-3p and miR-126-3p binding sites, into the 3' UTR of the construct. The mmRNA constructs were administered to mice to examine the effects of incorporating the miR binding sites on various immune parameters in the mice. The mmRNA constructs contained a Cap 1 5' Cap structure (7mG(5')ppp(5')NlmpNp), were fully modified with 5-methylcytosine and 1-methylpseudouridine and comprised a 100 nucleotide poly A tail. The control mmRNA construct lacked the presence of any known miR binding sites. The mmRNA constructs encoding luciferase (Luc) were formulated into MC3 lipid nanoparticles (LNP), which include MC3 50%, DSPC 10%, Cholesterol 38.5%, PEG-DMG 1.5%, N: P~5.5. (Values are based on mol. %).

In an initial study, groups of 24 mice each were assigned to the following treatment groups: (i) Luciferase (Luc) construct without any miR binding sites (the sequence of which is shown in SEQ ID NO: 30): (ii) Luc construct with miR-142-3p binding site (the sequence of which is shown in SEQ ID NO: 31): (iii) Luc construct with miR-126-3p binding site (the sequence of which is shown in SEQ ID NO: 32); and (iv) Luc construct with miR-142-3p and miR-126-3p binding sites (the sequence of which is shown in SEQ ID NO: 33). The mmRNAs were administered intravenously to C57Bl/6 mice at a dose of 0.2 mg/kg. In each group, 15 mice were selected to be dosed on days 1, 8, 15, 22, 29 and 36, 3 mice were dosed only once on Day 22, and 3 mice were dosed only once on Day 36. From the 15 mice selected for repeat dosing, 5 each were sacrificed for spleen collection 6h after dose on Day 1, 6h after dose on Day 22 and 6h after dose on Day 36.

Following treatment, mice were examined for: (i) luciferase expression from the mmRNA construct by measuring whole body luminescence: (ii) B cell frequency by measuring % of splenic CD19+ cells: (iii) activated B cell frequency by measuring % of activated CD19+ cells in splenic CD19+ cells; and (iv) cytokine production (IL-6, IFN-γ, TNF-α).

Figure 30:
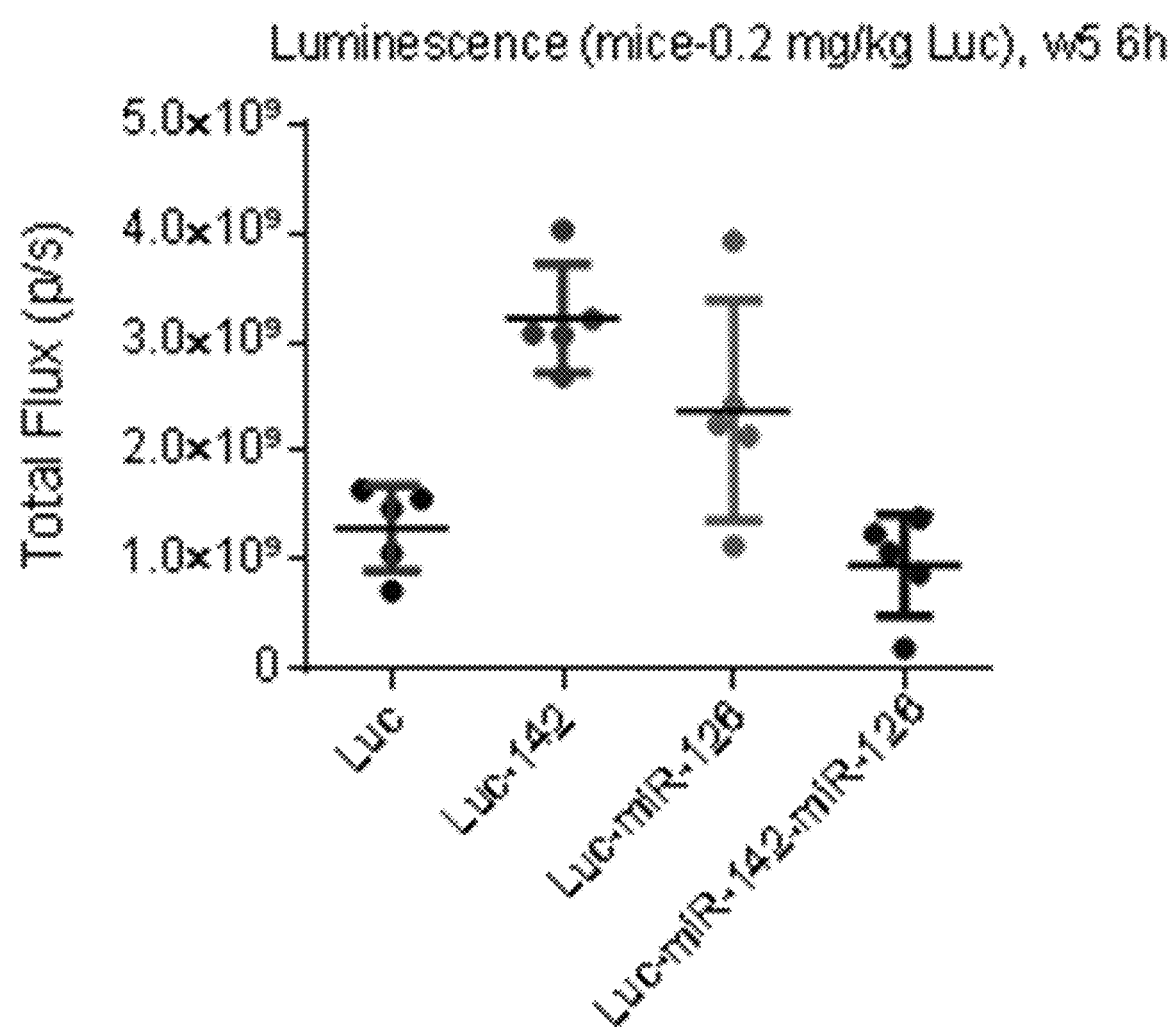
FIG. 30 is a graph showing Luciferase (Luc) expression levels in the serum of mice treated for 5 weeks with 0.2 mg/kg mmRNA encoding Luc either lacking or containing a miR-142-3p binding site, a miR-126 binding site, or both the miR-142-3p and miR-126 binding sites, in the 3' UTR of the construct.
Figure 32A:
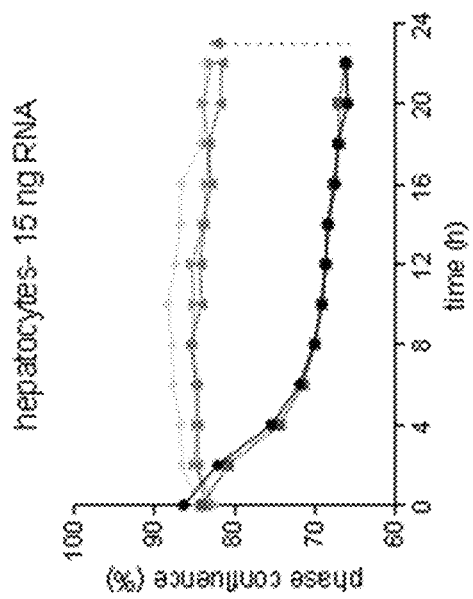
FIGS. 32A-D are graphs showing the percent phase confluence (as a measure of caspase-mediated toxicity) of primary hepatocytes transfected with caspase mRNA constructs containing either no recognizable miR sites (control), 1× or 3× miR-122 binding sites or a putative mRNA with a caspase-like sequence (control) with no start codon, at doses of 7.5 ng (FIG. 32A), 15 ng (FIG. 32B), 50 ng (FIG. 32C) or 100 ng (FIG. 32D).
Figure 32B:
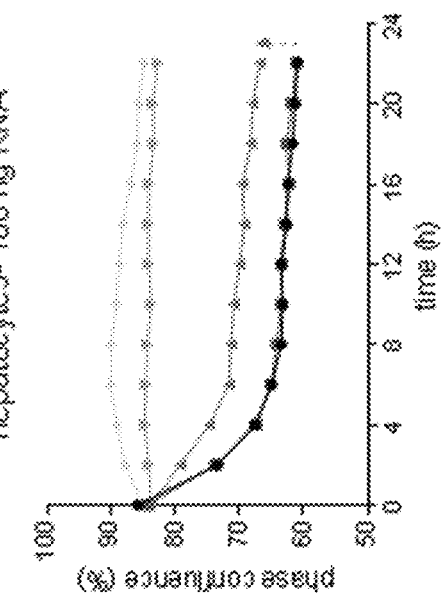
Figure 32C:
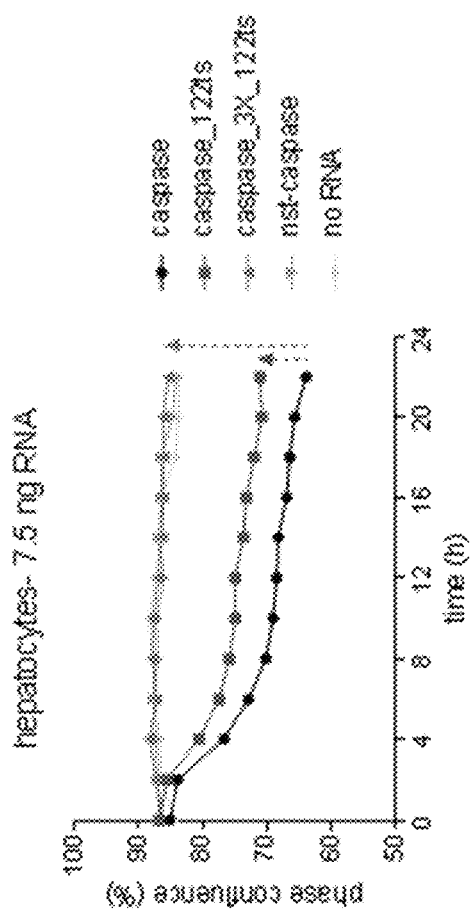
Figure 32D:
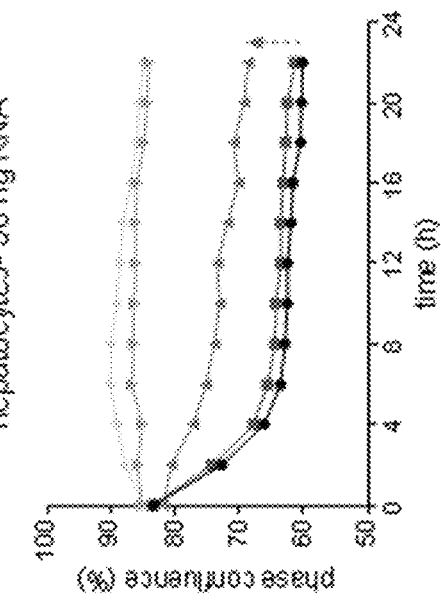

The results for the Luciferase expression are shown in FIGS. 15A and 15B. FIG. 15A shows results after 1 week (1 dose) and FIG. 15B shows results after 2 weeks (or 2 doses). The levels of Luc were much more variable that the hEPO levels discussed in Example 1. However, the results demonstrated that the level of expression of the protein of interest (Luc) encoded by the mmRNA construct is not significantly affected by the inclusion of the miR binding site(s) (miR-142-3p, miR-126-3p or both) in the construct. Protein expression was further monitored through week 6 of the study. Lucierfase expression showed modest to no change through the 6 weeks. FIG. 30 shows expression at week 5.

The results for the B cell frequency and the activated B cell frequency are shown in FIGS. 16 and 17, respectively. The results shown are at week 1 (1 dose). These results showed that overall total B cell frequency was not significantly affected by the inclusion of the miR binding site(s) in the Luc mmRNA constructs, but that frequency of activated B cells is slightly decreased in the presence of the miR-142-3p binding site and significantly reduced by the presence of the miR-126-3p binding site (alone or in combination with the miR-142-3p binding site). The reduced activated B cell frequency was not due to reduced numbers of CD19+ cells as (i) we measured the percentage of activated B cells inside the total B cell population, and (ii) the B cell frequencies did not fluctuate between groups. B cell frequency and activated B cell frequency were measured weekly through week 6 of the study and similar results were observed throughout the course of the study, with total B cell frequencies not being significantly affected by inclusion of the miR binding site(s) but with activated B cell frequencies being inhibited by the presence of either the miR-142-3p or miR-126-3p binding site alone, or both miR binding sites in combination.

Figure 18B:
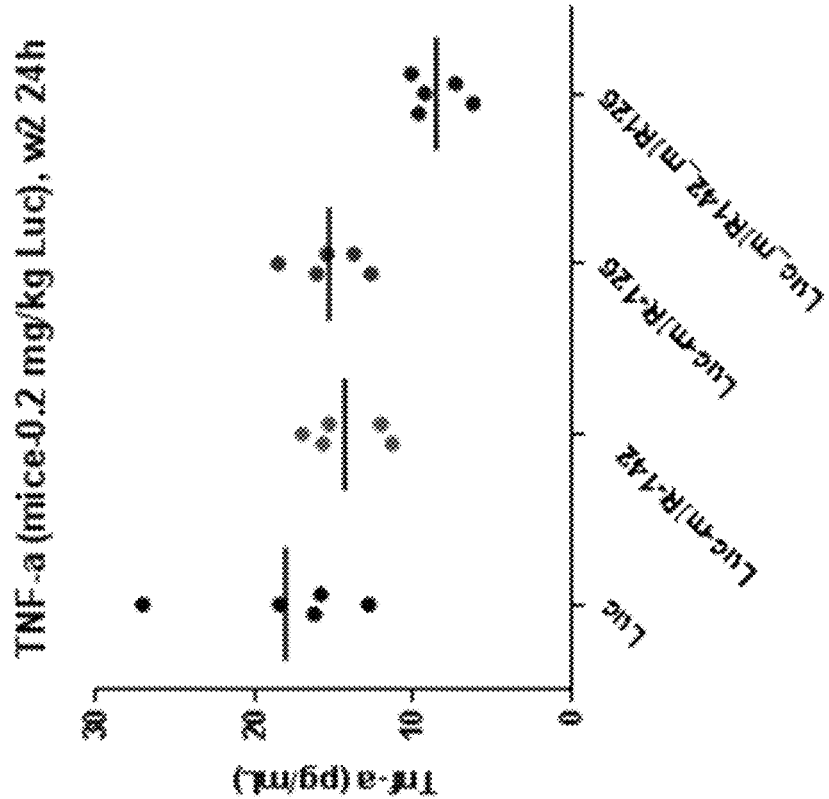
FIGS. 18A-C are graphs showing secreted IL-6 levels (FIG. 18A), TNF-α levels (FIG. 18B) and IFN-γ levels (FIG. 18C) in mice treated with 0.2 mg/kg mmRNA encoding Luc either lacking or containing a miR-142-3p binding site, a miR-126 binding site, or both the miR-142-3p and miR-126 binding sites, in the 3' UTR of the construct.
Figure 18A:
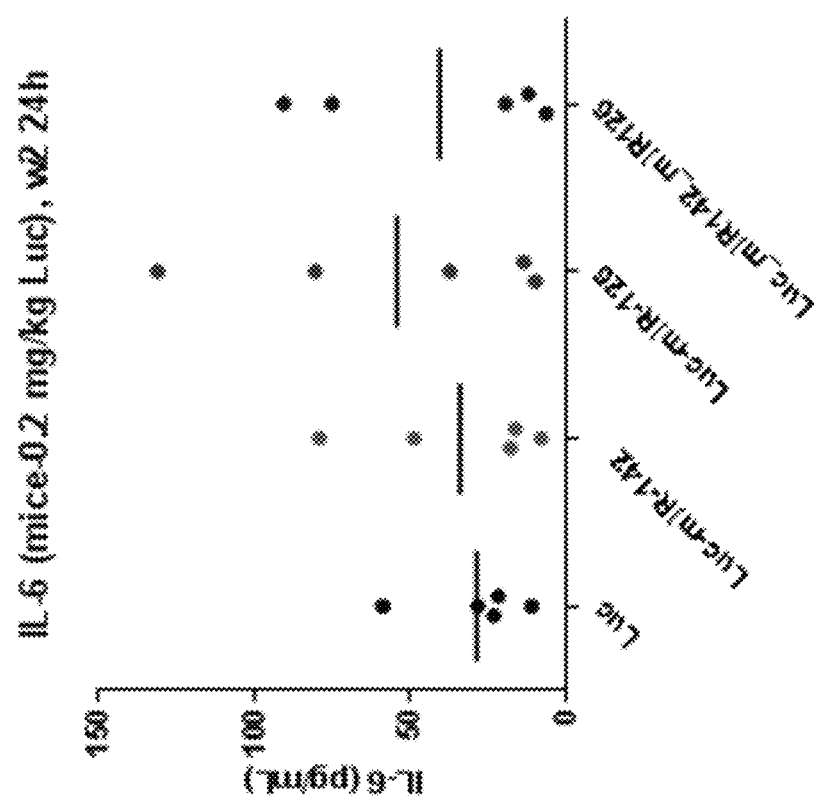
Figure 18C:
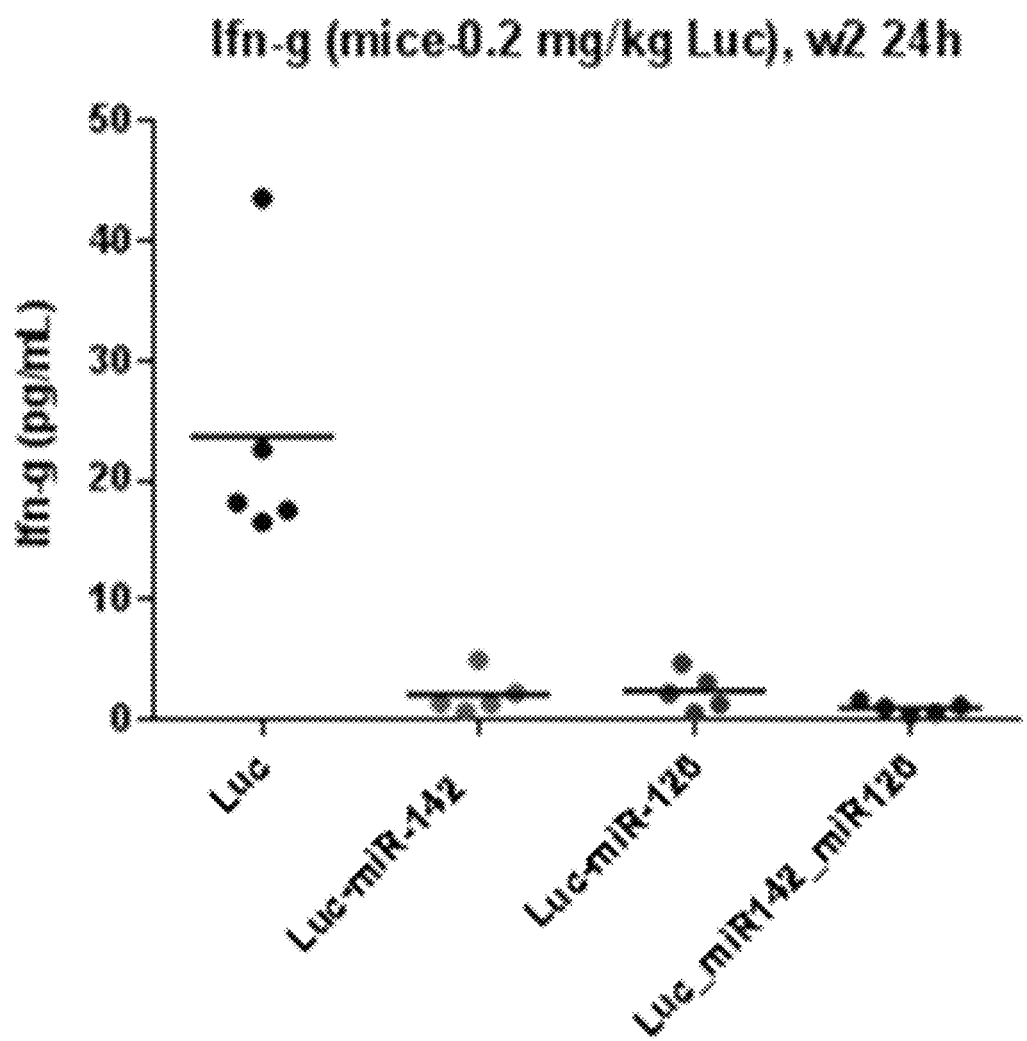

Cytokine expression was examined by measuring IL-6, IFN-γ and TNF-α levels in serum. The results for these three cytokines for mice treated with 0.2 mg/kg mmRNA are shown in FIGS. 18A (IL-6), 18B (IFN-γ) and 18C (TNF-α). The results shown are for week 2: similar results were observed at week 1 and week 3. Again, more variability in cytokine expression was observed in the Luc treated animals as compared to the hEPO treated animals described in Example 1. However, these results demonstrate that expression of at least some cytokines (most markedly with IFN-γ and TNF-α) is decreased in the presence of the miR-142-3p binding site and/or the miR-126-3p binding site, alone or in combination. Cytokine expression was further monitored through week 6 of the study, which demonstrated that levels of all three cytokines in the serum, IL-6, IFN-γ and TNF-α, were significantly inhibited by the presence of either the miR-142-3p or miR-126-3p binding site alone, or both miR binding sites in combination, in the mRNA construct.

Thus, the studies described above demonstrate that incorporation into an mRNA construct of a miR-126-3p binding site, a miR-142-3p binding site or both miR binding sites in combination, results in a reduced frequency of B cell activation and in reduced secretion of a panel of different immune-stimulating cytokines (TNF-α, IFN-γ) in vivo in animals treated with the mRNA construct, while having a minimal impact on the expression of a protein of interest encoded by the mRNA construct in the treated animal.

Example 5: Additional Studies Incorporating miR-142 and/or miR-155 Binding Sites into mmRNA Constructs In this example, EPO-encoding mmRNA constructs were prepared that incorporated a miR-142-3p binding site, a miR-142-5p binding site, a miR-155-5p binding site, or combinations thereof, and/or multiple copies thereof, into the 3' UTR of the construct. The miR-155-5p sequence upon which the binding site insertion was designed is as follows: uuaaugcuaauugugauaggggu (SEQ ID NO: 34). The miR-155-5p binding site inserted into the 3' UTR has the sequence as follows: ACCCCTATCACAATTAGCATTAA (SEQ ID NO: 35).

The mmRNA constructs were administered to mice to examine the effects of incorporating the miR binding sites on various immune parameters in the mice. The mmRNA constructs contained a Cap 1 5' Cap structure (7 mG (5')ppp(5') NlmpNp), were fully modified with 5-methylcytosine and 1-methylpseudouridine and comprised a 100 nucleotide poly A tail. The control mmRNA construct lacked the presence of any inserted miR binding sites. The mmRNA constructs encoding EPO were formulated into MC3 lipid nanoparticles (LNP), which include MC3 50%, DSPC 10%, Cholesterol 38.5%, PEG-DMG 1.5%, N: P~5.5. (Values are based on mol. %).

In this study, mice were assigned to one of the following treatment groups: (i) EPO construct without any miR binding sites (the sequence of which is shown in SEQ ID NO: 36): (ii) EPO construct with one miR-142-3p binding site (the sequence of which is shown in SEQ ID NO: 37); (iii) EPO construct with three miR-142-3p binding sites (EPO_3X-miR-142-3p) (the sequence of which is shown in SEQ ID NO: 38): (iv) EPO construct with one miR-142-5p binding site (the sequence of which is shown in SEQ ID NO: 39): (v) EPO construct with three miR-142-5p binding sites (EPO_3X-miR-142-5p) (the sequence of which is shown in SEQ ID NO: 40): (vi) EPO construct with two miR-142-5p binding sites and one miR-142-3p binding sites (EPO_2X-miR-142-5p_1X-miR-142-3p) (the sequence of which is shown in SEQ ID NO: 41): (vii) EPO construct with one miR-155-5p binding site (the sequence of which is shown in SEQ ID NO: 42): (viii) EPO construct with three miR-155-5p binding sites (EPO_3X-miR-155) (the sequence of which is shown in SEQ ID NO: 43): (ix) EPO construct with two miR-155-5p binding sites and one miR-142-3p binding sites (EPO_2X-miR-155-5p_1X-miR-142-3p) (the sequence of which is shown in SEQ ID NO: 44); and (x) LNP with non-translating control sequence ("empty"). The mmRNAs were administered intravenously to C57Bl/6 mice at a dose of 0.2 mg/kg. The dosing regimen was Days 1 and 8.

Following treatment, mice were examined for: (i) protein expression from the mmRNA construct by measuring levels of the encoded EPO (in ng/ml): (ii) total B cell frequency by measuring % of splenic CD19$^+$ cells: (iii) activated B cell frequency by measuring % of activated CD19$^+$ cells in splenic CD19$^+$ cells; and (iv) cytokine production (IL-6, IFN-$\gamma$, TNF-$\alpha$).

The results for the EPO protein expression are shown in FIGS. 19A-B, with FIG. 19A showing the results at week 1 and FIG. 19B showing the results for week 2. The results demonstrated that the level of expression of the protein of interest (EPO) encoded by the mmRNA construct is not significantly affected by the inclusion of the miR binding site(s) (miR-142-3p, miR-142-5p, miR-155-5p or multiple copies and/or combinations thereof) in the construct.

Figure 23:
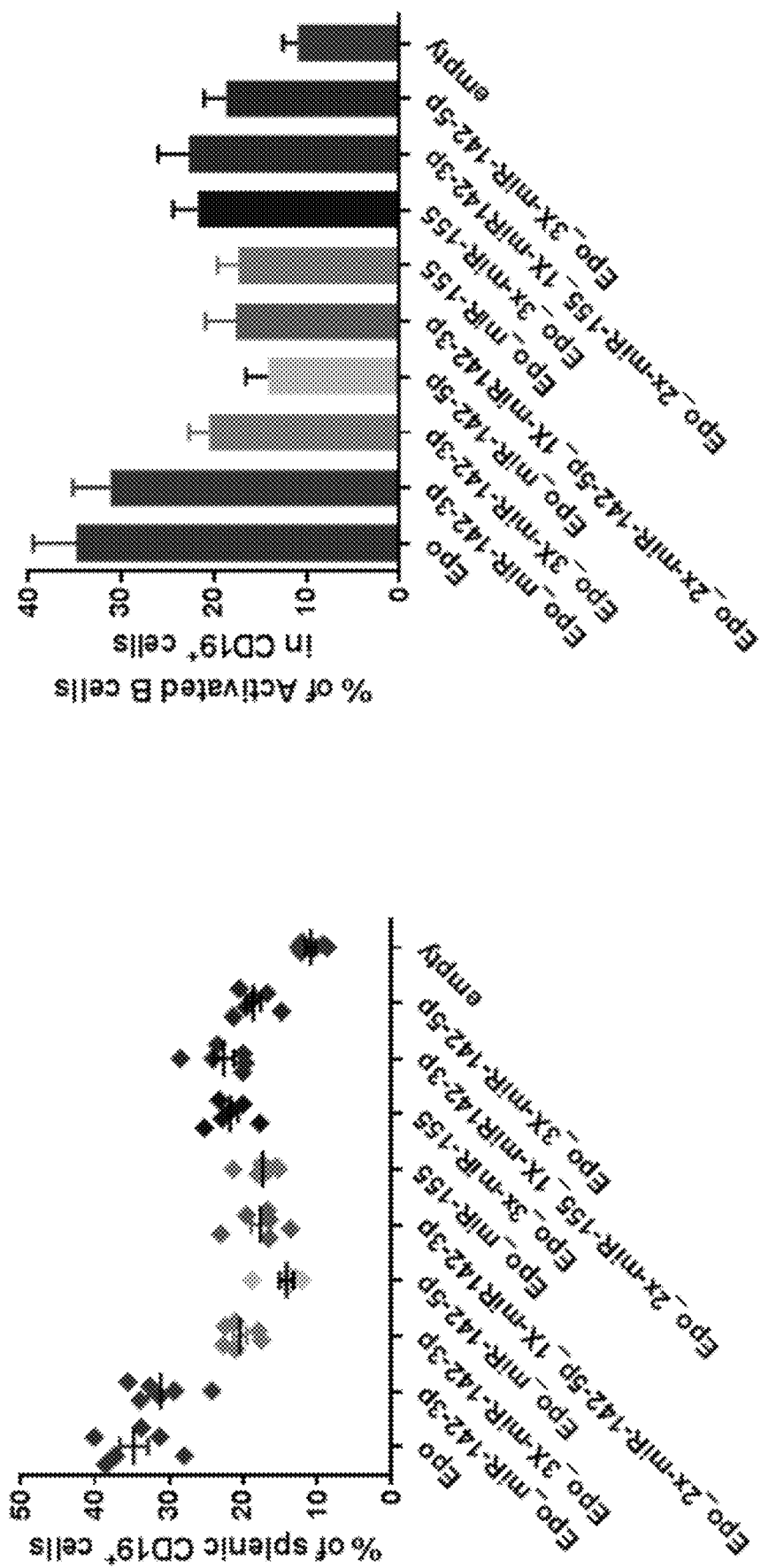
FIG. 23 are graphs showing activated B cell frequency in mice treated for 2 weeks with 0.2 mg/kg mmRNA encoding EPO either lacking or containing a miR-142-3p binding site, a miR-142-5p binding site, a miR-155-5p binding site, or multiple copies or combinations thereof.

The results for the B cell frequency and the activated B cell frequency are shown in FIGS. 20 and 21, respectively, for week 1, and FIGS. 22 and 23, respectively, for week 2. These results showed that overall total B cell frequency was not significantly affected by the inclusion of the miRs in the EPO mmRNA constructs, but that the frequency of activated B cells is decreased in the presence of the miR-142-3p binding site, the miR-142-5p binding site, the miR-155-5p binding site, or multiple copies thereof and/or combinations thereof.

Cytokine expression was examined by measuring IL-6, TNF-$\alpha$ and IFN-$\gamma$ levels in the serum. The results for these three cytokines for mice treated with 0.2 mg/kg mmRNA are shown in FIGS. 24A (IL-6), 24B (TNF-$\alpha$) and 24C (IFN-$\gamma$). The results shown are for week 2. Variability in cytokine expression was observed in the EPO treated animals. However, these results demonstrate that expression of at least some cytokines is decreased in the presence of the miR-142-3p binding site, the miR-142-5p binding site, the miR-155-5p binding site, or multiple copies thereof and/or combinations thereof.

Thus, the studies described above demonstrate that incorporation into an mRNA construct of a miR-142-3p binding site, a miR-142-5p binding site, a miR-155-5p binding site, or multiple copies thereof and/or combinations thereof, results in a reduced frequency of B cell activation and in reduced secretion of a panel of different immune-stimulating cytokines in vivo in animals treated with the mRNA construct, while having a minimal impact on the expression of a protein of interest encoded by the mRNA construct in the treated animal.

Example 6: Effect of miR Binding Sites on Particular Immune Cell Populations

In this example, studies were performed to examine the effect of the inclusion in mRNA constructs of a miR binding site expressed in immune cells (miR-142, miR-126 or both miR-142+miR-126) on the frequency and activation of particular immune cell populations. Balb/c mice were treated with mRNA constructs encoding EPO as described above in Example 3, which constructs either lacked miR binding sites or contained either a miR-142-3p binding site, a miR-126-3p binding site or both a miR-142-3p binding site and a miR-126-3p binding site. Mice were treated intravenously on days 1, 8 and 15 with 0.2 mg/kg of mRNA construct formulated into MC3 lipid nanoparticles.

Figure 25A:
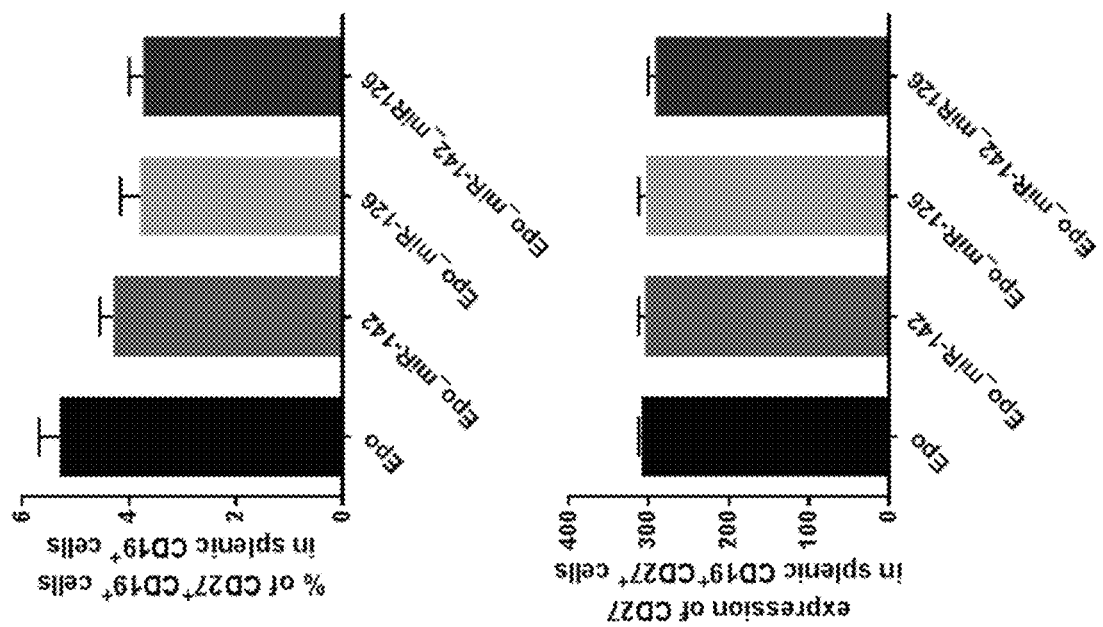
FIGS. 25A-B are graphs showing the percentage of $CD27^+$ $CD19^+$ B cells in splenic $CD19^+$ B cells (FIG. 25A) and the level of CD27 expression in $CD27^+$ $CD19^+$ B cells (FIG. 25B) in mice treated with mmRNA encoding EPO either lacking or containing a miR-142 binding site, a miR-126 binding site or miR-142 and miR-126 binding sites.
Figure 25B:
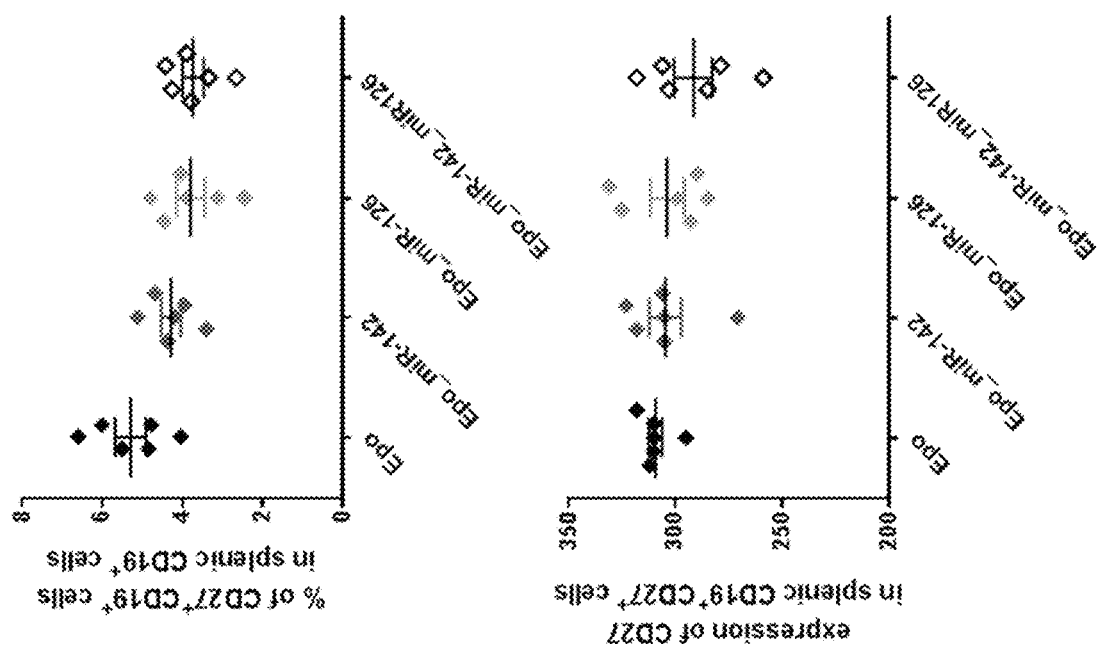

A first set of experiments examined whether the miRs had any effect on the frequency of CD27$^+$ B cells or the level of CD27 expression in these cells. The results are shown in FIGS. 25A-B. FIG. 25A shows the frequency of CD27$^+$ CD19$^+$B cells in splenic CD19$^+$ B cells, demonstrating that the CD27$^+$ B cell population was not affected by the inclusion of the miR binding site(s) in the mRNA constructs. FIG. 25B shows the level of CD27 expression in the CD27$^+$ B cell population and, likewise, shows that this expression was not affected by the inclusion of the miR binding site(s) in the mRNA constructs. Thus, this first set of experiments demonstrated that the effect of the miR binding site(s) in inhibiting B cell activation and/or inhibiting cytokine production was not resulting from the miR binding site(s) affecting either the frequency of CD27$^+$ CD19$^+$B cells or the level of CD27 expression in these cells.

Figure 26A:
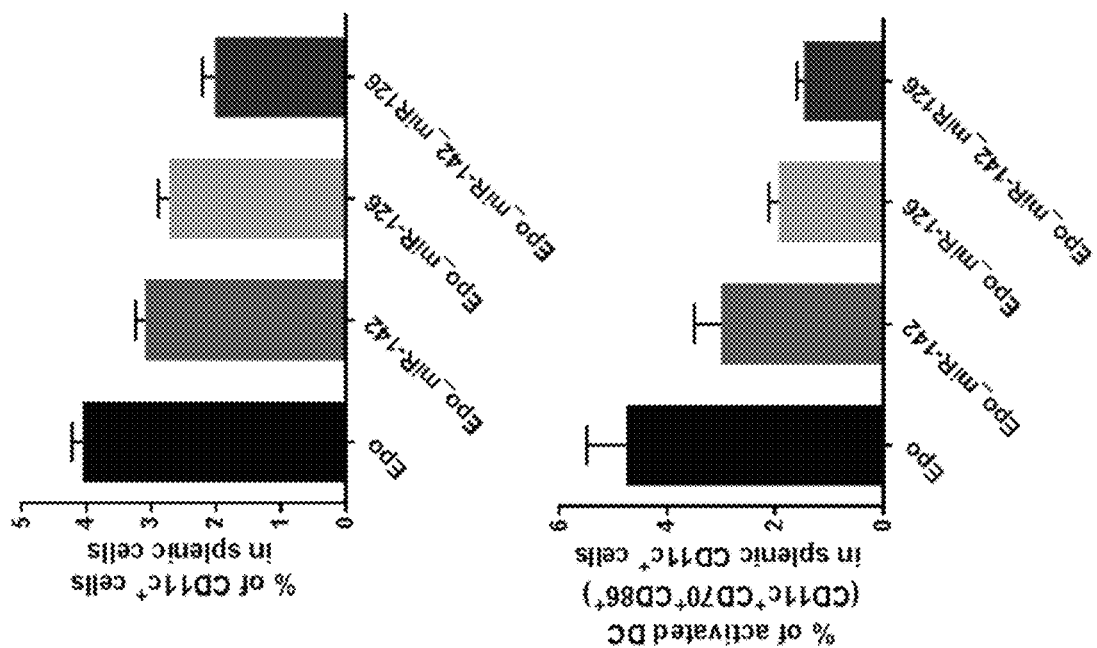
FIGS. 26A-B are graphs showing the total $CD11c^+$ cell frequency in splenic cells (FIG. 26A) and the percentage of activated dendritic cells ($CD11c^+$ $CD70^+$ $CD86^+$ cells) (FIG. 26B) in mice treated with mmRNA encoding EPO either lacking or containing a miR-142 binding site, a miR-126 binding site or miR-142 and miR-126 binding sites.
Figure 26B:
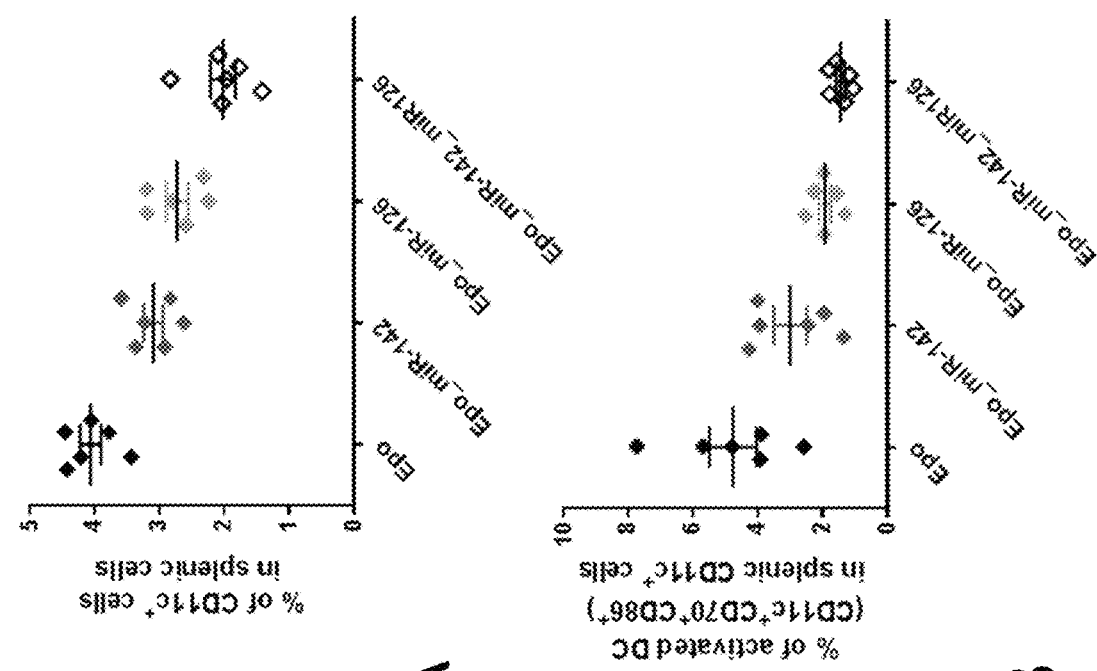

A second set of experiments examined whether the miRs had any effect on the frequency of CD11c$^+$ cells, as a marker of dendritic cells, and/or the frequency of activated dendritic cells (CD11c$^+$CD70$^+$CD86' cells). The results are shown in FIGS. 26A-B. FIG. 26A shows the percentage of CD11c$^+$ cells in splenic cells from the mice, demonstrating that the total frequency of CD11c$^+$ cells was inhibited by the inclusion of the miR-142-3p binding site, the miR-126-3p binding site, or both binding sites, in the mRNA constructs. FIG. 26B shows the frequency of activated dendritic cells (CD11c$^+$CD70+CD86' cells) within the CD11c$^+$ splenic cell population and, likewise, shows that the frequency of activated dendritic cells was inhibited by the inclusion of the miR binding site(s) in the mRNA constructs. Thus, this second set of experiments demonstrated that the inclusion of the miR binding site(s) inhibited both the total frequency of dendritic cells and the frequency of activated dendritic cells, thereby implicating this cell population in the mechanism of how inclusion of the miR binding site(s) leads to inhibition of B cell activation and inhibition of cytokine production. While not intending to be limited by mechanism, these results suggest that in the mice, decreased levels of activated CD70$^+$ dendritic cells leads to decreased interaction with CD27$^+$ B cells, thereby leading to decreased B cell activation and decreased cytokine production.

Figure 27:
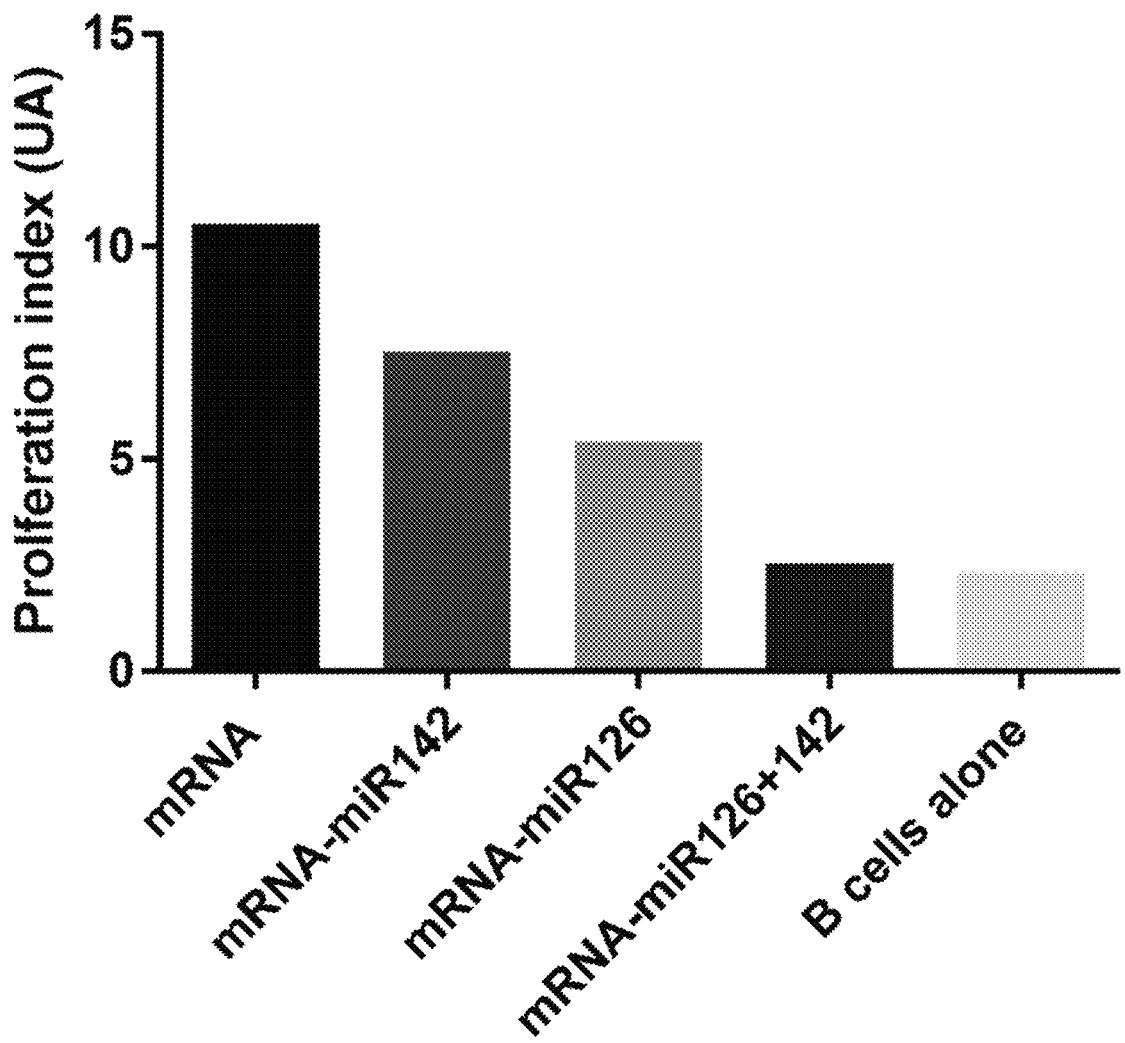
FIG. 27 is a graph showing the level of proliferation of naïve B cells in the presence of plasmacytoid dendritic cells (pDCs) isolated from mice treated with mmRNA encoding EPO either lacking or containing a miR-142 binding site, a miR-126 binding site or miR-142 and miR-126 binding sites.

To further investigate this, a third set of experiments were performed in which the ability of plasmacytoid dendritic cells (pDCs) from the mice to stimulate proliferation of naïve B cells was examined. For these experiments, 2×10$^5$ naïve B cells labeled with CFSE were incubated with 4×10$^4$ pDCs purified from the spleens of mice injected either with hEPO mRNA or hEPO mRNA-miR142, hEPO mRNA-miR126 or hEPO mRNA-miR126+142 in the presence of anti IgM at 10 μg/ml. After 5 days of culture, cells were harvested and analyzed by flow cytometry for CFSE expression. Levels of proliferation of the naïve B cells incubated with the pDCs are shown in the graph of FIG. 27. The results demonstrate that naïve B cells proliferate less in the presence of pDCs from mice treated with the mRNA constructs including the miR-142 binding site, the miR-126 binding site or both binding sites. These experiments further support the mechanism that in mice treated with the miR-containing constructs, decreased levels of activated pDCs leads to decreased B cell stimulation, thereby leading to inhibition of B cell activation and inhibition of cytokine production.

Example 7: Effect of miR Binding Sites on IgM

In this example, studies were performed to examine the effect of the inclusion in mRNA constructs of a miR binding site expressed in immune cells (miR-142, miR-126 or both miR-142+miR-126) on the levels of IgM that binds to PEG (anti-PEG IgM). Since PEG is a component of the LNP in which the mRNA construct is encapsulated, the presence of anti-PEG IgM in the serum of the mice contributes to Accelerated Blood Clearance (ABC) of the LNP/mRNA composition.

Figure 28B:
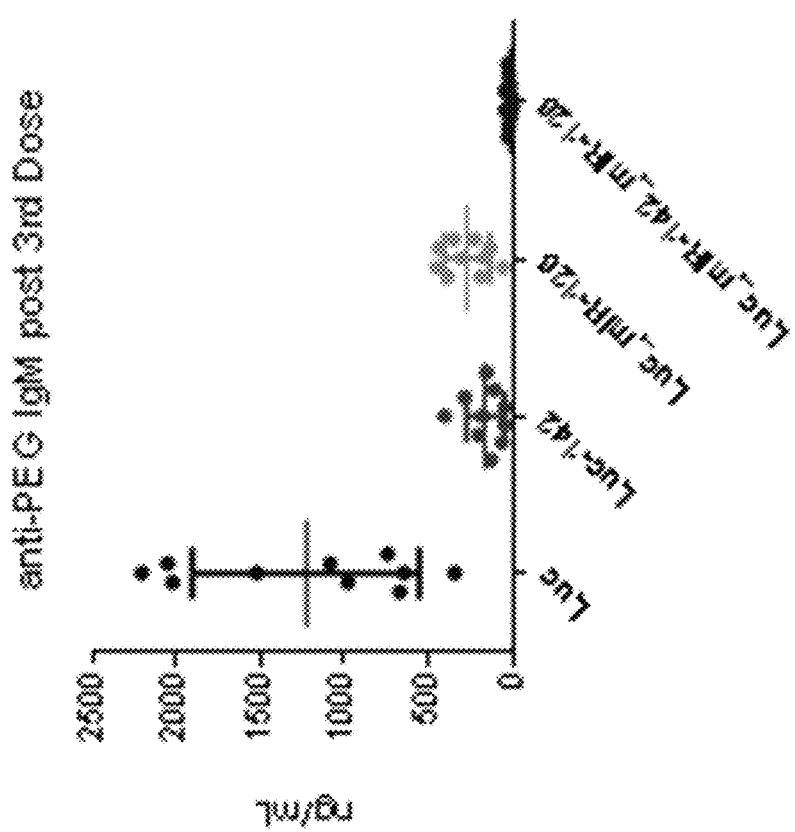
FIGS. 28A-C are graphs showing the level of serum anti-PEG IgM antibodies in mice treated with two doses (FIG. 28A), three doses (FIG. 28B) or four doses (FIG. 28C) of mmRNA encoding EPO either lacking or containing a miR-142 binding site, a miR-126 binding site or miR-142 and miR-126 binding sites.
Figure 28A:
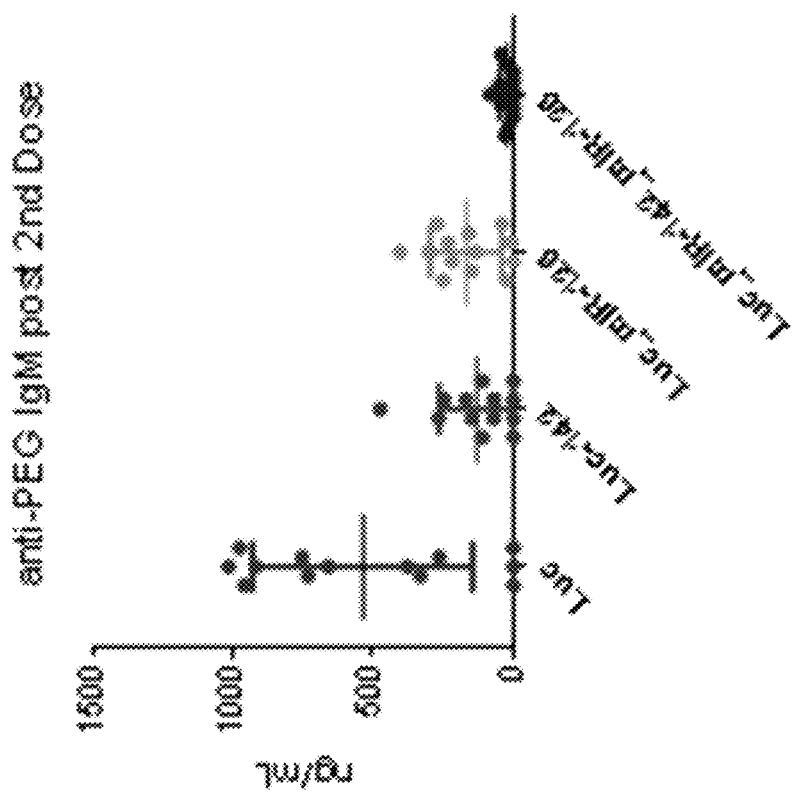
Figure 28C:
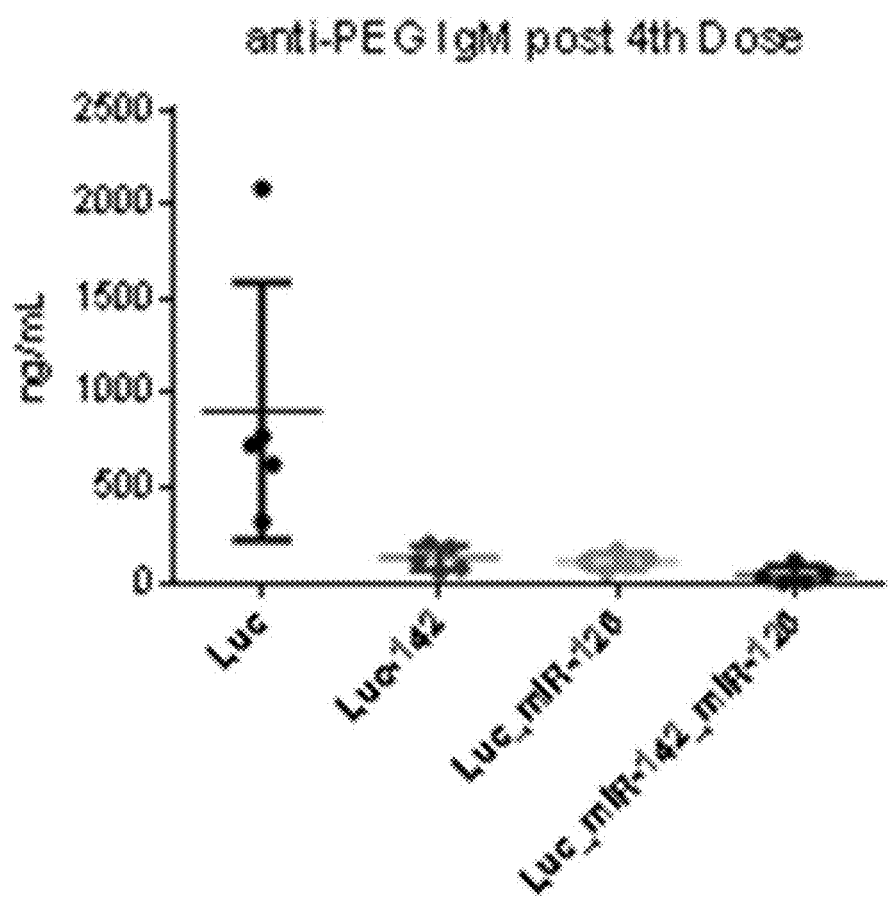

Mice were treated with the Luciferase-encoding mRNA constructs as described in Example 2. Serum was collected from the mice after the second, third and fourth doses of treatment and the levels of anti-PEG IgM in the serum (in ng/ml) was measured. The results are shown in the graphs of FIGS. 28A-C. FIG. 28A shows anti-PEG IgM levels after the second dose, FIG. 28B shows anti-PEG IgM levels after the third dose and FIG. 28C shows anti-PEG IgM levels after the fourth dose. The results demonstrate that inclusion of the miR binding site(s) significantly decreased the level of anti-PEG IgM in the mice. This effect was already observed after treatment with the second dose and the effect continued through treatment with the fourth dose. This reduction of anti-PEG IgM in the mice treated with the miR binding site-containing mRNA constructs indicates that ABC, which is mediated at least in part by anti-PEG IgM, is expected to be reduced in these mice.

Example 8: Effect of Single Versus Multiple miR Binding Sites

In this example, studies were performed to examine the effect of the inclusion in mRNA constructs of a single miR binding site (1×) versus multiple miR binding sites (e.g., 3×, having 3 miR binding sites).

A first series of studies were performed examining miR-122, which is known to regulate mRNA expression in liver cells. To determine the effect of inclusion of one versus three miR-122 binding sites on expression of a protein encoded by an mRNA construct, primary hepatocytes were co-transfected using Lipofectamine 2000 with a luciferase mRNA construct (Luc) and an enhanced green fluorescent protein mRNA construct (eGFP), wherein the 3' UTR of each construct either (i) lacked any miR-122 binding sites (control): (ii) contained one miR-122 binding site: or (iii) contained three miR-122 binding sites. Another control included transfection with Luc-like and eGFP-like RNA sequences with no ATG in the putatative coding sequence. The mRNA sequences of these four eGFP constructs are shown in SEQ ID NOs: 61-64, respectively. The mRNA sequences of these four Luc constructs are shown in SEQ ID NOs: 65-68, respectively. The sequence of the 3' UTR containing three miR-122 bindings sites is shown in SEQ ID NO: 54.

Cells were transfected with either 7.5 ng. 15 ng, 50 ng or 100 ng of mRNA. Total green integrated intensity was measured over time for 24 hours. The results are shown in FIGS. 31A-D, which demonstrate that at lower mRNA doses (7.5 ng and 15 ng, in FIGS. 31A and 31B, respectively), both the 1× miR-122 and the 3× miR-122 constructs led to significant reduction in expression of eGFP in the primary hepatocytes, whereas at the higher mRNA doses (50 ng and 100 ng, in FIGS. 31C and 31D, respectively), the 3× miR-122 constructs exhibited greater inhibition of eGFP expression than the 1× miR-122 constructs, and at the higher doses the 3× miR-122 constructs were able to maintain that loss of protein expression over time. Luciferase luminescence was also examined in the primary hepatocytes and similar results were observed: that the 3× miR-122 constructs led to higher knock-down of protein expression, particularly at higher mRNA doses.

In a second series of experiments examining the effect of inclusion of one versus three miR-122 binding sites on expression of a protein encoded by an mRNA construct, primary hepatocytes were transfected using Lipofectamine 2000 with an mRNA construct encoding a caspase and having in its 3' UTR either (i) no miR-122 binding sites (control): (ii) one miR-122 binding site: or (iii) three miR-122 binding sites. Another control included transfection with Caspase-like RNA sequences with no ATG in the putatative coding sequence. The mRNA sequences of these four caspase constructs are shown in SEQ ID NOs: 69-72, respectively. Caspase-mediated toxicity was measured over time for 24 hours. The results are shown in FIGS. 32A-D, which demonstrate that at the lower mRNA dose (7.5 ng, in FIG. 32A), both the 1× miR-122 and the 3× miR-122 constructs inhibited caspase-mediated toxicity, with the 3× miR-122 construct having a much stronger effect in inhibiting toxicity. Moreover, at the higher mRNA doses (15 ng. 50 ng and 100 ng, in FIGS. 32B, 32C and 32D, respectively), only the 3× miR-122 construct was able to inhibit caspase-mediated toxicity. Studies were also performed transfecting primary hepatocytes with the caspase mRNA construct in an MC3 lipid nanoparticle and similar results were observed: the alleviation of caspase-mediated toxicity was significantly stronger with the 3× miR-122 construct than with the 1× miR-122 construct.

To confirm these in vitro study results in vivo, Balb/c mice were co-adminstered the Luc and eGFP mRNA con-structs (0.5 mg/kg), in MC3 nanoparticles, containing either zero, one or three miR-122 binding sites. eGFP fluorescence in the liver was examined, the results of which showed that inclusion of one miR-122 binding site led to modest knock-down of eGFP expression in the liver, while inclusion of three miR-122 binding sites led to significant knock-down of eGFP expression in the liver. Similar results were observed for luciferase expression, with 1× site reducing luciferase expression and 3× sites leading to greater knock-down of protein expression.

Figure 33:
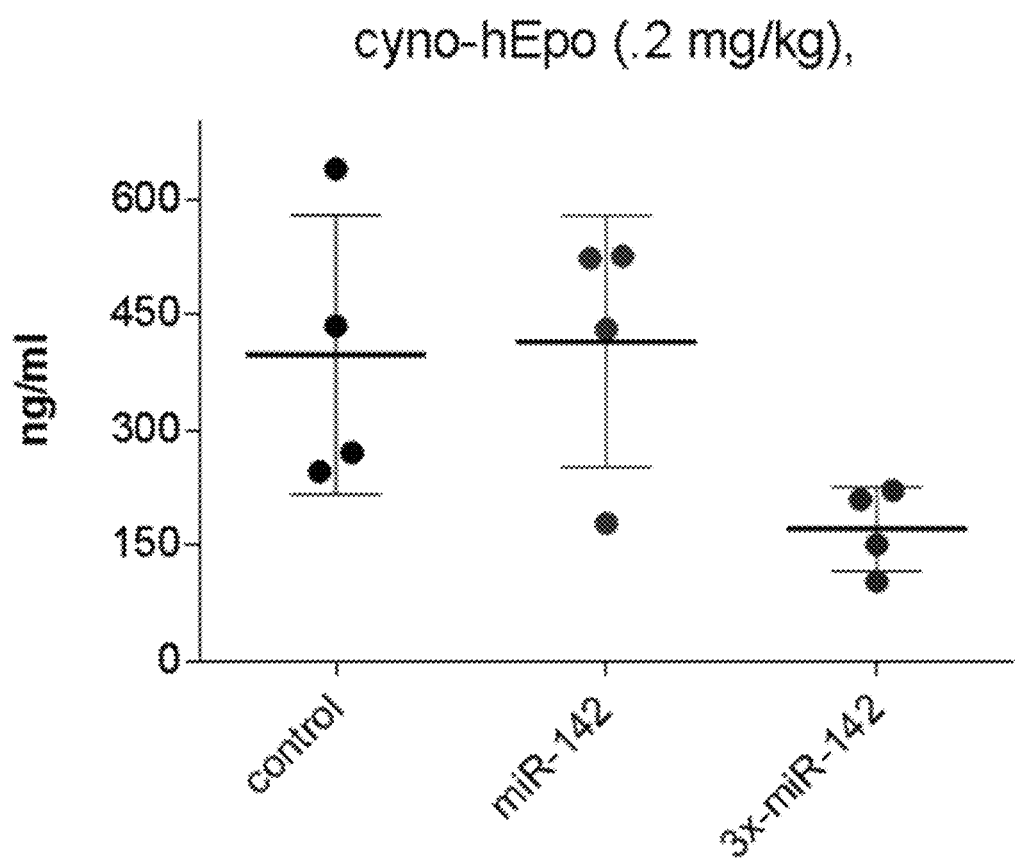
FIG. 33 is a graph showing the level of expression of hEPO in cynomologus monkeys administered mRNA constructs containing either no recognizable miR sites (control), 1× or 3× miR-142-3p binding sites.

In a third series of experiments, cynomolgus monkeys were administered hEPO mRNA constructs (0.2 mg/kg), in MC3 nanoparticles, containing either zero, one or three miR-142-3p binding sites in the 3' UTR. The levels of expression of hEPO (in ng/ml) in the monkeys was measured by ELISA, the results of which are shown in FIG. 33. The results show that inclusion of 3× miR-142-3p binding sites in the hEPO construct led to significantly lower expression of hEPO compared to the constructs with zero or one miR-142-3p binding site.

Overall, the studies described above demonstrate the benefit of inclusion of at least one miR binding site in the mRNA constructs and the enhanced effect of inclusion of three miR binding sites in the construct.

Example 9: Effect of miR Binding Sites in the 5' Untranslated Region (5' UTR)

In this example, studies were performed to examine the effect of the inclusion in mRNA constructs of a miR binding site in one of three different insertion sites within the 5' UTR of the mRNA construct. The 5'UTR sequence used is shown below:
GGGAAATAAGAG^AGAAAAGAAGAGTA^AGAAGA AATATA^AGAGCCACC (SEQ ID NO: 53), with the three possible insertions sites (P1, P2, P3) indicated by a caret sign (^). The sequences of 5' UTRs having a miR-142-3p binding site inserted into either P1, P2 or P3 are shown in SEQ ID NOs: 55-57, respectively. The sequences of 5' UTRs having a miR-122 binding site inserted into either P1, P2 or P3 are shown in SEQ ID NOs: 58-60, respectively.

Figure 34:
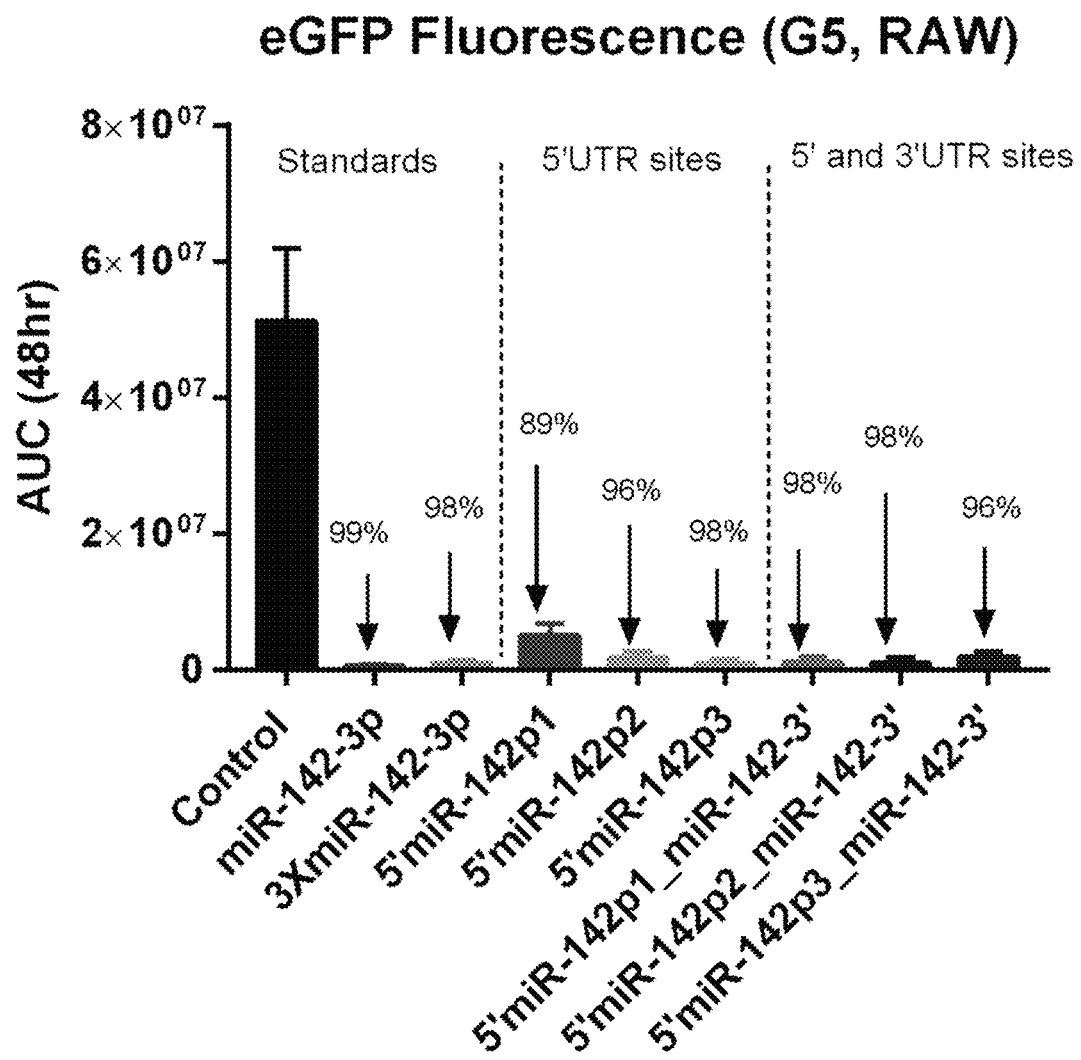
FIG. 34 is a bar graph showing the level of expression of eGFP in RAW264.7 cells transfected with mRNA constructs containing either no recognizable miR sites (control), a miR-142-3p binding site in the 3' UTR (1× or 3×), a miR-142-3p binding site in the 5' UTR (inserted at P1, P2 or P3), or a miR-142-3p binding site in both the 3' UTR and the 5' UTR.

In a first series of experiments, enhanced green fluorescent protein (eGFP) mRNA constructs were transfected into RAW264.7 murine macrophage cells using Lipofectamine 2000, wherein the constructs contained either 1× or 3× miR-142-3p binding sites in the 3' UTR, or contained a miR-142-3p binding site inserted into either P1, P2 or P3 of the 5' UTR, or contained a miR-142-3p binding site inserted into either P1, P2 or P3 of the 5' UTR combined with a single miR-142-3p binding site in the 3' UTR. eGFP fluorescence was measured at 48 hours post-transfection. The results are shown in FIG. 34. The results demonstrate that all of the constructs tested, including those with the miR-142-3p binding site inserted at P1, P2 or P3, alone or in combination with a miR-142-3p binding site in the 3' UTR, led to significantly reduced protein expression in the cells.

Similar constructs were made using hEPO as the encoded protein and similar experiments were conducted with transfected RAW264.7 cells. The results with the hEPO constructs were very similar to those with the eGFP constructs, with all constructs tested, including those with the miR binding site inserted at P1, P2 or P3, alone or in combination with a miR binding site in the 3' UTR, leading to significantly reduced protein expression in the cells. With the hEPO constructs, however, the degree of inhibition by the P1, P2 and P3 5' UTR constructs was slightly less (60%, 73% and 93%, respectively) compared to the degree of inhibition with the eGFP constructs (89%, 96% and 98%, respectively).

Figure 35:
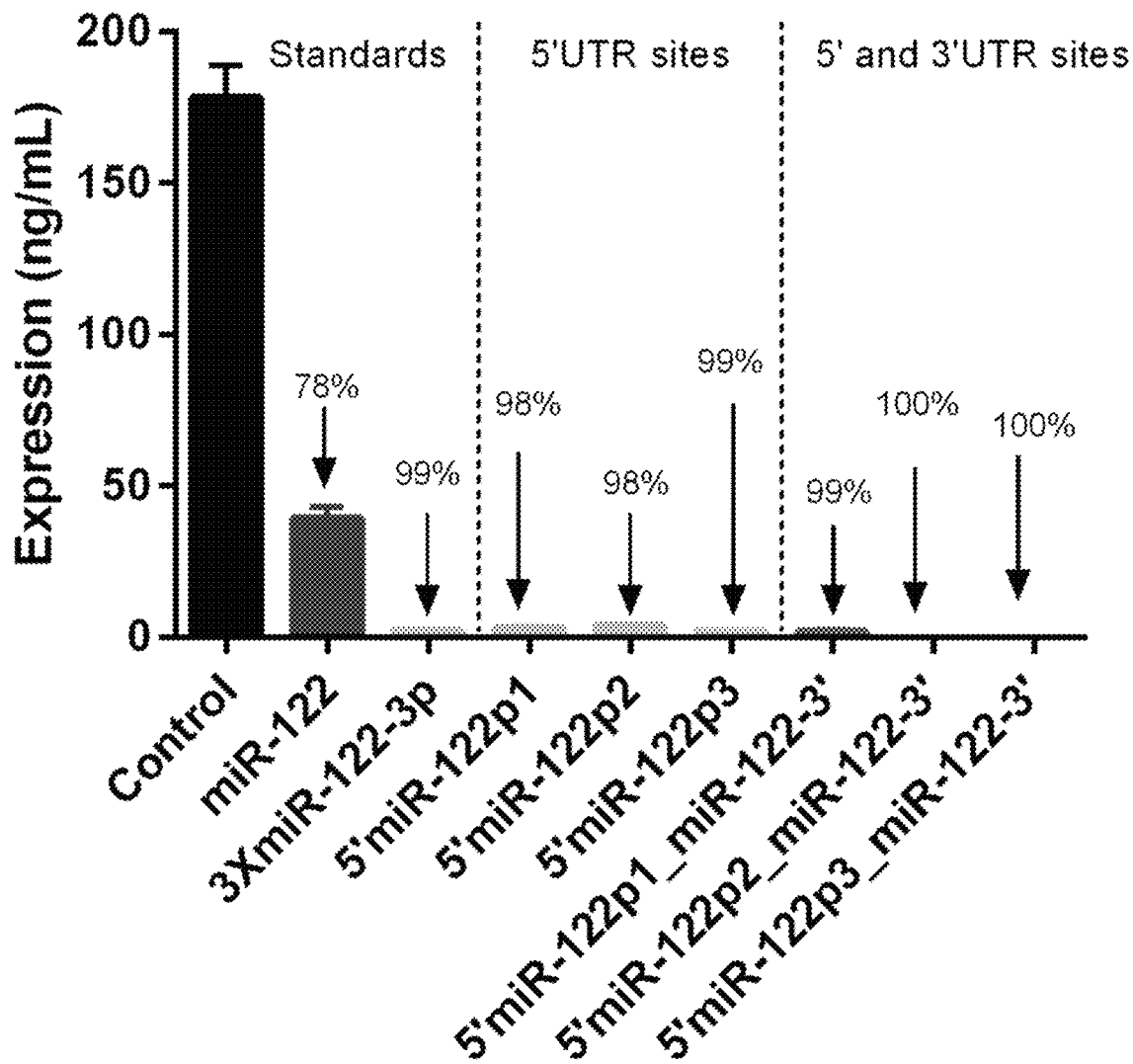
FIG. 35 is a bar graph showing the level of expression of hEPO in primary hepatocytes cells transfected with mRNA constructs containing either no recognizable miR sites (control), a miR-122 binding site in the 3' UTR (1× or 3×), a miR-122 binding site in the 5' UTR (inserted at P1, P2 or P3), or a miR-122 binding site in both the 3' UTR and the 5' UTR.

In a second series of experiments, hEPO mRNA constructs were made similar to those described above, except that the constructs contained either 1× or 3× miR-122 binding sites in the 3' UTR, or contained a miR-122 binding site inserted into either P1, P2 or P3 of the 5' UTR, or contained a miR-122 binding site inserted into either P1, P2 or P3 of the 5' UTR combined with a single miR-122 binding site in the 3' UTR. The mRNA constructs were transfected into primary hepatocytes using Lipofectamine 2000. hEPO expression (in ng/ml) was measured by ELISA, the results of which are shown in FIG. 35. The results demonstrate that all of the constructs tested, including those with the miR-122 binding site inserted at P1, P2 or P3, alone or in combination with a miR-122 binding site in the 3' UTR, led to significantly reduced protein expression in the cells.

To confirm these in vitro study results in vivo, Balb/c mice were administered the panel of hEPO/miR-122 mRNA constructs in MC3 nanoparticles or were administered the panel of hEPO/miR-142-3p constructs using Lipofectamine 2000. The results showed that, similar to the in vitro observations, all of the constructs tested, including those with a miR-122 or miR-142-3p binding site inserted at P1, P2 or P3, alone or in combination with a miR-122 or miR-142-3p binding site in the 3' UTR, led to significantly reduced protein expression in the mice.

Overall, these studies demonstrate the benefit of inclusion of at least one miR binding site in either the 3' UTR or the 5' UTR of the mRNA construct, or a combination of miR binding sites in both the 3 UTR and the 5' UTR.

What is claimed is:

1. A messenger RNA (mRNA) encoding a polypeptide of interest, wherein the mRNA comprises a 3' untranslated region (UTR) comprising at least one miR-142 binding site and at least one miR-126 binding site, and wherein the mRNA comprises one or more modified nucleobases.

2. The mRNA of claim 1, wherein the 3'UTR comprises 2, 3, or 4 miR-142 binding sites.

3. The mRNA of claim 1, wherein the 3'UTR comprises 2, 3, or 4 miR-126 binding sites.

4. The mRNA of claim 1, wherein the at least one miR-142 binding site is a miR-142-3p binding site.

5. The mRNA of claim 1, wherein the at least one miR-142 binding site is a miR-142-5p binding site.

6. The mRNA of claim 1, wherein the at least one miR-126 binding site a miR-126-3p binding site.

7. The mRNA of claim 1, wherein the at least one miR-126 binding site is a miR-126-5p binding site.

8. The mRNA of claim 1, wherein the one or more modified nucleobases is selected from pseudouridine ($\psi$), pseudouridine ($\psi$) and 5-methyl-cytidine ($m^5C$), 1-methyl-pseudouridine ($m^1\psi$), 1-methyl-pseudouridine ($m^1\psi$) and 5-methyl-cytidine ($m^5C$), 2-thiouridine ($s^2U$), 2-thiouridine and 5-methyl-cytidine ($m^5C$), 5-methoxy-uridine ($mo^5U$), 5-methoxy-uridine ($mo^5U$) and 5-methyl-cytidine ($m^5C$), 2'-O-methyl uridine, 2'-O-methyl uridine and 5-methyl-cytidine ($m^5C$), N6-methyl-adenosine ($m^6A$) or N6-methyl-adenosine ($m^6A$) and 5-methyl-cytidine ($m^5C$).

9. The mRNA of claim 1, wherein all uracil nucleobases in the mRNA are modified uracil nucleobases.

10. The mRNA of claim 9, wherein the modified uracil nucleobases are selected from pseudouridines ($\psi$), 1-methyl-pseudouridines ($m^1\psi$), and 5-methoxy-uridines ($mo^5U$).

11. The mRNA of claim 9, wherein the modified uracil nucleobases are 1-methyl-pseudouridines ($m^1\psi$).

12. The mRNA of claim 1, wherein all cytosine nucleobases in the mRNA are modified cytosine nucleobases.

13. The mRNA of claim 12, wherein the modified cytosine nucleobases are 5-methyl-cytidine.

14. The mRNA of claim 1, wherein the polypeptide of interest is a therapeutic protein, cytokine, growth factor, antibody or fusion protein.

15. A mRNA encoding a polypeptide of interest, wherein the mRNA comprises a 3' UTR comprising at least one miR-142-3p binding site and at least one miR-126-3p binding site, and wherein the mRNA comprises one or more modified nucleobases.

16. The mRNA of claim 15, wherein the 3'UTR comprises 2, 3, or 4 miR-142-3p binding sites.

17. The mRNA of claim 15, wherein the 3'UTR comprises 2, 3, or 4 miR-126-3p binding sites.

18. The mRNA of claim 15, wherein the miR-142-3p binding site comprises the sequence of SEQ ID NO: 3.

19. The mRNA of claim 15, wherein the miR-126-3p binding site comprises the sequence of SEQ ID NO: 26.

20. The mRNA of claim 15, wherein the one or more modified nucleobases is selected from pseudouridine ($\psi$), pseudouridine ($\psi$) and 5-methyl-cytidine ($m^5C$), 1-methyl-pseudouridine ($m^1\psi$), 1-methyl-pseudouridine ($m^1\psi$) and 5-methyl-cytidine ($m^5C$), 2-thiouridine ($s^2U$), 2-thiouridine and 5-methyl-cytidine ($m^5C$), 5-methoxy-uridine ($mo^5U$), 5-methoxy-uridine ($mo^5U$) and 5-methyl-cytidine ($m^5C$), 2'-O-methyl uridine, 2'-O-methyl uridine and 5-methyl-cytidine ($m^5C$), N6-methyl-adenosine ($m^6A$) or N6-methyl-adenosine ($m^6A$) and 5-methyl-cytidine ($m^5C$).

21. The mRNA of claim 15, wherein all uracil nucleobases in the mRNA are modified uracil nucleobases.

22. The mRNA of claim 21, wherein the modified uracil nucleobases are selected from pseudouridines ($\psi$), 1-methyl-pseudouridines ($m^1\psi$), and 5-methoxy-uridines ($mo^5U$).

23. The mRNA of claim 21, wherein the modified uracil nucleobases are 1-methyl-pseudouridines ($m^1\psi$).

24. The mRNA of claim 15, wherein all cytosine nucleobases in the mRNA are modified cytosine nucleobases.

25. The mRNA of claim 24, wherein the modified cytosine nucleobases are 5-methyl-cytidine.

26. The mRNA of claim 15, wherein the polypeptide of interest is a therapeutic protein, cytokine, growth factor, antibody or fusion protein.

27. A lipid nanoparticle comprising the mRNA of claim 1, wherein the lipid nanoparticle comprises an ionizable lipid, a structural lipid, a phospholipid, and a PEG lipid.

28. A pharmaceutical composition comprising the lipid nanoparticle of claim 27 and a pharmaceutically acceptable carrier, diluent or excipient.

29. A lipid nanoparticle comprising the mRNA of claim 15, wherein the lipid nanoparticle comprises an ionizable lipid, a structural lipid, a phospholipid, and a PEG lipid.

30. A pharmaceutical composition comprising the lipid nanoparticle of claim 29 and a pharmaceutically acceptable carrier, diluent or excipient.

31. The mRNA of claim 15, wherein the 3'UTR comprises one miR-142-3p binding site comprising the sequence of SEQ ID NO: 3 and one miR-126-3p binding site comprising the sequence of SEQ ID NO: 26.

32. The mRNA of claim 31, wherein all uracil nucleobases in the mRNA are modified uracil nucleobases, and wherein the modified uracil nucleobases are 1-methyl-pseudouridines (m1$\psi$).

* * * * *

SEQUENCE LISTING

```
Sequence total quantity: 86
SEQ ID NO: 1            moltype = RNA   length = 768
FEATURE                 Location/Qualifiers
misc_feature            1..768
                        note = Synthetic: EPO with miR 142-3p binding site
source                  1..768
                        mol_type = other RNA
                        organism = synthetic construct
SEQUENCE: 1
gggaaataag agagaaaaga agagtaagaa gaaatataag agccaccatg ggagtgcacg    60
agtgtcccgc gtggttgtgg ttgctgctgt cgctcttgag cctcccactg ggactgcctg   120
tgctgggggc accacccaga ttgatctgcg actcacgggt acttgagagg taccttcttg   180
aagccaaaga agccgaaaac atcacaaccg gatgcgccga gcactgctcc ctcaatgaga   240
acattactgt accggataca aaggtcaatt tctatgcatg gaagagaatg gaagtaggac   300
agcaggccgt cgaagtgtgg caggggctcg cgcttttgtc ggaggcggtg ttgcggggtc   360
aggccctcct cgtcaactca tcacagccgt gggagcccct ccaacttcat gtcgataaag   420
cggtgtcggg gctccgcagc ttgacgacgt tgcttcgggc tctgggcgca caaaggagg    480
ctatttcgcc gcctgacgcg gcctccgcgg caccccctccg aacgatcacc gcggacacgt   540
ttaggaagct ttttagagtg tacagcaatt tcctccgcgg aaagctgaaa ttgtatactg   600
gtgaagcgtg taggacaggg gatcgctgat aataggctgg agcctcggtg gccatgcttc   660
ttgccccttg ggcctccccc cagcccctcc tccccttcct gcacccgtac cccctccata   720
aagtaggaaa cactacagtg gtctttgaat aaagtctgag tgggcggc                768

SEQ ID NO: 2            moltype = RNA   length = 133
FEATURE                 Location/Qualifiers
misc_feature            1..133
                        note = Synthetic: 3'UTR with miR 142-3p binding site
source                  1..133
                        mol_type = other RNA
                        organism = synthetic construct
SEQUENCE: 2
gctggagcct cggtggccat gcttcttgcc ccttgggcct cccccagcc cctcctcccc      60
ttcctgcacc cgtaccccct ccataaagta ggaaacacta cagtggtctt tgaataaagt   120
ctgagtgggc ggc                                                      133
```

```
SEQ ID NO: 3              moltype = RNA   length = 23
FEATURE                   Location/Qualifiers
misc_feature              1..23
                          note = Synthetic: miR 142-3p binding site
source                    1..23
                          mol_type = other RNA
                          organism = synthetic construct
SEQUENCE: 3
tccataaagt aggaaacact aca                                                23

SEQ ID NO: 4              moltype = AA   length = 22
FEATURE                   Location/Qualifiers
REGION                    1..22
                          note = Synthetic: 2A peptide
source                    1..22
                          mol_type = protein
                          organism = synthetic construct
SEQUENCE: 4
GSGATNFSLL KQAGDVEENP GP                                                 22

SEQ ID NO: 5              moltype = DNA   length = 66
FEATURE                   Location/Qualifiers
misc_feature              1..66
                          note = Synthetic: polynucleotide encoding 2A peptide
source                    1..66
                          mol_type = other DNA
                          organism = synthetic construct
SEQUENCE: 5
ggaagcggag ctactaactt cagcctgctg aagcaggctg agacgtgga ggagaaccct         60
ggacct                                                                   66

SEQ ID NO: 6              moltype = DNA   length = 108
FEATURE                   Location/Qualifiers
misc_feature              1..108
                          note = Synthetic: polynucleotide encoding 2A peptide
source                    1..108
                          mol_type = other DNA
                          organism = synthetic construct
SEQUENCE: 6
tccggactca gatccgggga tctcaaaatt gtcgctcctg tcaaacaaac tcttaacttt        60
gatttactca aactggctgg ggatgtagaa agcaatccag gtccactc                    108

SEQ ID NO: 7              moltype = RNA   length = 745
FEATURE                   Location/Qualifiers
misc_feature              1..745
                          note = Synthetic: human EPO no miR binding sites
source                    1..745
                          mol_type = other RNA
                          organism = synthetic construct
SEQUENCE: 7
gggaaataag agagaaaaga agagtaagaa gaaatataag agccaccatg ggagtgcacg        60
agtgtcccgc gtggttgtgg ttgctgctgt cgctcttgag cctcccactg ggactgcctg      120
tgctggggc accacccaga ttgatctgcg actcacgggt acttgagagg taccttcttg       180
aagccaaaga agccgaaaac atcacaaccg gatgcgccga gcactgctcc ctcaatgaga      240
acattactgt accggataca aaggtcaatt tctatgcatg gaagagaatg gaagtaggac      300
agcaggccgt cgaagtgtgg caggggctcg cgcttttgtc ggaggcgtg ttgcggggtc       360
aggccctcct cgtcaactca tcacagccgt gggagcccct ccaacttcat gtcgataaag      420
cggtgtcggg gctccgcagc ttgacgacgt tgcttcgggc tctgggcgca caaaaggagg      480
ctatttcgcc gcctgacgcg gcctccgcgg caccccctccg aacgatcacc ggacacgt       540
ttaggaagct ttttagagtg tacagcaatt tcctccgcgg aaagctgaaa ttgtatactg      600
gtgaagcgtg taggacaggg gatcgctgat aataggctgg agcctcggtg gccatgcttc     660
ttgccccttg ggcctccccc cagccctcc tcccttcct gcacccgtac cccgtggtc       720
tttgaataaa gtctgagtgg gcggc                                            745

SEQ ID NO: 8              moltype = RNA   length = 23
FEATURE                   Location/Qualifiers
misc_feature              1..23
                          note = Synthetic: miR 142-3p sequence
source                    1..23
                          mol_type = other RNA
                          organism = synthetic construct
SEQUENCE: 8
tgtagtgttt cctactttat gga                                                23

SEQ ID NO: 9              moltype = RNA   length = 21
FEATURE                   Location/Qualifiers
misc_feature              1..21
                          note = Synthetic: miR 142-5p sequence
source                    1..21
```

```
                        mol_type = other RNA
                        organism = synthetic construct
SEQUENCE: 9
cataaagtag aaagcactac t                                              21

SEQ ID NO: 10           moltype = RNA   length = 22
FEATURE                 Location/Qualifiers
misc_feature            1..22
                        note = Synthetic: miR 146-3p sequence
source                  1..22
                        mol_type = other RNA
                        organism = synthetic construct
SEQUENCE: 10
cctctgaaat tcagttcttc ag                                             22

SEQ ID NO: 11           moltype = RNA   length = 22
FEATURE                 Location/Qualifiers
misc_feature            1..22
                        note = Synthetic: miR 146-5p sequence
source                  1..22
                        mol_type = other RNA
                        organism = synthetic construct
SEQUENCE: 11
tgagaactga attccatggg tt                                             22

SEQ ID NO: 12           moltype = RNA   length = 22
FEATURE                 Location/Qualifiers
misc_feature            1..22
                        note = Synthetic: miR 155-3p sequence
source                  1..22
                        mol_type = other RNA
                        organism = synthetic construct
SEQUENCE: 12
ctcctacata ttagcattaa ca                                             22

SEQ ID NO: 13           moltype = RNA   length = 23
FEATURE                 Location/Qualifiers
misc_feature            1..23
                        note = Synthetic: miR 155-5p sequence
source                  1..23
                        mol_type = other RNA
                        organism = synthetic construct
SEQUENCE: 13
ttaatgctaa tcgtgatagg ggt                                            23

SEQ ID NO: 14           moltype = RNA   length = 22
FEATURE                 Location/Qualifiers
misc_feature            1..22
                        note = Synthetic: miR 126-3p sequence
source                  1..22
                        mol_type = other RNA
                        organism = synthetic construct
SEQUENCE: 14
tcgtaccgtg agtaataatg cg                                             22

SEQ ID NO: 15           moltype = RNA   length = 21
FEATURE                 Location/Qualifiers
misc_feature            1..21
                        note = Synthetic: miR 126-5p sequence
source                  1..21
                        mol_type = other RNA
                        organism = synthetic construct
SEQUENCE: 15
cattattact tttggtacgc g                                              21

SEQ ID NO: 16           moltype = RNA   length = 22
FEATURE                 Location/Qualifiers
misc_feature            1..22
                        note = Synthetic: miR 16-3p sequence
source                  1..22
                        mol_type = other RNA
                        organism = synthetic construct
SEQUENCE: 16
ccagtattaa ctgtgctgct ga                                             22

SEQ ID NO: 17           moltype = RNA   length = 22
FEATURE                 Location/Qualifiers
misc_feature            1..22
                        note = Synthetic: miR 16-5p sequence
```

```
source                  1..22
                        mol_type = other RNA
                        organism = synthetic construct
SEQUENCE: 17
tagcagcacg taaatattgg cg                                              22

SEQ ID NO: 18           moltype = RNA   length = 21
FEATURE                 Location/Qualifiers
misc_feature            1..21
                        note = Synthetic: miR 21-3p sequence
source                  1..21
                        mol_type = other RNA
                        organism = synthetic construct
SEQUENCE: 18
caacaccagt cgatgggctg t                                               21

SEQ ID NO: 19           moltype = RNA   length = 22
FEATURE                 Location/Qualifiers
misc_feature            1..22
                        note = Synthetic: miR 21-5p sequence
source                  1..22
                        mol_type = other RNA
                        organism = synthetic construct
SEQUENCE: 19
tagcttatca gactgatgtt ga                                              22

SEQ ID NO: 20           moltype = RNA   length = 22
FEATURE                 Location/Qualifiers
misc_feature            1..22
                        note = Synthetic: miR 223-3p sequence
source                  1..22
                        mol_type = other RNA
                        organism = synthetic construct
SEQUENCE: 20
tgtcagtttg tcaaataccc ca                                              22

SEQ ID NO: 21           moltype = RNA   length = 22
FEATURE                 Location/Qualifiers
misc_feature            1..22
                        note = Synthetic: miR 223-5p sequence
source                  1..22
                        mol_type = other RNA
                        organism = synthetic construct
SEQUENCE: 21
cgtgtatttg acaagctgag tt                                              22

SEQ ID NO: 22           moltype = RNA   length = 22
FEATURE                 Location/Qualifiers
misc_feature            1..22
                        note = Synthetic: miR 24-3p sequence
source                  1..22
                        mol_type = other RNA
                        organism = synthetic construct
SEQUENCE: 22
tggctcagtt cagcaggaac ag                                              22

SEQ ID NO: 23           moltype = RNA   length = 22
FEATURE                 Location/Qualifiers
misc_feature            1..22
                        note = Synthetic: miR 24-5p sequence
source                  1..22
                        mol_type = other RNA
                        organism = synthetic construct
SEQUENCE: 23
tgcctactga gctgatatca gt                                              22

SEQ ID NO: 24           moltype = RNA   length = 21
FEATURE                 Location/Qualifiers
misc_feature            1..21
                        note = Synthetic: miR 27-3p sequence
source                  1..21
                        mol_type = other RNA
                        organism = synthetic construct
SEQUENCE: 24
ttcacagtgg ctaagttccg c                                               21

SEQ ID NO: 25           moltype = RNA   length = 22
FEATURE                 Location/Qualifiers
misc_feature            1..22
```

```
                        note = Synthetic: miR 27-5p sequence
source                  1..22
                        mol_type = other RNA
                        organism = synthetic construct
SEQUENCE: 25
agggcttagc tgcttgtgag ca                                            22

SEQ ID NO: 26           moltype = RNA   length = 22
FEATURE                 Location/Qualifiers
misc_feature            1..22
                        note = Synthetic: miR 126-3p binding site
source                  1..22
                        mol_type = other RNA
                        organism = synthetic construct
SEQUENCE: 26
cgcattatta ctcacggtac ga                                            22

SEQ ID NO: 27           moltype = RNA   length = 141
FEATURE                 Location/Qualifiers
misc_feature            1..141
                        note = Synthetic: 3'UTR with miR 126-3p binding site
source                  1..141
                        mol_type = other RNA
                        organism = synthetic construct
SEQUENCE: 27
tgataatagg ctggagcctc ggtggccatg cttcttgccc cttgggcctc ccccagccc    60
ctcctcccct tcctgcaccc gtaccccccg cattattact cacggtacga gtggtctttg   120
aataaagtct gagtgggcgg c                                             141

SEQ ID NO: 28           moltype = RNA   length = 767
FEATURE                 Location/Qualifiers
misc_feature            1..767
                        note = Synthetic: hEPO with miR 126-3p binding site
source                  1..767
                        mol_type = other RNA
                        organism = synthetic construct
SEQUENCE: 28
gggaaataag agagaaaaga agagtaagaa gaaatataag agccaccatg ggagtgcacg   60
agtgtcccgc gtggttgtgg ttgctgctgt cgctcttgag cctcccactg ggactgcctg   120
tgctgggggc accacccaga ttgatctgcg actcacgggt acttgagagg taccttcttg   180
aagccaaaga agccgaaaac atcacaaccg gatgcgccga gcactgctcc ctcaatgaga   240
acattactgt accggataca aaggtcaatt tctatgcatg gaagagaatg gaagtaggac   300
agcaggccgt cgaagtgtgg caggggctcg cgcttttgtc ggaggcggtg ttgcggggtc   360
aggccctcct cgtcaactca tcacagccgt gggagcccct ccaacttcat gtcgataaag   420
cggtgtcggg gctccgcagc ttgacgacgt tgcttcgggc tctgggcgca caaaaggagg   480
ctatttcgcc gcctgacgcg gcctccgcgg caccccctccg aacgatcacc gcggacacgt   540
ttaggaagct ttttagagtg tacagcaatt tcctccgcgg aaagctgaaa ttgtatactg   600
gtgaagcgtg taggacaggg gatcgctgat aataggctgg agcctcggtg gccatgcttc   660
ttgcccctlg ggcctccccc agccccctcc tcccttcct gcacccgtac ccccgcatt   720
attactcacg gtacgagtgg tctttgaata aagtctgagt gggcggc                 767

SEQ ID NO: 29           moltype = RNA   length = 790
FEATURE                 Location/Qualifiers
misc_feature            1..790
                        note = Synthetic: hEPO with miR 142-3p and miR 126-3p
                        binding sites
source                  1..790
                        mol_type = other RNA
                        organism = synthetic construct
SEQUENCE: 29
gggaaataag agagaaaaga agagtaagaa gaaatataag agccaccatg ggagtgcacg   60
agtgtcccgc gtggttgtgg ttgctgctgt cgctcttgag cctcccactg ggactgcctg   120
tgctgggggc accacccaga ttgatctgcg actcacgggt acttgagagg taccttcttg   180
aagccaaaga agccgaaaac atcacaaccg gatgcgccga gcactgctcc ctcaatgaga   240
acattactgt accggataca aaggtcaatt tctatgcatg gaagagaatg gaagtaggac   300
agcaggccgt cgaagtgtgg caggggctcg cgcttttgtc ggaggcggtg ttgcggggtc   360
aggccctcct cgtcaactca tcacagccgt gggagcccct ccaacttcat gtcgataaag   420
cggtgtcggg gctccgcagc ttgacgacgt tgcttcgggc tctgggcgca caaaaggagg   480
ctatttcgcc gcctgacgcg gcctccgcgg caccccctccg aacgatcacc gcggacacgt   540
ttaggaagct ttttagagtg tacagcaatt tcctccgcgg aaagctgaaa ttgtatactg   600
gtgaagcgtg taggacaggg gatcgctgat aatagtccat aaagtaggaa acactacagc   660
tggagcctcg gtggccatgc ttcttgcccc ttgggcctcc cccagcccc tcctcccctt    720
cctgcacccg taccccccgc attattactc acggtacgag tggtctttga ataaagtctg   780
agtgggcggc                                                          790

SEQ ID NO: 30           moltype = DNA   length = 119
FEATURE                 Location/Qualifiers
misc_feature            1..119
                        note = Synthetic: 3 UTR, no miR binding sites
```

```
source                   1..119
                         mol_type = other DNA
                         organism = synthetic construct
SEQUENCE: 30
tgataatagg ctggagcctc ggtggccatg cttcttgccc cttgggcctc ccccagccc    60
ctcctcccct tcctgcaccc gtaccccgt ggtctttgaa taaagtctga gtgggcggc    119

SEQ ID NO: 31            moltype = DNA   length = 142
FEATURE                  Location/Qualifiers
misc_feature             1..142
                         note = Synthetic: 3 UTR with miR 142-3p binding site
source                   1..142
                         mol_type = other DNA
                         organism = synthetic construct
SEQUENCE: 31
tgataatagg ctggagcctc ggtggccatg cttcttgccc cttgggcctc ccccagccc    60
ctcctcccct tcctgcaccc gtacccctc cataaagtag gaaacactac agtggtcttt   120
gaataaagtc tgagtgggcg gc                                           142

SEQ ID NO: 32            moltype = DNA   length = 141
FEATURE                  Location/Qualifiers
misc_feature             1..141
                         note = Synthetic: 3 UTR with miR 126-3p binding site
source                   1..141
                         mol_type = other DNA
                         organism = synthetic construct
SEQUENCE: 32
tgataatagg ctggagcctc ggtggccatg cttcttgccc cttgggcctc ccccagccc    60
ctcctccct tcctgcaccc gtacccccg cattattact cacggtacga gtggtctttg   120
aataaagtct gagtgggcgg c                                            141

SEQ ID NO: 33            moltype = DNA   length = 164
FEATURE                  Location/Qualifiers
misc_feature             1..164
                         note = Synthetic: 3 UTR with miR 142-3p and miR 126-3p
                          binding sites
source                   1..164
                         mol_type = other DNA
                         organism = synthetic construct
SEQUENCE: 33
tgataatagt ccataaagta ggaaacacta cagctggagc ctcggtggcc atgcttcttg    60
ccccttgggc ctcccccag ccctcctcc ccttcctgca cccgtacccc ccgcattatt   120
actcacggta cgagtggtct ttgaataaag tctgagtggg cggc                   164

SEQ ID NO: 34            moltype = RNA   length = 23
FEATURE                  Location/Qualifiers
misc_feature             1..23
                         note = Synthetic: miR 155-5p sequence
source                   1..23
                         mol_type = other RNA
                         organism = synthetic construct
SEQUENCE: 34
ttaatgctaa ttgtgatagg ggt                                           23

SEQ ID NO: 35            moltype = DNA   length = 23
FEATURE                  Location/Qualifiers
misc_feature             1..23
                         note = Synthetic: miR 155-5p binding site
source                   1..23
                         mol_type = other DNA
                         organism = synthetic construct
SEQUENCE: 35
accccctatca caattagcat taa                                          23

SEQ ID NO: 36            moltype = DNA   length = 119
FEATURE                  Location/Qualifiers
misc_feature             1..119
                         note = Synthetic: 3UTR with no miR binding site
source                   1..119
                         mol_type = other DNA
                         organism = synthetic construct
SEQUENCE: 36
tgataatagg ctggagcctc ggtggccatg cttcttgccc cttgggcctc ccccagccc    60
ctcctcccct tcctgcaccc gtaccccgt ggtctttgaa taaagtctga gtgggcggc    119

SEQ ID NO: 37            moltype = DNA   length = 142
FEATURE                  Location/Qualifiers
misc_feature             1..142
                         note = Synthetic: 3UTR with miR 142-3p binding site
```

```
source                  1..142
                        mol_type = other DNA
                        organism = synthetic construct
SEQUENCE: 37
tgataatagg ctggagcctc ggtggccatg cttcttgccc cttgggcctc ccccagccc      60
ctcctcccct tcctgcaccc gtaccccctc cataaagtag gaaacactac agtggtcttt    120
gaataaagtc tgagtgggcg gc                                             142

SEQ ID NO: 38           moltype = DNA  length = 188
FEATURE                 Location/Qualifiers
misc_feature            1..188
                        note = Synthetic: 3 UTR with 3 miR 142-3p binding sites
source                  1..188
                        mol_type = other DNA
                        organism = synthetic construct
SEQUENCE: 38
tgataatagt ccataaagta ggaaacacta cagctggagc ctcggtggcc atgcttcttg     60
cccccttggg ctccataaag taggaaacac tacatccccc cagcccctcc tcccttcct    120
gcacccgtac cccctccata aagtaggaaa cactacagtg tctttgaat aaagtctgag    180
tgggcggc                                                             188

SEQ ID NO: 39           moltype = DNA  length = 140
FEATURE                 Location/Qualifiers
misc_feature            1..140
                        note = Synthetic: 3UTR with miR 142-5p binding site
source                  1..140
                        mol_type = other DNA
                        organism = synthetic construct
SEQUENCE: 39
tgataatagg ctggagcctc ggtggccatg cttcttgccc cttgggcctc ccccagccc      60
ctcctcccct tcctgcaccc gtaccccag tagtgctttc tactttatgg tggtctttga   120
ataaagtctg agtgggcggc                                                140

SEQ ID NO: 40           moltype = DNA  length = 182
FEATURE                 Location/Qualifiers
misc_feature            1..182
                        note = Synthetic: 3UTR with 3 miR 142-5p binding sites
source                  1..182
                        mol_type = other DNA
                        organism = synthetic construct
SEQUENCE: 40
tgataataga gtagtgcttt ctactttatg gctggagcct cggtggccat gcttcttgcc     60
ccttgggcca gtagtgcttt ctactttatg tccccccagc ccctcctccc cttcctgcac   120
ccgtacccccc agtagtgctt tctactttat ggtggtcttt gaataaagtc tgagtgggcg   180
gc                                                                   182

SEQ ID NO: 41           moltype = DNA  length = 184
FEATURE                 Location/Qualifiers
misc_feature            1..184
                        note = Synthetic: 3UTR with 2 miR 142-5p binding sites and
                        1 miR 142-3p binding site
source                  1..184
                        mol_type = other DNA
                        organism = synthetic construct
SEQUENCE: 41
tgataataga gtagtgcttt ctactttatg gctggagcct cggtggccat gcttcttgcc     60
ccttgggcct ccataaagta ggaaacacta catcccccca gccctcctc cccttcctgc    120
acccgtaccc ccagtagtgc tttctacttt atggtggtct ttgaataaag tctgagtggg   180
cggc                                                                 184

SEQ ID NO: 42           moltype = DNA  length = 142
FEATURE                 Location/Qualifiers
misc_feature            1..142
                        note = Synthetic: 3UTR with miR 155-5p binding site
source                  1..142
                        mol_type = other DNA
                        organism = synthetic construct
SEQUENCE: 42
tgataatagg ctggagcctc ggtggccatg cttcttgccc cttgggcctc ccccagccc      60
ctcctcccct tcctgcaccc gtaccccac ccctatcaca attagcatta agtggtcttt    120
gaataaagtc tgagtgggcg gc                                             142

SEQ ID NO: 43           moltype = DNA  length = 188
FEATURE                 Location/Qualifiers
misc_feature            1..188
                        note = Synthetic: 3 UTR with 3 miR 155-5p binding sites
source                  1..188
                        mol_type = other DNA
                        organism = synthetic construct
```

```
SEQUENCE: 43
tgataataga ccctatcac aattagcatt aagctggagc ctcggtggcc atgcttcttg    60
cccctgggc cacccctatc acaattagca ttaatcccc cagcccctcc tccccttcct    120
gcacccgtac cccaccccct atcacaatta gcattaagtg gtctttgaat aaagtctgag   180
tgggcggc                                                             188

SEQ ID NO: 44          moltype = DNA   length = 188
FEATURE                Location/Qualifiers
misc_feature           1..188
                       note = Synthetic: 3UTR with 2 miR 155-5p binding sites and
                       1 miR 142-3p binding site
source                 1..188
                       mol_type = other DNA
                       organism = synthetic construct
SEQUENCE: 44
tgataataga ccctatcac aattagcatt aagctggagc ctcggtggcc atgcttcttg    60
cccctgggc ctccataaag taggaaacac tacatcccc cagcccctcc tccccttcct    120
gcacccgtac cccaccccct atcacaatta gcattaagtg gtctttgaat aaagtctgag   180
tgggcggc                                                             188

SEQ ID NO: 45          moltype = RNA   length = 22
FEATURE                Location/Qualifiers
misc_feature           1..22
                       note = Synthetic: miR 122 binding site
source                 1..22
                       mol_type = other RNA
                       organism = synthetic construct
SEQUENCE: 45
tatttagtgt gataatggcg tt                                             22

SEQ ID NO: 46          moltype = RNA   length = 22
FEATURE                Location/Qualifiers
misc_feature           1..22
                       note = Synthetic: miR 122 binding site
source                 1..22
                       mol_type = other RNA
                       organism = synthetic construct
SEQUENCE: 46
caaacaccat tgtcacactc ca                                             22

SEQ ID NO: 47          moltype = DNA   length = 164
FEATURE                Location/Qualifiers
misc_feature           1..164
                       note = Synthetic: 3'UTR with miR 142-3p and miR 122-5p
                       binding sites
source                 1..164
                       mol_type = other DNA
                       organism = synthetic construct
SEQUENCE: 47
tgataatagt ccataaagta ggaaacacta cagctggagc ctcggtggcc atgcttcttg    60
cccctgggc ccaaacacca ttgtcacact ccatccccc agcccctcct cccttcctg     120
cacccgtacc ccgtggtct tgaataaag tctgagtggg cggc                      164

SEQ ID NO: 48          moltype = DNA   length = 142
FEATURE                Location/Qualifiers
misc_feature           1..142
                       note = Synthetic: 3'UTR with miR 142-3p binding site, P1
                       insertion
source                 1..142
                       mol_type = other DNA
                       organism = synthetic construct
SEQUENCE: 48
tgataatagt ccataaagta ggaaacacta cagctggagc ctcggtggcc atgcttcttg    60
cccctgggc ctccccccag ccctcctcc cttcctgca cccgtacccc cgtggtcttt     120
gaataaagtc tgagtgggcg gc                                             142

SEQ ID NO: 49          moltype = DNA   length = 142
FEATURE                Location/Qualifiers
misc_feature           1..142
                       note = Synthetic: 3'UTR with miR 142-3p binding site, P2
                       insertion
source                 1..142
                       mol_type = other DNA
                       organism = synthetic construct
SEQUENCE: 49
tgataatagg ctggagcctc ggtggctcca taaagtagga acactacac atgcttcttg    60
cccctgggc ctccccccag ccctcctcc cttcctgca cccgtacccc cgtggtcttt     120
gaataaagtc tgagtgggcg gc                                             142
```

-continued

```
SEQ ID NO: 50              moltype = DNA   length = 142
FEATURE                    Location/Qualifiers
misc_feature               1..142
                           note = Synthetic: 3'UTR with miR 142-3p binding site, P3
                            insertion
source                     1..142
                           mol_type = other DNA
                           organism = synthetic construct
SEQUENCE: 50
tgataatagg ctggagcctc ggtggccatg cttcttgccc cttgggcctc cataaagtag    60
gaaacactac atcccccag ccctcctcc ccttcctgca cccgtacccc cgtggtcttt     120
gaataaagtc tgagtgggcg gc                                            142

SEQ ID NO: 51              moltype = RNA   length = 21
FEATURE                    Location/Qualifiers
misc_feature               1..21
                           note = Synthetic: miR-142-5p binding site
source                     1..21
                           mol_type = other RNA
                           organism = synthetic construct
SEQUENCE: 51
agtagtgctt tctactttat g                                             21

SEQ ID NO: 52              moltype = RNA   length = 87
FEATURE                    Location/Qualifiers
misc_feature               1..87
                           note = Synthetic: miR-142
source                     1..87
                           mol_type = other RNA
                           organism = synthetic construct
SEQUENCE: 52
gacagtgcag tcacccataa agtagaaagc actactaaca gcactggagg gtgtagtgtt   60
tcctactttta tggatgagtg tactgtg                                      87

SEQ ID NO: 53              moltype = DNA   length = 47
FEATURE                    Location/Qualifiers
misc_feature               1..47
                           note = Synthetic: 5 UTR
source                     1..47
                           mol_type = other DNA
                           organism = synthetic construct
SEQUENCE: 53
gggaaataag agagaaaaga agagtaagaa gaaatataag agccacc                 47

SEQ ID NO: 54              moltype = DNA   length = 185
FEATURE                    Location/Qualifiers
misc_feature               1..185
                           note = Synthetic: 3'UTR with 3X miR122 binding sites
source                     1..185
                           mol_type = other DNA
                           organism = synthetic construct
SEQUENCE: 54
tgataatagc aaacaccatt gtcacactcc agctggagcc tcggtggcca tgcttcttgc    60
cccttgggcc caaacaccat tgtcacactc catcccccca gccctcctc ccttcctgc     120
acccgtaccc cccaaacacc attgtcacac tccagtggtc tttgaataaa gtctgagtgg   180
gcggc                                                               185

SEQ ID NO: 55              moltype = DNA   length = 70
FEATURE                    Location/Qualifiers
misc_feature               1..70
                           note = Synthetic: 5' UTR with miR142-3p binding site at
                            position p1
source                     1..70
                           mol_type = other DNA
                           organism = synthetic construct
SEQUENCE: 55
gggaaataag agtccataaa gtaggaaaca ctacaagaaa agaagagtaa gaagaaatat    60
aagagccacc                                                          70

SEQ ID NO: 56              moltype = DNA   length = 70
FEATURE                    Location/Qualifiers
misc_feature               1..70
                           note = Synthetic: 5' UTR with miR142-3p binding site at
                            position p2
source                     1..70
                           mol_type = other DNA
                           organism = synthetic construct
SEQUENCE: 56
gggaaataag agagaaaaga agagtaatcc ataaagtagg aaacactaca gaagaaatat    60
```

```
SEQ ID NO: 57         moltype = DNA   length = 70
FEATURE               Location/Qualifiers
misc_feature          1..70
                      note = Synthetic: 5' UTR with miR142-3p binding site at
                        position p3
source                1..70
                      mol_type = other DNA
                      organism = synthetic construct
SEQUENCE: 57
gggaaataag agagaaaaga agagtaagaa gaaatataat ccataaagta ggaaacacta    60
cagagccacc                                                          70

SEQ ID NO: 58         moltype = DNA   length = 69
FEATURE               Location/Qualifiers
misc_feature          1..69
                      note = Synthetic: 5' UTR with miR122-3p binding site at
                        position p1
source                1..69
                      mol_type = other DNA
                      organism = synthetic construct
SEQUENCE: 58
gggaaataag agcaaacacc attgtcacac tccaagaaaa gaagagtaag aagaaatata    60
agagccacc                                                           69

SEQ ID NO: 59         moltype = DNA   length = 69
FEATURE               Location/Qualifiers
misc_feature          1..69
                      note = Synthetic: 5' UTR with miR122-3p binding site at
                        position p2
source                1..69
                      mol_type = other DNA
                      organism = synthetic construct
SEQUENCE: 59
gggaaataag agagaaaaga agagtaacaa acaccattgt cacactccag aagaaatata    60
agagccacc                                                           69

SEQ ID NO: 60         moltype = DNA   length = 69
FEATURE               Location/Qualifiers
misc_feature          1..69
                      note = Synthetic: 5' UTR with miR122-3p binding site at
                        position p3
source                1..69
                      mol_type = other DNA
                      organism = synthetic construct
SEQUENCE: 60
gggaaataag agagaaaaga agagtaagaa gaaatataac aaacaccatt gtcacactcc    60
agagccacc                                                           69

SEQ ID NO: 61         moltype = DNA   length = 883
FEATURE               Location/Qualifiers
misc_feature          1..883
                      note = Synthetic: eGFP mRNA construct with no miR binding
                        sites
source                1..883
                      mol_type = other DNA
                      organism = synthetic construct
SEQUENCE: 61
gggaaataag agagaaaaga agagtaagaa gaaatataag agccaccatg gtgtccaagg    60
gtgaggaatt gtttaccggg gtggtgccta ttctcgtcga acttgacggg gatgtgaatg   120
gacacaagtt ttcggtatcc ggagaaggag agggtgacgc cacatacgga aagcttacac   180
tcaaattcat ctgtacgacg gggaaactgc ccgtaccctg gctacgctc gtaaccacgc    240
tgacttatgg agtgcagtgc tttagcagat acccgacca tatgaagcag cacgacttct   300
tcaagtcggc gatgcccgag gggtacgtgc aagagaggac catttcttc aaagacgatg    360
gcaattacaa aacacgcgca gaagtcaagt ttgagggcga tactctggtc aatcggatcg   420
aattgaaggg aatcgatttc aaagaagatg gaaacatcct tggccataag ctcgagtaca   480
actataactc gcataatgtc tatatcatgg ctgacaagca gaaaacggt atcaaagtca    540
actttaagat ccgacacaat attgaggacg gttcggtgca gcttgcggac cactatcaac   600
agaatacgcc gattgggat ggtccggtcc ttttgcgga taaccattat ctctcaaccc     660
agtcagccct gagcaaagat ccaaacgaga gagggacca catggtcttg ctcgaattcg    720
tgacagcgga agggatcact ctgggaatgg acgagttgta caagtgataa taggctggag   780
cctcggtggc catgcttctt gccccttggg cctcccccca gccctcctc ccttcctgc     840
acccgtaccc ccgtggtctt tgaataaagt ctgagtgggc ggc                     883

SEQ ID NO: 62         moltype = DNA   length = 905
FEATURE               Location/Qualifiers
misc_feature          1..905
                      note = Synthetic: eGFP mRNA construct with 1X miR122
```

```
                            binding site in 3 UTR
source                      1..905
                            mol_type = other DNA
                            organism = synthetic construct
SEQUENCE: 62
gggaaataag agagaaaaga agagtaagaa gaaatataag agccaccatg gtgtccaagg    60
gtgaggaatt gtttaccggg gtggtgccta ttctcgtcga acttgacggg gatgtgaatg   120
gacacaagtt ttcggtatcc ggagaaggag agggtgacgc cacatacgga aagcttacac   180
tcaaattcat ctgtacgacg gggaaactgc ccgtacccty gcctacgctc gtaaccacgc   240
tgacttatgg agtgcagtgc tttagcagat accccgacca tatgaagcag cacgacttct   300
tcaagtcggc gatgcccgag gggtacgtgc aagagaggac catttttcttc aaagacgatg   360
gcaattacaa aacacgcgca gaagtcaagt ttgagggcga tactctggtc aatcggatcg   420
aattgaaggg aatcgatttc aaagaagatg gaaacatcct tggccataag ctcgagtaca   480
actataactc gcataatgtc tatatcatgg ctgacaagca gaaaaacggt atcaaagtca   540
actttaagat ccgacacaat attgaggacg gttcggtgca gcttgcggac cactatcaac   600
agaatacgcc gattggggat ggtccggtcc ttttgccgga taaccattat ctctcaaccc   660
agtcagccct gagcaaagat ccaaacgaga gagggacca catggtcttg ctcgaattcg   720
tgacagcggc agggatcact ctgggaatgg acgagttgta caagtgataa taggctgagg   780
cctcggtggc catgcttctt gcccccttgg gcctccccca gccccctcctc cccttcctgc   840
acccgtaccc cccaaacacc attgtcacac tccagtggtc tttgaataaa gtctgagtgg   900
gcggc                                                                905

SEQ ID NO: 63           moltype = DNA   length = 949
FEATURE                 Location/Qualifiers
misc_feature            1..949
                        note = Synthetic: eGFP mRNA construct with 3X miR122
                         binding site in 3 UTR
source                  1..949
                        mol_type = other DNA
                        organism = synthetic construct
SEQUENCE: 63
gggaaataag agagaaaaga agagtaagaa gaaatataag agccaccatg gtgtccaagg    60
gtgaggaatt gtttaccggg gtggtgccta ttctcgtcga acttgacggg gatgtgaatg   120
gacacaagtt ttcggtatcc ggagaaggag agggtgacgc cacatacgga aagcttacac   180
tcaaattcat ctgtacgacg gggaaactgc ccgtacccty gcctacgctc gtaaccacgc   240
tgacttatgg agtgcagtgc tttagcagat accccgacca tatgaagcag cacgacttct   300
tcaagtcggc gatgcccgag gggtacgtgc aagagaggac catttttcttc aaagacgatg   360
gcaattacaa aacacgcgca gaagtcaagt ttgagggcga tactctggtc aatcggatcg   420
aattgaaggg aatcgatttc aaagaagatg gaaacatcct tggccataag ctcgagtaca   480
actataactc gcataatgtc tatatcatgg ctgacaagca gaaaaacggt atcaaagtca   540
actttaagat ccgacacaat attgaggacg gttcggtgca gcttgcggac cactatcaac   600
agaatacgcc gattggggat ggtccggtcc ttttgccgga taaccattat ctctcaaccc   660
agtcagccct gagcaaagat ccaaacgaga gagggacca catggtcttg ctcgaattcg   720
tgacagcggc agggatcact ctgggaatgg acgagttgta caagtgataa tagcaaaac   780
cattgtcaca ctccagctgg agcctcggtg gccatgcttc ttgccccttg ggcccaaaca   840
ccattgtcac actccatccc cccagcccct cctcccctte ctgcacccgt accccccaaa   900
caccattgtc acactccagt ggtctttgaa taaagtctga gtgggcggc                949

SEQ ID NO: 64           moltype = DNA   length = 883
FEATURE                 Location/Qualifiers
misc_feature            1..883
                        note = Synthetic: control nst-eGFP mRNA construct
source                  1..883
                        mol_type = other DNA
                        organism = synthetic construct
SEQUENCE: 64
gggaaataag agagaaaaga agagtaagaa gaaatataag agccaccatc gtctccaagg    60
gtcaggaatt ctctaccggg gtcgtcccta ttctcgtcga acttgacggg gatctcaatc   120
gacacaactc ttcgatctcc ggagaaggag agggtcacga cacatacgga aagcttacac   180
tcaaattcat ctatccgacg gggaaactcc ccatccccctc gcctacgctc atcaccacgc   240
tcacttatcg agtccagtcc tttagcagat accccgacca tatcaagcag cacgacttct   300
tcaagtcggc gatccccgag ggatccgtcc aagagaggac catttttcttc aaagacgatc   360
gcaattacaa aacacgcgca gaagtcaact ttgagggcga tactctcgtc aatcggatcg   420
aattgaaggg aatcgatttc aaagaagatc gaaacatcct tggccataag ctcgagtaca   480
actataactc gcataatctc tatatcatcg ctcacaagca gaaaaacgat ctcaaagtca   540
actttaagat ccgacacaat attgaggacg ctccggtcca gcttgcggac cactatcaac   600
agaatacgcc gattggggat cgtccggtcc ttttgccgga taaccattat ctctcaaccc   660
agtcagccct cagcaaagat ccaaacgaga gagggacca catcgtcttg ctcgaattcg   720
tcacagcggc agggatcact ctcggaatcg acgactcatc caagtgataa taggctggag   780
cctcggtggc catgcttctt gcccccttgg gcctccccca gccccctcctc cccttcctgc   840
acccgtaccc ccgtggtctt tgaataaagt ctgagtgggc ggc                      883

SEQ ID NO: 65           moltype = DNA   length = 1816
FEATURE                 Location/Qualifiers
misc_feature            1..1816
                        note = Synthetic: Luc mRNA construct with no miR binding
                         sites
source                  1..1816
                        mol_type = other DNA
```

```
                        organism = synthetic construct
SEQUENCE: 65
gggaaataag agagaaaaga agagtaagaa gaaatataag agccaccatg gaagatgcga    60
agaacatcaa gaagggacct gccccgtttt acccttggga ggacggtaca gcaggagaac   120
agctccacaa ggcgatgaaa cgctacgccc tggtccccgg aacgattgcg tttaccgatg   180
cacatattga ggtagacatc acatacgcag aatacttcga aatgtcggtg aggctggcgg   240
aagcgatgaa gagatatggt cttaacacta atcaccgcat cgtggtgtgt tcggagaact   300
cattgcagtt tttcatgccg gtccttggag cacttttcat cggggtcgca gtcgcgccag   360
cgaacgacat ctacaatgag cgggaactct tgaatagcag gggaatctcc cagccgacgg   420
tcgtgtttgt ctccaaaaag gggctgcaga aaatcctcaa cgtgcagaag aagctcccca   480
ttattcaaaa gatcatcatt atggatagca agacagatta ccaagggttc cagtcgatgt   540
ataccttttgt gacatcgcat ttgccgccag ggtttaacga gtatgacttc gtccccgagt   600
catttgacag agataaaacc atcgcgctga ttatgaattc ctcgggtagc accggtttgc   660
caaagggggt ggcgttgccc caccgcactg ctttgtgtgcg gttctcgcac gctagggatc   720
ctatctttgg taatcagatc attcccgaca cagcaatcct gtccgtggta ccttttcatc   780
acggttttgg catgttcacg actctcggct atttgatttg cggtttcagg gtcgtactta   840
tgtatcggtt cgaggaagaa ctgttttttga gatccttgca agattacaag atccagtcgg   900
ccctccttgt gccaacgctt ttctcattct ttgcgaaatc gacacttatt gataagtatg   960
acctttccaa tctgcatgag attgcctcag ggggagcgcc gcttagcaag gaagtcgggg  1020
aggcagtggc caagcgcttc caccttcccg gaattcggca gggatacggg ctcacggaga  1080
caacatccgc gatccttatc acgcccgagg gtgacgataa gccgggagcc gtcggaaaag  1140
tggtcccctt ctttgaagcc aaggtcgtag acctcgacac gggaaaaacc ctcggagtga  1200
accagagggg cgagctctgc gtgagagggc cgatgatcat gtcaggttac gtgaataacc  1260
ctgaagcgac gaatgcgctg atcgacaagg atgggtggtt gcattcggga gacattgcct  1320
attgggatga ggatgagcac ttctttatcg tagatcgact taagagcttg atcaaataca  1380
aaggctatca ggtagcgcct gccgagctcg agtcaatcct gctccagcac cccaacattt  1440
tcgacgccgg agtggccggg ttgcccgatg acgacgcggg tgagctgcca gcggccgtgg  1500
tagtcctcga acatgggaaa acaatgaccg aaaaggagat cgtggactac gtagcatcac  1560
aagtgacgac tgcgaagaaa ctgaggggag gggtagtctt tgtggacgag gtcccgaaag  1620
gcttgactgg gaagcttgac gctcgcaaaa tccgggaaat cctgattaag gcaaagaaag  1680
gcgggaaaat cgctgtctga taataggctg gagcctcggt ggccatgctt cttgcccctt  1740
gggcctcccc ccagccctc ctccccttcc tgcacccgta cccccgtggt ctttgaataa  1800
agtctgagtg ggcggc                                                   1816

SEQ ID NO: 66            moltype = DNA  length = 1838
FEATURE                  Location/Qualifiers
misc_feature             1..1838
                         note = Synthetic: Luc mRNA construct with 1X miR122 binding
                         site in 3 UTR
source                   1..1838
                         mol_type = other DNA
                         organism = synthetic construct
SEQUENCE: 66
gggaaataag agagaaaaga agagtaagaa gaaatataag agccaccatg gaagatgcga    60
agaacatcaa gaagggacct gccccgtttt acccttggga ggacggtaca gcaggagaac   120
agctccacaa ggcgatgaaa cgctacgccc tggtccccgg aacgattgcg tttaccgatg   180
cacatattga ggtagacatc acatacgcag aatacttcga aatgtcggtg aggctggcgg   240
aagcgatgaa gagatatggt cttaacacta atcaccgcat cgtggtgtgt tcggagaact   300
cattgcagtt tttcatgccg gtccttggag cacttttcat cggggtcgca gtcgcgccag   360
cgaacgacat ctacaatgag cgggaactct tgaatagcag gggaatctcc cagccgacgg   420
tcgtgtttgt ctccaaaaag gggctgcaga aaatcctcaa cgtgcagaag aagctcccca   480
ttattcaaaa gatcatcatt atggatagca agacagatta ccaagggttc cagtcgatgt   540
ataccttttgt gacatcgcat ttgccgccag ggtttaacga gtatgacttc gtccccgagt   600
catttgacag agataaaacc atcgcgctga ttatgaattc ctcgggtagc accggtttgc   660
caaagggggt ggcgttgccc caccgcactg ctttgtgtgcg gttctcgcac gctagggatc   720
ctatctttgg taatcagatc attcccgaca cagcaatcct gtccgtggta ccttttcatc   780
acggttttgg catgttcacg actctcggct atttgatttg cggtttcagg gtcgtactta   840
tgtatcggtt cgaggaagaa ctgttttttga gatccttgca agattacaag atccagtcgg   900
ccctccttgt gccaacgctt ttctcattct ttgcgaaatc gacacttatt gataagtatg   960
acctttccaa tctgcatgag attgcctcag ggggagcgcc gcttagcaag gaagtcgggg  1020
aggcagtggc caagcgcttc caccttcccg gaattcggca gggatacggg ctcacggaga  1080
caacatccgc gatccttatc acgcccgagg gtgacgataa gccgggagcc gtcggaaaag  1140
tggtcccctt ctttgaagcc aaggtcgtag acctcgacac gggaaaaacc ctcggagtga  1200
accagagggg cgagctctgc gtgagagggc cgatgatcat gtcaggttac gtgaataacc  1260
ctgaagcgac gaatgcgctg atcgacaagg atgggtggtt gcattcggga gacattgcct  1320
attgggatga ggatgagcac ttctttatcg tagatcgact taagagcttg atcaaataca  1380
aaggctatca ggtagcgcct gccgagctcg agtcaatcct gctccagcac cccaacattt  1440
tcgacgccgg agtggccggg ttgcccgatg acgacgcggg tgagctgcca gcggccgtgg  1500
tagtcctcga acatgggaaa acaatgaccg aaaaggagat cgtggactac gtagcatcac  1560
aagtgacgac tgcgaagaaa ctgaggggag gggtagtctt tgtggacgag gtcccgaaag  1620
gcttgactgg gaagcttgac gctcgcaaaa tccgggaaat cctgattaag gcaaagaaag  1680
gcgggaaaat cgctgtctga taataggctg gagcctcggt ggccatgctt cttgcccctt  1740
gggcctcccc ccagccctc ctccccttcc tgcacccgta ccccccaaac accattgtca  1800
cactccagtg gtctttgaat aaagtctgag tgggcggc                          1838

SEQ ID NO: 67            moltype = DNA  length = 1882
FEATURE                  Location/Qualifiers
misc_feature             1..1882
                         note = Synthetic: Luc mRNA construct with 3X miR122 binding
```

|  |  |
|---|---|
| | site in 3 UTR |
| source | 1..1882 |
| | mol_type = other DNA |
| | organism = synthetic construct |

SEQUENCE: 67

```
gggaaataag agagaaaaga agagtaagaa gaaatataag agccaccatg gaagatgcga    60
agaacatcaa gaagggacct gccccgtttt acccttggga ggacggtaca gcaggagaac   120
agctccacaa ggcgatgaaa cgctacgccc tggtccccgg aacgattgcg tttaccgatg   180
cacatattga ggtagacatc acatacgcag aatacttcga aatgtcggtg aggctggcgg   240
aagcgatgaa gagatatggt cttaacacta atcaccgcat cgtggtgtgt tcggagaact   300
cattgcagtt tttcatgccg gtccttgagg cacttttcat cggggtcgca gtcgcgccag   360
cgaacgacat ctacaatgag cgggaactct tgaatagcat gggaatctcc cagccgacgg   420
tcgtgtttgt ctccaaaaag gggctgcaga aaatcctcca cgtgcagaag aagctcccca   480
ttattcaaaa gatcatcatt atggatagca agacagatta ccaagggttc cagtcgatgt   540
atacctttgt gacatcgcat ttgccgccag ggtttaacga gtatgacttc gtccccgagt   600
catttgacag agataaaacc atcgcgctga ttatgaattc ctcgggtagc accggtttgc   660
caaagggggt ggcgttgccc caccgcactg cttgtgtgcg gttctcgcac gctagggatc   720
ctatctttgg taatcagatc attcccgaca cagcaatcct gtccgtggta ccttttcatc   780
acggttttgg catgttcacg actctcggct atttgatttg cggtttcagg gtcgtactta   840
tgtatcggtt cgaggaagaa ctgtttttga gatcctttgca agattacaag atccagtcgg   900
ccctccttgt gccaacgctt ttctcattct tgcgaaatc gacactttat gataagtatg   960
acctttccaa tctgcatgag attgcctcag ggggagcgcc gcttagcaag gaagtcgggg  1020
aggcagtggc caagcgcttc caccttcccg gaattcggac gggatacggg ctcacggaga  1080
caacatccgc gatccttatc acgcccgagg tgacgataa gccgggagcc gtcggaaaag  1140
tggtcccctt ctttgaagcc aaggtcgtag acctcgacac gggaaaaacc ctcggagtga  1200
accagagggg cgagctctgc gtgagagggc cgatgatcat gtcaggttac gtgaataacc  1260
ctgaagcgac gaatgcgctg atcgacaagg atgggtggt gcattcggga gacattgcct  1320
attgggatga ggatgagcac ttctttatcg tagatcgact taagagcttg atcaaataca  1380
aaggctatca ggtagcgcct gccgagctcg agtcaatcct gctccagcac ccaacatttt  1440
tcgacgccga agtggccggg ttgcccgatg acgacgcggg tgagctgcca gcggccgtgg  1500
tagtcctcga acatgggaaa acaatgaccg aaaaggagat cgtggactac gtagcatcac  1560
aagtgacgac tgcgaagaaa ctgaggggag gggtagtctt tgtggacgag gtcccgaaag  1620
gcttgactgg gaagcttgac gctcgcaaaa tccgggaaat cctgattaag gcaaagaaag  1680
gcgggaaaat cgctgtctga taatagcaaa caccattgtc acactccagc tggagcctcc  1740
gtggccatgc ttcttgcccc ttgggcccaa acaccattgt cacactccat cccccccagcc  1800
cctcctcccc ttcctgcacc cgtaccccc aaacaccatt gtcacactcc agtggtcttt  1860
gaataaagtc tgagtgggcg gc                                           1882
```

| | |
|---|---|
| SEQ ID NO: 68 | moltype = DNA length = 1816 |
| FEATURE | Location/Qualifiers |
| misc_feature | 1..1816 |
| | note = Synthetic: control nst-Luc mRNA construct |
| source | 1..1816 |
| | mol_type = other DNA |
| | organism = synthetic construct |

SEQUENCE: 68

```
gggaaataag agagaaaaga agagtaagaa gaaatataag agccaccata gaagatacga    60
agaacatcaa gaagggacct accccgtttt acccttggga ggacggtaca gcaggagaac   120
agctccacaa ggcgataaaa cgctacgccc tagtccccgg aacgattgcg tttaccgata   180
cacatattga ggtagacatc acatacgcag aatacttcga aatatcggtc aggctagcgg   240
aagcgataaa gagatatagt cttaacacta atcaccgcat cgtcgtctat tcggagaact   300
cattgcagtt tttcataccg gtccttgagg cacttttcat cggggtcgca gtcgcgccag   360
cgaacgacat ctacaataag cgggaactct tgaatagcat aggaatctcc cagccgacgg   420
tcgtctttgt ctccaaaaag gggctacaga aaatcctcaa cgtccagaag aagctcccca   480
ttattcaaaa gatcatcatt atagatagca agacagatta ccaagggttc cagtcgatat   540
atacctttgt cacatcgcat ttgccgccag ggtttaacga gtataacttc gtccccgagt   600
catttgacag agataaaacc atcgcgctaa ttataaattc ctcgggtagc accggtttgc   660
caaagggggt cgcgttgccc caccgcacta cttgtctacg gttctcgcac gctagggatc   720
ctatctttgg taatcagatc attcccgaca cagcaatcct atcgtcgta ccttttcatc   780
acggttttgg catattcacg actctcggct atttgatttg cggtttcagg gtcgtactta   840
tatatcggtt cgaggaagaa ctatttttga gatcctttgca agattacaag atccagtcgg   900
ccctccttgt cccaacgctt ttctcattct tgcgaaatc gacactttat gataagtata   960
acctttccaa tctacataag attgcctcag ggggagcgcc gcttagcaag gaagtcgggg  1020
aggcagtcgc caagcgcttc caccttcccg gaattcggac gggatacggg ctcacggaga  1080
caacatccgc gatccttatc acgcccgagg tcacgataa gccgggagcc gtcggaaaag  1140
tcgtcccctt ctttgaagcc aaggtcgtag acctcgacac gggaaaaacc ctcggagtca  1200
accagagggg cgagctctac gtcagagggc gataatcat atcaggttac gtcaataacc  1260
ctaaagcgac gaatacgcta atcgacaagg ataggtcgtt gcattcggga gacattgcct  1320
attgggataa ggataagcac ttctttatcg tagatcgact taagagcttg atcaaataca  1380
aaggctatca ggtagcgcct accgagctcg agtcaatcct actccagcac ccaacatttt  1440
tcgacgccga agtcgccggg ttgcccgata cgacgcggg tcagctacca gcggccgtcg  1500
tagtcctcga acataggaaa acaataaccg aaaaggagat cgtcgactac gtagcatcac  1560
aagtcacgac tacgaagaaa ctaaggggag gggtagtctt tgtcgacgag gtcccgaaag  1620
gcttgactgg gaagcttgac gctcgcaaaa tccgggaaat cctaattaag gcaaagaaag  1680
gcgggaaaat cgctatctga taataggctg agcctcggg ggccatgctt cttgcccctt  1740
gggcctcccc ccagcccctc ctcccctttcc tgcacccgta ccccgtggt ctttgaataa  1800
agtctgagtg ggcggc                                                  1816
```

| | |
|---|---|
| SEQ ID NO: 69 | moltype = DNA length = 1066 |

```
FEATURE              Location/Qualifiers
misc_feature         1..1066
                     note = Synthetic: Caspase mRNA construct with no miR
                     binding sites
source               1..1066
                     mol_type = other DNA
                     organism = synthetic construct
SEQUENCE: 69
gggaaataag agagaaaaga agagtaagaa gaaatataag agccaccatg gtagaaatag   60
atgcagcctc cgtttacacg ctgcctgctg gagctgactt cctcatgtgt tactctgttg  120
cagaaggata ttattctcac cgggaaactg tgaacggctc atggtacatt caagatttgt  180
gtgagatgtt gggaaaatat ggctcctcct tagagttcac agaactcctc acactggtga  240
acaggaaagt ttctcagcgc cgagtggact tttgcaaaga cccaagtgca attggaaaga  300
agcaggttcc ctgttttgcc tcaatgctaa ctaaaaagct gcatttcttt ccaaaatcta  360
atctcgagca ccaccaccac caccacgttg aaattgatgg gggatccccc atgagctcgg  420
cctcggggct ccgcagggg cacccggcag gtggggaaga aaacatgaca gaaacagatg   480
ccttctataa aagagaaatg tttgatccgg cagaaaagta caaatggac cacaggagga   540
gaggaattgc tttaatcttc aatcatgaga ggttctttg gcacttaaca ctgccagaaa   600
ggcggggcac ctgcgcagat agagacaatc ttacccgcag gttttcagat ctaggatttg  660
aagtgaaatg ctttaatgat cttaaagcag aagaactact gctcaaaatt catgaggtgt  720
caactgttag ccacgcagat gccgattgct tgtgtgtgt cttcctgagc catggcgaag   780
gcaatcacat ttatgcatat gatgctaaaa tcgaaattca gacattaact ggcttgttca  840
aaggagacaa gtgtcacagc ctggttggaa aacccaagat atttatcatc caggcatgtc  900
ggggaaacca gcacgatgtg ccagtcattc ctttggatgt agtagattga taataggctg  960
gagcctcggt ggccatgctt cttgcccctt gggcctcccc ccagcccctc ctcccttcc  1020
tgcacccgta ccccgtggt ctttgaataa agtctgagtg gcggc                 1066

SEQ ID NO: 70        moltype = DNA  length = 1088
FEATURE              Location/Qualifiers
misc_feature         1..1088
                     note = Synthetic: Caspase mRNA construct with 1X miR122
                     binding site in 3 UTR
source               1..1088
                     mol_type = other DNA
                     organism = synthetic construct
SEQUENCE: 70
gggaaataag agagaaaaga agagtaagaa gaaatataag agccaccatg gtagaaatag   60
atgcagcctc cgtttacacg ctgcctgctg gagctgactt cctcatgtgt tactctgttg  120
cagaaggata ttattctcac cgggaaactg tgaacggctc atggtacatt caagatttgt  180
gtgagatgtt gggaaaatat ggctcctcct tagagttcac agaactcctc acactggtga  240
acaggaaagt ttctcagcgc cgagtggact tttgcaaaga cccaagtgca attggaaaga  300
agcaggttcc ctgttttgcc tcaatgctaa ctaaaaagct gcatttcttt ccaaaatcta  360
atctcgagca ccaccaccac caccacgttg aaattgatgg gggatccccc atgagctcgg  420
cctcggggct ccgcagggg cacccggcag gtggggaaga aaacatgaca gaaacagatg   480
ccttctataa aagagaaatg tttgatccgg cagaaaagta caaatggac cacaggagga   540
gaggaattgc tttaatcttc aatcatgaga ggttctttg gcacttaaca ctgccagaaa   600
ggcggggcac ctgcgcagat agagacaatc ttacccgcag gttttcagat ctaggatttg  660
aagtgaaatg ctttaatgat cttaaagcag aagaactact gctcaaaatt catgaggtgt  720
caactgttag ccacgcagat gccgattgct tgtgtgtgt cttcctgagc catggcgaag   780
gcaatcacat ttatgcatat gatgctaaaa tcgaaattca gacattaact ggcttgttca  840
aaggagacaa gtgtcacagc ctggttggaa aacccaagat atttatcatc caggcatgtc  900
ggggaaacca gcacgatgtg ccagtcattc ctttggatgt agtagattga taataggctg  960
gagcctcggt ggccatgctt cttgcccctt gggcctcccc ccagcccctc ctcccttcc  1020
tgcacccgta cccccaaac accattgtca cactccagtg gtctttgaat aaagtctgag  1080
tgggcggc                                                          1088

SEQ ID NO: 71        moltype = DNA  length = 1132
FEATURE              Location/Qualifiers
misc_feature         1..1132
                     note = Synthetic: Caspase mRNA construct with 3X miR122
                     binding site in 3 UTR
source               1..1132
                     mol_type = other DNA
                     organism = synthetic construct
SEQUENCE: 71
gggaaataag agagaaaaga agagtaagaa gaaatataag agccaccatg gtagaaatag   60
atgcagcctc cgtttacacg ctgcctgctg gagctgactt cctcatgtgt tactctgttg  120
cagaaggata ttattctcac cgggaaactg tgaacggctc atggtacatt caagatttgt  180
gtgagatgtt gggaaaatat ggctcctcct tagagttcac agaactcctc acactggtga  240
acaggaaagt ttctcagcgc cgagtggact tttgcaaaga cccaagtgca attggaaaga  300
agcaggttcc ctgttttgcc tcaatgctaa ctaaaaagct gcatttcttt ccaaaatcta  360
atctcgagca ccaccaccac caccacgttg aaattgatgg gggatccccc atgagctcgg  420
cctcggggct ccgcagggg cacccggcag gtggggaaga aaacatgaca gaaacagatg   480
ccttctataa aagagaaatg tttgatccgg cagaaaagta caaatggac cacaggagga   540
gaggaattgc tttaatcttc aatcatgaga ggttctttg gcacttaaca ctgccagaaa   600
ggcggggcac ctgcgcagat agagacaatc ttacccgcag gttttcagat ctaggatttg  660
aagtgaaatg ctttaatgat cttaaagcag aagaactact gctcaaaatt catgaggtgt  720
caactgttag ccacgcagat gccgattgct tgtgtgtgt cttcctgagc catggcgaag   780
gcaatcacat ttatgcatat gatgctaaaa tcgaaattca gacattaact ggcttgttca  840
```

```
aaggagacaa gtgtcacagc ctggttggaa acccaagat atttatcatc caggcatgtc   900
ggggaaacca gcacgatgtg ccagtcattc ctttggatgt agtagattga taatagcaaa   960
caccattgtc acactccagc tggagcctcg gtggccatgc ttcttgcccc ttgggccaa   1020
acaccattgt cacactccat cccccagcc cctcctcccc ttcctgcacc cgtaccccc   1080
aaacaccatt gtcacactcc agtggtcttt gaataaagtc tgagtgggcg gc          1132

SEQ ID NO: 72          moltype = DNA   length = 1066
FEATURE                Location/Qualifiers
misc_feature           1..1066
                       note = Synthetic: control nst-Caspase mRNA construct
source                 1..1066
                       mol_type = other DNA
                       organism = synthetic construct
SEQUENCE: 72
gggaaataag agagaaaaga agagtaagaa gaaatataag agccaccagg gtagaaatag    60
atccagcctc cgtttacacg ttgcttgttg gagttgactt cctcttgtct tactttgttg   120
cagaaggata ttattctcac cgggaaattg tcaacggctc attgtacatt caagatttgt   180
ctcagatctt ggaaaatag cgctcctcct tagagttcac agaactcctc acattggtca    240
acaggaaagt ttctcagcgc cgagtcgact tttgcaaaga cccaagtcca attggaaaga   300
agcaggttcc ttgttttgcc tcattgctaa ctaaaaagtt gcatttcttt ccaaaatcta   360
atctcgagca ccaccaccac caccacgttg aaattgattg gggatccccc attagctcgg   420
cctcgggggct ccgcagggggg cacccggcag gtcgggaaga aacattaca gaaacagatt   480
ccttctataa aagagaaatc tttgatccgg cagaaaagta caaatcgac cacaggagga   540
gaggaattgc tttaatcttc aatcatcaga ggttctttg gcacttaaca ttgccagaaa   600
ggcgggggcac ttgcgcagat agagacaatc ttacccgcag gttttcagat ctaggatttg   660
aagtcaaatc ctttaatcat cttaaagcag aagaactctc gctcaaaatt catcaggtct   720
caattgttag ccacgcagat cccgattgct ttgtctctct cttcttgagc catcgcgaag   780
gcaatcacat ttatccatat catcctaaaa tcgaaattca gacattaatt ggcttgttca   840
aaggagacaa gtctcacagc ttggttggaa acccaagat atttatcatc caggcatctc   900
ggggaaacca gcacgatttg ccagtcattc ctttggatct agtagattga taataggctg   960
gagcctcggt ggccatgctt cttgcccctt gggcctcccc ccagcccctc ctcccttcc   1020
tgcacccgta ccccgtggt ctttgaataa agtctgagtg ggcggc                  1066

SEQ ID NO: 73          moltype = RNA   length = 164
FEATURE                Location/Qualifiers
misc_feature           1..164
                       note = Synthetic: 3 UTR with miR 142-3p and miR 126-3p
                        binding sites
source                 1..164
                       mol_type = other RNA
                       organism = synthetic construct
SEQUENCE: 73
tgataatagt ccataaagta ggaaacacta cagctggagc ctcggtggcc atgcttcttg    60
cccccttggg ctcccccccag cccctcctcc ccttcctgca cccgtacccc ccgcattatt   120
actcacggta cgagtggtct ttgaataaag tctgagtggg cggc                     164

SEQ ID NO: 74          moltype = RNA   length = 23
FEATURE                Location/Qualifiers
misc_feature           1..23
                       note = Synthetic: miR 155-5p binding site
source                 1..23
                       mol_type = other RNA
                       organism = synthetic construct
SEQUENCE: 74
accccctatca caattagcat taa                                            23

SEQ ID NO: 75          moltype = RNA   length = 188
FEATURE                Location/Qualifiers
misc_feature           1..188
                       note = Synthetic: 3 UTR with 3 miR 142-3p binding sites
source                 1..188
                       mol_type = other RNA
                       organism = synthetic construct
SEQUENCE: 75
tgataatagt ccataaagta ggaaacacta cagctggagc ctcggtggcc atgcttcttg    60
cccccttggg ctccataaag taggaaacac tacatcccc cagcccctcc tcccccttcct   120
gcacccgtac cccctccata aagtaggaaa cactacagtg gtctttgaat aaagtctgag   180
tgggcggc                                                            188

SEQ ID NO: 76          moltype = RNA   length = 140
FEATURE                Location/Qualifiers
misc_feature           1..140
                       note = Synthetic: 3UTR with miR 142-5p binding site
source                 1..140
                       mol_type = other RNA
                       organism = synthetic construct
SEQUENCE: 76
tgataatagg ctggagcctc ggtggccatg cttcttgccc cttgggcctc ccccagccc    60
ctcctcccct tcctgcaccc gtaccccag tagtgctttc tactttatgg tggtctttga   120
```

```
ataaagtctg agtgggcggc                                              140

SEQ ID NO: 77          moltype = RNA   length = 181
FEATURE                Location/Qualifiers
misc_feature           1..181
                       note = Synthetic: 3UTR with 3 miR 142-5p binding sites
source                 1..181
                       mol_type = other RNA
                       organism = synthetic construct
SEQUENCE: 77
tgataataga gtagtgcttt ctactttatg gctggagcct cggtggccat gcttcttgcc   60
ccttgggcca gtagtgcttt ctactttatg tcccccagc ccctctcccc ttcctgcacc   120
cgtaccccca gtagtgcttt ctactttatg gtggtctttg aataaagtct gagtgggcgg  180
c                                                                  181

SEQ ID NO: 78          moltype = RNA   length = 184
FEATURE                Location/Qualifiers
misc_feature           1..184
                       note = Synthetic: 3UTR with 2 miR 142-5p binding sites and
                       1 miR 142-3p binding site
source                 1..184
                       mol_type = other RNA
                       organism = synthetic construct
SEQUENCE: 78
tgataataga gtagtgcttt ctactttatg gctggagcct cggtggccat gcttcttgcc   60
ccttgggcct ccataaagta ggaaacacta catcccccca gccctcctc ccttcctgc    120
acccgtaccc ccagtagtgc tttctacttt atggtggtct ttgaataaag tctgagtggg  180
cggc                                                               184

SEQ ID NO: 79          moltype = RNA   length = 142
FEATURE                Location/Qualifiers
misc_feature           1..142
                       note = Synthetic: 3UTR with miR 155-5p binding site
source                 1..142
                       mol_type = other RNA
                       organism = synthetic construct
SEQUENCE: 79
tgataatagg ctggagcctc ggtggccatg cttcttgccc cttgggcctc ccccagccc   60
ctcctcccct tcctgcaccc gtaccccac ccctatcaca attagcatta agtggtcttt   120
gaataaagtc tgagtgggcg gc                                           142

SEQ ID NO: 80          moltype = RNA   length = 188
FEATURE                Location/Qualifiers
misc_feature           1..188
                       note = Synthetic: 3 UTR with 3 miR 155-5p binding sites
source                 1..188
                       mol_type = other RNA
                       organism = synthetic construct
SEQUENCE: 80
tgataataga ccctatcac aattagcatt aagctggagc ctcggtggcc atgcttcttg    60
cccttgggc caccctatc acaattagca ttaatcccc cagccctcc tccttcct       120
gcaccgtac ccccaccct atcacaatta gcattaagtg gtctttgaat aaagtctgag    180
tgggcggc                                                           188

SEQ ID NO: 81          moltype = RNA   length = 188
FEATURE                Location/Qualifiers
misc_feature           1..188
                       note = Synthetic: 3UTR with 2 miR 155-5p binding sites and
                       1 miR 142-3p binding site
source                 1..188
                       mol_type = other RNA
                       organism = synthetic construct
SEQUENCE: 81
tgataataga ccctatcac aattagcatt aagctggagc ctcggtggcc atgcttcttg    60
ccccttgggc ctccataaag taggaaacac tacatccccc cagccctcc tcccttcct   120
gcacccgtac ccccacccct atcacaatta gcattaagtg gtctttgaat aaagtctgag  180
tgggcggc                                                           188

SEQ ID NO: 82          moltype = RNA   length = 142
FEATURE                Location/Qualifiers
misc_feature           1..142
                       note = Synthetic: 3'UTR with miR 142-3p binding site, P2
                       insertion
source                 1..142
                       mol_type = other RNA
                       organism = synthetic construct
SEQUENCE: 82
tgataatagg ctggagcctc ggtggctcca taaagtagga acactacac atgcttcttg    60
cccttgggc ctcccccag ccctcctcc ccttcctgca ccgtacccc cgtggtcttt      120
```

```
                                        -continued
gaataaagtc tgagtgggcg gc                                             142

SEQ ID NO: 83           moltype = RNA   length = 142
FEATURE                 Location/Qualifiers
misc_feature            1..142
                        note = Synthetic: 3'UTR with miR 142-3p binding site, P3
                          insertion
source                  1..142
                        mol_type = other RNA
                        organism = synthetic construct
SEQUENCE: 83
tgataatagg ctggagcctc ggtggccatg cttcttgccc cttgggcctc cataaagtag    60
gaaacactac atcccccag ccctcctcc ccttcctgca cccgtacccc cgtggtcttt     120
gaataaagtc tgagtgggcg gc                                             142

SEQ ID NO: 84           moltype = RNA   length = 70
FEATURE                 Location/Qualifiers
misc_feature            1..70
                        note = Synthetic: 5' UTR with miR142-3p binding site at
                          position p1
source                  1..70
                        mol_type = other RNA
                        organism = synthetic construct
SEQUENCE: 84
gggaaataag agtccataaa gtaggaaaca ctacaagaaa agaagagtaa gaagaaatat    60
aagagccacc                                                            70

SEQ ID NO: 85           moltype = RNA   length = 70
FEATURE                 Location/Qualifiers
misc_feature            1..70
                        note = Synthetic: 5' UTR with miR142-3p binding site at
                          position p2
source                  1..70
                        mol_type = other RNA
                        organism = synthetic construct
SEQUENCE: 85
gggaaataag agagaaaaga agtaatcc ataaagtagg aaacactaca gaagaaatat      60
aagagccacc                                                            70

SEQ ID NO: 86           moltype = RNA   length = 70
FEATURE                 Location/Qualifiers
misc_feature            1..70
                        note = Synthetic: 5' UTR with miR142-3p binding site at
                          position p3
source                  1..70
                        mol_type = other RNA
                        organism = synthetic construct
SEQUENCE: 86
gggaaataag agagaaaaga agtaagaa gaaatataat ccataaagta ggaaacacta     60
cagagccacc                                                            70
```